US008465755B2

(12) United States Patent
Curtiss, III et al.

(10) Patent No.: US 8,465,755 B2
(45) Date of Patent: Jun. 18, 2013

(54) RECOMBINANT BACTERIUM CAPABLE OF ELICITING AN IMMUNE RESPONSE AGAINST ENTERIC PATHOGENS

(75) Inventors: Roy Curtiss, III, Paradise Valley, AZ (US); Melha Mellata, Tempe, AZ (US); Bereket Zekarias, Mesa, AZ (US); Zhaoxing Shi, Tempe, AZ (US); Christine Branger, Phoenix, AZ (US); Kenneth Roland, Mesa, AZ (US)

(73) Assignee: The Arizona Board of Regents for and on Behalf of Arizona State University, Tempe, AZ (US)

( * ) Notice: Subject to any disclaimer, the term of this patent is extended or adjusted under 35 U.S.C. 154(b) by 3 days.

(21) Appl. No.: 12/681,721

(22) PCT Filed: Oct. 6, 2008

(86) PCT No.: PCT/US2008/078991
§ 371 (c)(1),
(2), (4) Date: Oct. 26, 2010

(87) PCT Pub. No.: WO2009/046449
PCT Pub. Date: Apr. 9, 2009

(65) Prior Publication Data
US 2011/0033501 A1 Feb. 10, 2011

Related U.S. Application Data

(60) Provisional application No. 60/978,084, filed on Oct. 5, 2007.

(51) Int. Cl.
*A61K 39/112* (2006.01)
*C12N 1/21* (2006.01)

(52) U.S. Cl.
USPC ..................................... 424/258.1; 435/252.3

(58) Field of Classification Search
None
See application file for complete search history.

(56) References Cited

U.S. PATENT DOCUMENTS

| | | |
|---|---|---|
| 4,190,495 A | 2/1980 | Curtiss, III |
| 4,888,170 A | 12/1989 | Curtiss, III |
| 4,968,619 A | 11/1990 | Curtiss, III |
| 5,210,035 A | 5/1993 | Stocker |
| 5,294,441 A | 3/1994 | Curtiss, III |
| 5,387,744 A | 2/1995 | Curtiss |
| 5,389,368 A | 2/1995 | Curtiss, III |
| 5,424,065 A | 6/1995 | Curtiss, III |
| 5,468,485 A | 11/1995 | Curtiss, III |
| 5,654,184 A | 8/1997 | Curtiss, III |
| 5,656,488 A | 8/1997 | Curtiss, III |
| 5,672,345 A | 9/1997 | Curtiss, III |
| 5,679,880 A | 10/1997 | Curtiss, III |
| 5,686,079 A | 11/1997 | Curtiss, III |
| 5,817,317 A | 10/1998 | Titball |
| 5,840,483 A | 11/1998 | Curtiss, III |
| 5,855,879 A | 1/1999 | Curtiss, III |
| 5,855,880 A | 1/1999 | Curtiss, III |
| 6,024,961 A | 2/2000 | Curtiss, III |
| 6,180,614 B1 | 1/2001 | Davis |
| 6,248,329 B1 * | 6/2001 | Chandrashekar et al. . 424/191.1 |
| 6,350,454 B1 | 2/2002 | Thune |
| 6,383,496 B1 | 5/2002 | Curtiss, III |
| 6,399,074 B1 | 6/2002 | Roland |
| 6,403,094 B1 | 6/2002 | Titball |
| 6,610,529 B1 | 8/2003 | Curtiss, III |
| 6,780,405 B1 | 8/2004 | Curtiss, III |
| 6,872,547 B1 | 3/2005 | Curtiss, III |
| 6,969,513 B2 | 11/2005 | Galen |
| 7,083,794 B2 | 8/2006 | Curtiss, III |
| 7,195,757 B2 | 3/2007 | Curtiss, III |
| 7,205,125 B2 | 4/2007 | Castillo |
| 7,341,860 B2 | 3/2008 | Curtiss, III |
| 7,871,604 B1 | 1/2011 | Curtiss, III |
| 7,968,101 B2 | 6/2011 | Kawaoka |
| 8,133,493 B2 | 3/2012 | Curtiss, III |
| 2003/0031683 A1 | 2/2003 | Curtiss, III |
| 2003/0175772 A1 | 9/2003 | Wang |
| 2004/0101531 A1 | 5/2004 | Curtiss, III |
| 2004/0120962 A1 | 6/2004 | Curtiss, III |
| 2004/0137003 A1 | 7/2004 | Curtiss, III |
| 2004/0203039 A1 | 10/2004 | Hensel |
| 2005/0036987 A1 | 2/2005 | Pawelek |
| 2005/0106175 A1 | 5/2005 | Montanes |
| 2005/0106176 A1 | 5/2005 | Curtiss, III |
| 2006/0140975 A1 | 6/2006 | Curtiss, III |
| 2006/0171917 A1 | 8/2006 | Campbell |

(Continued)

FOREIGN PATENT DOCUMENTS

| | | |
|---|---|---|
| EP | 0315682 B1 | 12/1993 |
| EP | 0381706 B1 | 4/1995 |

(Continued)

OTHER PUBLICATIONS

Houghten et al. (Vaccines, 1986, Edited by Fred Brown: Cold Spring Harbor Laboratory).*
Ellis (Chapter 29 of Vaccines, Plotkin, et al. (eds) WB Saunders, Philadelphia, 1988.*
Greenspan et al. (Nature Biotechnology 7: 936-937, 1999).*
International Search Report and Written Opinion from related International application No. PCT/US2008/078991, 6 pgs.
PCT/US2008/063303 (WO 2008/141226)—International Search Report and Written Opinion of the International Searching Authority, Nov. 26, 2008.
PCT/US2008/063293 (WO 2009/025888)—International Search Report and Written Opinion of the International Searching Authority, Feb. 12, 2009.
PCT/US2008/078991 (WO 2009/046449)—International Search Report and Written Opinion of the International Searching Authority, Dec. 15, 2008.
PCT/US2008/078993 (WO 2009/046451)—International Search Report and Written Opinion of the International Searching Authority, Dec. 15, 2008.

(Continued)

*Primary Examiner* — Padma V Baskar
(74) *Attorney, Agent, or Firm* — Polsinelli Shughart PC

(57) ABSTRACT

The present invention relates to a recombinant bacterium that is capable of eliciting an immune response against at least two enteric pathogens, without substantially inducing an immune response specific to the serotype of the bacterium. The invention also relates to methods of making such a bacterium and vaccines and methods of using such a bacterium.

28 Claims, 46 Drawing Sheets

U.S. PATENT DOCUMENTS

| | | | |
|---|---|---|---|
| 2006/0206961 A1 | 9/2006 | Cirpus | |
| 2006/0233829 A1 | 10/2006 | Curtiss, II | |
| 2006/0234346 A1 | 10/2006 | Retallack | |
| 2006/0275255 A1 | 12/2006 | Gudkov | |
| 2007/0025981 A1 | 2/2007 | Szalay | |
| 2008/0248066 A1 | 10/2008 | Dubensky, Jr. | |
| 2009/0175829 A1 | 7/2009 | Forbes | |
| 2010/0124558 A1 | 5/2010 | Curtiss, III | |
| 2010/0285592 A1 | 11/2010 | Curtiss, III | |
| 2010/0317084 A1 | 12/2010 | Curtiss, II | |
| 2011/0256181 A1 | 10/2011 | Curtiss, III | |
| 2012/0087946 A1 | 4/2012 | Curtiss, III | |

FOREIGN PATENT DOCUMENTS

| | | |
|---|---|---|
| EP | 0465560 B1 | 6/1996 |
| EP | 0500699 B1 | 6/1998 |
| EP | 0558631 B1 | 3/1999 |
| EP | 0433372 B1 | 6/2002 |
| EP | 1030690 B1 | 7/2002 |
| EP | 0556333 B1 | 3/2003 |
| EP | 1326960 B1 | 12/2004 |
| EP | 0832255 B1 | 12/2005 |
| EP | 1537214 B1 | 3/2006 |
| EP | 1292687 B1 | 8/2006 |
| WO | 88/09669 A1 | 12/1988 |
| WO | 89/03427 A1 | 4/1989 |
| WO | 90/02484 A1 | 3/1990 |
| WO | 90/11687 A1 | 10/1990 |
| WO | 90/11688 A1 | 10/1990 |
| WO | 90/12086 A1 | 10/1990 |
| WO | 91/06317 A1 | 5/1991 |
| WO | 92/08486 A1 | 5/1992 |
| WO | 92/09684 A1 | 6/1992 |
| WO | 93/04202 A1 | 9/1993 |
| WO | 94/24291 A2 | 10/1994 |
| WO | 94/24291 A3 | 12/1994 |
| WO | 96/40947 A1 | 12/1996 |
| WO | 91/25387 A1 | 5/1999 |
| WO | 01/83785 A2 | 11/2001 |
| WO | 02/30457 A2 | 4/2002 |
| WO | 01/83785 A3 | 6/2002 |
| WO | 02/059292 A2 | 8/2002 |
| WO | 02/030457 A3 | 1/2003 |
| WO | 02/030457 A3 | 7/2003 |
| WO | 02/059292 A3 | 7/2003 |
| WO | 03/079792 A1 | 10/2003 |
| WO | 03/096812 A1 | 11/2003 |
| WO | 2004/020643 A2 | 3/2004 |
| WO | 2004/020643 A3 | 4/2004 |
| WO | 2005/001069 A1 | 1/2005 |
| WO | 2008/141226 A2 | 11/2008 |
| WO | 2009/025888 A2 | 2/2009 |
| WO | 2009/046449 A1 | 4/2009 |
| WO | 2009/046451 A1 | 4/2009 |
| WO | 2010/045620 A1 | 4/2010 |
| WO | 2010/078584 A1 | 8/2010 |
| WO | 2010/135563 A1 | 11/2010 |
| WO | 2011/091291 A1 | 7/2011 |
| WO | 2011/150421 A2 | 12/2011 |
| WO | 2012087483 A1 | 6/2012 |

OTHER PUBLICATIONS

PCT/US2010/035630 (WO 2010/135563)—International Search Report and Written Opinion of the International Searching Authority, Sep. 29, 2010.
PCT/US2009/061100 (WO 2010/045620)—International Search Report and Written Opinion of the International Searching Authority, Dec. 4, 2009.
PCT/US2010/020137 (WO 2010/078584)—International Search Report and Written Opinion of the International Searching Authority, Mar. 9, 2010.
PCT/US2011/022110 (WO 2011/091291)—International Search Report and Written Opinion of the International Searching Authority, Apr. 11, 2011.
PCT/US2011/038588 (WO 2011/150421)—International Search Report and Written Opinion of the International Searching Authority, Nov. 22, 2011.
PCT/US98/24295—International Preliminary Examination Report, Dec. 26, 2000.
PCT/US2001/013915—International Preliminary Examination Report, Aug. 16, 2002.
European Patent Application No. 89910552.2 (EP0433372), Intention to Grant dated Jun. 19, 2001.
European Patent Application No. 89910552.2 (EP0433372), Office Action dated Oct. 10, 1994.
European Patent Application No. 89910552.2 (EP0433372), Office Action dated Sep. 12, 1995.
European Patent Application No. 89910552.2 (EP0433372), Office Action dated Jun. 20, 2000.
European Patent Application No. 89910552.2 (EP0433372), Decision to Grant dated May 6, 2002.
European Patent Application No. 90905859.6 (EP0465560), Office Action dated Feb. 19, 1992.
European Patent Application No. 90905859.6 (EP0465560), Office Action dated Feb. 9, 1994.
European Patent Application No. 90905859.6 (EP0465560), Intention to Grant dated Jan. 4, 1995 by A. Ormerod.
European Patent Application No. 90905859.6 (EP0465560), Decision to Grant dated Apr. 25, 1996.
European Patent Application No. 96919292.1 (EP0832255), Office Action dated Sep. 30, 2003.
European Patent Application No. 96919292.1 (EP0832255), Office Action dated Jul. 13, 2004.
European Patent Application No. 96919292.1 (EP0832255), Intention to Grant dated May 25, 2005.
European Patent Application No. 96919292.1 (EP0832255), Decision to Grant dated Nov. 4, 2005.
European Patent Application No. 98958581.5 (EP1030690), Office Action dated Jan. 31, 2001.
European Patent Application No. 98958581.5 (EP1030690), Intention to Grant dated Sep. 7, 2001.
European Patent Application No. 98958581.5 (EP1030690), Decision to Grant dated May 24, 2002.
European Patent Application No. 01944119.5 (EP1292687), Office Action dated Oct. 18, 2004.
European Patent Application No. 01944119.5 (EP1292687), Office Action dated Aug. 4, 2005.
European Patent Application No. 01944119.5 (EP1292687), Intention to Grant dated Jan. 26, 2006.
European Patent Application No. 01944119.5 (EP1292687), Decision to Grant dated Jul. 20, 2006.
European Patent Application No. 01979646.5 (EP1326960), Intention to Grant dated Apr. 8, 2004.
European Patent Application No. 01979646.5 (EP1326960), Decision to Grant dated Oct. 28, 2004.
European Patent Application No. 03721711.4 (EP1499191), Search Report dated May 23, 2006.
European Patent Application No. 03721711.4 (EP1499191), Office Action dated Aug. 24, 2006.
European Patent Application No. 03721711.4 (EP1499191), Office action dated Jan. 17, 2007.
European Patent Application No. 03721711.4 (EP1499191), Office action dated Mar. 23, 2009.
European Patent Application No. 03721711.4 (EP1499191), Office action dated Jun. 15, 2010.
European Patent Application No. 03721711.4 (EP1499191), Intention to Grant dated Oct. 21, 2011.
European Patent Application No. 03770256.0 (EP1537214), Intention to Grant dated Aug. 12, 2005.
U.S. Appl. No. 08/473,789, Office Action dated Apr. 15, 1997.
U.S. Appl. No. 08/473,789, Office Action dated Dec. 23, 1997.
U.S. Appl. No. 08/473,789, Office Action dated Nov. 13, 1998.
U.S. Appl. No. 08/473,789, Office Action dated Jun. 14, 1999.
U.S. Appl. No. 08/473,789, Office Action dated Jan. 21, 2000.
U.S. Appl. No. 08/473,789, Office Action dated Jul. 25, 2000.
U.S. Appl. No. 08/473,789, Office Action dated Sep. 27, 2001.
U.S. Appl. No. 08/761,769, Office Action dated Jul. 20, 1998.
U.S. Appl. No. 08/761,769, Office Action dated Mar. 3, 1999.
U.S. Appl. No. 08/761,769, Office Action dated Aug. 9, 2000.
U.S. Appl. No. 08/761,769, Office Action dated Sep. 25, 2001.

U.S. Appl. No. 08/761,769, Office Action dated Aug. 8, 2002.
U.S. Appl. No. 08/761,769, Notice of Allowance and Fees Due dated Jan. 22, 2003.
U.S. Appl. No. 09/120,970, Office Action dated Sep. 6, 2000.
U.S. Appl. No. 09/120,970, Office Action dated Jun. 5, 2001.
U.S. Appl. No. 09/120,970, Office Action dated Jan. 12, 2005.
U.S. Appl. No. 09/120,970, Office Action dated Nov. 8, 2005.
U.S. Appl. No. 09/120,970, Notice of Allowance and Fees Due dated Aug. 6, 2010.
U.S. Appl. No. 09/560,539, Office Action dated Feb. 12, 2002.
U.S. Appl. No. 09/560,539, Office Action dated Mar. 25, 2003.
U.S. Appl. No. 09/560,539, Office Action dated Aug. 29, 2003.
U.S. Appl. No. 09/560,539, Notice of Allowance and Fees Due dated Mar. 30, 2004.
U.S. Appl. No. 09/686,499, Office Action dated Jun. 20, 2001.
U.S. Appl. No. 09/686,499, Office Action dated Jan. 29, 2002.
U.S. Appl. No. 09/686,499, Office Action dated Dec. 16, 2002.
U.S. Appl. No. 09/686,499, Office Action dated Aug. 27, 2003.
U.S. Appl. No. 09/686,499, Notice of Allowance and Fees Due dated Nov. 2, 2004.
U.S. Appl. No. 10/138,239, Office Action dated Mar. 15, 2005.
U.S. Appl. No. 10/138,239, Office Action dated Sep. 21, 2005.
U.S. Appl. No. 10/138,239, Notice of Allowance and Fees Due dated Mar. 16, 2006.
U.S. Appl. No. 10/414,533, Office Action dated Apr. 12, 2006.
U.S. Appl. No. 10/414,533, Notice of Allowance and Fees Due dated Dec. 8, 2006.
U.S. Appl. No. 10/511,616, Office Action dated Nov. 27, 2009.
U.S. Appl. No. 10/511,616, Office Action dated Jun. 23, 2010.
U.S. Appl. No. 10/511,616, Office Action dated Dec. 27, 2010.
U.S. Appl. No. 10/511,616, Notice of Allowance and Fees Due dated Oct. 26, 2011.
U.S. Appl. No. 10/620,777, Office Action dated Nov. 14, 2006.
U.S. Appl. No. 10/620,777, Office Action dated Oct. 31, 2007.
U.S. Appl. No. 10/924,574, Office Action dated Feb. 28, 2007.
U.S. Appl. No. 10/924,574, Notice of Allowance and Fees Due dated Oct. 1, 2007.
European Patent Application No. 08827622.5, Search Report dated Jun. 27, 2011.
European Patent Application No. 08827622.5, Office action dated Feb. 22, 2012.
U.S. Appl. No. 12/615,872, Office Action dated Mar. 14, 2012.
U.S. Appl. No. 12/759,842, Office Action dated Oct. 4, 2011.
U.S. Appl. No. 12/789,869, Office Action dated Mar. 22, 2011.
U.S. Appl. No. 12/789,869, Office Action dated Dec. 7, 2011.
Bang et al, OmpR regulates the stationary-phase acid tolerance response of *Salmonella enterica* serovar Typhimurium. J Bacteriol, 2000, pp. 2245-2252, vol. 182.
Bang et al., Autoinduction of the ompR response regulator by acid shock and control of the *Salmonella enterica* acid tolerance response. Mol Microbiol, 2002, pp. 1235-1250, vol. 44.
Bartlett et al., Influenza A (H5N1): will it be the next pandemic influenza? Are we ready? Ann. Intern. Med., 2005, pp. 460-462, vol. 143.
Bartlett, Planning for avian influenza. Ann. Intern. Med., 2006, pp. 141-144, vol. 145.
Bearson et al., A low pH-inducible, PhoPQ-dependent acid tolerance response protects *Salmonella typhimurium* against inorganic acid stress. J Bacteriol, 1998, pp. 2409-2417, vol. 180.
Bertani, Studies on lysonucleic acid sequencesis. I. The mode of phage liberation by lysogenic *Escherichia coli*. J Bacteriol, 1951, pp. 293-300, vol. 62, No. 3.
Black et al., Aspartic-semialdehydedehydrogenase and aspartic-semialdehyde J. Biol. Chem., 1955, pp. 39-50, vol. 213.
Briles et al., Immunization of humans with recombinant pneumococcal surface protein A (rPspA) elicits antibodies that passively protect mice from fatal infection with *Streptococcus pneumoniae* bearing heterologous PspA. J. Infect. Dis., 2000, pp. 1694-1701, vol. 182.
Brooks-Walter et al., The pspC gene of *Streptococcus pneumoniae* encodes a polymorphic protein, PspC, which elicits cross-reactive antibodies to PspA and provides immunity to pneumococcal bacteremia. Infect. Immun., 1999, pp. 6533-6542, vol. 67.

Brosius et al., Spacing of the -10 and -35 regions in the tac promoter. Effect on its in vivo activity. J Biol Chem, 1985, pp. 3539-3540, vol. 260, No. 6.
Brown et al., MurA (MurZ), the enzyme that catalyzes the first committed step in peptidoglycan biosynthesis, is essential in *Escherichia coli*. J. Bacteriol., 1995, pp. 4194-4197, vol. 177.
Buchanan et al., IL-12 Enhances Antibody Responses to T-Independent Polysaccharide Vaccines in the Absence of T and NK Cells. J Immunol, 1998, pp. 5525-5533, vol. 161.
Buchmeier, et al., DNA repair is more important than catalase for Salmonella virulence in mice. J. Clin. Invest., 1995, pp. 1047-1053, vol. 95.
Bumann, Regulated antigen expression in live recombinant *Salmonella enterica* serovar Typhimurium strongly affects colonization capabilities and specific CD4(+)-T-cell responses. Infect Immun, 2001. pp. 7493-7500, vol. 69, No. 12.
CDC, Update: influenza activity—United States, Sep. 30, 2007-Apr. 5, 2008, and composition of the 2008-09 influenza vaccine. MMWR Morb. Mortal. Wkly Rep., 2008, pp. 404-409, vol. 57.
Chen et al., Genetic mapping of the cold-adapted phenotype of B/Ann Arbor/1/66, the master donor virus for live attenuated influenza vaccines (FluMist). Virology, 2006, pp. 416-423, vol. 345.
Collins et al., Mutations at rfc or pmi attenuate *Salmonella typhimurium* virulence for mice. Infect. Immun., 1991, pp. 1079-1085, vol. 59.
Curtiss et al., Avirulent *Salmonella typhimurium* delta cya delta crp oral vaccine strains expressing a streptococcal colonization and virulence antigen. Vaccine, 1988, pp. 155-160, vol. 6.
Curtiss et al., New technologies in using recombinant attenuated *Salmonella* vaccine vectors. Crit. Rev. Immunol., 2010, pp. 255-270, vol. 30.
Curtiss et al., *Salmonella* strains with regulated delayed attenuation in vivo. Infect. Immun., 2009, pp. 1071-1082, vol. 77.
Curtiss et al., *Salmonella typhimurium* deletion mutants lacking adenylate cyclase and cyclic AMP receptor protein are avirulent and immunogenic. Infect Immun, 1987, pp. 3035-3043, vol. 55.
Curtiss et al., Stabilization of recombinant avirulent vaccine strains in vivo. Res Microbiol, 1990, pp. 797-805, vol. 141.
Curtiss, Bacterial infectious disease control by vaccine development. J. Clin. Investig., 2002, pp. 1061-1066, vol. 110.
Curtiss, Chromosomal aberrations associated with mutations to bacteriophage resistance in *Escherichia coli*. J. Bacteriol., 1965, pp. 28-40, vol. 89.
Daigle et al., Identification of *Salmonella typhi* genes expressed within macrophages by selective capture of transcribed sequences (SCOTS). Mol Microbiol, 2001, pp. 1211-1222, vol. 41.
Darzins. Nucleotide-sequence analysis of the phosphomannose isomerase gene (PMI) of *Pseudomonas aeruginosa* and comparison with the corresponding *Escherichia-coli* gene mana. Gene, 1986, pp. 293-302, vol. 42, No. 3.
Dean, 1997. Import of plasmid DNA into the nucleus is sequence specific. Exp. Cell Res., 1997, pp. 293-302, vol. 230.
Doggett et al., Immune responses to *Streptococcus sobrinus* surface protein antigen A expressed by recombinant *Salmonella typhimurium*. Infect Immun, 1993, pp. 1859-1866, vol. 61.
Dunstan et al., Comparison of the Abilities of Different Attenuated *Salmonella typhimurium* Strains to Elicit Humoral Immune Responses against a Heterologous Antigen. Infect. Immun., 1998, pp. 732-740, vol. 66.
Dusek et al., Brown, Systemic and mucosal immune responses in mice orally immunized with avirulent *Salmonella typhimurium* expressing a cloned *Porphyromonas gingivalis* hemagglutinin. Infect Immun, 1994, pp. 1652-1657, vol. 62, No. 5.
Egan et al., A regulatory cascade in the induction of rhaBAD. J Mol Biol, 1993, pp. 97-98, vol. 234.
Egorov et al., Transfectant influenza A viruses with long deletions in the NS1 protein grow efficiently in Vero cells. J. Virol., 1998, pp. 6437-6441, vol. 72.
Enami et al., Introduction of site-specific mutations into the genome of influenza virus. Proc. Natl. Acad. Sci. USA, 1990, pp. 3802-3805, vol. 87.
Fodor et al., Rescue of influenza A virus from recombinant DNA. J. Virol., 1999, pp. 9679-9682, vol. 73.

Formal et al., Construction of a potential bivalent vaccine strain: introduction of *Shigella sonnei* form I antigen genes into the galE *Salmonella typhi* Ty21a typhoid vaccine strain. Infect. Immun., 1981, pp. 746-750, vol. 34.

Fraser et al., The amino acid composition of T3 bacteriophage. J Biol Chem, 1953, pp. 291-295, vol. 205, No. 1.

Galan et al., Cloning and molecular characterization of genes whose products allow *Salmonella typhimurium* to penetrate tissue culture cells. Proc Natl Acad Sci U S A, 1989, pp. 6383-6387, vol. 86.

Galen et al., Optimization of Plasmid Maintenance in the Attenuated Live Vector Vaccine Strain *Salmonella typhi* CVD 908-htrA. Infect. Immun., 1999, pp. 6424-6433, vol. 67.

Garmory et al., Antibiotic-free plasmid stabilization by operator-repressor titration for vaccine delivery by using live *Salmonella enterica* serovar *typhimurium*. Infect. Immun., 2005, pp. 2005-2011, vol. 73.

Gay et al., Positive selection procedure for entrapment of insertion sequence elements in gram-negative bacteria. J Bacteriol, 1985, pp. 918-921, vol. 164, No. 2.

Gentschev et al., Delivery of the p67 sporozoite antigen of *Theileria parva* by using recombinant *Salmonella dublin*: secretion of the product enhances specific antibody responses in cattle. Infect. Immun., 1998, pp. 2060-2064, vol. 66.

Gerdil, The annual production cycle for influenza vaccine. Vaccine, 2003, pp. 1776-1779, vol. 21.

Ghany et al. Candidate live, attenuated *Salmonella enterica* serotype *typhimurium* vaccines with reduced fecal shedding are immunogenic and effective oral vaccines. Infect. Immun., 2007, pp. 1835-1842, vol. 75.

Greenwood, The epidemiology of pneumococcal infection in children in the developing world. Philos. Trans. R. Soc. Lond. B. Biol. Sci., 1999, pp. 777-785, vol. 354.

Gulig et al., Plasmid-associated virulence of *Salmonella typhimurium*. Infect Immun, 1987, pp. 2891-2901, vol. 55.

Guzman et al., Tight regulation, modulation, and high-level expression by vectors containing the arabinose PBAD promoter. J Bacteriol, 1995, pp. 4121-4130, vol. 177.

Hall et al., The role of fur in the acid tolerance response of *Salmonella typhimurium* is physiologically and genetically separable from its role in iron acquisition. J Bacteriol, 1996, pp. 5683-5691, vol. 178.

Hess et al., Superior efficacy of secreted over somatic antigen display in recombinant *Salmonella* vaccine induced protection against listeriosis. Proc. Natl. Acad. Sci. USA, 1996, pp. 1458-1463, vol. 93.

Hicks et al., Incidence of pneumococcal disease due to non-pneumococcal conjugate vaccine (PCV7) serotypes in the United States during the era of widespread PCV7 vaccination, 1998-2004. J Infect Dis, 2007, pp. 1346-1354, vol. 196.

Hitchcock et al., Morphological heteronucleic acid sequenceity among *Salmonella* lipopolysaccharide chemotypes in silver-stained polyacrylamide gels. J Bacteriol, 1983, pp. 269-277, vol. 154, No. 1.

Hoffmann et al., "Ambisense" approach for the generation of influenza A virus: vRNA and mRNA synthesis from one template. Virology, 2000, pp. 310-317, vol. 267.

Hohmann et al., Macrophage-inducible expression of a model antigen in *Salmonella typhimurium* enhances immunogenicity. Proc Natl Acad Sci U S A, 1995, pp. 2904-2908, vol. 92, No. 7.

Hollingshead et al., Diversity of PspA: mosaic genes and evidence for past recombination in *Streptococcus pneumoniae*. Infect Immun., 2000, pp. 5889-5900, vol. 68.

Hopkins et al., A recombinant *Salmonella typhimurium* vaccine induces local immunity by four different routes of immunization. Infect Immun, 1995, pp. 3279-3286, vol. 63.

Jin et al., Multiple amino acid residues confer temperature sensitivity to human influenza virus vaccine strains (FluMist) derived from cold-adapted A/Ann Arbor/6/60. Virology, 2003, pp. 18-24, vol. 306.

Kang et al., Immune responses dependent on antigen location in recombinant attenuated *Salmonella typhimurium* vaccines following oral immunization. FEMS Immunol. Med. Microbiol. Lett., 2003, pp. 99-104, vol. 37.

Kang et al., Immune responses to recombinant pneumococcal PspA antigen delivered by live attenuated *Salmonella enterica* serovar typhimurium vaccine. Infect. Immun., 2002, pp. 1739-1749, vol. 70.

Kang et al., Transduction-mediated transfer of unmarked deletion and point mutations through use of counterselectable suicide vectors. J Bacteriol, 2002, pp. 307-312, vol. 184.

Katzman et al., Invertebrate connective tissue. Isolation of D-arabinose from sponge acidic polysaccharide. Biochem J, 1970, pp. 17-19, vol. 119, No. 1.

Kennedy et al., Attenuation and immunogenicity of Delta cya Delta crp derivatives of *Salmonella choleraesuis* in pigs. Infection and Immunity, 1999, pp. 4628-4636, vol. 67, No. 9.

Kilbourne, Studies on influenza in the pandemic of 1957-1958. III. Isolation of influenza A (Asian strain) viruses from influenza patients with pulmonary complications; details of virus isolation and characterization of isolates, with quantitative comparison of isolation methods. J. Clin. Invest., 1959, pp. 266-274, vol. 38.

Klumpp et al., Roles of the influenza virus polymerase and nucleoprotein in forming a functional RNP structure. EMBO J., 1997, pp. 1248-1257, vol. 16.

Kong et al, Regulated programmed lysis of recombinant *Salmonella* in host tissues to release protective antigens and confer biological containment. PNAS, 2008, pp. 9361-9366, vol. 105, No. 27.

Konjufca et al., A Recombinant Attenuated *Salmonella enterica* Serovar *typhimurium* Vaccine Encoding Eimeria acervulina Antigen Offers Protection against *E. acervulina* Challenge. Infect. Immun., 2006, pp. 6785-6796, vol. 74.

Song et al., Organization and regulation of the D-xylose operons in *Escherichia coli* K-12: XylR acts as a transcriptional activator. J Bacteriol, 1997, pp. 7025-7032, vol. 179.

Spellberg et al., Type 1/type 2 immunity in infectious diseases. Clin. Infect. Dis., 2001, pp. 76-102, vol. 32.

Schnaitman et al., Genetics of Lipopolysaccharide Biosynthesis in Enteric Bacteria. Microbiological Reviews, 1993, pp. 655-682, vol. 57, No. 3.

Srinivasan et al., Oral immunization with attenuated *Salmonella* expressing human sperm antigen induces antibodies in serum and the reproductive tract. Biol Reprod, 1995, pp. 462-471, vol. 53.

Steel et al., Live attenuated influenza viruses containing NS1 truncations as vaccine candidates against H5N1 highly pathogenic avian influenza. J. Virol., 2009, pp. 1742-1753, vol. 83.

Tacket et al., Safety and immunogenicity in humans of an attenuated *Salmonella typhi* vaccine vector strain expressing plasmid-encoded hepatitis B antigens stabilized by the asd-balanced lethal vector system. Infect Immun, 1997, pp. 3381-3385, vol. 65.

Taubenberger et al., 1918 Influenza: the mother of all pandemics. Emerg. Infect. Dis., 2006, pp. 15-22, vol. 12.

Török et al., Accumulation of ppGpp in a relA mutant of *Escherichia coli* during amino acid starvation. J. Biol. Chem., 1980, pp. 3838-3840, vol. 255.

Tu et al., The PhoP/PhoQ two-component system stabilizes the alternative sigma factor RpoS in *Salmonella enterica*. Proc Natl Acad Sci U S A., 2006, pp. 13503-13508, vol. 103.

Tumpey et al., Characterization of the reconstructed 1918 Spanish influenza pandemic virus. Science, 2005, pp. 77-80, vol. 310.

Van Rossum et al., Host and bacterial factors contributing to the clearance of colonization by *Streptococcus pneumoniae* in a murine model. Infect Immun, 2005, pp. 7718-7726, vol. 73.

Van Velkinburgh et al., PhoP-PhoQ-regulated loci are required for enhanced bile resistance in *Salmonella* spp. Infect Immun, 1999, pp. 1614-1622, vol. 67.

Webster et al., Evolution and ecology of influenza A viruses. Microbiol Rev, 1992, pp. 152-179, vol. 56.

Wilmes-Riesenberg et al., Role of acid tolerance response in virulence of *Salmonella typhimurium*. Infect.Immun, 1996, pp. 1085-1092, vol. 64.

Wu et al., The mechanism underlying T cell help for induction of an antigen-specific in vivo humoral immune response to intact *Streptococcus pneumoniae* is dependent on the type of antigen. J Immunol, 2002, pp. 5551-5557, vol. 168.

Zahn, Overexpression of an mRNA dependent on rare codons inhibits protein synthesis and cell growth. J Bacteriol, 1996, pp. 2926-2933, vol. 178, No. 10.

Zhang et al., Characterization and immunogenicity of *Salmonella typhimurium* SL1344 and UK-1 crp and cdt deletion mutants. Infect. Immun., 1997, pp. 5381-5387, vol. 65.

Zobel et al., RNA polymerase I catalysed transcription of insert viral cDNA. Nucleic. Acids. Res., 1993, pp. 3607-3614, vol. 21.

Baek et al., Leucine-Responsive Regulator Protein (Lrp) Acts as a Virulence Respressor in *Salmonella enterica* Servoar Typhimurium. Journal of Bacteriology, 2009, pp. 1278-1292, vol. 191, No. 4.

PCT/US2011/061896—International Search Report and Written Opinion of the International Searching Authority, Apr. 5, 2012.

Byl et al, Sequence of the Genomore of Salmonella Bacteriophage P22. Journal of Bacteriology, 2000, pp. 6472-6484, vol. 182, 22.

Houng et al., Expression of Vi antigen in *Escherichia coli* K-12: characterization of ViaB from Citrobacter freundii and identity of ViaA with RcsB. J.Bacterio, 1992, pp. 5910-5915, vol. 174, No. 18.

Hori et al, Constructionof selt-disruptive *Bacillus megaterium* in response to substrate exhaustion for polyhydroxybutryrate production. Appl Microbiol Biotechnol, 2002, pp. 211-216, vol. 59.

Hurme et al, A Proteinaceous Gene Regulator Thermameter in *Salmonella*. Cell, 1997, pp. 55-64, vol. 90.

Kong et al., Salmonelle synthesizing 1-Monophosphorylated Lipopolysaccharide Exhibits Low Endotoxic while Retaining Its Immunogenicity. J Immunol, 2011, pp. 412-423, vol. 187.

Pickard et al., Characterization of defined ompR mutants of *Salmonella typhi*: ompR is involved in the regulation of Vi polysaccharide expression. Infect Immun, 1994, pp. 3984-3993, vol. 62, No. 9.

Reed et al., The W-Beijing Lineage of *Mycobacterium tuberculosis* Overproduces Triglycerides and Has the DosR Dormancy Regulon Constitutively Upregulated. Journal of Bacteriology, 2007, pp. 2583-2589, vol. 189, No. 7.

Takaya et al., The ATP-Dependent Lon Protease of *Salmonella enterica* Serovar Typhimurium Regulates Invasion and Expression of Genes Carried on Salmonella Pathogenicity Island 1. Journal of Bacteriology, 2002, pp. 224-232, vol. 184, No. 1.

Waltman et al., Biochemical Characteristics of *Edwardsiella ictaluri*. Applied and Enviornmental Microbiology, 1986, pp. 101-104, vol. 51, No. 1.

U.S. Appl. No. 12/681,711, Office Action dated Jan. 31, 2012.

Verjan et al, Genetic Loci of Major Antigenic Protein Genes of *Edwardsiella tarda*. Applied and Environmental Microbiology, 2005, pp. 5654-5658, vol. 71, No. 9.

Nieto et al., Complex Structure of the nuclear translocation signal of influenza virus polymerase PA subunit. Journal of General Nirology, 1994, pp. 29-36, vol. 75.

Stevens et al, Immunization with the C-Domain of alpha-Toxin Prevents Lethal Infection, Localizes Tissue Injury, and Promotes Host Response to Challenge with Clostridium perfringens. JID, 2004, pp. 767-773, vol. 190.

U.S. Appl. No. 13/006,072, Office Action issued Apr. 19, 2012.

Sun et al, Highly Efficient Method for Introducing Successive Multiple Scarless Gene Deletions and Markerless Gene Insertions into the *Yersinia pestis* Chromosome. Applied and Environment Microbiology, 2008, pp. 4241-4245, vol. 74, No. 13.

Sheehan et al., Generation and characterization of hamster monoclonal antibodies that neutralize murine tumor necrosis factors. J Immunol, 1989, pp. 3884-3893, vol. 142.

Sizemore et al., Attenuated bacteria as a DNA delivery vehicle for DNA-mediated immunization. Vaccine, 1997, pp. 804-807, vol. 15.

Snapper et al., Distinct types of T-cell help for the induction of a humoral immune response to *Streptococcus pneumoniae*. Trends Immunol, 2001, pp. 308-311, vol. 22.

Sodeinde et al., Plasminogen activator/coagulase gene of *Yersinia pestis* is responsible for degradation of plasmid-encoded outer membrane proteins. Infect Immun, 1988, pp. 2749-2752, vol. 56.

Sternberg et al., Bacteriophage-mediated nucleic acid sequenceralized transduction in *Escherichia coli* and *Salmonella typhimurium*. Methods Enzymol, 1991, pp. 18-43, vol. 204.

Straley et al., Virulence genes regulated at the transcriptional level by Ca2+ in *Yersinia pestis* include structural genes for outer membrane proteins. Infect Immun, 1986, pp. 445-454, vol. 51.

Sun et al., The role of relA and spoT in *Yersinia pestis* KIM5+ pathogenicity. PLoS One, 2009, pp. E6720, vol. 4.

Thompson et al., The bacterial signal molecule, ppGpp, mediates the environmental regulation of both the invasion and intracellular virulence gene programs of *Salmonella*. J Biol Chem, 2006, pp. 30112-30121, vol. 281.

Une et al., In vivo comparison of avirulent Vwa- and Pgm- or Pstr phenotypes of Yersiniae. Infect Immun, 1984, pp. 895-900, vol. 43.

Uzzau et al., Epitope tagging of chromosomal genes in *Salmonella*. Proc Natl Acad Sci U S A, 2001, pp. 15264-15269, vol. 98.

Viboud et al., Yersinia outer proteins: role in modulation of host cell signaling responses and pathogenesis. Annu Rev Microbiol, 2005, pp. 69-89, vol. 59.

Wasserman et al., Two alanine racemase genes in *Salmonella typhimurium* that differ in structure and function. J. Bacteriol., 1983, pp. 1439-1450, vol. 153.

Whitfield, Biosynthesis and assembly of capsular polysaccharides in *Escherichia coli*. Annu Rev. Biochem., 2006, pp. 39-68, vol. 75.

Winter et al., The *Salmonella enterica* serotype Typhi regulator TviA reduces interleukin-8 production in intestinal epithelial cells by repressing flagellin secretion. Cell Microbiol, 2008, pp. 247-261, vol. 10, No. 1.

Wolf et al., Evolution of aminoacyl tRNA synthetases—analysis of unique domain architectures and phylogenetic trees reveals a complex history of horizontal gene transfer events. Genome Res, 1999, pp. 689-710, vol. 9.

Xiao et al., Residual guanosine 39,59-bispyrophosphate synthetic activity of relA null mutants can be eliminated by spoT null mutations. J Biol Chem, 1991, pp. 5980-5990, vol. 266.

Zahorchak et al., Effect of exogenous nucleotides on Ca2+ dependence and V antigen synthesis in *Yersinia pestis*. Infect Immun, 1982, pp. 953-959, vol. 38.

Zhang et al., A "one-plasmid" system to generate influenza virus in cultured chicken cells for potential use in influenza vaccine. J. Virol., 2009, pp. 9296-9303, vol. 83.

Zhang et al., Transcription activation parameters at ara pBAD. J Mol Biol, 1996, pp. 14-24, vol. 258, No. 1.

Zinkernagel et al., Antigen localisation regulates immune responses in a dose- and time-dependent fashion: a geographical view of immune reactivity. Immunol Rev, 1997, pp. 199-209, vol. 156.

Briles et al., PspA, a protection-eliciting pneumococcal protein: immunogenicity of isolated native PspA in mice. Vaccine, 1996, pp. 858-867, vol. 14.

Hanisch, et al, The *Ralstonia eutropha* H16 phasin PhaP1 is targeted to intracellular triacylglycerol inclusions in *Rhodococcus opacus* PD630 and *Mycobacterium smegmatis* mc2155, and provides an anchor to target other proteins, 2006, Microbiology 152:3271-3280.

Kong et al, Regulated Delayed Expression of rfaH in an Attenuated *Salmonella enterica* Serovar *typhimurium* Vaccine Enhances Immunogenicity of Outer Membrane Proteins and Heterologous Antigen. Infec Immun. 2009, pp. 5572-5582, vol. 77, No. 12.

Lefman et al, Three-Dimensional Electron Microscopic Imaging of Membrane Invaginations in *Escherichia coli* Overproducing the Chemotaxis Receptor Tsr. Journal of Bacteriology, 2004, pp. 5052-5061, vol. 186, No. 15.

Morita et al., Antibacterial Activity of Bacillus amyloliquefaciencs Phage Endolysin without Holin Conjugation. Journal of Biosciences and Bioengineering, 2001, pp. 469-473, vol. 91, No. 5.

Navasa et al, Temperature has reciprocal effects on colanic acid and polysialic acid biosynthesis in *E. coli* K92. Appl Microbiol Biotechnol, 2009, pp. 721-729, vol. 82.

U.S. Appl. No. 12/759,843, Office Action dated Jun. 7, 2012.

U.S. Appl. No. 12/599,655, Office Action dated Jul. 2, 2012.

Alonso et al, Anti-polysaccharide immunoglobulin isotype levels and opsonic activity of antisera: relationships with protection against *Streptococcus pneumoniae* infection in mice. J Infect Dis, 1995, pp. 562-565, vol. 172.

Amann et al., Tightly regulated tac promoter vectors useful for the expression of unfused and fused proteins in *Escherichia coli*. Nucleic acid sequence, 1988. pp. 301-315, vol. 69, No. 2.

Anderson et al., Delivery of the Pertactin/p. 69 polypeptide of *Bordetella pertussis* using an attenuated *Salmonella typhimurium* vaccine strain: expression levels and immune response. Vaccine, 1996, pp. 1384-1390, vol. 14, No. 14.

Aravind et al., The HD domain defines a new superfamily of metal-dependent phosphohydrolases. Trends Biochem Sci, 1998, pp. 469-472, vol. 23.

Arricau et al., The RcsB-RcsC regulatory system of *Salmonella typhi* differentially modulates the expression of invasion proteins, flagellin and Vi antigen in response to osmolarity., Mol Microbiol, 1998, pp. 85-50, vol. 29, No. 3.

Arulanandam et al., Intranasal vaccination with pneumococcal surface protein A and interleukin-12 augments antibody-mediated opsonization and protective immunity against *Streptococcus pneumoniae* infection. Infect Immun, 2001, pp. 6718-6724, vol. 69.

Audia et al., Breaking through the acid barrier: an orchestrated response to proton stress by enteric bacteria. Int J Med Microbiol, 2001, pp. 97-106, vol. 291.

Battesti et al., Acyl carrier protein/SpoT interaction, the switch linking SpoT-dependent stress response to fatty acid metabolism. Mol Microbiol, 2006, pp. 1048-1063, vol. 62.

Blattner et al., The complete genome sequence of *Escherichia coli* K-12. Science, 1997, pp. 1453-1474, vol. 277.

Branger et al., Oral vaccination with different antigens from *Yersinia pestis* KIM delivered by live attenuated *Salmonella typhimurium* elicits a protective immune response against plague. Adv Exp Med Biol, 2007, pp. 387-399, vol. 603.
Briles et al. The potential for using protein vaccines to protect against otitis media caused by *Streptococcus pneumoniae*. Vaccine, 2001, pp. S87-S95, vol. 19, Suppl 1.
Brubaker, Interleukin-10 and inhibition of innate immunity to *Yersiniae*: roles of Yops and LcrV (V antigen). Infect Immun, 2003, pp. 3673-3681, vol. 71.
Brubaker, The Vwa+ virulence factor of *Yersiniae*: the molecular basis of the attendant nutritional requirement for Ca2+. Rev Infect Dis, 1983,pp. S748-S758, vol. 5, Suppl 4.
Brumell et al., (2004) *Salmonella* redirects phagosomal maturation. Curr Opin Microbiol, 2004, pp. 78-84, vol. 7.
Cárdenas et al., Oral immunization using live attenuated *Salmonella* spp. as carriers of foreign antigens. Clin. Microbiol. Rev., 1992, pp. 328-342, vol. 5, No. 3.
Charnetzky et al., RNA synthesis in *Yersinia pestis* during growth restriction in calcium-deficient medium. J Bacteriol, 1982, pp. 108-195, vol. 149.
Chatfield et al., Use of the nirB promoter to direct the stable expression of heterologous antigens in Salmonella oral vaccine strains: development of a single-dose oral tetanus vaccine. Biotechnology (N Y), 1992, pp. 888-892, vol. 10, No. 8.
Cheng et al., Simultaneous analyses of neutral carbohydrates and amino sugars in freshwaters with HPLC-PAD. J. Chromatogr. Sci., 2003, pp. 434-438, vol. 41.
Chipman et al., The ACT domain family. Curr Opin Struct Biol, 2001, pp. 694-700, vol. 11.
Chromy et al., Proteomic characterization of *Yersinia pestis* virulence. J Bacteriol, 2005, pp. 8172-8180, vol. 187.
Coombes et al., SseL Is a Salmonella-Specific Translocated Effector Integrated into the SsrB-Controlled *Salmonella* Pathogenicity Island 2 Type III Secretion System. Infection and Immunity, 2007, pp. 574-580, vol. 75, No. 2.
Cornelis et al., The virulence plasmid of *Yersinia*, an antihost genome. Microbiol Mol Biol Rev, 1998, pp. 1315-1352, vol. 62.
Curtiss et al. Nonrecombinant and recombinant avirulent *Salmonella* vaccines for poultry. Vet Immunol Immunopathol, 1996, pp. 365-372, vol. 54.
Curtiss et al., Live oral avirulent *Salmonella* vaccines. Vet. Microbiol., 1993, pp. 397-405, vol. 37.
Curtiss et al., Recombinant *Salmonella* vectors in vaccine development. Dev Biol Stand., 1994, pp. 23-33, vol. 82.
Datsenko et al., One-step inactivation of chromosomal genes in *Escherichia coli* K-12 using PCR products. Proc Natl Acad Sci U S A, 2000, pp. 6640-6645, vol. 97.
Davison, Towards safer vectors for the field release of recombinant bacteria. Environ. Biosafety Res., 2002, pp. 9-18, vol. 1.
De Groote et al., Homocysteine antagonism of nitric oxide-related cytostasis in *Salmonella typhimurium*. Science, 1996, pp. 414-417, vol. 272.
Dekruyff et al., Induction of immunoglobulin synthesis by CD4+ T cell clones. Seminars in Immunology, 1993, pp. 421-430, vol. 5.
Del Beccaro et al., Bacteriology of acute otitis media: a new perspective. J Pediatr, 1992, pp. 81-84, vol. 120.
Deng et al., Genome sequence of *Yersinia pestis* KIM. J Bacteriol, 2002, pp. 4601-4611, vol. 184.
Doggett et al., Delivery of antigens by recombinant avirulent *Salmonella* strains. Adv. Exp. Med. Biol., 1992, pp. 165-173, vol. 327.
Doublet et al., The murl gene of *Escherichia coli* is an essential gene that encodes a glutamate racemase activity. J. Bacteriol., 1993, pp. 2970-2979, vol. 175.
Dubnau, DNA uptake in bacteria. Annu. Rev. Microbiol., 1999, pp. 217-244, vol. 53.
Edwards et al., Improved allelic exchange vectors and their use to analyze 987P fimbria nucleic acid sequence expression. Gene, 1998, pp. 149-157, vol. 207, No. 2.
Fooks, Development of oral vaccines for human use. Curr Opin Mol Ther, 2000, pp. 80-86, vol. 2, No. 1.
Foster et al., How *Salmonella* survive against the odds. Annu Rev Microbiol, 1995, pp. 145-174, vol. 49.
Galen et al., Can a 'flawless' live vector vaccine strain be engineered? Trends Microbiol, 2001, pp. 372-376, vol. 9, No. 8.
Garmory et al., The Use of Live Attenuated Bacteria as a Delivery System for Heterologous Antigens. Journal of Drug Targeting, 2003, pp. 471, vol. 11.
Garzon et al., recB recJ mutants of *Salmonella typhimurium* are deficient in transductional recombination, DNA repair and plasmid maintenance. Mol. Gen. Genet., 1996, pp. 570-580, vol. 250.
Gentry et al., Mutational analysis of the *Escherichia coli* spoT gene identifies distinct but overlapping regions involved in ppGpp synthesis and degradation. Mol Microbiol, 1996, pp. 1373-1384, vol. 19.
Gentschev et al., The *E. coli* alpha-hemolysin secretion system and its use in vaccine development. Trends Microbiol, 2002, pp. 39-45, vol. 10, No. 1.
Giannella et al., Gastric acidity and cholera. Ann Intern Med, 1973, p. 780, vol. 78.
Gilbert, The lac repressor and the lac operator. Ciba Found Symp, 1972, pp. 24-59, vol. 7.
Gong et al., Characterization of the *Yersinia pestis* Yfu ABC inorganic iron transport system. Infect Immun, 2001, pp. 2829-2837, vol. 69.
Gor et al., TH1-TH2: a Procrustean paradigm. Nat Immunol, 2003, p. 503-5, vol. 4.
Grillot-Courvalin et al., Functional gene transfer from intracellular bacteria to mammalian cells. Nat. Biotechnol., 1998, pp. 862-866, vol. 16.
Guerrant et al., Magnitude and Impact of Diarrheal Diseases. Arch. Med. Res., 2002, pp. 351-355, vol. 33.
Gunn, Mechanisms of bacterial resistance and response to bile. Microbes Infect, 2000, pp. 907-913, vol. 2.
Hengge-Aronis et al., Identification and molecular analysis of glgS, a novel growth-phase-regulated and rpoS-dependent gene involved in glycogen synthesis in *Escherichia coli*. Mol Microbiol, 1992, pp. 1877-1886, vol. 6.
Kotton et al., Enteric pathogens as vaccine vectors for foreign antigen delivery. Infect. Immun., 2004, pp. 5535-5547, vol. 72.
Lee et al., Characterization of recent H5 subtype avian influenza viruses from US poultry. Avian Pathol., 2004, pp. 288-297, vol. 33.
Lee et al., Mechanism of araC autoregulation and the domains of two overlapping promoters, PC and PBAD, in the L-arabinose regulatory region of *Escherichia coli*. Proc. Natl. Acad. Sci. U S A, 1981, pp. 752-756, vol. 78.
Li et al., A sopB Deletion Mutation Enhances the Immunogenicity and Protective Efficacy of a Heterologous Antigen Delivered by Live Attenuated *Salmonella enterica* Vaccines. Infection and Immunity, 2008, pp. 5238-5246, vol. 76, No. 11.
Lee et al., Trigger factor retards protein export in *Escherichia coli*. J Biol Chem, 2002, pp. 43527-43535, vol. 277.
Lefeber et al., Th1-directing adjuvants increase the immunogenicity of oligosaccharide-protein conjugate vaccines related to *Streptococcus pneumoniae* type 3. Infect Immun, 2003, pp. 6915-6920, vol. 71.
Loessner et al., Differential effect of auxotrophies on the release of macromolecules by *Salmonella enterica* vaccine strains. FEMS Microbiol. Lett., 2006, pp. 81-88, vol. 265.
Loewen et al., Genetic mapping of katF, a locus that with katE affects the synthesis of a second catalase species in *Escherichia coli*. J Bacteriol, 1984, pp. 668-675, vol. 160.

Luytjes et al., Amplification, expression, and packaging of foreign gene by influenza virus. Cell, 1989, pp. 1107-1113, vol. 59.

Malley et al., CD4+ T cells mediate antibody-independent acquired immunity to pneumococcal colonization. PNAS, 2005, pp. 4848-4853, vol. 102.

Massin et al., Cloning of the chicken RNA polymerase I promoter and use for reverse genetics of influenza A viruses in avian cells. J. Virol., 2005, pp. 13811-13816, vol. 79.

Matthay et al., Evaluation of the opsonic requirements for phagocytosis of Streptococcus pneumoniae serotypes VII, XIV, and XIX by chemiluminescence assay. Infect Immun, 1981, pp. 228-235, vol. 31.

McClelland et al., Complete genome sequence of Salmonella enterica serovar Typhimurium LT2. Nature, 2001, pp. 852-856, vol. 413, No. 6858.

McDaniel et al., Monoclonal antibodies against protease sensitive pneumococcal antigens can protect mice from fatal infection with Streptococcus pneumoniae. J. Exp. Med., 1984, pp. 368-397, vol. 160.

McDaniel et al., Use of insertional inactivation to facilitate studies of biological properties of pneumococcal surface protein A (PspA). J. Exp. Med., 1987, pp. 381-394, vol. 165.

Mesika et al., A regulated, NF κB-assisted import of plasmid DNA into mammalian cell nuclei. Mol. Ther., 2001, pp. 653-657, vol. 3.

Miller et al., A novel suicide vector and its use in construction of insertion mutations: osmoregulation of outer membrane proteins and virulence determinants in Vibrio cholerae requires toxR. J Bacteriol, 1988, pp. 2575-2583, vol. 170.

Miller et al., Bacteriophage T4 genome. Microbiol Mol Biol Rev, 2003, pp. 86-156, vol. 67, No. 1.

Molinari et al., The annual impact of seasonal influenza in the US: measuring disease burden and costs. Vaccine, 2007, pp. 5086-5096, vol. 25.

Mulvey et al., Regulation of transcription of katE and katF in Escherichia coli. J Bacteriol, 1990, pp. 6713-6720, vol. 172.

Murti et al., Localization of RNA polymerases on influenza viral ribonucleoproteins by immunogold labeling. Virology, 1988, pp. 562-566, vol. 164.

Nardelli-Haefliger et al., Human papillomavirus type 16 virus-like particles expressed in attenuated Salmonella typhimurium elicit mucosal and systemic neutralizing antibodies in mice. Infect Immun, 1997, pp. 3328-3336, vol. 65.

Nayak et al., A live recombinant avirulent oral Salmonella vaccine expressing pneumococcal surface protein A induces protective responses against Streptococcus pneumoniae. Infect Immun., 1998, pp. 3744-3751, vol. 66.

Neumann et al., An improved reverse genetics system for influenza A virus generation and its implications for vaccine production. Proc. Natl. Acad. Sci. USA, 2005, pp. 16825-16829, vol. 102.

Neumann et al., Generation of influenza A viruses entirely from cloned cDNAs. Proc. Natl. Acad. Sci. USA, 1999, pp. 9345-9350, vol. 96.

Neumann et al., RNA polymerase I-mediated expression of influenza viral RNA molecules. Virology, 1994, pp. 477-479, vol. 202.

Nickerson et al., Role of sigma factor RpoS in initial stages of Salmonella typhimurium infection. Infect Immun, 1997, pp. 1814-1823, vol. 65.

Noda et al., Architecture of ribonucleoprotein complexes in influenza A virus particles. Nature, 2006, pp. 490-492, vol. 439.

Oehler et al., The three operators of the lac operon cooperate in repression. EMBO J, 1990, pp. 973-979, vol. 9, No. 4.

Ogunniyi et al., Contributions of Pneumolysin, Pneumococcal Surface Protein A (PspA), and PspC to Pathogenicity of Streptococcus pneumoniae D39 in a Mouse Model. Infect. Immun., 2007, pp. 1843-1851, vol. 75.

Osterholm, Preparing for the next pandemic. N. Engl. J. Med., 2005, pp. 1839-1842, vol. 352.

Ozaki et al., Generation of high-yielding influenza A viruses in African green monkey kidney (Vero) cells by reverse genetics. J. Virol., 2004, pp. 1851-1857, vol. 78.

Park et al., Engineered viral vaccine constructs with dual specificity: avian influenza and Newcastle disease. Proc. Natl. Acad. Sci. USA, 2006, pp. 8203-8208, vol. 103.
Pascual et al., Expression of Recombinant Enterotoxigenic *Escherichia coli* Colonization Factor Antigen I by *Salmonella typhimurium* Elicits a Biphasic T Helper Cell Response. Infect. Immun., 1999, pp. 6249-6256, vol. 67.
Pashine et al., Th1 dominance in the immune response to live *Salmonella typhimurium* requires bacterial invasiveness but not persistence. Int. Immunol., 1999, pp. 481-489, vol. 11.
Peterson et al., RpoS proteolysis is regulated by a mechanism that does not require the SprE (RssB) response regulator phosphorylation site. J Bacteriol, 2004, pp. 7403-7410, vol. 186.
Pizarro-Cerda et al., The bacterial signal molecule, ppGpp, regulates Salmonella virulence nucleic acid sequence expression. Mol Microbiol, 2004, pp. 1827-1844, vol. 52, No. 6.
Prouty et al., *Salmonella enterica* serovar Typhimurium invasion is repressed in the presence of bile. Infect Immun, 2000, pp. 6763-6769, vol. 68.
Quinlivan et al., Attenuation of equine influenza viruses through truncations of the NS1 protein. J. Virol., 2005, pp. 8431-8439, vol. 79.
Rand, Crystal violet can be used to visualize DNA bands during gel electrophoresis and to improve cloning efficiency. Tech. Tips Online, 1996 http://www.science-direct.com/science/journal/13662120.
Roberts et al., Oral vaccination against tetanus: comparison of the immunogenicities of Salmonella strains expressing fragment C from the nirB and htrA promoters. Infect. Immun., 1998, pp. 3080-3087, vol. 66.
Romeo et al., Genetic regulation of glycogen biosynthesis in *Escherichia coli*: in vitro effects of cyclic AMP and guanosine 5'-diphosphate 3'-diphosphate and analysis of in vivo transcripts. J Bacteriol, 1989, pp. 2773-2782, vol. 171.
Sadler et al., A perfectly symmetric lac operator binds the lac repressor very tightly. Proc Natl Acad Sci U S A, 1983, pp. 6785-6789, vol. 80, No. 22.
Saeland et al., Serum samples from infants vaccinated with a pneumococcal conjugate vaccine, PncT, protect mice against invasive infection caused by *Streptococcus pneumoniae* serotypes 6A and 6B. J Infect Dis, 2001, pp. 253-260, vol. 183.
Schodel et al., Hybrid hepatitis B virus core-pre-S proteins synthesized in avirulent *Salmonella typhimurium* and *Salmonella typhi* for oral vaccination. Infect Immun, 1994, pp. 1669-1676, vol. 62, No. 5.
Schodel, Recombinant avirulent Salmonellae as oral vaccine carriers. Infection, 1992, pp. 1-8, vol. 20.
Schuchat et al., Bacterial meningitis in the United States in 1995. Active Surveillance Team. N Engl J Med, 1997, pp. 970-976, vol. 337.
Schulman et al., Independent variation in nature of hemagglutinin and neuraminidase antigens of influenza virus: distinctiveness of hemagglutinin antigen of Hong Kong-68 virus. Proc. Natl. Acad. Sci. USA, 1969, pp. 326-333, vol. 63.
Siegele et al., Gene Expression from plasmids containing the araBAD promoter at subsaturating inducer concentrations represents mixed populations. Proc Natl Acad Sci U S A, 1997, pp. 8168-8172, vol. 94, No. 15.
Simonsen et al., The impact of influenza epidemics on hospitalizations. J. Infect. Dis., 2000, pp. 831-837, vol. 181.
Hess et al., Secretion of different listeriolysin cognates by recombinant attenuated *Salmonella typhimurium*: superior efficacy of haemolytic over non-haemolytic constructs after oral vaccination. Microbes Infect, 2000, pp. 1799-1806, vol. 2.
Hohmann et al., Evaluation of a phoP/phoQ-deleted, aroA-deleted live oral *Salmonella typhi* vaccine strain in human volunteers. Vaccine, 1996, pp. 19-24, vol. 14.
Hu et al., The inducible lac operator-repressor system is functional in mammalian cells. Cell, 1987, pp. 555-566, vol. 48, No. 4.
Hu et al., The inducible lac operator-repressor system is functional for control of expression of injected DNA in Xenopus oocytes. Gene, 1988, pp. 301-313, vol. 62, No. 2.
Huang et al., Genome-wide screen of *Salmonella* nucleic acid sequences expressed during infection in pigs, using in vivo expression technology. Appl Environ Microbiol, 2007, pp. 7522-7530, vol. 73, No. 23.
Iannelli et al., Allelic variation in the highly polymorphic locus pspC of *Streptococcus pneumoniae*. Gene, 2002, pp. 63-71, vol. 284.

In Soo Lee et al., The stationary-phase sigma factor sS (RpoS) is required for a sustained acid tolerance response in virulent *Salmonella typhimurium*. Molecular Microbiology, 1995, pp. 155-167, vol. 17.
Isoda et al., Expression of a *Porphyromonas gingivalis* hemagglutinin on the surface of a *Salmonella* vaccine vector. Vaccine, 2007, pp. 117-126, vol. 25, No. 1.
Ivancic-Bace et al, Effects of recJ, recQ, and recFOR mutations on recombination in nuclease-deficient recB recD double mutants of *Escherichia coli*. J. Bacteriol., 2005, pp. 1350-1356, vol. 187.
Kaufmann et al., Impact of intracellular location of and antigen display by intracellular bacteria: implications for vaccine development. Immunol. Lett., 1999, pp. 81-84, vol. 65.
Khan et al., Immunogenicity and protective efficacy of DnaJ (hsp40) of *Streptococcus pneumoniae* against lethal infection in mice. Vaccine, 2006, pp. 6225-6231, vol. 24.
Kim et al., Direct transcriptional control of the plasminogen activator gene of Yersinia pestis by the cyclic AMP receptor protein. J Bacteriol, 2007, pp. 8890-8900, vol. 189.
Kolodrubetz et al., Regulation of the L-arabinose transport operons in *Escherichia coli*. J Mol Biol, 1981, pp. 215-227, vol. 151, No. 2.
Kwon et al., Salmonella-based vaccines for infectious diseases. Expert Review of Vaccines, 2007, pp. 147-152, vol. 6.
Lange et al., Identification of a central regulator of stationary-phase gene expression in *Escherichia coli*. Mol Microbiol, 1991, pp. 49-59, vol. 5.
Lee et al., Regulation of L-arabinose transport in *Salmonella typhimurium* LT2. Mol Gen Genet, 1982, pp. 136-141, vol. 185, No. 1.
Lee et al., Surface-displayed viral antigens on *Salmonella* carrier vaccine. Nat Biotechnol, 2000, pp. 645-648, vol. 18, No. 6.
Lewis, The lac repressor. C R Biol, 2005, pp. 521-548, vol. 328, No. 6.
Lobell et al., AraC-DNA looping: orientation and distance-dependent loop breaking by the cyclic AMP receptor protein. J Mol Biol, 1991, pp. 45-54, vol. 218.
Lobocka et al., Organization and expression of the *Escherichia coli* K-12 dad operon encoding the smaller subunit of D-amino acid dehydrogenase and the catabolic alanine racemase. J. Bacteriol., 1994, pp. 1500-1510, vol. 176.
Loessner et al., Bacteria-mediated DNA transfer in gene therapy and vaccination. Expert. Opin. Biol. Ther., 2004, pp. 157-168, vol. 4.
Loessner et al., Remote control of tumour-targeted *Salmonella enterica* serovar Typhimurium by the use of L-arabinose as inducer of bacterial gene expression in vivo. Cell Microbiol, 2007, pp. 1529-1537, vol. 9.
Marshall et al., Use of the stationary phase inducible promoters, spy and dps, to drive heterologous antigen expression in *Salmonella* vaccine strains. Vaccine, 2000, pp. 1298-1306, vol. 18, No. 14.
Medina et al., Use of live bacterial vaccine vectors for antigen delivery: potential and limitations. Vaccine, 2001, pp. 1573-1580, vol. 19.
Mehigh et al., Expression of the low calcium response in *Yersinia pestis*. Microb Pathog, 1989, pp. 203-217, vol. 6.
Moore et al., Enhanced protective immunity against pneumococcal infection with PspA DNA and protein. Vaccine, 2006, p. 5755, vol. 24.
Mossing et al., Upstream operators enhance repression of the lac promoter. Science, 1986, pp. 889-892, vol. 233, No. 4766.
Motin et al., Passive immunity to Yersiniae mediated by anti-recombinant V antigen and protein A-V antigen fusion peptide. Infect Immun, 1994, pp. 4192-4201, vol. 62.
Muller et al., Repression of lac promoter as a function of distance, phase and quality of an auxiliary lac operator. J Mol Biol, 1996, pp. 21-29, vol. 257, No. 1.
Muller-Hill et al., Mutants that mke more lac repressor. Proc Natl Acad Sci U S A, 1968, pp. 1259-1264, vol. 59, No. 4.
Muller-Hill, Lac repressor and lac operator. Prog Biophys Mol Biol, 1975, pp. 227-252, vol. 30, No. 2-3.
Nabors et al., Immunization of healthy adults with a single recombinant pneumococcal surface protein A (PspA) variant stimulates broadly cross-reactive antibodies to heterologous PspA molecules. Vaccine, 2000, p. 1743, vol. 18.
Nakayama et al., Construction of an Asd+ expression-cloning vector: stable maintenance and high level expression of cloned nucleic acid sequences in a *Salmonella* vaccine strain. BioTechnology, 1988, pp. 693-697, vol. 6.
Nedialkov et al., Resistance to lipopolysaccharide mediated by the *Yersinia pestis* V antigen-polyhistidine fusion peptide: amplification of interleukin-10. Infect Immun, 1997, pp. 1196-1203, vol. 65.
Neutra et al., Antigen sampling across epithelial barriers and induction of mucosal immune responses. Annu Rev Immunol, 1996, pp. 275-300, vol. 14.
O'Callaghan et al., High efficiency transformation of *Salmonella typhimurium* and *Salmonella typhi* by electroporation. Mol Gen Genet, 1990, pp. 156-158, vol. 223, No. 1.
Ortqvist et al., Randomised trial of 23-valent pneumococcal capsular polysaccharide vaccine in prevention of pneumonia in middle-aged and elderly people. Swedish Pneumococcal Vaccination Study Group. Lancet, 1998, pp. 399-403, vol. 351.
Perry et al., Temperature regulation of the hemin storage (Hms+) phenotype of *Yersinia pestis* is posttranscriptional. J Bacteriol, 2004, pp. 1638-1647, vol. 186.
Petersen et al., Essential role for cyclic AMP and its receptor protein in *Yersinia enterocolitica* virulence. Infect Immun, 2004, pp. 3665-3672, vol. 70.
Ramarathinam et al., *Salmonella typhimurium* induces IFN-gamma production in murine splenocytes. Role of natural killer cells and macrophages. J Immunol, 1993, pp. 3973-3981, vol. 150.
Raupach et al., Bacterial virulence, proinflammatory cytokines and host immunity: how to choose the appropriate *Salmonella* vaccine strain? Microbes and Infection, 2001, p. 1261, vol. 3.
Roland et al., Construction and evaluation of a delta cya delta crp *Salmonella typhimurium* strain expressing avian pathogenic *Escherichia coli* O78 LPS as a vaccine to prevent airsacculitis in chickens. Avian Dis, 1999, pp. 429-441, vol. 43, No. 3.
Sarubbi et al., (1989) Characterization of the spoT gene of *Escherichia coli*. J Biol Chem, 1989, pp. 15074-15082, vol. 264.
Schmieger et al., Altered cotransduction frequencies exhibited by HT-mutants of *Salmonella*-phage P22. Mol Gen Genet, 1976, pp. 307-309, vol. 143.
Schmieger, Phage P22-mutants with increased or decreased transduction abilities. Mol Gen Genet, 1972, pp. 75-88, vol. 119.
Schödel et al., Hybrid hepatitis B virus core antigen as a vaccine carrier moiety. II. Expression in avirulent *Salmonella* spp. for mucosal immunization. Adv Exp Med Biol., 1996, pp. 15-21, vol. 397.
Schodel, Prospects for oral vaccination using recombinant bacteria expressing viral epitopes. Adv. Virus Res., 1992, pp. 409-446, vol. 41.
Schwyn et al., Universal chemical assay for the detection and determination of siderophores. Analytical Biochemistry, 1987, p. 47, vol. 160.
Sedgwick et al., A solid-phase immunoenzymatic technique for the enumeration of specific antibody-secreting cells. Journal of Immunological Methods, 1983, p. 301, vol. 57.
Shalaby, Development of oral vaccines to stimulate mucosal and systemic immunity: barriers and novel strategies. Clin Immunol Immunopathol, 1995, pp. 127-134, vol. 74, No. 2.

* cited by examiner

```
    1  GCG CCC GCC ACG GTA CTG TTC TTC AAA GGC GCG CTG TGT AAC TGG CTG GTT TGT
   55  CTG GCA ATC TGG ATG GCA ATC CGC ACC GAA GGC ACG GCA AAA TTT CTT GCT ATC
  109  TGG TGG TGT CTG CTG GCG TTT ATC GCT TCC GGC TAC GAG CAC TCC GTC GCG AAT
  163  ATG ACG CTG TTC GCC CTC TCC TGG TTT GGT CAT CAC AGC GAC GCC TAT ACC CTG
  217  GCC GGA ATT GGT CAT AAC CTG TTG TGG GTG ACA CTC GGT AAT ACT TTG TCC GGT
  271  GTC GTA TTC ATG GGA TTG GGT TAT TGG TAT GCT ACG CCA AAA TCG GAG CGT CCG
  325  GCT CCG GCA AAA ATC AAT CAG CCA GAG GCT GCT GCC AAT AAT TAA GGG GTA ATG
  379  TCG CTA GCG AAA CTG AAT AAC GGT GAC TAT GAC GGC GCA GCG AAT CCT CCG CAC
       -35                          -10                            SD
```

```
                                                                                                      spvA
  433  AGT TGA CAC TAC CGC GCT CCG CTA TAA TTC AGA CGG CCA GTT TTA GGA GGT
                                                           M   N   M   N   Q   T   T   S   P   A   L   S   Q   V   E   T   A
  487  AGT GTA TGA ATA TGA ATC AGA CCA CCA GTC GGG CAC TTT CAC AGG TCG AAA CCG
         I   R   V   P   A   G   N   F   A   K   Y   N   Y   S   V   F   D
  541  CCA TCC GGG TCC CCG CAG GGA ATT TTG CAA AAT ATA ATT ATT ATT CCG TGT TTG
         I   V   R   Q   T   R   K   Q   F   I   N   A   N   M   S   W   P   G
  595  ATA TTG TCC GTC AGA CCC GTA AAC AGT TTA TTA ACG CCA ATA TGT CAT GGC CGG
         S   R   G   K   T   W   D   L   A   M   G   Q   A   Q   Y   I   R
  649  GCT CCC GCG GAG GTA AAA CCT GGG ACC TGG CGA TGG GCC AGG CGC AGT ATA TCC
         C   M   F   R   E   N   Q   L   T   R   R   V   R   G   T   L   Q   Q
  703  GCT GCA TGT TCC GAG AAA ATC AAT TGA CCC GCA GAG TTC GGG GGA CCT TGC AGC
         T   P   D   N   G   T   N   L   S   S   A   V   G   G   I   Q   G
  757  AGA CAC CGG ACA ATG GCA CGA ACC TGA GCA GTT CCG CTG TCG GCG GTA TTC AGG
         Q   A   E   R   R   F   D   L   A   T   L   M   V   V   N   D   A   I
  811  GAC AGG CAG AGC GTC GGC CGG ACC TGG CCA CCC TGA TGG TGG TTA ATG ATG CCA
         N   Q   Q   I   P   T   L   L   P   Y   H   F   P   H   D   Q   V   E
  865  TTA ACC AGC AAA TAC CGA CCC TGC TGC CGT ATC ATT TCC ACG ACC AGG TGG
         L   S   L   L   N   T   D   V   S   L   E   D   I   I   S   E   S   S
  919  AGT TAT CTC TGC TGA ATA CCG ATG TGT CGC TGG AAG ATA TTA TCA GCG AGA GCA
         I   D   N   P   W   F   L   S   N   S   L   T   G   D   N   S   N   Y
  973  GCA TTG ACT GGC CGT GGT TCC TGA GCA ACT CGC TGA CCG GCG ATA ACA GTA ACT
         A   M   E   L   A   S   R   L   S   P   E   Q   Q   T   L   P   T   E
 1027  ATG CCA TGG AGC TCG CCA GCC GGC TGT CAC CAG AGC AGC AGA CAC TGC CGA CCG
         P   D   N   S   T   A   T   D   L   T   S   F   Y   Q   T   N   L   G
 1081  AGC CGG ACA ACA GTA CCG CCA CTG ACC TGA CCT CTT TTT ACC AGA CCA ATC TGG
         L   K   T   A   D   Y   T   P   F   E   A   L   N   T   F   A   R   Q
 1135  GGC TGA AAA CCG CCG ACT ATA CGC CAT TTG AAG CAC TGA ATA CCT TTG CCC GAC
         L   A   I   T   V   P   P   G   G   T   V   D   C   G   Y   S   A   C
 1189  AGT TAG TTA CCG TTC CCC CAG GTG GAA CAG TTG ATT GCG GGT ACT CTG CGT
         Q   P   A   V
 1243  GCC AGC CGG CAG TTT AGC TTC CCG CGC TAC CAG AGT AGT GAG CAG CAG ACC ATT
 1297  CTG CAG AAT CTG AGC GAC GTC ATT GTT CAG GTG CAT TCT ACC GCG CTG TAC GGC
 1351  GGC AGC ACT TTT GAA CAG GCC GTA GAG CAG ACG CTG TAA GCA GAA AAT ATA CCT
                                                                                                      spvB
                                                                  M   L   I   L   N   G
 1405  GGC CAT CGT CAG ACG GCC AGT TTC AGG AGA TAG TGT ATG TTG ATA CTA AAT GGT
         F   S   S   A   T   L   A   L   I   T   P   P   F   L   P   K   G   G
 1459  TTT TCA TCT GCC ACT TTA GCG CTG ATC ACT CCC CCT TTC CTG CCA AAA GTG GGC
         K   A   L   S   Q   S   G   P   D   G   L   A   S   I   T   L   P   L
 1513  AAG GCG CTG AGT CAG TCA GGC CCT GAC GGC AGT GCC AGT ATA ACG CTG CCT CTG
         P   I   S   A   E   R   G   F   A   P   A   L   A   L   H   Y   S   S
 1567  CCC ATC AGC GCC GAA CGC GGC TTT GCG CCT GCG CTG GCG CTG CAC TAC AGC AGC
         G   G   G   N   G   P   F   G   V   G   W   S   C   A   T   M   S   I
 1621  GGT GGC GGC AAT GGC CCC TTC GGC GTG GGC TGG TCC TGC GCG ACA ATG AGC ATT
         A   R   R   T   S   H   G   V   P   Q   Y   N   D   S   D   E   F   L
 1675  GCC CGC CGC ACC AGC CAT GGC GTG CCG CAG TAT AAC GAC AGC GAT GAG TTT CTG
         G   P   D   G   E   V   L   V   Q   T   L   S   T   G   D   A   P   N
 1729  GGG CCG GAC GGA GAA GTG CTG GTT CAA ACG CTC AGC ACC GGT GAT GCC CCC AAT
         P   V   T   C   F   A   Y   G   D   V   S   F   P   Q   S   Y   T   V
```

FIG. 7A

```
1783    CCC GTC ACC TGC TTC GCG TAC GGT GAC GTA TCG TTC CCG CAA AGC TAC ACG GTG
         T   R   Y   Q   P   R   T   E   S   S   F   Y   R   L   E   Y   W   V
1837    ACC CGC TAT CAG CCC CGC ACG GAG AGC AGT TTT TAT CGC CTG GAG TAC TGG GTG
         Q   N   S   N   G   D   D   F   W   L   L   H   D   S   N   G   I   L
1891    GGC AAC AGC AAC GGC GAT GAT TTC TGG TTA CTG CAT GAC AGT AAC GGC ATC CTG
         H   L   L   G   K   T   A   A   A   R   L   S   D   P   Q   A   A   S
1945    CAC CTG CTG GGG AAA ACC GCC GCA GCA CGC CTC AGC GAT CCG CAG GCC GCC TCT
         H   T   A   Q   W   L   V   E   E   S   V   T   P   T   G   E   H   I
1999    CAT ACG GCG CAA TGG CTG GTT GAG GAG TCG GTG ACC CCT ACC GGC GAG CAT ATC
         Y   Y   S   Y   L   A   E   N   G   D   N   V   D   L   N   G   N   E
2053    TAT TAC TCC TAC TTG GCG GAG AAC GGT GAC AAT GTG GAC CTC AAT GGG AAC GAG
         A   G   R   D   R   S   A   M   R   Y   L   S   K   V   Q   Y   G   N
2107    GCC GGA CGC GAT CGC AGC GCC ATG CGC TAT CTC AGC AAG GTA CAG TAT GGC AAC
         A   T   P   A   A   D   L   Y   L   W   T   S   A   T   P   A   V   Q
2161    GCG ACC CCC GCC GCC GAT CTG TAC CTC TGG ACT AGC GCC ACA CCC GCG GTA CAG
         W   L   F   T   L   V   F   D   Y   G   E   R   G   V   D   P   Q   V
2215    TGG CTG TTC ACC CTA GTG TTT GAC TAC GGC GAA CGT GGT GTA GAT CCA CAG GTA
         P   P   A   F   T   A   Q   N   S   W   L   A   R   Q   D   P   F   S
2269    CCG CCT GCA TTC ACT GCT CAG AAC AGC TGG CTC GCC GGC CAG GAT CCC TTC TCC
         L   Y   G   F   E   I   R   L   H   R   L   C   R   Q   V   L
2323    CTG TAT AAC TAC GGC TTT GAG ATC CGC CTC CAT CGC CTG TGC CGC CAA GTC CTG
         M   F   H   H   F   P   D   E   L   G   E   A   D   T   L   V   S   R
2377    ATG TTC CAC CAC TTT CCT GAT GAA CTG GGT GAA GCC GAT ACG CTG GTT TCC CGT
         L   L   L   E   Y   D   E   N   P   I   L   T   Q   L   C   A   A   R
2431    CTG CTG CTG GAG TAT GAC GAA AAT CCG ATA CTG ACA CAG CTT TGC GCT GCT CGG
         T   L   A   Y   E   G   D   G   Y   R   R   A   P   V   N   N   M   M
2485    ACG CTG GCC TAT GAA GGC GAC GGT TAT AGA AGA GCT CCC GTC AAC AAT ATG ATG
         P   P   P   P   P   M   M   G   G   N   S   S   R   P   K   S   K   W
2539    CCG CCG CCT CCT CCG ATG ATG GGA GGT AAT TCA TCT CGA CCA AAA TCA AAA TGG
         A   I   V   E   E   S   K   Q   I   Q   A   L   R   Y   Y   S   A   Q
2593    GCG ATT GTA GAG GAA TCA AAG CAG ATT CAA GCT CTG AGG TAC TAT TCA GCT CAA
         G   Y   S   V   I   N   K   Y   L   R   G   D   D   Y   P   E   T   Q
2647    GGG TAC AGT GTG ATT AAT AAA TAT TTA CGT GGG GAT GAT TAT CCT GAA ACA CAG
         A   K   E   T   L   L   S   R   D   Y   L   S   T   N   E   P   S   D
2701    GCA AAA GAA ACT CTG CTC TCC AGA GAC TAT CTT TCC ACA AAT GAA CCC AGT GAT
         E   E   F   K   N   A   M   S   V   Y   I   N   D   I   A   E   G   L
2755    GAG GAG TTT AAA AAT GCC ATG TCA GTT TAT ATA AAT GAT ATT GCG GAG GGA TTA
         S   S   L   P   E   T   D   H   R   V   V   T   G   L   K   L   D
2809    AGT TCA CTT CCC GAA ACA GAT CAC AGA GTC GTA TAC CGG GGC CTG AAG CTT GAT
         K   P   A   L   S   D   V   L   K   E   Y   T   T   I   G   N   I   I
2863    AAG CCC GCA TTA TCG GAT GTG CTG AAG GAA TAC ACT ACT ATA GGT AAT ATA ATA
         I   D   K   A   F   M   S   T   S   P   D   K   A   W   I   N   D   T
2937    ATA GAT AAA GCT TTT ATG AGT ACA TCG CCA GAT AAG GCA TGG ATA AAT GAC ACT
         I   L   N   I   Y   L   E   K   G   Y   K   G   R   I   L   G   D   V
2971    ATT CTC AAC ATA TAC CTA GAA AAA GGA TAT AAA GGT AGA ATA CTC GGA GAT GTT
         A   H   F   K   G   E   A   E   M   L   F   P   P   N   T   K   L   K
3025    GCA CAT TTT AAG GGA GAG GCA GAG ATG CTT TTC CCT CCA AAT ACT AAA CTC AAA
         I   E   S   I   V   N   C   G   S   Q   D   F   A   S   Q   L   S   K
3079    ATC GAA AGC ATT GTA AAT TGT GGA TCC CAA GAC TTT GCA AGC CAG CTT AGT AAG
         L   R   L   S   D   D   A   T   A   D   T   N   R   I   K   R   Y   I
3133    CTG AGA TTA AGT GAT GAT GCA ACT GCT GAC ACA AAC AGG ATA AAA AGA ATA ATA
         N   M   R   V   L   N   S
3187    AAC ATG AGG GTA CTC AAC TCA TAG ATA CTA AGA ATC TAT TCC AGA AGT GGT ATG
3241    AGC GGC CTA GCT CTA TAA GGG GTT ATA CTC CGG AAC CCC AGA TTT TTC CGT CAC
3295    CCT AGG CCC GCA AAG TAG TGC ATC TAA ACT TTT GCC ATT ACC CTT CTT TAA CTT
3349    TCT GCT CGG AAC GGA CCG AAA TAT CAT TTT TTC GCC TGA TAA AAA ATG AGG TTT
```

FIG. 7B

```
       3403           TCT GGA TAA CTA ATC GTT TTA TTA AAA AAA ACT GAG AAT TTA TAT CTA ATA ATA
spvC                                                                     M   P   I   N   R   P   N
       3457           TGG CGA TAT ATC CAT ATC GCA AAG GAG ATT TCC CAT GCC CAT AAA TAG GCC TAA
                       L   N   L   N   I   S   P   L   N   I   V   A   A   Y   D   G   A   E
       3511           TCT AAA TCT AAA CAT CTC TCC TTT GAA TAT TGT AGC TGC TTA TGA TGG GGC GGA
                       I   P   S   T   N   K   H   L   K   N   F   N   S   L   H   N   Q
       3565           AAT ACC ATC TAC AAA TAA GCA CCT GAA AAA TAA TTT CAA CTC CTT GCA CAA CCA
                       M   R   K   M   P   V   S   H   F   K   E   A   L   D   V   P   D   Y
       3619           AAT GCG GAA GAT GCC GGT ATC CCA CTT TAA AGA GGC GCT GGA TGT GCC TGA CTA
                       S   G   M   R   Q   S   G   F   F   A   M   S   Q   G   F   Q   L   N
       3673           TTC AGG GAT GCG CCA GAG TGG TTT CTT TGC TAT GAG CCA AGG TTT TCA GCT GAA
                       N   H   G   Y   D   V   F   I   H   A   R   R   E   S   P   Q   S   Q
       3727           TAA CCA TGG TTA CGA TGT TTT CAT CCA TGC TCG TCG AGA ATC ACC TCA GTC TCA
                       G   K   F   A   G   D   K   F   H   I   S   V   L   R   D   M   V   P
       3781           GGG CAA ATT TGC CGG TGA CAA GTT CCA CAT CAG TGT GCT CAG GGA TAT GGT GCC
                       Q   A   F   Q   A   L   S   G   L   L   F   S   E   D   S   P   V   D
       3835           ACA AGC ATT TCA AGC GCT GTC CGG ATT GCT GTT TTC AGA GGA CAG TCC GGT AGA
                       K   W   V   T   D   M   E   K   V   V   Q   Q   A   R   V   S   L
       3889           TAA GTG GAA AGT GAC CGA TAT GGA GAA GGT CGT TCA ACA AGC CCG TGT TAG CCT
                       G   A   Q   F   T   L   Y   I   K   P   D   Q   E   N   S   Q   Y   S
       3943           GGG CGC TCA GTT CAC GTT GTA TAT AAA ACC AGA CCA GGA AAA TTC GCA GTA CAG
                       A   S   F   L   H   K   T   R   Q   F   I   E   C   L   E   S   R   L
3997  TGC GTC GTT TCT CCA CAA GAC ACG GCA ATT TAT AGA GTG TCT GGA ATC CAG ACT
       S   E   N   G   V   I   S   G   Q   C   P   E   S   D   V   H   P   E
       4051           ATC CGA AAA TGG GGT TAT TTC AGG ACA GTG TCC TGA GTC AGA CGT TCA TCC TGA
                       N   W   K   Y   L   S   Y   R   N   E   L   R   S   G   R   D   G
       4105           AAA TTG GAA ATA TCT CAG TTA TCG TAA TGA ACT ACG AAG TGG GCG TGA TGG TGG
                       L   M   Q   R   Q   A   L   R   E   S   P   Y   R   L   M   T   E
       4159           CGA AAT GCA GAG ACA GGC TTT ACG TGA GGA ACC GTT TTA TCG TTT GAT GAC AGA
                       E
       4213           GTA AGT ATG GGT TTG GGG AGC AAC GGA ACA GTA AAC GCC GTT AAA CAG CTA TTT
       4267           TAA ATG CTC ATT AAT TTA TTA ATC AAT AAA TTA CAA ATT TTC ATT GAA GGC TCC
       4321           CCC CTT ACT GAC GAA TTC CGG CAC CGT AAA GGA ATA ACG CTC ATG CAT ATT GAT
       4375           ATG TCC GCA CTG TAA TGG TGA AAA TTA CAT AAG CAA GAG CGT TTT TTG AAA AAT
spvD                                                                                         M   R
       4429           ATT ATA TTT AAT GTT TTG TAA TAT GCA TTT TAT TGA GGT AGT GTA ACT ATG AGA
                       V   S   G   S   A   S   S   Q   D   I   I   S   R   I   N   S   K   N
       4483           GTT TCT GGT AGT GCG TCA TCC CAA GAT ATA ATA TCA CGT ATA AAT TCA AAA AAT
                       I   N   N   N   D   S   N   E   V   K   R   I   K   D   A   L   C   I
       4537           ATC AAT AAT AAT GAT TCA AAT GAA GTC AAG AGA ATT AAA GAT GCG CTT TGT ATT
                       E   S   K   E   R   I   L   Y   P   Q   N   L   S   R   D   N   L   K
       4591           GAA TCA AAA GAG AGA ATT TTG TAT CCA CAA AAT TTG AGT CGA GAT AAT TTA AAA
                       Q   M   A   R   Y   V   N   N   T   Y   V   H   Y   S   G   N   C   V
       4645           CAA ATG GCT AGA TAT GTA AAT AAT ACA TAC GTC CAT TAC TCT GGG AAC TGC GTT
                       L   L   S   A   C   L   H   Y   N   I   H   H   R   Q   D   I   L   S
       4699           TTA TTA TCA GCG TGT TTA CAT TAT AAC ATA CAT CAC CGA CAG GAT ATA TTA AGT
                       S   K   N   T   A   S   P   T   V   G   L   D   S   A   I   V   D   K
       4753           TCG AAG AAC ACT GCC TCT CCT ACA GTG GGA TTA GAC AGC GCC ATT GTT GAT AAA
                       I   I   F   G   H   E   L   N   Q   S   Y   C   L   N   S   I   D   E
       4807           ATC ATT TTT GGT CAT GAG CTT AAC CAA TCA TAT TGT TTA AAT TCC ATC GAT GAG
                       V   E   K   E   I   L   N   R   H   D   I   K   R   E   S   S   F   I
       4861           GTG GAA AAA GAA ATA TTA AAC CGT CAT GAC ATT AAG AGG GAA AGT TCT TTT ATC
                       I   S   A   E   N   Y   I   A   P   I   I   G   E   C   R   H   D   F
       4915           ATT AGC GCA GAG AAC TAC ATA GCT CCA ATA ATT GGC GAA TGT AGA CAT GAT TTC
                       N   A   V   V   I   C   E   Y   D   K   K   P   Y   V   Q   F   I   D
       4969           AAC GCT GTG GTT ATC TGT GAA TAT GAT AAA AAA CCA TAT GTA CAA TTC ATT GAT
                       S   W   K   T   S   N   I   L   P   S   L   Q   E   I   K   K   H   F
       5023           TCT TGG AAA ACA TCC AAC ATA CTT CCT AGC TTA CAA GAA ATA AAA AAA CAC TTC
                       S   S   S   G   E   F   Y   V   R   A   Y   D   E   K   H   D
       5077           TCA TCA TCA GGG GAA TTT TAT GTC AGG GCT TAT GAT GAA AAA CAC GAT TGA TAA
       5131           CTC GAG CGG AAG ATC TTA ATT AAA ATA ACG CCC TGT TAT TCA GGG CTT TAT TTT
       5185           ACA ACT ACT CGT AAT CTC AAA TTA TTT TTA CTT AA
```

FIG. 7C

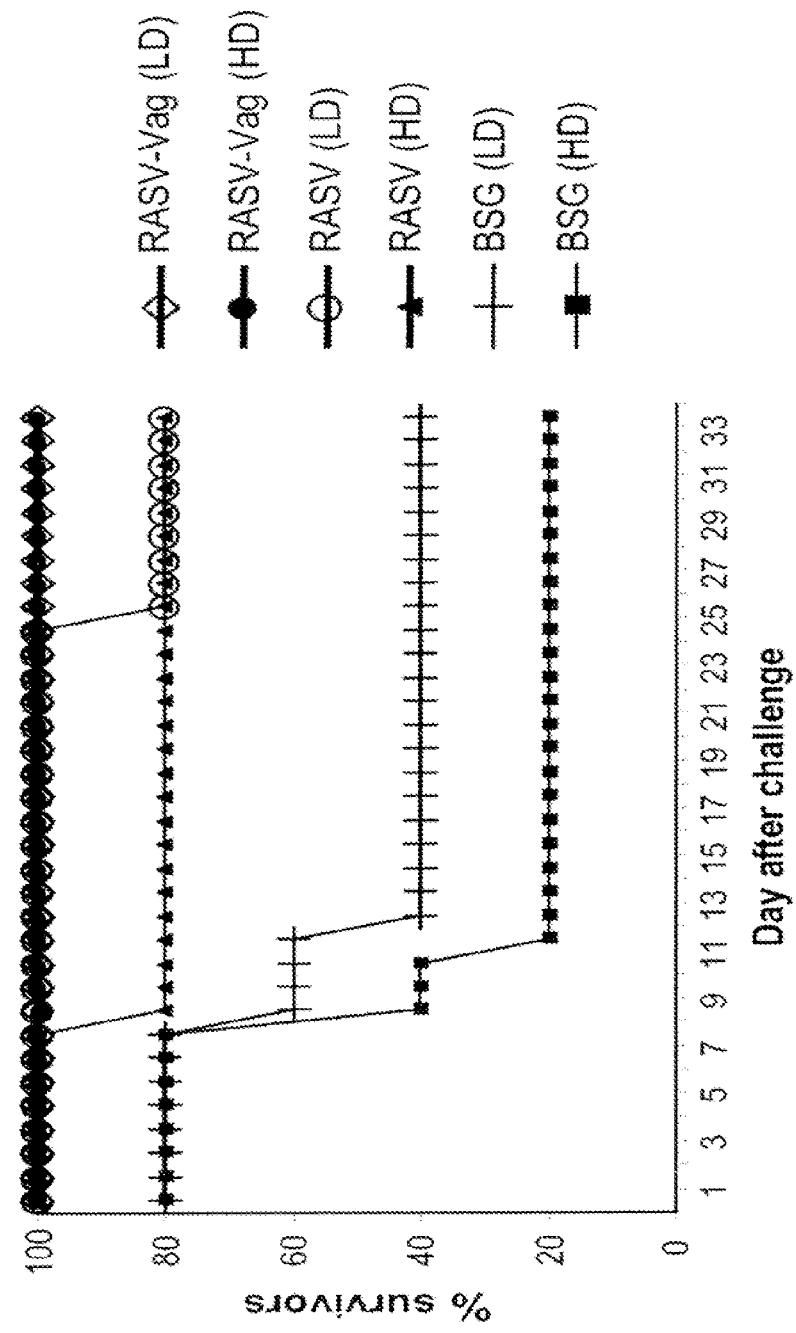

|  |  |
|---|---|
| 1 | ATG GAA GGC GGC ACT CCG CTG TTT CAT ATG ATA CCG CCG AAG CCC GAT GTA AGC |
| 55 | CGC TAC AGT CGT CCG AAA GTC ACC AGC CTC CTC CCC CCT GCC GTC ATC CGT GCA |
| 109 | TCA GCT ATG CAC TGA GTA TGC CTG CCC TTC CCT AGA GAA TCC TGC CAG GCT TGC |
| 163 | CAC ACT GAT ATA TCT TGA CTT TAT GTA AAC GAT ATG ACA CTT TAA CAT GAT AAT |
| 217 | GAT TAC CAT TCT CTT TTA ATA TAC AGA GAA ACT AGG AAA TAG ATG AAT GAG TTA |
| 271 | TGT TAC TTT AAT ATT CTC TGA CAA TAA CCT AAA TCA GTT AGA TTA TTG TCA TTT |
| 325 | AAT AAA TAA TGA CAT TCT TTC ATC ATA AAT AAA AAG ACT ATT GTT TAT AAT ATT |
| 379 | GTT CTC AGC ATT ATA TGA TTA TTT ATC CTG ATA ACT CTC CTA TGT TGT ATG TTT |
| 433 | ATA TGA TTT TCC TTG AAA CAT ATA ATG CAA ATT TTC GAT TTA TTT TCC ATC ATT |
| 487 | AAT CCA GAT AAA CAA CAA ACT AAT AGT ATG CAA GGA GAC ATT ATA GCG CGT GGA |
| 541 | AAA TTC CTG ACC AAA TCG AGT TTC TGG ACC ACT GGC CGC TCA CCG CCG TCG GCA |
| 595 | AGA TAG ACA AAA AAC GCC TGA CGG CTC TCG CCG TCG ACC GTT ATC GCC ATT CTG |
| 649 | CCC AAT AAG CGC AAA CCG ACC CGA AAC AGG TTG AAA TAA ACC CGT TTC GGG TAG |
| 703 | CAC CAC TAT TAG AAA TAG TTA TCA TTT TCA ATT CAC CAT TGT CGG TAT TTT TGG | pan

|  |  |
|---|---|
|  |                          M   K   M   T   R   L   Y   P |
| 757 | CGT TTC GCC GTC TTA CAG GGA CTC ACA ACA ATG AAA ATG ACA CGC CTT TAT CCT |
|  | L  A  L  G  L  L  P  A  I  A  N  A  Q  T  S  Q |
| 811 | CTG GCC TTG GGG GGC TTA TTG CTC CCT GCC ATT GCT AAT GCC CAG ACT TCA CAG |
|  | Q  D  E  S  T  L  V  V  T  A  S  K  Q  S  S  R  S  A |
| 865 | CAA GAC GAA AGC ACG CTG GTG GTT ACC GCC AGT AAA CAA TCT TCC CGC TCG GCA |
|  | S  A  N  N  V  S  E  T  V  V  S  A  F  L  S  D  A |
| 919 | TCA GCC AAC AAC GTC TCG TCT ACT GTT GTC AGC GCG CCG GAA TTA AGC GAC GCC |
|  | G  V  T  A  S  D  K  L  P  S  V  L  P  G  L  N  I  E |
| 973 | GGC GTC ACC GCC AGC GAC AAA CTC CCT AGC GTC TTG CCT GGG CTC AAT ATT GAA |
|  | N  S  G  N  M  L  F  S  T  I  S  L  R  G  V  S  S  A |
| 1027 | AAT AGC GGC AAC ATG CTT TTT TCG ACG ATC TCG CTC CGC GGC GTC TCT TCA GCG |
|  | Q  D  F  Y  N  P  A  V  T  L  Y  V  D  G  V  P  Q  L |
| 1081 | CAG GAC TTC TAT AAC CCT GCC GTC ACC CTG TAT GTC GAT GGC GTC CCT CAG CTT |
|  | S  T  N  T  I  Q  A  L  T  D  V  Q  S  V  E  L  L  R |
| 1135 | TCC ACC AAC ACC ATC CAG GCG CTT ACC GAT GTG CAA AGC GTG GAG TTG CTG CGC |
|  | G  P  Q  G  T  L  Y  G  K  S  A  G  G  I  I  N  I |
| 1189 | GGC CCA CAG GGC ACG TTA TAT GGC AAA AGC GCT CAG GGC GGG ATC ATC AAC ATC |
|  | V  T  Q  Q  P  D  S  T  P  R  G  Y  I  E  G  G  V  S |
| 1243 | GTC ACC CAG CAG CCG GAC AGC ACG CCG CGC GGC TAT ATT GAA GGC GGC GTC AGT |
|  | S  R  D  S  Y  R  S  K  F  N  L  S  G  P  I  Q  D  G |
| 1297 | AGC CGC GAC AGT TAT CGC AGT AAG TTC AAC CTG AGC GGC CCT ATT CAG GAT GGC |
|  | L  L  Y  G  S  V  T  L  R  Q  V  D  D  G  D  M  I |
| 1351 | CTG CTG TAC GGC AGC GTC ACC CTG TTA CGC CAG GTT GAT GAC GGC GAC ATG ATT |
|  | N  P  A  T  G  S  D  D  L  G  G  T  R  A  S  I  G  N |
| 1405 | AAC CCT GCG ACG GGC AGC GAT GAC TTA GGC GGC ACC CGC GCC AGC ATT GGG AAT |
|  | V  K  L  R  L  A  P  D  D  Q  P  W  E  M  G  F  A  A |
| 1459 | GTG AAA CTG CGT CTG GCG CCG GAC GAT CAG CCT TGG GAA ATG GGC TTT GCC GCC |
|  | S  R  E  C  T  R  A  T  Q  D  A  Y  V  G  W  N  D  I |
| 1513 | TCA CGC GAA TGT ACC CGC GCC ACC CAG GAC GCC TAT GTG GGC TGG AAT GAT ATT |
|  | K  G  R  K  L  S  I  S  D  G  S  P  D  P  Y  M  R  R |
| 1567 | AAG GGC CGT AAG CTG TCG ATC AGC GAT GGT TCA CCA GAC CCG TAC ATG CGC CGC |
|  | C  T  D  S  Q  T  L  S  G  K  Y  T  T  D  D  W  V  F |
| 1621 | TGC ACT GAC AGC CAG ACC CTG AGT GGG AAA TAC ACC ACC GAT GAC TGG GTT TTC |
|  | N  L  I  S  A  N  Q  Q  H  Y  S  R  T  F  P  S  G |
| 1675 | AAC CTG ATC AGC GCC TGG CAG CAG CAG CAT TAT TCG CGC ACC TTC CCT TCC GGT |
|  | S  L  I  V  N  M  P  Q  R  N  Q  D  V  Q  E  L  R |
| 1729 | TCG TTA ATC GTC AAT ATG CCT CAG CGC TGG AAT CAG GAT GTG CAG GAG CTG CGC |
|  | A  A  T  L  G  D  A  R  T  V  D  M  V  F  G  L  Y  R |

FIG. 9A

```
1783  GCC GCA ACC CTG GGC GAT GCG CGT ACC GTT GAT ATG GTG TTT GGG CTG TAC CGC
       Q   N   T   R   E   K   L   N   S   A   Y   D   M   P   T   M   P   Y
1837  CAG AAC ACC CGC GAG AAG TTA AAT TCA GCC TAC GAC ATG CCG ACA ATG CCT TAT
       L   S   S   T   G   Y   T   T   A   E   T   L   A   A   Y   S   D   L
1891  TTA AGC AGT ACC GGC TAT ACC ACC GCT GAA ACG CTG GCC GCA TAC AGT GAC CTG
       T   N   H   L   T   D   R   F   D   I   G   G   G   V   R   F   S   H
1945  ACC TGG CAT TTA ACC GAT CGT TTT GAT ATC GGC GGC GGC GTG CGC TTC TCG CAT
       D   K   S   S   T   Q   Y   H   G   S   N   L   G   N   P   F   G   D
1999  GAT AAA TCC AGT ACA CAA TAT CAC GGC AGC ATG CTC GGC AAC CCG TTT GGC GAC
       Q   G   K   S   N   D   D   Q   V   L   G   Q   L   S   A   G   Y   M
2053  CAG GGT AAG AGC AAT GAC GAT CAG GTG CTC GGG CAG CTC TCC GCA GGC TAT ATG
       L   T   D   D   W   S   V   Y   T   R   V   A   Q   G   Y   K   P   S
2107  CTG ACC GAT GAC TGG AGC GTG TAT ACC CGT GTA GCC CAG GGC TAT AAA CCT TCC
       G   Y   N   I   V   P   T   A   G   L   D   A   K   P   F   V   A   E
2161  GGG TAC AAC ATC GTG CCT ACT GCG GGT CTT GAT GCC AAA CCG TTC GTC GCC GAG
       K   S   I   N   Y   E   L   G   T   R   Y   E   T   A   D   V   T   L
2215  AAA TCC ATC AAC TAT GAA CTT GGC ACC CGC TAC GAA ACC GCT GAC GTC ACG CTG
       Q   A   A   T   F   Y   T   H   T   K   D   M   Q   L   Y   S   G   P
2269  CAA GCC GCG ACG TTT TAT ACC CAC ACC AAA GAC ATG CAG CTT TAC TCT GGC CCG
       V   S   M   Q   T   L   S   N   A   G   K   A   D   A   T   G   V   E
2323  GTC AGC ATG CAG ACA TTA AGC AAT GCG GGT AAA GCC GAC GCC ACC GGC GTT GAG
       L   E   A   K   W   R   F   A   P   G   W   S   W   D   I   N   G   N
2377  CTT GAA GCG AAG TGG CGC TTT GCG CCA GGC TGG TCA TGG GAT ATC AAT GGC AAC
       V   I   R   S   E   F   T   N   D   S   E   L   Y   H   G   N   R   V
2431  GTG ATC CGT TCC GAA TTC ACC AAT GAC AGT GAG TTG TAT CAC GGT AAC CGC GTG
       P   F   V   P   R   Y   G   A   G   S   S   V   N   G   V   I   D   T
2485  CCG TTC GTA CCA CGT TAT GGC GCG GGC AGC AGC GTG AAC GGC GTG ATT GAT ACG
       R   Y   G   A   L   M   P   R   L   A   V   N   L   V   G   P   H   Y
2539  CGC TAT GGC GCA CTG ATG CCT CGC CTG GCG GTT AAT CTC GTC GGG CCG CAT TAT
       F   D   G   D   N   Q   L   R   Q   G   T   Y   A   T   L   D   S   S
2593  TTC GAT GGC GAC AAC CAG TTG CGC CAA GGC ACC TAT GCC ACC CTG GAC AGC AGC
       L   G   W   Q   A   T   E   R   M   N   I   S   V   Y   V   D   N   L
2647  CTG GGC TGG CAG GCG ACT GAA CGC ATG AAC ATT TCC GTC TAT GTC GAT AAC CTG
       F   D   R   R   Y   R   T   Y   G   Y   M   N   G   S   S   A   V   A
2701  TTC GAC CGT CGT TAC CGT ACC TAT GGC TAC ATG AAC GGC AGC AGC GCC GTC GCG
       Q   V   N   M   G   R   T   V   G   I   N   T   R   I   D   F   F   *
2755  CAG GTC AAT ATG GGT CGC ACC GTC GGT ATC AAT ACG CGC ATT GAT TTC TTC TGA
2809  ACC ATA GAG GAA TTA CAA GCG TAT GAG GAA TAT TTC TTC CTG TTA TAA TTC CTC
2863  GTT ATG CTC AGA TAT CTG TTG GAG GTG GAA TGG AAG ATA GAC AAT CCA CCA AGA
2917  AGA AAT ATC ATT CTG TGT GGA TTG TCC AAT AAC TGT TCT TTC TTA TAT TAA ATA
       *   L   C   V   D   S   L   N   N   P   S   W   N   C   L   R  -
2971  ATA CTA TTT ATA AAC AAA CAT CAC TAA GAT TAT TTG GAC TCC AAT TAC ACA ATC
      - G   A   A   Y   N   W   A   E   S   P   I   G   E   P   K   Q   I  -
3025  TTC CCG CAG CAT AGT TCC ATG CTT CTG AAG GTA TCC CTT CGG GTT TTT GCT TAA
      - T   G   G   L   G   S   P   S   M   A   P   N   P   K   H   T   S  A -
3079  TTG TTC CCC CTA AAC CGG ATG GAG ACA TTG CAG GAT TAG GTT TGT GAG TGG ATG
      - V   D   Y   I   A   G   G   A   A   V   G   A   A   A   G   I   G  G -
3133  CAT AGT CAT ATA TTG CAC CTC CAG CCA CAC CCC CAG CAG CTG CTC CAA TTC CTC
      - A   V   F   Q   G   S   L   T   G   I   A   M   A   I   D   R   G  S -
3187  CTG CAA CAA ATT GCC CGG ATA GTG TTC CTA TAG CCA TCG CAA TAT CAC GCC CTG
cvi   - A   G   G   S   V   S   D   L   E   N   L   T   L   T   R   M
3241  AAG CAC CAC CAG AAA CAG AAT CTA ATT CAT TTA GAG TCA GAG TTC TCA TAT GAT
3295  CTC CTT TTT ATC CTA TCG GAT ATT GAA TTA TAA TAA TTA TCA CCA ACA AAG TAA CAT
3349  ATT GCA GAC ATT AAT GCA GAG AAG CAA AAT GTA TGC CAA GCA TCA GCA GGG CAG
3403  CCC ATA CAG ACA GAC TCA GAT TTG TCT GTA TGA CCA GAA CAG GGA GCA CAA CCA
3457  GCA GAC CGT TCT GTC CGA TAC CGA GAA GCC CGG CAC TGA ACG CAA GTG GCC AGC
```

FIG. 9B

```
3511       AGG ACA GTG GTT TTT GGG GCG TAT CTT CGA TCC CTG GTG ACA TTA TAA TGT TTC
3565       AAC TCC ATG TAT TAA TTG TGT TTA TTT GTA AAA TTA ATT TAT CTG ACA ATA ACA
lucA                   M   R   I   I   I   D   I   I   V   I   I   L   L   C
3619       TTT ATT GTT GAT AAT GAG AAT CAT TAT TGA CAT AAT TGT TAT TAT TTT ACT GTG
           · G   S   C   L   T   M   T   L   P   S   E   K   P   T   D   V   A ·
3673       TGG CAG CTG TTT GAC TAT GAC CCT GCC CTC TGA AAA ACC AGC CAC AGA TGT GGC
           · A   Q   C   F   L   N   A   L   I   R   E   T   T   D   W   K   L   T ·
3727       TGC GCA GTG CTT CCT GAA TGC ACT GAT TCG TGA AAC CAC AGA CTG GAA ACT GAC
           · E   Y   P   P   D   E   L   L   I   P   L   D   E   Q   K   S   L   H ·
3781       AGA ATA CCC GCC AGA CGA ATT GCT CAT CCC GCT GGA TGA GCA GAA ATC GCT CCA
           · F   R   V   A   Y   F   S   P   T   Q   H   R   F   A   F   P   A ·
3835       TTT CAG AGT GGC TTA TTT CTC CCC AAC CCA GCA TCA CCG CTT TGC ATT CCC TGC
           · R   L   V   T   A   S   G   S   Y   P   V   P   F   T   T   L   S   R ·
3889       ACG TCT GGT CAC GGC ATC AGG CAG TTA TCC TGT CGA CTT TAC CAC TCT CTC CCG
           · L   I   I   D   K   L   R   H   Q   L   F   L   P   V   P   L   C   E ·
3943       GCT TAT TAT TGA TAA GCT ACG CCA TCA ACT GTT TCT GCC CGT TCC CCT CTG CGA
           · T   F   H   Q   R   V   L   E   S   H   V   H   T   Q   A   I   D ·
3997       AAC TTT CCA CCA GCG CGT GCT GGA AAG CCA TGT CCA TAC ACA CAA GGC AAT TGA
           · A   R   H   D   W   A   A   L   R   E   K   A   L   N   F   G   E   A ·
4051       TGC CCG TCA TGA CTG GGC CGC TCT GCG TGA AAA AGC GTT GAA TTT TGG CGA GGC
           · E   Q   A   L   L   T   G   H   A   F   H   P   A   P   K   S   H   E ·
4105       TGA GCA GGC GCT GCT GAC AGG ACA CGC TTT CCA CCC TGC GCC TAA GTC TCA TGA
           · P   F   N   R   R   E   A   E   R   Y   L   P   D   M   A   P   H   F ·
4159       ACC GTT TAA CCG GCG GGA GGC TGA ACG CTA CCT GCC TGA TAT GGC ACC CCA CTT
           · P   L   R   N   F   S   V   D   K   T   Q   I   A   G   E   S   L   H ·
4213       CCC ACT GCG GTG GTT TTC GGT GGA TAA AAC GCA AAT CGC CGG TGA AAG TTT GCA
           · L   N   L   Q   Q   R   L   T   R   F   A   A   E   N   A   P   Q   L ·
4267       TCT CAA CCT TCA ACA GCG GCT GAC GCG AAT TGC CGC AGA GAA TGC GCC TCA GTT
           · L   N   E   L   S   D   N   Q   W   L   F   P   L   H   P   W   Q   G ·
4321       ACT CAA CGA ATT AAG TGA CAA CCA ATG GCT GTT CCC GTT GCA CCC GTG GCA GGG
           · E   Y   L   L   Q   Q   G   W   C   Q   A   L   V   A   K   G   L   I ·
4375       GGA ATA TCT TTT GCA GCA GGG GTG GTG CCA GGC ACT TGT TGC TAA AGG GCT GAT
           · K   D   L   S   E   A   G   T   T   S   W   L   P   T   T   S   R   S ·
4429       TAA AGA CTT AGG TGA GGC CGG CAC GTC GTG GCT GCC GAC CAC CTC TTC CCG TTC
           · L   Y   C   A   T   S   R   D   M   I   K   F   S   L   S   V   R   L ·
4483       CCT CTA CTG TGC CAC CAG CCG CGA TAT GAT CAA GTT CTC CCT GAG CGT ACG GCT
           · T   N   S   I   R   T   L   S   V   K   E   V   K   R   G   M   R   L ·
4537       GAC CAA CTC CAT CCG TAC TCT GTC CGT GAA AGA AGT GAA GCG TGG AAT GCG CCT
           · A   R   L   A   Q   T   D   G   W   M   L   Q   V   R   F   P   T ·
4591       GGC ACG CCT GGC TCA AAC CGA CGG CTG GCA GAT GCT ACA GGT CCG CTT CCC GAC
           · F   R   V   M   Q   E   D   G   W   A   G   L   L   D   L   N   G   N ·
4645       TTT CCG GGT AAT GCA GGA GGA TGG CTG GGC CGG GCT GCT CGA TCT AAC GGC AAT
           · I   M   Q   E   S   L   F   A   L   R   E   N   L   L   V   D   Q   P ·
4699       CAT GAT GCA GGA AAG TCT GTT TGC CCT GCG TGA AAA TCT GCT GGT GGA TCA GCC
           · K   S   Q   T   N   V   L   V   S   L   T   Q   A   A   P   D   G   G ·
4753       GAA AAG CCA GAC TAA CGT ACT GGT CTC CCT GAC TCA GGC CGC ACC TGA TGG CGG
           · D   S   L   L   V   S   A   V   K   R   L   S   D   R   L   G   I   T ·
4807       TGA TTC GCT GCT GGT TTC GGC GGT AAA ACG CCT GAG CGA TCG CCT CGG TAT CAC
           · V   Q   A   A   H   Y   W   V   D   A   Y   C   Q   Q   V   L   K ·
4861       TGT GCA ACA GGC CGC CCA TGC ATG GGT TGA TGC ATA CTG TCA GCA AGT GCT AAA
           · P   L   F   T   A   E   A   D   Y   G   L   V   L   L   A   R   Q   Q ·
4915       GCC GCT GTT TAC GGC TGA AGC GGA TTA CGG CCT GGT GCT GGC GCA TCA GCA
           · N   I   L   V   Q   M   L   G   D   L   P   V   G   F   I   Y   R   D ·
4969       AAA TAT TCT TGT CCA GAT GCT TGG GGA TCT GCC GGT CGG ATT TAT TTA CCG TGA
           · C   Q   G   S   A   F   M   P   H   A   T   D   W   L   D   S   I   G ·
5023       CTG TCA GGG CAG CGC TTT TAT GCC TCA CGC GAC AGA CTG GCT CGA TTC TAT TGG
           · E   A   Q   A   E   N   I   F   T   H   E   Q   L   L   R   Y   F   P ·
5077       CGA GGC GCA GGC CGA AAA TAT TTT CAC CCA TGA GCA GTT GCT GCG CTA TTT CCC
           · Y   Y   L   L   V   N   S   T   F   A   V   T   A   A   L   G   A   A ·
```

FIG. 9C

```
        5131  TTA TTA CCT GCT GGT TAA CTC CAC TTT TGC TGT GAC CGC TGC GCT GGG GGC TGC
               ·  G   L   D   S   E   N   L   M   A   R   V   R   A   S   L   A   E  ·
        5185  CGG GCT GGA CAG CGA ATC GAA TCT GAT GGC TCG TGT ACG AGC ATC GCT GGC TGA
               ·  V   R   D   Q   V   T   H   K   T   C   L   N   Y   V   L   E   S   P  ·
        5239  AGT GCG TGA TCA GGT GAC TCA TAA AAC CTG TCT CAA CTA CGT GCT GGA AAG TCC
               ·  Y   W   N   V   K   G   N   F   C   Y   L   N   D   H   N   E   N  ·
        5293  GTA CTG GAA CGT AAA AGG TAA CTT TTT CTG TTA TCT GAA CGA TCA TAA CGA GAA
               ·  T   I   V   D   P   S   V   I   Y   F   D   F   A   N   P   L   Q   A  ·
        5347  CAC CAT TGT TGA CCC TTC GGT GAT CTA TTT CGA TTT CGC TAA CCC GCT GCA GGC
iucB           ·  Q   E   V           M   S   E   A   N   I   I   H   S   R   Y   G   L   R  ·
        5401  TCA GGA GGT CTG AAT GTC TGA GGC AAA CAT TAT TCA CAG CAG ATA TGG ACT GCG
               ·  C   D   K   L   D   K   P   L   N   L   G   W   G   L   D   N   S   A  ·
        5455  CTG TGA TAA ACT CGA CAA GCC CCT GAA TCT TGG CTG GGG ACT GGA CAA TAG CGC
               ·  V   L   H   C   P   G   E   L   P   T   G   W   L   C   D   A   L   D  ·
        5509  GGT GTT GCA CTG TCC CGG GGA GCT GCC GAC AGG GTG GCT GTG CGA TGC GTT GGA
               ·  Q   I   F   I   A   A   P   Q   L   S   A   V   A   L   P   W   A   E  ·
        5563  TCA GAT ATT TAT CGC CGC ACC ACA ACT GTC AGC AGT GGC TCT CCC CTG GGC CGA
               ·  W   R   E   E   F   Q   A   L   T   L   F   G   Q   V   K   S   D   I  ·
        5617  ATG GCG TGA GGA GCC ACA GGC GCT GAC GCT TTT TGG GCA GGT AAA AAG CGA CAT
               ·  I   H   R   T   A   F   W   Q   L   P   L   W   L   S   S   P   A   N  ·
        5671  TAT CCA TCG TAC TGC CTT CTG GCA GTT ACC GTT ATG GTT GAG TTC ACC GGC AAA
               ·  R   A   S   G   E   M   V   F   D   A   E   R   E   I   Y   F   P   Q  ·
        5725  CCG GGC CTC CGG TGA AAT GGT TTT TGA TGC AGA GCG TGA GAT TTA TTT CCC GCA
               ·  R   P   P   R   P   Q   G   E   V   Y   R   R   Y   D   P   R   I   R  ·
        5779  GCG CCC ACC CCG TCA GGG TGA GGT TTA CCG CCG TTA CGA TCC ACG TAT TCG
               ·  R   M   L   S   F   R   I   A   D   P   V   S   D   A   E   R   F   T  ·
        5833  CAG GAT GCT GAG TTT CCG CAT TGC CGA TCC CGT TTC TGA TGC AGA ACG TTT CAC
               ·  R   W   M   N   D   P   R   V   E   Y   F   W   E   Q   S   G   S   L  ·
        5887  CCG CTG GAT GAA TGA TCC GCG CGT TGA GTA TTT CTG GGA GCA AAG TGG CTC ACT
               ·  E   V   Q   T   A   Y   L   E   R   Q   L   T   G   K   H   A   F   P  ·
        5941  GGA GGT ACA GAC CGC CTA TCT GGA GCG CCA GCT CAC CGG TAA ACA TGC ATT CCC
               ·  L   I   G   C   F   D   D   R   P   F   S   Y   F   E   I   Y   W   A  ·
        5995  GCT GAT TGG GTG CTT CGA CGA TCG CCC ATT CAG CTA TTT CGA AAT CTA CTG GGC
               ·  A   E   D   R   I   G   R   H   Y   S   W   Q   P   F   D   R   G   L  ·
        6049  GGC GGA AGA CCG CAT TGG TCG TCA CTA TTC GTG GCA GCC CTT TGA CCG TGG CCT
               ·  H   L   V   G   E   Q   Q   W   R   G   A   H   Y   V   Q   S   W  ·
        6103  GCA TCT GCT GGT TGG TGA ACA GCA ATG GCG CGG GGC CCA CTA TGT GCA AAG CTG
               ·  L   R   G   L   T   H   Y   L   L   D   E   P   R   T   Q   R   T  ·
        6157  GCT GCG CGG GCT GAC ACA TTA CCT GCT GCT GGA TGA GCC CCG TAC GCA GCG CAC
               ·  V   L   E   P   R   T   D   N   Q   R   L   F   R   H   L   P   A  ·
        6211  AGT ACT GGA GCC ACG CGA TAA CCA GCG CCT GTT CCG CCA TCT TGA GCC TGC
               ·  G   Y   R   T   I   K   E   F   D   F   F   K   R   S   R   M   V  ·
        6265  GGG ATA CCG GAC AAT AAA GAG TTT GAA CTT CCC ACA TAA GCG CTC GCG CAT GGT
               ·  M   A   D   R   H   H   F   F   T   E   V   G   L
iucC                                                                    M   N   H   K
        6319  GAT GGC GGA TCG TCA TCA CTT CTT CAC GGA GGT CGG TCT GTA ATG AAT CAC AAG
               D   W   D   F   V   N   R   R   L   V   A   K   M   L   S   E   M   E
        6373  GAC TGG GAT TTT GTT AAC CGT CGG CTG GTG GCA AAA ATG TTG TCT GAG ATG GAG
               Y   E   Q   V   F   H   A   E   S   Q   G   D   D   H   Y   C   I   N
        6427  TAT GAG CAG GTT TTC CAC GCG GAA TCT CAG GGT GAT GAC CAC TAC TGC ATT AAC
               L   P   G   A   Q   W   R   F   I   A   E   R   G   I   W   G   W   L
        6481  CTG CCG GGA GCA CAA TGG CGC TTC ATC GCT GAA CGT GGT ATC TGG GGC TGG CTG
               W   L   D   A   Q   T   L   R   C   T   D   E   P   V   L   A   Q   T
        6535  TGG ATT GAT GCC CAA ACG TTG CGC TGC ACG GAC GAA CCA GTA CTG GCG CAG ACG
               L   L   M   Q   L   K   P   V   L   S   M   S   D   A   T   V   A   E
        6589  CTG CTG ATG CAG CTA AAG CCG GTG CTG TCT ATG AGT GAT GCC ACT GTT GCA GAG
               H   M   Q   D   L   Y   A   T   L   L   G   D   L   Q   L   L   K   A
```

FIG. 9D

```
6643  CAT ATG CAG GAT TTG TAT GCC ACG CTA CTG GGC GAC CTG CAA CTG CTG AAG GCC
       R   R   G   L   S   A   T   D   L   I   N   L   D   A   D   R   L   Q
6697  CGT CGC GGA CTG AGT GCC ACT GAC CTG ATT AAT CTT GAT GCC GAT CGT CTG CAA
       C   L   L   S   G   H   P   K   F   V   F   N   K   G   R   R   G   W
6751  TGC CTG CTG AGC GGT CAT CCT AAA TTC GTT TTT AAT AAA GGT CGC CGT GGC TGG
       G   K   K   A   L   E   Q   Y   A   P   E   Y   T   N   T   F   R   L
6805  GGC AAA AAG GCG CTG GAA CAA TAT GCG CCA GAG TAT ACC AAC ACC TTC AGA CTG
       H   W   L   A   V   K   R   E   H   M   I   W   R   C   D   N   D   L
6859  CAC TGG CTG GCG GTA AAA CGT GAA CAT ATG ATC TGG CGC TGC GAT AAC GAT CTG
       D   I   Q   Q   L   L   T   A   A   M   D   P   Q   E   F   T   R   F
6913  GAT ATT CAG CAG TTG TTG ACT GCC GCA ATG GAT CCG CAG GAG TTT ACA CGC TTC
       S   Q   V   W   Q   E   N   G   L   D   H   N   W   L   P   L   P   V
6967  AGT CAG GTC TGG CAG GAA AAC GGG CTG GAT CAC AAC TGG CTG CCG CTG CCG GTA
       H   P   W   Q   W   Q   Q   K   I   A   T   D   F   I   A   D   F   A
7021  CAT CCG TGG CAG TGG CAG CAA AAA ATC GCC ACA GAC TTC ATC GCT GAT TTT GCC
       E   G   R   M   V   S   L   G   E   F   G   D   Q   W   L   A   Q   Q
7075  GAA GGC AGG ATG GTG TCT CTC GGC GAG TTT GGC GAC CAG TGG CTC GCC CAG CAG
       S   L   R   T   L   T   N   A   S   R   G   G   L   D   I   K   L
7129  TCG CTG CGT ACC CTG ACC AAC GCC AGC CGG CGG GGA GGG CTG GAT ATC AAG CTG
       P   L   T   I   Y   N   T   S   C   Y   R   G   I   P   G   R   Y   I
7183  CCG CTG ACC ATC TAC AAT ACC TCA TGC TAC CGG GGG ATC CCT GGC AGA TAT ATC
       A   A   G   P   L   A   S   R   W   L   Q   Q   V   F   A   T   D   A
7237  GCT GCC GGA CCA CTG GCT TCA CGC TGG CTG CAA CAG GTT TTT GCG ACC GAC GCC
       T   L   V   Q   S   G   A   M   I   L   G   E   P   A   A   G   Y   V
7291  ACC CTG GTG CAA AGC GGC GCA ATG ATC CTT GGT GAA CCG GCT GCA GGC TAT GTG
       S   H   E   G   Y   A   A   L   A   R   A   P   Y   R   Y   Q   K   M
7345  TCC CAT GAA GGC TAT GCC GCG CTT GCC CGG GCT CCC TAT CGC TAC CAG AAA ATG
       L   G   V   I   W   R   E   N   P   C   R   W   L   K   P   D   E   S
7399  CTT GGT GTT ATC TGG CGG GAG AAT CCG TGC CGC TGG CTG AAA CCG GAT GAA AGT
       P   V   L   M   A   T   L   M   E   C   D   E   N   N   Q   P   L   A
7453  CCT GTT CTG ATG GCA ACA CTG ATG GAG TGC GAC GAA AAC AAT CAG CCG CTG GCA
       G   A   Y   I   D   R   S   G   L   D   A   E   T   W   L   T   Q   L
7507  GGC GCA TAT ATC GAC CGC TCC GGA CTG GAC GCT GAA ACC TGG CTT ACG CAA TTG
       F   R   V   V   V   P   L   Y   H   L   L   C   R   Y   G   V   A
7561  TTC CGG GTG GTT GTG GTT CCG CTG TAT CAC CTG CTT TGC CGC TAC GGT GTC GCG
       L   I   A   H   G   Q   N   I   T   L   A   M   K   E   G   V   F   Q
7615  CTT ATT GCA CAC GGA CAA AAT ATA ACG CTC GCC ATG AAA GAG GGG GTA CCA CAG
       R   V   L   K   N   F   Q   G   D   M   R   L   V   K   E   A   F
7669  CGT GTT CTG CTG AAA AAC TTC CAG GGC GAT ATG CGG CTG GTG AAA GAA GCG TTT
       P   E   M   D   S   L   P   Q   E   V   R   D   V   T   S   R   L   S
7723  CCC GAA ATG GAC TCT TTG CCT CAG GAG GTG CGT GAT GTC ACA TCC CGT CTG AGT
       A   D   Y   L   I   H   D   L   Q   T   G   H   F   V   T   V   L   R
7777  GCG GAC TAC TTA ATC CAT GAT TTG CAG ACG GGT CAC TTC GTG ACA GTA CTG CGT
       F   I   S   P   L   M   V   R   L   G   V   P   E   R   R   F   Y   Q
7831  TTT ATT TCG CCA CTG ATG GTT CGT CTT GGC GTA CCT GAA AGG CGA TTT TAT CAA
       L   L   A   A   V   L   S   D   Y   M   N   K   H   P   Q   M   A   E
7885  CTG CTG GCA GCA GTG TTG AGT GAT TAC ATG AAC AAA CAT CCA CAA ATG GCA GAG
       R   F   A   L   F   S   L   F   R   P   Q   I   I   R   V   V   L   N
7939  CGT TTT GCG CTT TTC TCA CTC TTC AGG CCA CAA ATC ATT CGC GTG GTG CTG AAC
       P   V   K   L   T   W   P   D   L   D   G   G   S   R   M   L   P   N
7993  CCG GTA AAA CTG ACC TGG CCG GAC CTG GAT GGC GGC AGT CGC ATG CTG CCG AAT
iucD                                                                          M
       Y   L   E   N   L   Q   N   P   L   W   L   V   T   Q   E   Y   E   S
```

FIG. 9E

```
8047       TAC CTT GAG AAT CTG CAA AAT CCG CTG TGG CTG GTA ACT CAG GAA TAT GAA TCA
             · R   K   S   V   D   F   I   G   V   G   T   G   P   F   N   L   S   I ·
8101  TGA AAA AAA GTG TCG ATT TTA TTG GTG TCG GGA CAG GGC CAT TTA ATC TCA GCA
             · A   A   L   S   H   Q   I   E   E   L   N   C   L   F   F   D   E   H ·
8155       TTG CTG CAT TGT CAC ATC AGA TCG AAG AAC TGA ACT GTC TCT TCT TTG ACG AAC
             · P   H   F   S   W   H   P   G   M   L   V   P   D   C   H   M   Q   T ·
8209       ATC CTC ATT TTT CCT GGC ATC CGG GTA TGC TGG TAC CGG ATT GTC ATA TGC AGA
             · V   F   L   K   D   L   V   S   A   V   A   P   T   N   P   Y   S   F ·
8263       CCG TCT TTC TGA AAG ATC TGG TCA GTG CAG TTG CAC CTA CAA ATC CCT ACA GCT
             · V   N   Y   L   V   K   H   K   K   F   Y   R   F   L   T   S   R   L ·
8317       TTG TTA ACT ATC TGG TGA AGC ACA AAA AGT TCT ATC GCT TCC TTA CAA GCA GGC
             · R   T   V   S   R   E   F   S   D   Y   L   R   W   A   A   E   D ·
8371       TAC GTA CAG TAT CCC GTG AAG AGT TTT CTG ACT ATC CCT GGG CTG CTG AAG
             · M   N   N   L   Y   F   S   H   T   V   E   N   I   D   F   D   K   K ·
8425       ATA TGA ATA ACC TGT ATT TCA GTC ATA CCG TTG AAA ATA TTG ATT CCG ACA AAA
             · S   R   L   F   L   V   Q   T   S   R   G   E   Y   F   A   H   N   I ·
8479       AAA GTC GAT TGT TTC TGG TTC AGA CCA GTC GGG GAG AAT ATT TTG CCC ACA ATA
             · C   L   G   T   S   K   Q   P   Y   L   P   P   C   V   K   H   V   T ·
8533       TCT GCC TTG GTA CAG GAA AAC AAC CTT ATT TAC CAC CCT GTG TGA AGC ATG TGA
             · Q   S   C   F   H   A   S   E   M   N   L   R   R   P   D   L   S   G ·
8587       CAC AAT CCT GTT TCC ATG CCA GTG AAA TGA ATC TTC GTC GGC CGG ACC TGA GTG
             · K   R   I   T   V   V   G   G   Q   S   G   A   D   L   F   L   N ·
8641       GAA AAC GGA TAA CCG TGG TTG GTG GAG CAC AGA GTG GTG CAG ACC TGT TCC TTA
             · A   L   R   G   E   W   G   E   A   A   E   I   N   W   V   S   R   R ·
8695       ATG CAT TAC GCG GGG AAT GGG GAG AAG CGG CGG AAA TAA ACT GGG TCT CAC GGC
             · N   N   F   N   A   L   D   E   A   A   F   A   D   E   Y   F   T   P ·
8749       GTA ATA ATT TTA ACG CAC TGG ATG AGG CTG CTT CTG ATG AGT ATT TTA CAC
             · E   Y   I   S   G   F   S   G   L   K   E   D   I   R   H   Q   L   L ·
8803       CTG AAT ATA TTT CAG GCT TCT CCG GAC TGA AGG AAG ATA TTC GCC ATC AGT TAC
             · D   E   Q   K   N   T   S   D   G   I   T   A   D   S   L   L   T   I ·
8857       TGG ATG AGC AGA AAA TGA CAT CGG ATG GCA TCA CTG CCG ATT CTT TAC TGA CCA
             · Y   R   E   L   Y   H   R   F   E   V   L   R   K   P   R   N   I   R ·
8911       TTT ATC GTG AGT TGT ACC ACC GTT TTG AAG TTC TGA GAA AAC CAA GAA ATA TCC
             · L   L   P   S   R   S   V   T   T   L   E   S   S   G   P   G   W   R ·
8965       GTC TGC TAC CCA GTC GTC GCT GGA TAA CAA CTC TGG AAA GTA GTG GTC CGG GCT GGA
             · L   L   M   E   H   H   L   D   Q   G   R   E   S   L   E   S   D   V ·
9019       GGT TAT TGA TGC AAC ATC ATC TGG ATC ACG GCA GAG AGA GCC TGG AAA GTG ATG
             · V   I   F   A   T   G   Y   R   S   A   L   P   Q   I   L   P   S   L ·
9073       TGG TGA TTT TCG CCA CAG GTT ACC GTT CTG CAT TGC CAC AAA TAC TTC CCT CAC
             · M   P   L   I   T   M   H   D   K   N   T   F   K   V   R   D   D   F ·
9127       TGA TGC CCT TGA TCA CCA TGC ACG ATA AGA ACA CCT TTA AAG TGC GTG ATG ACT
             · T   L   E   W   S   G   P   K   E   N   N   I   P   A   V   N   A   S ·
9181       TCA CTC TGG AAT GGA GTG GCC GGA AAG AAA ATA ACA TCT TTG CGG TCA ACG CCA
             · N   Q   T   H   G   I   A   E   P   Q   L   S   L   H   A   W   R   S ·
9235       GCA TGC AAA CTC ATG GCA TCG CCG AAC CCC AGC TCA GCC TGA TGG CCT GGC GAT
             · A   R   I   L   N   R   V   L   G   R   D   L   F   D   L   S   M   P ·
9289       CTG CAC GTA TTC TTA ATC GCG TAC TGG GCG TGA TTA TCG ATC TCA GTA TGC
             · P   A   L   I   Q   W   R   S   G   S   R   K   K   P   Q   P   E   A ·
iutA                                                                · V   A   Q   R   Q   P   E   K   T   T   A   G   G ·
9343       CGC CCG CAC TGA TTC AGT GGC GCA GCG GCA GCC GGA AAA ACA CAC AGC CGG AGG
             · A   S   L   T   H   Y   T   A   N   I   Q   E
             · C   F   F   N   S   L   Y   S   K   Y   S   G   I   T   M   M   R   K ·
9397       CTG CTT CTT TAA CTC ACT ATA CAG CAA ATA TTC AGG AAT AAC GAT GAT GCG CAA
             · K   Y   M   P   R   A   L   G   P   L   L   L   V   V   L   S   P   A ·
9451       AAA GTA TAT GCC CCG GGC TCT TGG TCC GCT GCT TCT TGT CGT GCT GTC ACC AGC
             · V   A   Q   Q   N   D   N   E   I   V   S   A   S   R   S   N ·
9505       TGT GGC CCA GCA AAA CGA TGA TAA TGA GAT CGT AGT GTC TGC AGC CGC AGC AA
             · R   T   V   A   E   M   A   Q   T   T   W   V   I   E   N   A   E   L ·
```

FIG. 9F

```
9559   TCG AAC TGT AGC GGA GAT GGC GCA AAC CAC CTG GGT TAT CGA AAA TGC CGA ACT
       · E   Q   Q   L   Q   G   G   K   E   L   K   D   A   L   A   Q   L   I ·
9613   GGA GCA GCA GAT TCA GGG CGG TAA AGA GCT GAA AGA CGC ACT GGC TCA GTT AAT
       · P   G   L   D   V   S   S   Q   S   R   T   N   Y   G   M   N   M   R ·
9667   CCC CGG CCT TGA TGT CAG CAG CCA GAG TCG AAC CAA CTA CGG TAT GAA CAT GCG
       · G   R   P   L   V   V   L   I   D   G   V   R   L   N   S   S   R   S ·
9721   TGG CCG CCC GCT GGT TGT CCT GAT TGA CGG TGT GCG CCT CAA CTC TTC ACG TTC
       · D   S   R   Q   L   D   S   V   D   P   F   N   I   D   H   F   E   V ·
9775   CGA CAG CCG ACA ACT GGA CTC TGT CGA TCC TTT TAA TAT CGA CCA TAT TGA AGT
       · I   S   G   A   T   L   Y   G   G   S   T   G   L   I   N ·
9829   GAT CTC CGG CGC GAC GGC CCT GTA CGG TGG CGG GAG TAC CGG AGG GTT GAT CAA
       · I   V   T   K   G   Q   P   E   T   M   M   E   F   E   A   G   T ·
9883   CAT CGT GAC CAA AAA AGG TCA GCC GGA AAC CAT GAT GGA GTT TGA GGC TGG CAC
       · K   S   G   F   N   S   S   K   D   H   D   E   R   I   A   G   A   V ·
9937   AAA AAG TGG CTT TAA CAG CAG TAA AGA TCA CGA TGA GCG CAT TGC CGG TGC TGT
       · S   G   G   N   D   H   I   S   G   R   L   S   V   A   Y   Q   K   F ·
9991   CTC CGG CGG AAA TGA CCA TAT CTC CGG ACG TCT TTC CGT GGC ATA TCA GAA ATT
       · G   W   F   D   G   N   G   D   A   T   L   L   D   N   T   Q   T ·
10045  TGG CGG CTG GTT TGA CGG TAA CGG CGA TGC CAC CCT GCT TGA TAA CAC CCA GAC
       · G   L   Q   H   S   N   R   L   D   I   M   G   T   G   T   L   N   I ·
10099  CGG CCT GCA GCA CTC CAA TCG GCT GGA CAT CAT GGG AAC CGG TAC GCT GAA CAT
       · D   E   S   R   Q   L   Q   L   I   T   Q   Y   Y   K   S   Q   G   D ·
10153  CGA TGA ATC CCG GCA GCT TCA ACT GAT TAC GCA GTA CTA TAA AAG TCA GGG AGA
       · D   N   Y   G   L   N   L   G   K   G   F   S   A   I   S   G   S ·
10207  CGA CAA TTA CGG GCT TAA TCT CGG GAA AGG CTT TTC CGC CAT CAG CGG GAG CAG
       · T   P   Y   V   S   K   G   L   N   S   D   R   I   P   G   T   E   R ·
10261  CAC ACC ATA CGT CAG TAA GGG GCT GAA TTC TGA CCG CAT TCC CGG CAC TGA GCG
       · H   L   I   S   L   Q   Y   S   D   F   L   G   Q   E   L   V ·
10315  GCA TTT GAT CAG CCT GCA GTA CTC TGA CAG TGA TTT CCT GGG ACA GGA ACT GGT
       · G   Q   V   Y   R   D   E   S   L   R   Y   Y   P   F   P   T   V ·
10369  CGG TCA GGT TTA CTA CCG CGA TGA GTC GTT GCG GTA CTA CCC GTT CCC GAC GGT
       · N   A   N   K   Q   A   T   F   S   S   Q   Q   D   T   D   Q ·
10423  AAA TGC GAA TAA ACA GGC GAC GGC TTT CTC CTC GTC ACA GCA GGA TAC CGA CCA
       · Y   G   M   K   L   T   L   N   G   F   L   M   D   G   W   Q   I   T ·
10477  GTA CGG CAT GAA ACT GAC TCT GAA CAG CCA ACT GAT GGA CGG CTG GCA AAT CAC
       · W   G   L   D   A   E   H   E   R   F   T   S   N   Q   M   F   F   D ·
10531  CTG GGG GCT GGA TGC TGA GCA TGA GCG CTT TAC CTC AAC CAA GAT GTT CTT CGA
       · L   A   Q   A   S   A   S   G   G   L   N   N   H   K   I   Y   T   T ·
10585  TCT GGC TCA GGC AAG TGC TTC CGG AGG GCT AAC AAC CAC TAA GAT TTA CAC CAC
       · G   R   Y   P   S   Y   D   I   T   N   L   A   F   L   Q   S   S ·
10639  CGG GCG CTA TCC GTC ATA TGA CAT CAC CAA TCT GGC GGC TTT CCT GCA ATC CAG
       · Y   D   I   N   D   I   F   T   V   S   G   V   R   Y   Q   Y   T ·
10693  CTA TGA CAT TAA TGA TAT TTT TAC CGT TAG CGG TGG CGT ACG CTA TCA GTA TAC
       · E   N   R   V   D   D   F   I   D   Y   T   Q   Q   K   I   A   A ·
10747  TGA GAA CAG GGT AGA TGA TTT CAT CGA CTA CAC GCA GCA ACA GAA GAT TGC TGC
       · G   K   A   I   S   A   D   A   I   P   G   Q   S   V   D   Y   D   N ·
```

FIG. 9G

```
10803   CGG GAA GGC GAT ATC TGC CGA CGC CAT TCC TGG TGG TTC GGT AGA TTA CGA TAA
        · F   L   F   N   A   G   L   L   M   H   I   T   E   R   Q   A   L ·
10855   CTT TCT GTT CAA TGC TGG TCT GCT GAT GCA CAT CAC CGA ACG TCA GCA GGC ATT
        · F   N   F   S   Q   G   V   A   L   P   D   P   G   K   Y   Y   G   R ·
10909   GTT CAA TTT TTC CCA GGG CGT GGC ATT GCC GGA TCC GGG GAA ATA TTA TGG TCG
        · G   I   Y   G   A   A   V   N   G   H   L   P   L   T   K   S   V   N ·
10963   CGG CAT CTA TGG TGC AGC AGT GAA CGG CCA TCT TCC CCT GAC AAA GAG CGT GAA
        · V   S   D   S   F   L   E   G   V   K   V   D   S   Y   E   L   G   W ·
11017   CGT CAG CGA CAG TAA GCT GGA AGG CGT GAA AGT CGA TTC TTA TGA ACT GGG CTG
        · R   F   I   G   D   H   L   R   T   Q   I   A   A   Y   Y   S   L   S ·
11071   GCG CTT TAT CGG TGA CAA CCT GCG GAC TCA AAT CGC GGC ATA TTA CTC GCT TTC
        · N   K   S   V   E   R   N   K   D   L   T   I   S   V   K   D   D   R ·
11125   CAA TAA GAG CGT GGA AAG GAA TAA AGA TCT GAC CAT CAG TGT GAA GGA CGA CAG
        · R   R   I   Y   G   V   E   G   A   V   D   Y   L   I   P   D   T   D ·
11179   GCG CCG TAT TTA CGG CGT GGA AGG TGC GGT GGA CTA CCT GAT CCC GGA TAC TGA
        · W   S   T   G   V   N   F   N   V   L   K   T   E   S   K   V   N   G ·
11233   CTG GAG TAC CGG TGT GAA CTT CAA TGT GCT GAA AAC GGA GTC GAA AGT GAA CGG
        · Q   W   Q   K   Y   D   V   K   E   S   S   P   S   K   A   T   A   Y ·
11287   TCA ATG GCA AAA ATA TGA CGT GAA GGA ATC AAG TCC ATC GAA AGC GAC AGC TTA
        · I   N   W   A   P   E   P   W   S   L   R   V   Q   S   T   S   F ·
11341   CAT TAA CTG GGC GCC GGA ACC GTG GAG TCT GCG TGT ACA GAG CAC CAG TTC TTT
        · D   V   S   D   A   E   G   N   D   I   N   G   Y   T   T   V   D   F ·
11395   CGA CGT AAG CGA TGC AGA GGG TAA CGA TAT TAA TGG TTA CAC TAC CGT CGA TTT
        · I   S   S   W   Q   L   P   V   G   T   L   S   F   S   V   E   N   L ·
11449   TAT CAG TAG TTG GCA GCT TCC GGT GGG AAC ACT CAG CTT CAG CGT TGA GAA CCT
        · P   G   Y   G   P   A   S   L   Y   D   K   G   R   G   R   T   F ·
11503   CTT CGA CCG TGA CTA TAC CAC TGT CTG GGG ACA GCG TGC ACC TCT GTA CTA CAG
        · G   L   N   Y   S   V   L   F   * ·
11557   CCC GGG TTA CGG CCC TGC TTC ACT GTA CGA CTA CAA AGG CCG GGG CCG AAC CTT
11611   TGG TCT GAA CTA CTC AGT GCT GTT CTG A
```

FIG. 9H

Sequence Range: 1 to 999

```
             10           20          30          40          50
 ATG AAT ATA ACA ACT CTG ACT AAT AGT ATT TCC ACC TCA TCA TTC AGT CCA AAC
 TAC TTA TAT TGT TGA GAC TGA TTA TCA TAA AGG TGG AGT AGT AAG TCA GGT TTG
  M   N   I   T   T   L   T   N   S   I   S   T   S   S   F   S   P   N>

60           70          80          90         100
 AAT ACC AAC GGT TCA TCA ACC GAA ACA GTT AAT TCT GAT ATA AAA ACA ACG ACC
 TTA TGG TTG CCA AGT AGT TGG CTT TGT CAA TTA AGA CTA TAT TTT TGT TGC TGG
  N   T   N   G   S   S   T   E   T   V   N   S   D   I   K   T   T   T>

110         120          130         140         150         160
 AGT TCT CAT CCT GTA AGT TCC CTT ACT ATG CTC AAC GAC ACC CTT CAT AAT ATC
 TCA AGA GTA GGA CAT TCA AGG GAA TGA TAC GAG TTG CTG TGG GAA GTA TTA TAG
  S   S   H   P   V   S   S   L   T   M   L   N   D   T   L   H   N   I>

170          180         190         200         210
 AGA ACA ACA AAT CAG GCA TTA AAG AAA GAG CTT TCA CAA AAA ACG TTG ACT AAA
 TCT TGT TGT TTA GTC CGT AAT TTC TTT CTC GAA AGT GTT TTT TGC AAC TGA TTT
  R   T   T   N   Q   A   L   K   K   E   L   S   Q   K   T   L   T   K>

220         230          240         250         260         270
 ACA TCG CTA GAA GAA ATA GCA TTA CAT TCA TCT CAG ATT AGC ATG GAT GTA AAT
 TGT AGC GAT CTT CTT TAT CGT AAT GTA AGT AGA GTC TAA TCG TAC CTA CAT TTA
  T   S   L   E   E   I   A   L   H   S   S   Q   I   S   M   D   V   N>

280          290         300         310         320
 AAA TCC GCT CAA CTA TTG GAT ATT CTT TCC AGG AAC GAA TAT CCA ATT AAT AAA
 TTT AGG CGA GTT GAT AAC CTA TAA GAA AGG TCC TTG CTT ATA GGT TAA TTA TTT
  K   S   A   Q   L   L   D   I   L   S   R   N   E   Y   P   I   N   K>

330          340         350         360         370
 GAC GCA AGA GAA TTA TTA CAT TCA GCC CCG AAA GAA GCC GAG CTT GAT GGA GAT
 CTG CGT TCT CTT AAT AAT GTA AGT CGG GGC TTT CTT CGG CTC GAA CTA CCT CTA
  D   A   R   E   L   L   H   S   A   P   K   E   A   E   L   D   G   D>

380         390          400         410         420         430
 CAA ATG ATA TCT CAT AGA GAA CTG TGG GCT AAA ATT GCA AAC TCC ATC AAT GAT
 GTT TAC TAT AGA GTA TCT CTT GAC ACC CGA TTT TAA CGT TTG AGG TAG TTA CTA
  Q   M   I   S   H   R   E   L   W   A   K   I   A   N   S   I   N   D>

440          450         460         470         480
 ATT AAT GAA CAG TAT CTG AAA GTA TAT GAA CAT GCC GTT AGT TCA TAT ACT CAA
 TAA TTA CTT GTC ATA GAC TTT CAT ATA CTT GTA CGG CAA TCA AGT ATA TGA GTT
  I   N   E   Q   Y   L   K   V   Y   E   H   A   V   S   S   Y   T   Q>

490         500          510         520         530         540
 ATG TAT CAA GAT TTT AGC GCT GTT CTT TCC AGT CTT GCC GGC TGG ATC TCT CCC
 TAC ATA GTT CTA AAA TCG CGA CAA GAA AGG TCA GAA CGG CCG ACC TAG AGA GGG
  M   Y   Q   D   F   S   A   V   L   S   S   L   A   G   W   I   S   P>
```

FIG. 11A

```
             550           560           570           580           590
GGA GGT AAC GAC GGA AAC TCC GTG AAA TTA CAA GTC AAC TCG CTT AAA AAG GCA
CCT CCA TTG CTG CCT TTG AGG CAC TTT AAT GTT CAG TTG AGC GAA TTT TTC CGT
 G   G   N   D   G   N   S   V   K   L   Q   V   N   S   L   K   K   A>

600           610           620           630           640
TTG GAA GAA CTC AAG GAA AAA TAT AAA GAT AAA CCG CTA TAT CCA GCA AAT AAT
AAC CTT CTT GAG TTC CTT TTT ATA TTT CTA TTT GGC GAT ATA GGT CGT TTA TTA
 L   E   E   L   K   E   K   Y   K   D   K   P   L   Y   P   A   N   N>

650           660           670           680           690           700
ACT GTT AGT CAG GAA CAA GCA AAT AAA TGG CTT ACA GAA TTA GGT GGA ACA ATC
TGA CAA TCA GTC CTT GTT CGT TTA TTT ACC GAA TGT CTT AAT CCA CCT TGT TAG
 T   V   S   Q   E   Q   A   N   K   W   L   T   E   L   G   G   T   I>

710           720           730           740           750
GGC AAG GTA TCT CAA AAA AAC GGG GGA TAT GTT GTC AGT ATA AAC ATG ACC CCA
CCG TTC CAT AGA GTT TTT TTG CCC CCT ATA CAA CAG TCA TAT TTG TAC TGG GGT
 G   K   V   S   Q   K   N   G   G   Y   V   V   S   I   N   M   T   P>

760           770           780           790           800           810
ATA GAC AAT ATG TTA AAA AGC TTA GAT AAT CTA GGT GGA AAT GGC GAG GTT GTG
TAT CTG TTA TAC AAT TTT TCG AAT CTA TTA GAT CCA CCT TTA CCG CTC CAA CAC
 I   D   N   M   L   K   S   L   D   N   L   G   G   N   G   E   V   V>

820           830           840           850           860
CTA GAT AAT GCA AAA TAT CAG GCA TGG AAT GCC GGA TTC TCT GCC GAA GAT GAA
GAT CTA TTA CGT TTT ATA GTC CGT ACC TTA CGG CCT AAG AGA CGG CTT CTA CTT
 L   D   N   A   K   Y   Q   A   W   N   A   G   F   S   A   E   D   E>

870           880           890           900           910
ACA ATG AAA AAT AAT CTT CAA ACT TTA GTT CAA AAA TAC AGT AAT GCC AAT AGT
TGT TAC TTT TTA TTA GAA GTT TGA AAT CAA GTT TTT ATG TCA TTA CGG TTA TCA
 T   M   K   N   N   L   Q   T   L   V   Q   K   Y   S   N   A   N   S>

920           930           940           950           960           970
ATT TTT GAT AAT TTA GTA AAG GTT TTG AGT AGT ACA ATA AGC TCA TGT ACA GAT
TAA AAA CTA TTA AAT CAT TTC CAA AAC TCA TCA TGT TAT TCG AGT ACA TGT CTA
 I   F   D   N   L   V   K   V   L   S   S   T   I   S   S   C   T   D>

980           990
ACA GAT AAA CTT TTT CTC CAT TTC TGA
TGT CTA TTT GAA AAA GAG GTA AAG ACT
 T   D   K   L   F   L   H   F   *>
```

```
1567  GGG TGA TTA TTC CGC AGG CCT TCA GTC AGG CGC TTC AGG ACG GCA TGA GCG TCC
      ·  L   Y   I   H   L   A   G   S   Q   G   R   Q   D   D   Q   R   I   G ·
1621  CGC TCT ATA TTC ATC TCG CCG GTA GCC AGG GTC GCC AGG ACG ATC AGC GAA TCG
      ·  S   A   F   I   W   L   D   D   G   Q   L   R   I   K   I   Q   L   ·
1675  GCA GCC CTT TTA TCT GGT TGG ATG ATG GAC AGC TAC GCA TCC GGA AAA TAC AGC
      ·  E   E   S   E   D   N   A   S   V   S   E   Q   T   R   G   Q   L   M ·
1729  TGG AAG AGA GTG AAG ATA ACG CCA GTG TCA GCG AAC AAA CTC GAC AGC AGC TGA
      ·  A   L   A   N   A   P   F   N   E   A   L   T   I   P   L   T   D   N ·
1783  TGG CTC TGG CGA ACG CCC CGT TCA ATG AGG CCC TTA CCA TCC CCC TGA CTG ACA
      ·  A   Q   L   D   L   S   L   R   Q   L   L   L   Q   L   V   V   K   R ·
1837  ACG CGC AGC TGG ATC TCA GCT TGC GCC AAC TGC TGC TGC AGC TGG TGG TCA AGC
      ·  E   A   L   G   T   V   L   R   S   R   S   E   D   I   G   G   Q   S ·
1891  GCG AAG CGC TGG CCA CTC TAC TAC GCT CAC GTA GCG AAG ACA TCG GGC AGT CCA
      ·  V   N   T   L   S   S   N   L   S   Y   N   F   G   I   Y   N   N   Q ·
1945  GTG TTA ACA CCC TCA GCA GTA ATC TGA GCT ATA ACT TCG GCA TCT ATA ACA ACC
      ·  L   R   N   G   G   S   N   T   S   S   Y   L   S   L   N   N   V   T ·
1999  AGT TGC GTA ACG GCG GGA GCA ACA CAT CCA GCT ATC TGT CGC TGA ATA ACG TTA
      ·  A   L   R   E   H   H   V   L   D   G   S   L   Y   G   I   G   S   ·
2053  CTG CAC TGC GCG AAC ATC ATG TGG TGC TGC ACG GCT CGC TGT ACC GGA TCG GTA
      ·  G   Q   Q   D   S   E   L   Y   K   A   M   Y   E   R   D   F   A   G ·
2107  GCG GTC AAC AGG ACA GTG AAT TAT ATA AAG CGA TGT ATG AAC GCG ATT TTG CCG
      ·  H   R   F   A   G   G   T   L   D   T   W   N   L   Q   S   L   G   P ·
2161  GTC ACC GAT TTG CCG GTG GAA CGC TCG ACA CCT GGA ACT TGC AGT CCT TAG GGC
      ·  M   T   A   I   S   A   G   K   I   Y   G   L   S   W   G   N   Q   A ·
2215  CGA TGA CCG CCA TTT CAG CAG GGA AGA TTT ACG GCC TTT CCT GGG GAA ACC AGG
      ·  S   T   I   F   D   S   S   Q   S   A   T   P   V   I   A   F   L   ·
2269  CCA GCT CCA CCA TCT TCG ACA GCA GCC AGT CAG CCA CGC CAG TGA TCG CCT TTT
      ·  P   A   A   G   E   V   H   L   T   R   D   G   R   L   L   S   V   Q ·
2323  TAC GCG CGG GTG AAG TAC ATC TCA CCC GTG ATC GGC GGT TAC TAA GCG TTC
      ·  N   F   T   M   G   N   H   E   V   D   T   R   G   L   P   Y   G   I ·
2377  AGA ACT TCA CCA TGG GCA ATC ATC AAG TGG ATA CCC GGG GTC TAC CAT ACG GTA
      ·  Y   D   V   E   V   E   V   I   V   N   G   R   V   I   S   K   R   T ·
2431  TTT ACG ATG TGG AAG TTG AGG TGA TCG TTA ACG GTC GCG TGA TCA GCA AAC GCA
      ·  Q   R   V   N   K   L   F   S   R   G   R   G   V   G   A   P   L   A ·
2485  CCC AGC GGG TCA ATA AGC TGT TTA GCC GGG GGC GCG GCG TCG GTG CAC CAC TGG
      ·  N   Q   V   W   G   G   S   F   H   M   D   R   W   S   E   N   G   K ·
2539  CGT GGC AGG TAT GGG GCG GTA GCT TTC ATA TGG ATC GCT GGT CGG AAA ACG GGA
      ·  K   T   R   P   A   K   E   S   W   L   A   G   A   S   T   S   G   S ·
2593  AAA AGA CGC GAC CAG CTA AAG AGA GTT GGC TGG CAG GTG CCT GGA CCT CCG GCT
      ·  L   S   T   L   S   W   A   A   T   G   Y   G   Y   D   N   Q   A   V ·
2647  CAC TGA GTA CGC TTA GCT GGG CGG CAA CGG GAT ATG GAT ACG ATA ATC AGG CGG
      ·  G   E   T   R   L   T   L   P   L   G   G   A   I   N   V   N   L   Q ·
2701  TGG GTG AAA CCC GTC TGA CGC TGC CGC TTG GGG GAG CGA TCA ACG TTA ACC TGC
      ·  N   M   L   A   S   D   S   S   W   S   S   I   G   S   I   S   A   T ·
2755  AAA ATA TGC TGG CCA GTG ACA GCT CAT GGA GCA GCA TCG GCA GCA TCA GCG CCA
      ·  L   P   G   G   F   S   S   L   W   V   N   Q   E   K   T   R   I   G ·
2809  CTC TAC GGG GAG GCT TTA GTT CGC TGT GGG TTA ATC AGG AAA AAA CCC GCA TTG
      ·  N   Q   L   R   S   D   A   D   N   R   A   I   G   G   T   L   N ·
2863  GCA ATC AAT TGC GAC GTA GCG ATG CCG ACA ACC GTG CTA TCG GCG GCA CAC TCA
      ·  L   N   S   L   W   S   K   L   G   T   F   S   I   S   Y   N   D   D ·
2917  ACC TGA ACT CAC TGT GGT CGA AGC TGG GCA CAT TCA GCA TCA GCT ACA ATG ATG
      ·  R   R   Y   N   S   H   Y   Y   T   A   D   Y   Y   Q   N   V   Y   S ·
2971  ACC GCC GTT ACA ACA GCC ATT ATT ACA CGG CAG ATT ACT ATC AAA ATG TCT ACA
      ·  G   T   F   G   S   L   G   L   R   A   G   I   Q   R   Y   N   N   G ·
3025  GCG GTA CCT TTG GTT CGC TTG GCC TGC GGG CCG GTA TTC AGC GCT ATA ACA ACG
      ·  D   S   N   A   H   T   G   K   Y   I   A   L   D   L   S   L   P   L ·
```

FIG. 14B

```
3079  GCG ACA GCA ACG CCA ATA CAG GGA AAT ATA TCG CTC TCG ATC TCT CGC TAC CAC
       · G   N   W   F   S   A   G   M   T   H   Q   N   G   Y   T   M   A   N ·
3133  TGG GCA ACT GGT TTA GCG CAG GGA TGA CTC ATC AAA ACG GCT ACA CCA TGG CAA
       · L   S   A   R   K   Q   F   D   E   G   T   I   R   T   V   G   A   N ·
3187  ACC TGT CAG CAC GCA AGC AGT TTG ATG AAG GGA CCA TTC GCA CTG TTG GTG CCA
       · L   S   R   A   I   S   G   D   T   Q   D   D   K   T   L   S   G   G ·
3241  ATC TGT CAC GAG CCA TCT CCG GCG ATA CCG GTG ATG ACA AAA CTC ACA GTG GTG
       · A   Y   A   Q   F   D   A   R   Y   A   S   G   T   L   N   V   N   S ·
3295  GGG CGT ATG CAC AGT TCG ACG CTC GCT ACG CCA GCA GCG GAA CGC TGA ACG TCA ATA
       · A   A   D   G   Y   V   N   T   N   L   T   A   N   G   S   V   G   W ·
3349  GCG CGG CGG ACG GCT ACG TCA ATA CCA ATT AAC CCG CCA ATG GCA GCG TCG GCT
       · Q   G   K   N   I   A   A   S   G   R   T   D   G   N   A   G   V   I ·
3403  CGC ACG GTA AAA ACA TTG CTG CCA GCG GGC GGA CTG ATG GCA ACG CTG GGG TGA
       · F   N   T   G   L   E   D   D   G   Q   I   S   A   K   I   N   G   E ·
3457  TAT TCA ACA CCG GGC TGG AGG ACG ACG GTC AGA TCA GCG CCA AAA TCA ACG GGC
       · I   F   P   L   N   G   K   R   N   Y   L   P   L   S   P   Y   G   R ·
3511  GGA TTT TCC CGC TTA ACG GCA AGC GTA ACT ATC TCC CGC TCT CTC CCT ATG GAA
       · Y   E   V   E   L   Q   N   S   K   N   S   L   D   S   Y   D   I   V ·
3565  GAT ATG AGG TGG AGT TAC AGA ACA GCA AAA ACT CAC TCG ACA GTT ACG ATA TCG
       · S   G   R   K   S   H   L   T   L   Y   P   G   N   V   A   V   I   E ·
3619  TCA GCG GTC GCA AAA GTC ATC TGA CTC TCT ATC CAG GCA ATG TCG CTG TCA TTG
       · P   E   V   K   Q   M   V   T   V   S   G   R   I   R   A   E   D   G ·
3673  AGC CAG AGG TGA AGC AGA TGG TTA CCG TCT CCG GTC GTA TCC GTG CGG AAG ACG
       · T   L   L   A   N   A   R   I   N   N   H   T   G   R   T   R   T   D ·
3727  GCA CAC TGC TGG CTA ACG CAC GGA TTA ACA ACC ATA TCG GCC GAA CCC GAA CCG
       · E   N   G   E   F   V   M   D   V   D   K   K   Y   F   T   I   D   F ·
3781  ATG AAA ACG GCG AGT TTG TCA TGG ACG TGG ATA AGA AAT ACC CCA CTA TCG ATT
       · R   Y   S   G   N   K   T   C   E   V   A   L   E   L   N   Q   A   R ·
3835  TTC GCT ACA GTG GCA ATA AAA CCT GCG AAG TGG CAC TGG AAC TCA ACC AGG CGC
       · G   A   V   N   V   G   D   V   V   C   S   G   L   S   S   W   A   A ·
3889  GCG GTG CCG TCT GGG TGG GTG ATG TGG TCT GCA GCG GCC TCT CAT CGT GGG CGG
       · V   T   Q   T   G   E   F   N   S   *
yagN                                              M   R   V   N   L   L   I   A   M   I
3943  CGG TGA CGC AGA CAG GAG AAG AGA ATG AGA GTT AAC CTA CTG ATA GCG ATG ATA
       I   F   A   L   I   W   P   V   T   A   L   R   A   A   V   S   K   T
3997  ATC TTT GCG CCG CTA ATC TGG CCA GTA ACT GCG CTC GCA GCG GTG AGC AAA ACA
       T   W   A   D   A   P   A   R   E   F   V   F   V   E   N   N   S   D
4051  ACC TGG GCG GAT GCA CCG GCA CGC GAG TTT GTG TTT GTC GAA AAC AAC TCA GAC
       D   N   F   F   V   T   P   G   A   L   D   P   R   L   T   G   A
4105  GAC AAC TTT TTC GTC ACT CCT GGC GGG GCG CTG GAT CCG CGC CTG ACC GGT GCC
       N   R   W   T   G   L   K   Y   I   D   G   Y   N   T   G   L   Y   T   N   W   K   F
4159  AAC CGC TGG ACC GGT TTA AAA TAC AAT GGT TCA GGA ACC ATC TAT CAG CAA AGC
       L   G   Y   I   D   N   G   Y   N   T   G   L   Y   T   N   W   K   F
4213  CTC GGC TAC ATT GAT AAC GGT TAC AAC ACC GGC CTT TAT ACC AAC TGG AAG TTT
       D   M   W   L   E   N   S   P   V   S   S   P   L   T   G   L   R   C
4267  GAT ATG TGG CTG GAA AAT TCA CCA GTT TCA TCT CCT TTA ACT GGC TTG CGC TGC
       I   N   W   Y   A   G   C   N   M   T   T   S   L   I   L   P   Q   T
4321  ATC AAC TGG TAC GCT GCG TGT AAT ATG ACC ACC AGT CTT ATC CTG CCG CAA ACC
       T   D   T   S   G   F   Y   G   A   T   V   T   S   G   G   A   K   W
4375  ACC GAC ACC AGT GGA TTT TAT GGC GCA ACC GTC AGC GGC GGC GCG AAG TGG
       M   H   G   M   L   S   D   A   F   Y   Q   Y   L   Q   Q   M   P   V
4429  ATG CAC GGC ATG TTG TCA GAC GCG TTT TAC CAG TAT CTG CAA CAA ATG CCC GTC
       G   S   S   F   T   M   T   I   N   A   C   Q   T   S   V   N   Y   D
4483  GGC AGC AGC TTT ACA ATG ACC ATC AAT GCC TGC CAG ACC TCT GTG AAC TAT GAC
       A   S   S   G   A   R   C   K   D   Q   A   S   G   N   W   Y   V   R
```

FIG. 14C

```
4537  GCC AGC AGC GGC GCA CGC TGT AAG GAT CAG GCC TCC GGC AAC TGG TAT GTT CGC
       N   V   T   H   T   K   A   A   N   L   R   L   I   N   T   H   S   L
4591  AAC GTC ACC CAT ACG AAA GCA GCA AAT CTA CGG TTG ATA AAT ACC CAC TCG CTG
       A   E   V   F   I   N   S   D   G   V   P   T   L   G   E   G   N   A
4645  GCG GAA GTA TTT ATC AAC AGC GAC GGA GTA CCG ACT CTG GGC GAA GGG AAC GCC
       D   C   R   T   Q   T   I   G   S   R   S   G   L   S   C   K   M   V
4699  GAC TGC CGG ACG CAA ACC ATC GGC AGC CGT TCA GGA TTA AGT TGT AAG ATG GTT
       N   Y   T   L   Q   T   N   G   L   S   N   T   S   I   H   I   F   P
4753  AAC TAT ACC CTG CAA ACA AAC GGA CTC AGC AAC ACC TCA ATC CAT ATA TTC CCG
       A   I   A   N   S   S   L   A   S   A   V   G   A   Y   D   M   Q   F
4807  GCG ATC GCC AAC TCG TCG TTA GCC TCG GCC GTC GGG GCG TAC GAT ATG CAG TTC
       S   L   N   G   S   S   W   K   P   V   S   N   T   A   Y   Y   Y   T
4861  AGT CTG AAT GGC AGT TCA TGG AAA CCG GTG AGC AAT ACT GCC TAT TAC TAC ACC
       F   N   E   M   K   S   A   D   S   I   Y   V   F   F   S   S   N   F
4915  TTC AAC GAG ATG AAG AGC GCA GAC TCG ATC TAT GTT TTC TTC TCG AGC AAC TTC
       F   K   Q   M   V   N   Q   G   I   S   D   I   N   T   K   D   L   F
4969  TTT AAG CAG ATG GTG AAC CAG GGA ATC AGC GAT ATC AAC ACC AAA GAT CTA TTC
       N   F   R   F   Q   N   T   T   S   P   E   S   G   W   Y   E   F   S
5023  AAC TTT CGC TTT CAG AAC ACC ACA TCA CCG GAG TCT GGC TGG TAT GAA TTT TCT
       T   S   N   T   L   I   I   K   P   R   D   F   S   I   S   I   I   S
5077  ACC TCC AAC ACG CTG ATT ATC AAA CCC CGT GAT TTC AGC ATC AGT ATT ATC TCC
       D   E   Y   T   Q   T   P   S   R   E   G   Y   V   G   S   G   E   S
5131  GAT GAA TAT ACT CAG ACA CCG TCG CGG GAG GGA TAT GTC GGC AGC GGC GAG TCG
       A   L   D   F   G   Y   L   V   T   T   S   G   K   T   A   A   D   E
5185  GCA CTC GAT TTC GGC TAT ATC GTA ACC ACC AGC GGT AAA ACA GCT GCC GAC GAA
       V   L   I   K   V   T   G   P   A   Q   V   I   G   G   R   S   Y   C
5239  GTC CTG ATC AAG GTG ACC GGA CCC GCG CAG GTG ATT GGC GGG CGC TCC TAT TGT
       V   F   S   S   D   D   G   K   A   K   V   P   F   P   A   T   L   S
5293  GTC TTC AGC TCC GAT GAC GGT AAG GCG AAA GTA CCG TTC CCG GCG ACG CTT TCC
       F   I   T   R   N   G   A   T   K   T   Y   D   A   G   C   D   D   S
5347  TTT ATT ACC CGC AAC GGA GCT ACA AAA ACC TAC GAT GCC GGG TGC GAT GAT AGC
       W   R   D   M   T   D   A   L   W   L   T   T   P   W   T   D   I   S
5401  TGG CGG GAT ATG ACC GAT GCG CTG TGG TTG ACC ACA CCG TGG ACT GAT ATC TCT
       G   E   V   G   Q   M   D   K   T   T   V   K   F   S   I   P   M   D
5455  GGC GAA GTG GGG CAG ATG GAT AAG ACC ACA GTC AAA TTT TCG ATT CCA ATG GAT
       N   A   I   S   L   R   T   V   D   D   N   G   W   F   G   E   V   S
5509  AAC GCC ATT TCT CTG CGT ACG GTA GAT GAT AAC GGC TGG TTT GGC GAA GTC AGC
       A   S   G   E   I   H   V   Q   A   T   W   R   N   I   N
5563  GCT TCA GGA GAA ATT CAT GTT CAG GCG ACG TGG CGT AAC ATT AAC TAA AAG CTT
5617  GGC TGT TTT GGC GGA TGA GAG AAG ATT TTC AGC CTG ATA CAG ATT AAA TCA GAA
5671  CGC AGA AGC GGT CTG ATA AAA CAG AAT TTG CCT GGC GGC AGT AGC GCG GTG GTC
5725  CCA CCT GAC CCC ATG CCG AAC TCA GAA GTG AAA CGC CGT AGC GCC GAT GGT AGT
5779  GTG GGG TCT CCC CAT GCG AGA GTA GGG AAC TGC CAG GCA TCA AAT AAA ACG AAA
5833  GGC TCA GTC GAA AGA CTG GGC CTT TCG TTT TAT CTG TTG TTT GTC GGT GAA CGC
5887  TCT CCT GAG TAG GAC AAA TCC GCC GGG AGC GGA TTT GAA CGT TGC GAA GCA ACG
5941  GCC CGG AGG GTG GCG GGC AGG ACG CCC GCC ATA AAC TGC CAG GCA TCA AAT TAA
5995  GCA GAA GGC CAT CCT GAC GGA TGG CCT TTT TGC GTT TCT ACA AAC TCT TTT GTT
6049  TAT TTT TCT AAA TAC ATT CAA ATA TGT ATC CGC TCA TGA GAC AAT AAC CCT GAT
6103  AAA TGC TTC AAT AAT GGA AGA TCT CTC CTG TTC AGC TAC TGA CGG GGT GGT GCG
6157  TAA CGG CAA AAG CAC CGC CGG ACA TCA GCG CTA GCG GAG TGT GGA CCA GGC TGT
6211  CTA TGT GTG ACT GTT GAG CTG TAA CAA GTT GTC TCA GGT GTT CAA TTT CAT GTT
6265  CTA GTT GCT TTC TTT TAC TGG TTT CAC CTG TTC TAT TAG GTG TTA CAT GCT GTT
6319  CAT CTG TTA CAT TGT CGA TCT GTT CAT GGT GAA CAG CTT TGA ATG CAC CAA AAA
6373  CTC GTA AAA GCT CTG ATG TAT CTA TCT TTT TTA CAC CGT TTT CAT CTG TGC ATA
```

FIG. 14D

```
6427    TGG ACA GTT TTC CCT TTG ATA TGT AAC GGT GAA CAG TTG TTC TAC TTT TGT TTG
6481    TTA GTC TTG ATG CTT CAC TGA TAG ATA CAA GAG CCA TAA GAA CCT CAG ATC CTT
6535    CCG TAT TTA GCC AGT ATG TTC TCT AGT GTG GTT CGT TGT TTT TGC GTG AGC CAT
6589    GAG AAC GAA CCA TTG AGA TCA TAC TTA CTT TGC ATC TCA CTC AAA AAT TTT GCC
6643    TCA AAA CTC GTG AGC TGA ATT TTT CCA GTT AAA CCA TCG TCT AGT GTT TTT CTT
6697    AGT CCG TTA TGT AGG TAG GAA TCT GAT GTA ATG GTT GTT GGT ATT TTG TCA CCA
6751    TTC ATT TTT ATC TGG TTG TTC TCA AGT TCG GTT ACG AGA TCC ATT TGT CTA TCT
6805    AGT TCA ACT TGG AAA ATC AAC GTA TCA GTC GGG CGG CCT TTA TCA ACC ACC
6859    AAT TTC ATA TTG CTG TAA GTG TTT AAA TCT TTA CTT ATT GGT TTC AAA ACC CAT
6913    TGG TTA AGC CTT TTA AAC TCA TGG TAG TTA TTT TCA AGC ATT AAC ATG AAC TTA
6967    AAT TCA TCA AGG CTA ATC TCT ATA TTT GCC TTG TGA GTT TTC TTT TGT GTT AGT
7021    TCT TTT AAT AAC CAC TCA TAA ATC CTC ATA GAG TAT TTG TTT TCA AAA GAC TTA
7075    ACA TGT TCC AGA TTA TAT TTT ATG AAT TTT TTT AAC TGG AAA AGA TAA GGC AAT
7129    ATC TCT TCA CTA AAA ACT AAT TCT AAT TTT TCG CTT GAG AAC TTG GCA TAG TTT
7183    GTC CAC TGG AAA ATC TCA AAG CCT TTA ACC AAA GGA TTC CTG ATT TCC ACA GTT
7237    CTC GTC ATC AGC TCT CTG GTT GCT TTA GCT AAT ACA CCA TAA GCA TTT TCC CTA
7291    CTG ATG TTC ATC ATC TGA GCG TAT TGG TTA TAA GTG AAC GAT ACC GTC GGT TCT
7345    TTC CTT GTA GGG TTT TCA ATC GTG GGG TTG AGT AGT GCC ACA CAG CAT AAA ATT
7399    AGC TGT GTT TCA TGC TCC GTT AAG TCA TAG CCA CTA ATC GCT AGT TCA TTT GCT
7453    TTG AAA ACA ACT AAT TCA GAC ATA CAT CTC AAT TGG TCT AGG TGA TTT TAA TCA
7507    CTA TAC CAA TTG AGA TGG GCT AGT CAA TGA TAA TTA CTA GTC CTT TTC CTT TGA
7561    GTT GTG GGT ATC TGT AAA TTC TGC TAG ACC TTT GCT GGA AAA CTT GTA AAT TCT
7615    GCT AGA CCC TCT GTA AAT TCC GCT AGA CCT TTG TGT GTT TTT TTT GTT TAT ATT
7669    CAA GTC GTT ATA ATT TAT ACA ATA AAC AAA CAA TAA AAA AAC ATA AAA ACA ATA
7723    GAT CCC AGC CCT GTG TAT AAC TCA CTA CTT TGA TCA GTT CCG CAG TAT TAC AAA
7777    AGG ATG TCG CAA ACG CTG TTT GCT CCT CTA CAA AAC AGA CCT TAA AAC CCT AAA
7831    GGC TTA AGT AGC ACC CTC GCA AGC TCG GGC AAA TCG CTG AAT ATT CCT TTT GTC
7885    TCC GAC CAT CAG GCA CCT GAG TCG CTG TCT TTT TCG TGA CAT TCA GTT CGC TGC
7939    GCT CAC GTC TAG ATT TCA GTG CAA TTT ATC TCT TCA AAT GTA GCA CCT GAA GTC
7993    AGC CCG ATA CGA TAT AAG TTG TAA TTC TCA TGT TTG ACA GCT TAT CAT CGA AGA
8047    TCT TCC GTG CAT GGC AAT CGC CCA ACG ACA TTT GCC CTC GCC ATG TTT CAG TAC
8101    GCG CAT AAA AGC AGG CAA ATT TCT ACG CTG ATC CAT AAT TAG GAT CAA TAA AAC
8155    AGC GAC GGA AAT GAT TCC CTT CCT AAC GCA AAT TCC CTG ATA ATC GCC ACT GGA
8209    CTT TCT GCT TGC GCG GTA AGG CAG GAT AAG TCG CAT TAC TGA TGG CTT CGC TAT
                                                                    M   V   K   D   A
asd
8263    CAT TGA TTA ATT TCA CTT GCG ACT TTG GCT GCT TTT TGT GTG AAG GAT GCG
         P   Q   D   T   G   A   H   T   Q   H   I   S   L   Q   E   K   N   A
8317    CCA CAG GAT ACT CGC GCG CAT ACA CAG CAC ATC TCT TTG CAG GAA AAA AAC GCT
         M   K   N   V   G   F   I   G   W   R   G   M   V   G   S   V   L   M
8371    ATG AAA AAT GTT GGT TTT ATC GGC TGG CGC GGA ATG GTC GGC TCT GTT CTC ATG
         Q   R   M   V   E   E   R   D   F   D   A   I   R   P   V   F   S
8425    CAA CGC ATG GTA GAG GAG CGC GAT TTC GAC GCT ATT CGC CCT GTT TTC TTT TCT
         T   S   Q   F   G   Q   A   A   P   T   F   G   D   T   S   T   G   T
8479    ACC TCC CAG TTT GGA CAG GCG GCG CCC ACC TTC GGC GAC ACC TCC ACC GGC ACG
         L   Q   D   A   F   D   L   D   A   L   K   A   L   D   I   I   V   T
8533    CTA CAG GAC GCT TTT GAT CTC GAT GCG CTA AAA GCG CTC GAT ATC ATC GTC ACC
         C   Q   G   G   D   Y   T   N   E   I   Y   P   K   L   R   E   S   G
```

FIG. 14E

```
8587    TGC CAG GGC GGC GAT TAT ACC AAC GAA ATT TAT CCA AAG CTG CGC GAA AGC GGA
        W   Q   G   G   D   Y   T   N   E   I   Y   P   K   L   R   E   S   G
8641    TGG CAG GGT TAC TGG ATT GAT GCG GCT TCT ACG CTG CGC ATG AAA GAT GAT GCC
        W   Q   G   Y   W   I   D   A   A   S   T   L   R   M   K   D   D   A
8695    ATT ATT ATT CTC GAC CCG GTC AAC CAG GAC GTG ATT ACC GAC GGC CTG AAC AAT
        I   I   I   L   D   P   V   N   Q   D   V   I   T   D   G   L   N   N
8749    GGC GTG AAG ACC TTT GTC GGC GGT AAC TGT ACC GTT AGC CTG ATG TTG ATG TCG
        G   V   K   T   F   V   G   G   N   C   T   V   S   L   M   L   M   S
8803    CTG GGC GGT CTC TTT GCC CAT AAT CTC GTT GAC TGG GTA TCC GTC GCG ACC TAT
        L   G   G   L   F   A   H   N   L   V   D   W   V   S   V   A   T   Y
8857    CAG GCC GCC TCC GGC GGC GGC GCG CGC CAT ATG CGC GAG CTG TTA ACC CAG ATG
        Q   A   A   S   G   G   G   A   R   H   M   R   E   L   L   T   Q   M
8911    GGT CAG TTG TAT GGC CAT GTC GCC GAT GAA CTG GCG ACG CCG TCT TCC GCA ATT
        G   Q   L   Y   G   H   V   A   D   E   L   A   T   P   S   S   A   I
8965    CTT GAT ATT GAA CGC AAA GTT ACG GCA TTG ACC CGC AGC GGC GAG CTG CCG GTT
        L   D   I   E   R   K   V   T   A   L   T   R   S   G   E   L   P   V
9019    GAT AAC TTT GGC GTA CCG CTG GCG GGA AGC CTG ATC CCC TGG ATC GAC AAA CAG
        D   N   F   G   V   P   L   A   G   S   L   I   P   W   I   D   K   Q
9073    CTC GAT AAC GGC CAG AGC CGC GAA GAG TGG AAA GGC CAG GCG GAA ACC AAC AAG
        L   D   N   G   Q   S   R   E   E   W   K   G   Q   A   E   T   N   K
9127    ATT CTC AAT ACT GCC TCT GTG ATT CCG GTT GAT GGT TTG TGT GTG CGC GTC GGC
        I   L   N   T   A   S   V   I   P   V   D   G   L   C   V   R   V   G
9181    GCG CTG CGC TGT CAC AGC CAG GCG TTC ACC ATC AAG CTG AAA AAA GAG GTA TCC
        A   L   R   C   H   S   Q   A   F   T   I   K   L   K   K   E   V   S
9235    ATT CCG ACG GTG GAA GAA CTG CTG GCG GCA CAT AAT CCG TGG GCG AAA GTG GTG
        I   P   T   V   E   E   L   L   A   A   H   N   P   W   A   K   V   V
9289    CCG AAC GAT CGT GAT ATC ACT ATG CGC GAA TTA ACC CCG GCG GCG GTG ACC GGC
        P   N   D   R   D   I   T   M   R   E   L   T   P   A   A   V   T   G
9343    ACG TTG ACT ACG CCG GTT GGT CGT CTG CGT AAG CTG AAC ATG GGG CCA GAG TTC
        T   L   T   T   P   V   G   R   L   R   K   L   N   M   G   P   E   F
9397    TTG TCG GCG TTT ACC GTA GGC GAC CAG TTG TTA TGG GGC GCC GCC GAG CCG CTC
        L   S   A   F   T   V   G   D   Q   L   L   W   G   A   A   E   P   L
9451    CGT CGA ATG CTG CGC CAG TTG GCG TAG TGG CTA TTG CAG CGC TTA TCG GGC CTG
        R   R   M   L   R   Q   L   A
9505    CGT GTG GTT CTG TAG GCC GGA TAA GGC GCG TCA GCG CCG CCA TCC GGC GGG GAA
9559    ATT TGT GTT AAA CCA GGG GTG CAT CGT CAC CCT TTT TTT GCG TAA TAC AGG AGT
9613    AAA CGC AGA TGT TTC ATT TTT ATC AGG AGT TAA GCA GAG CAT TGG CTA TTC TTT
9667    AAG GGT AGC TTA ATC CCA CGG GTA TTA AGC CTA ACC TGA GGT AGG AGC AGC GCA
9721    GAT AGG ATG CAC AGT GTG CTG CGC CGT TCA GGT CAA AGA AGT GTC ACT ACC TGA
9775    TGT TGA ATT CGG AAG ATC T
```

FIG. 14F

Sequence Range: 1 to 462

```
              10           20           30           40           50
    GAATTC ATG TCC GTG ACC AAA CAA CTG CTG CAA ATG CAA GCA GAC GCT CAT CAT
    CTTAAG TAC AGG CAC TGG TTT GTT GAC GAC GTT TAC GTT CGT CTG CGA GTA GTA
            M   S   V   T   K   Q   L   L   Q   M   Q   A   D   A   H   H>

60           70           80           90          100
    CTG TGG GTG AAA TTC CAT AAC TAT CAC TGG AAC GTG AAA GGC CTG CAA TTC TTC
    GAC ACC CAC TTT AAG GTA TTG ATA GTG ACC TTG CAC TTT CCG GAC GTT AAG AAG
     L   W   V   K   F   H   N   Y   H   W   N   V   K   G   L   Q   F   F>

110          120          130          140          150          160
    TCT ATC CAC GAG TAC ACC GAA AAA GCG TAT GAA GAA ATG GCA GAA CTG TTC GAC
    AGA TAG GTG CTC ATG TGG CTT TTT CGC ATA CTT CTT TAC CGT CTT GAC AAG CTG
     S   I   H   E   Y   T   E   K   A   Y   E   E   M   A   E   L   F   D>

170          180          190          200          210
    AGC TGT GCT GAA CGC GTG CTG CAA CTG GGC GAA AAA GCT ATC ACT TGC CAA AAA
    TCG ACA CGA CTT GCG CAC GAC GTT GAC CCG CTT TTT CGA TAG TGA ACG GTT TTT
     S   C   A   E   R   V   L   Q   L   G   E   K   A   I   T   C   Q   K>

220          230          240          250          260          270
    GTG CTG ATG GAA AAC GCA AAA AGC CCG AAA GTG GCA AAA GAC TGC TTC ACT CCG
    CAC GAC TAC CTT TTG CGT TTT TCG GGC TTT CAC CGT TTT CTG ACG AAG TGA GGC
     V   L   M   E   N   A   K   S   P   K   V   A   K   D   C   F   T   P>

280          290          300          310          320
    CTG GAA GTC ATC GAA CTG ATC AAA CAA GAC TAT GAA TAT CTG CTG GCA GAA TTT
    GAC CTT CAG TAG CTT GAC TAG TTT GTT CTG ATA CTT ATA GAC GAC CGT CTT AAA
     L   E   V   I   E   L   I   K   Q   D   Y   E   Y   L   L   A   E   F>

330          340          350          360          370
    AAA AAA CTG AAC GAA GCA GCA GAA AAA GAA AGC GAC ACT ACC ACC GCT GCT TTC
    TTT TTT GAC TTG CTT CGT CGT CTT TTT CTT TCG CTG TGA TGG TGG CGA CGA AAG
     K   K   L   N   E   A   A   E   K   E   S   D   T   T   T   A   A   F>

380          390          400          410          420          430
    GCA CAA GAA AAC ATC GCA AAA TAT GAA AAA AGC CTG TGG ATG ATC GGC GCT ACT
    CGT GTT CTT TTG TAG CGT TTT ATA CTT TTT TCG GAC ACC TAC TAG CCG CGA TGA
     A   Q   E   N   I   A   K   Y   E   K   S   L   W   M   I   G   A   T>

440          450          460
    TTA CAA GGC GCT TGC AAA ATG TAA AAGCTT
    AAT GTT CCG CGA ACG TTT TAC ATT TTCGAA
     L   Q   G   A   C   K   M   *>
```

FIG. 17

Sequence Range: 1 to 852

```
              10             20             30             40             50
     GAATTC ATG AAA AAA ATG CTG CTG AGC ATT TTC ACC ACC TTC GTT GCA GTA TTC
     CTTAAG TAC TTT TTT TAC GAC GAC TCG TAA AAG TGG TGG AAG CAA CGT CAT AAG
             M   K   K   M   L   L   S   I   F   T   T   F   V   A   V   F>

60             70             80             90            100
     CTG GCT GCT TGT GGC GGC AAC AGC GAT TCT GGT GCT AGC AAC TCT CTG GAA CGC
     GAC CGA CGA ACA CCG CCG TTG TCG CTA AGA CCA CGA TCG TTG AGA GAC CTT GCG
      L   A   A   C   G   G   N   S   D   S   G   A   S   N   S   L   E   R>

110            120            130            140            150            160
     ATC AAG CAA GAT GGC GTA GTA CGC ATC GGC GTT TTC GGC GAT AAA CCG CCG TTC
     TAG TTC GTT CTA CCG CAT CAT GCG TAG CCG CAA AAG CCG CTA TTT GGC GGC AAG
      I   K   Q   D   G   V   V   R   I   G   V   F   G   D   K   P   P   F>

170            180            190            200            210
     CGT TAT GTA GAT GAA AAA GGC GTA AAC CAA GGT TAT GAT ATC GTG CTG GCG AAA
     GCA ATA CAT CTA CTT TTT CCG CAT TTG GTT CCA ATA CTA TAG CAC GAC CGC TTT
      G   Y   V   D   E   K   G   V   N   Q   G   Y   D   I   V   L   A   K>

220            230            240            250            260            270
     CGT ATC GCA AAA GAA CTG CTG GGC GAT GAA AAC AAG GTG CAG TTC GTA CTG GTT
     GCA TAG CGT TTT CTT GAC GAC CCG CTA CTT TTG TTC CAC GTC AAG CAT GAC CAA
      R   I   A   K   E   L   L   G   D   E   N   K   V   Q   F   V   L   V>

280            290            300            310            320
     GAA GCT GCA AAC CGC GTG GAA TTT CTG AAA AGC AAC AAA GTT GAT ATT ATT CTG
     CTT CGA CGT TTG GCG CAC CTT AAA GAC TTT TCG TTG TTT CAA CTA TAA TAA GAC
      E   A   A   N   R   V   E   F   L   K   S   N   K   V   D   I   I   L>

330            340            350            360            370
     GCT AAC TTC ACT CAA ACC CCG GAA CGC GCA GAG CAA GTG GAT TTC TGC CTG CCG
     CGA TTG AAG TGA GTT TGG GGC CTT GCG CGT CTC GTT CAC CTA AAG ACG GAC GGC
      A   N   F   T   Q   T   P   E   R   A   E   Q   V   D   F   C   L   P>

380            390            400            410            420            430
     TAT ATG AAG GTA GCT CTC GGT GTG GCT GTG CCG CAA GAT AGC AAC ATC AGC AGC
     ATA TAC TTC CAT CGA GAC CCA CAC CGA CAC GGC GTT CTA TCG TTG TAG TCG TCG
      Y   M   K   V   A   L   G   V   A   V   P   Q   D   S   N   I   S   S>

440            450            460            470            480
     ATC GAA GAT CTG AAA GAT AAA ACT TTA CTG CTG AAC AAA GGC ACT ACT GCT GAT
     TAG CTT CTA GAC TTT CTA TTT TGA AAT GAC GAC TTG TTT CCG TGA TGA CGA CTA
      I   E   D   L   K   D   K   T   L   L   L   N   K   G   T   T   A   D>

490            500            510            520            530            540
     GCG TAT TTC ACC AAA GAA TAT CCG GAT ATT AAA ACC CTG AAA TAC GAT CAA AAC
     CGC ATA AAG TGG TTT CTT ATA GGC CTA TAA TTT TGG GAC TTT ATG CTA GTT TTG
      A   Y   F   T   K   E   Y   P   D   I   K   T   L   K   Y   D   Q   N>
```

FIG. 18A

```
       550           560           570           580           590
ACC GAA ACT TTC GCG GCT CTG ATC GAT CAA CGC GGT GAT GCT CTG AGC CAT GAC
TGG CTT TGA AAG CGC CGA GAC TAG CTA GTT GCG CCA CTA CGA GAC TCG GTA CTG
 T   E   T   F   A   A   L   I   D   Q   R   G   D   A   L   S   H   D>

600           610           620           630           640
AAC ACT CTG CTG TTC GCG TGG GTA AAA GAA CAT CCG GAA TTT AAA ATG GCG ATT
TTG TGA GAC GAC AAG CGC ACC CAT TTT CTT GTA GGC CTT AAA TTT TAC CGC TAA
 N   T   L   L   F   A   W   V   K   E   H   P   E   F   K   M   A   I>

650           660           670           680           690           700
AAA GAA CTG GGC AAC AAA GAT GTA ATT GCT CCG GCT GTT AAA AAA GGT GAT AAA
TTT CTT GAC CCG TTG TTT CTA CAT TAA CGA GGC CGA CAA TTT TTT CCA CTA TTT
 K   E   L   G   N   K   D   V   I   A   P   A   V   K   K   G   D   K>

710           720           730           740           750
GAG CTG AAA GAA TTT ATT GAT AAC TTA ATC ACC AAA CTG GGC GAA GAA CAA TTC
CTC GAC TTT CTT AAA TAA CTA TTG AAT TAG TGG TTT GAC CCG CTT CTT GTT AAG
 E   L   K   E   F   I   D   N   L   I   T   K   L   G   E   E   Q   F>

760           770           780           790           800           810
TTC CAT AAA GCG TAT GAT GAA ACT CTG AAA AGC CAT TTC GGC GAT GAT GTA AAA
AAG GTA TTT CGC ATA CTA CTT TGA GAC TTT TCG GTA AAG CCG CTA CTA CAT TTT
 F   H   K   A   Y   D   E   T   L   K   S   H   F   G   D   D   V   K>

820           830           840           850
GCG GAT GAT GTA GTT ATT GAA GGC GGT AAA ATT TAA AAGCTT
CGC CTA CTA CAT CAA TAA CTT CCG CCA TTT TAA ATT TTCGAA
 A   D   D   V   V   I   E   G   G   K   I   *>
```

FIG. 18B

MKRKICKALVCATLVTSLWAGVSTKVYAWDGKIDGTGTHAMIVTQGVSILENDMSKNEPE
SVRKNLEILKDNMHELQLGSTYPDYDKNAYDLYQDHFWDPDTNNNFSKDNSWYLAYSIPD
TGESQIRKFSALARYEWQRGNYKQATFYLGEAMHYFGDIDTPYHPANVTAVDSAGHVKFE
TFAEERKEQYKINTVGCKTNEDFYADILKNKDFNAWSKEYARGFAKTGKSIYYSHASMSH
SWDDWDYAAKVTLANSQKGTAGYIYRFLHDVSEGNDPSVGNNVKELVAYISTSGEKDAGT
DDYMYFGIKTKDGKTQEWEMDNPGNDFMAGSKDTYTFKLKDENLKIDDIQNMWIRKRKYT
AFPDAYKPENIKVIANGKVVVDKDINEWISGNSTYNIK*

FIG. 20

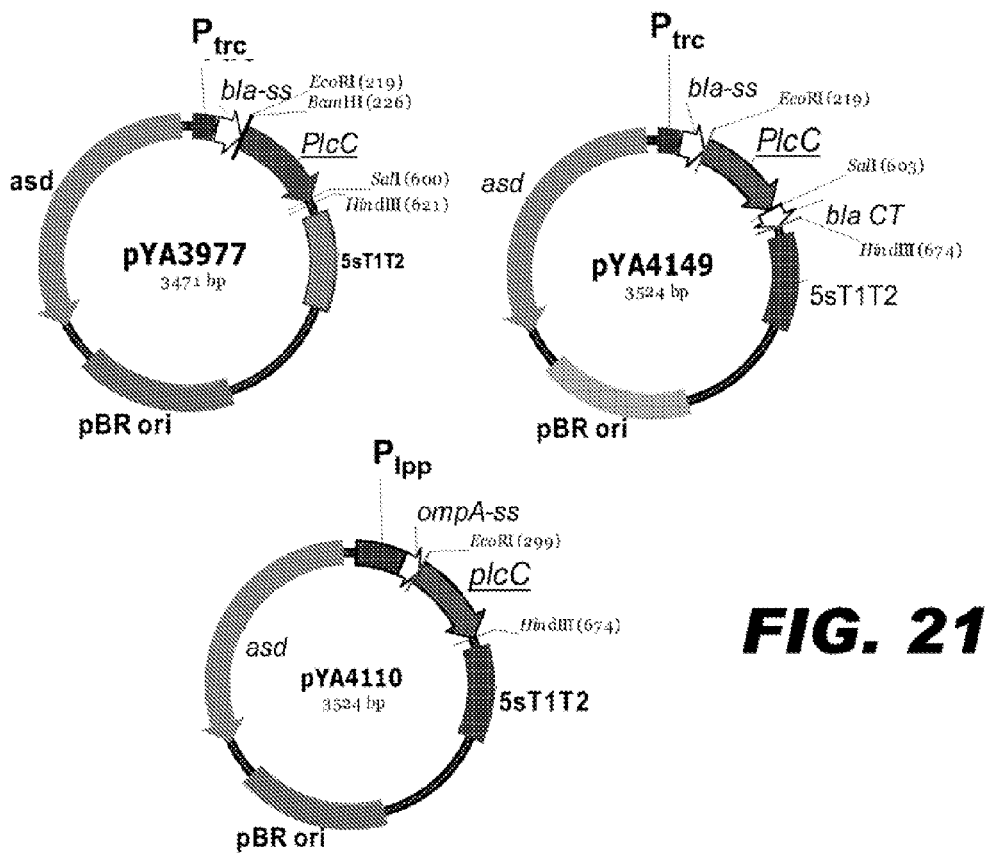

FIG. 21

```
            10              20              30              40              50
GAATTC GAC CCG TCC GTG GGC AAC AAC GTG AAA GAA CTG GTG GCT TAC ATC TCC
CTTAAG CTG GGC AGG CAC CCG TTG TTG CAC TTT CTT GAC CAC CGA ATG TAG AGG
        D   P   S   V   G   N   N   V   K   E   L   V   A   Y   I   S>

60              70              80              90             100
ACT AGC GGC GAA AAA GAC GCT GGC ACC GAC GAC TAC ATG TAT TTC GGC ATC AAA
TGA TCG CCG CTT TTT CTG CGA CCG TGG CTG CTG ATG TAC ATA AAG CCG TAG TTT
 T   S   G   E   K   D   A   G   T   D   D   Y   M   Y   F   G   I   K>

110             120             130             140             150             160
ACC AAG GAC GGC AAA ACT CAA GAA TGG GAA ATG GAC AAC CCG GGC AAC GAC TTC
TGG TTC CTG CCG TTT TGA GTT CTT ACC CTT TAC CTG TTG GGC CCG TTG CTG AAG
 T   K   D   G   K   T   Q   E   W   E   M   D   N   P   G   N   D   F>

170             180             190             200             210
ATG GCT GGC AGC AAA GAC ACT TAT ACT TTC AAA TTA AAA GAC GAA AAC CTG AAA
TAC CGA CCG TCG TTT CTG TGA ATA TGA AAG TTT AAT TTT CTG CTT TTG GAC TTT
 M   A   G   S   K   D   T   Y   T   F   K   L   K   D   E   N   L   K>

220             230             240             250             260             270
ATT GAC GAC ATC CAA AAC ATG TGG ATT CGC AAA CGT AAA TAT ACC GCA TTC CCG
TAA CTG CTG TAG GTT TTG TAC ACC TAA GCG TTT GCA TTT ATA TGG CGT AAG GGC
 I   D   D   I   Q   N   M   W   I   R   K   R   K   Y   T   A   F   P>

280             290             300             310             320
GAC GCT TAT AAG CCG GAA AAC ATC AAG GTG ATC GCA AAC GGC AAA GTG GTA GTG
CTG CGA ATA TTC GGC CTT TTG TAG TTC CAC TAG CGT TTG CCG TTT CAC CAT CAC
 D   A   Y   K   P   E   N   I   K   V   I   A   N   G   K   V   V   V>

330             340             350             360             370
GAC AAG GAC ATC AAC GAG TGG ATT TCC GGC AAC TCC ACT TAT AAC ATC AAA TAA
CTG TTC CTG TAG TTG CTC ACC TAA AGG CCG TTG AGG TGA ATA TTG TAG TTT ATT
 D   K   D   I   N   E   W   I   S   G   N   S   T   Y   N   I   K   *>

380
TAAAAGCTT
ATTTTCGAA
```

FIG. 22

```
         10          20          30          40          50
GAATTC AGC GAA CTG AAC GAC ATC AAC AAA ATT GAG CTG AAA AAC CTG AGC GGC
CTTAAG TCG CTT GAC TTG CTG TAG TTG TTT TAA CTC GAC TTT TTG GAC TCG CCG
        S   E   L   N   D   I   N   K   I   E   L   K   N   L   S   G>

60          70          80          90         100
GAA ATC ATC AAA GAA AAC GGC AAG GAA GCT ATT AAA TAT ACT TCC AGC GAC ACC
CTT TAG TAG TTT CTT TTG CCG TTC CTT CGA TAA TTT ATA TGA AGG TCG CTG TGG
 E   I   I   K   E   N   G   K   E   A   I   K   Y   T   S   S   D   T>

110         120         130         140         150         160
GCT TCC CAT AAA GGC TGG AAG GCA ACT CTG AGC GGC ACC TTC ATT GAA GAC CCG
CGA AGG GTA TTT CCG ACC TTC CGT TGA GAC TCG CCG TGG AAG TAA CTT CTG GGC
 A   S   H   K   G   W   K   A   T   L   S   G   T   F   I   E   D   P>

170         180         190         200         210
CAT TCC GAC AAG AAA ACT GCT CTG CTG AAC CTG GAA GGC TTT ATC CCG TCC GAC
GTA AGG CTG TTC TTT TGA CGA GAC GAC TTG GAC CTT CCG AAA TAG GGC AGG CTG
 H   S   D   K   K   T   A   L   L   N   L   E   G   F   I   P   S   D>

220         230         240         250         260         270
AAA CAG ATT TTC GGC TCT AAA TAT TAC GGC AAA ATG AAA TGG CCG GAA ACT TAT
TTT GTC TAA AAG CCG AGA TTT ATA ATG CCG TTT TAC TTT ACC GGC CTT TGA ATA
 K   Q   I   F   G   S   K   Y   Y   G   K   M   K   W   P   E   T   Y>

280         290         300         310         320
CGC ATT AAT GTG AAA AGC GCT GAC GTG AAC AAT AAC ATC AAA ATC GCA AAC TCC
GCG TAA TTA CAC TTT TCG CGA CTG CAC TTG TTA TTG TAG TTT TAG CGT TTG AGG
 R   I   N   V   K   S   A   D   V   N   N   N   I   K   I   A   N   S>

330         340         350         360         370
ATT CCG AAA AAT ACT ATC GAC AAA AAA GAC GTG TCC AAT TCC ATT GGC TAT TCC
TAA GGC TTT TTA TGA TAG CTG TTT TTT CTG CAC AGG TTA AGG TAA CCG ATA AGG
 I   P   K   N   T   I   D   K   K   D   V   S   N   S   I   G   Y   S>

380         390         400         410         420         430
ATC GGC GGT AAC ATC TCC GTG GAA GGC AAA ACT GCT GGC GCT GGC ATC AAC GCT
TAG CCG CCA TTG TAG AGG CAC CTT CCG TTT TGA CGA CCG CGA CCG TAG TTG CGA
 I   G   G   N   I   S   V   E   G   K   T   A   G   A   G   I   N   A>

440         450         460         470         480
TCC TAT AAC GTC CAA AAC ACT ATC AGC TAT GAA CAA CCG GAC TTC CGC ACC ATT
AGG ATA TTG CAG GTT TTG TGA TAG TCG ATA CTT GTT GGC CTG AAG GCG TGG TAA
 S   Y   N   V   Q   N   T   I   S   Y   E   Q   P   D   F   R   T   I>

490         500         510         520         530         540
CAA CGC AAA GAC GAT GCA AAC CTG GCA TCC TGG GAC ATC AAA TTC GTT GAG ACT
GTT GCG TTT CTG CTA CGT TTG GAC CGT AGG ACC CTG TAG TTT AAG CAA CTC TGA
 Q   R   K   D   D   A   N   L   A   S   W   D   I   K   F   V   E   T>
```

FIG. 23A

```
          550             560             570             580             590
AAG GAC GGC TAT AAC ATC GAC TCC TAT CAT GCT ATT TAT GGC AAC CAA CTG TTC
TTC CTG CCG ATA TTG TAG CTG AGG ATA GTA CGA TAA ATA CCG TTG GTT GAC AAG
 K   D   G   Y   N   I   D   S   Y   H   A   I   Y   G   N   Q   L   F>

600             610             620             630             640
ATG AAA TCC CGC CTG TAT AAC AAT GGC GAC AAA AAC TTC ACC GAC GAT CGC GAC
TAC TTT AGG GCG GAC ATA TTG TTA CCG CTG TTT TTG AAG TGG CTG CTA GCG CTG
 M   K   S   R   L   Y   N   N   G   D   K   N   F   T   D   D   R   D>

650             660             670             680             690             700
CTG TCC ACC CTG ATT TCC GGC GGC TTC TCC CCG AAC ATG GCT CTG GCA CTG ACC
GAC AGG TGG GAC TAA AGG CCG CCG AAG AGG GGC TTG TAC CGA GAC CGT GAC TGG
 L   S   T   L   I   S   G   G   F   S   P   N   M   A   L   A   L   T>

710             720             730             740             750
GCA CCT AAA AAT GCT AAA GAA TCC GTG ATC ATC GTG GAA TAT CAA CGC TTC GAC
CGT GGA TTT TTA CGA TTT CTT AGG CAC TAG TAG CAC CTT ATA GTT GCG AAG CTG
 A   P   K   N   A   K   E   S   V   I   I   V   E   Y   Q   R   F   D>

760             770             780             790             800             810
AAC GAC TAT ATT CTG AAT TGG GAA ACT ACT CAA TGG CGC GGC ACC AAC AAA CTT
TTG CTG ATA TAA GAC TTA ACC CTT TGA TGA GTT ACC GCG CCG TGG TTG TTT GAA
 N   D   Y   I   L   N   W   E   T   T   Q   W   R   G   T   N   K   L>

820             830             840             850             860
TCC TCA ACC AGC GAA TAT AAC GAA TTT ATG TTC AAA ATC AAC TGG CAA GAC CAT
AGG AGT TGG TCG CTT ATA TTG CTT AAA TAC AAG TTT TAG TTG ACC GTT CTG GTA
 S   S   T   S   E   Y   N   E   F   M   F   K   I   N   W   Q   D   H>

870             880             890
AAA ATC GAA TAT TAT CTG TAA AAGCTT
TTT TAG CTT ATA ATA GAC ATT TTCGAA
 K   I   E   Y   Y   L   *
```

FIG. 23B

```
ATG ATT CGC GCC TAC GAA CAA AAC CCA CAA CAT TTT ATT GAG GAT CTC GAA AAA GTT CGC   60
 M   I   R   A   Y   E   Q   N   P   Q   H   F   I   E   D   L   E   K   V   R    20

GTG GAA CAA CTT ACT GGT CAT GGT TCT TCA GTT TTA CAA CAA TTG GTT CAG TTA GTC AAA  120
 V   E   Q   L   T   G   H   G   S   S   V   L   Q   Q   L   V   Q   L   V   K    40

GAT CAA AAT ATT GAT ATT TCC ATT AAA TAT GAT CCT CGC AAA GAT TCG GAG GTT TTT GCC  180
 D   Q   N   I   D   I   S   I   K   Y   D   P   R   K   D   S   E   V   F   A    60

AAT CGC GTA ATT ACT GAT GAT ATC GAA TTG CTC AAG AAA ATC CTC GCT TAT TTT CTC CCT  240
 N   R   V   I   T   D   D   I   E   L   L   K   K   I   L   A   Y   F   L   P    80

GAG GAT GCC ATT CTT AAA GGC GGT CAT TAT GAC AAC CAA CTG CAA AAT GGC ATC AAG CGC  300
 E   D   A   I   L   K   G   G   H   Y   D   N   Q   L   Q   N   G   I   K   R   100

GTA AAA GAG TTC CTT GAA TCA TCG CCG AAT ACA CAA TGG GAA TTG CGC GCG TTC ATG GCA  360
 V   K   E   F   L   E   S   S   P   N   T   Q   W   E   L   R   A   F   M   A   120

GTA ATG CAT TTC TCT TTA ACC GCC GAT CGT ATC GAT GAT GAT ATT TTG AAA GTG ATT GTT  420
 V   M   H   F   S   L   T   A   D   R   I   D   D   D   I   L   K   V   I   V   140

GAT TCA ATG AAT CAT CAT GGT GAT GCC CGT AGC AAG TTG CGT GAA GAA TTA GCT GAG CTT  480
 D   S   M   N   H   H   G   D   A   R   S   K   L   R   E   E   L   A   E   L   160

ACC GCC GAA TTA AAG ATT TAT TCA GTT ATT CAA GCC GAA ATT AAT AAG CAT CTG TCT AGT  540
 T   A   E   L   K   I   Y   S   V   I   Q   A   E   I   N   K   H   L   S   S   180

AGT GGC ACC ATT AAT ATC CAT GAT AAA TCC ATT AAT CTC ATG GAT AAA AAT TTA TAT GGT  600
 S   G   T   I   N   I   H   D   K   S   I   N   L   M   D   K   N   L   Y   G   200

TAT ACA GAT CAA CAG ATT TTT AAA GCC AGC GCA GAG TAC AAA ATT CTC GAG AAA ATG CCT  660
 Y   T   D   Q   Q   I   F   K   A   S   A   E   Y   K   I   L   E   K   M   P   220

CAA ACC ACC ATT CAG GTG GAT GGG AGC GAG AAA AAA ATT GTC TCG ATT AAG GAC TTT CTT  720
 Q   T   T   I   Q   V   D   G   S   E   K   K   I   V   S   I   K   D   F   L   240

GGC AGT GAG AAT AAA CGC ACC GGG GCG TTG GGT AAT CTG AAA AAC TCA TAC TCT TAT AAT  780
 G   S   E   N   K   R   T   G   A   L   G   N   L   K   N   S   Y   S   Y   N   260

AAA GAT AAT AAT GAA TTA TCT CAC TTT GCC ACC ACC TGC TCG GAT AAG TCC AGG CCG CTC  840
 K   D   N   N   E   L   S   H   F   A   T   T   C   S   D   K   S   R   P   L   280

AAC GAC TTG GTT AGC CAA AAA ACA ACT CAG CTG TCT GAT ATT ACA TCA CGT TTT AAT TCA  900
 N   D   L   V   S   Q   K   T   T   Q   L   S   D   I   T   S   R   F   N   S   300

GCT ATT GAA GCA CTG AAC CGT TTC ATT CAG AAA TAT GAT TCA GTG ATG CAA CGT CTG CTC  960
 A   I   E   A   L   N   R   F   I   Q   K   Y   D   S   V   M   Q   R   L   L   320

GAT GAC ACG TCT GGT AAA TGA                                                      981
 D   D   T   S   G   K   *                                                       326
```

FIG. 26

RECOMBINANT BACTERIUM CAPABLE OF ELICITING AN IMMUNE RESPONSE AGAINST ENTERIC PATHOGENS

GOVERNMENTAL RIGHTS

This invention was made with government support under Grant No. 5U01 A1060557, Grant No. 5RO1A124533, and Grant No. 5ROI A1057885 awarded by The National Institutes of Health. The government has certain rights in the invention.

FIELD OF THE INVENTION

The invention encompasses a recombinant bacterium and a vaccine comprising the recombinant bacterium. The recombinant bacterium may be used to elicit an immune response to one or more enteric pathogens.

BACKGROUND OF THE INVENTION

Global disease burden data from UNICEF and WHO show that the top two major causes of infant and child mortality are respiratory and diarrheal diseases. While diarrheal diseases caused by enteric pathogens constitute one of the major causes of morbidity and mortality globally, obtaining accurate epidemiological information about the causative agents is essentially impossible. WHO estimates are just that and the apportionment of disease due to bacteria versus viruses versus parasites are often educated guesses at best and are further complicated due to infections with more than one causative pathogen. Enteric fever due to *Salmonella Typhi* and *S. Paratyphi* A & B is still a major worldwide problem affecting at least 20-30 million people with a significant mortality in medically underprivileged countries. Experts on *Shigella* infections estimate 165 million annual episodes of infection with 1.1 million deaths. If one collects all these data and the information of diarrheal diseases due to *E. coli* pathovars, *C. perfringens* type A, *C. jejuni* plus the enteric viruses and parasites, the total annual mortality due to diarrheal diseases approaches 5 million. Guerrant et al., Arch. Med. Res. 33:351-355 (2002) estimate that there are 3 million annual deaths from diarrheal diseases and thus might be closer to the truth. The WHO estimate that children in Africa experience an average of five diarrheal episodes per year with 800,000 deaths due to fluid loss and dehydration nevertheless indicates the magnitude of the problem. The results of a 4-year WHO study found that between 2000 and 2003, diarrheal diseases accounted for 18% of the 10.6 million annual deaths in children under 5 years of age.

The problem is exacerbated by cessation in use of subtherapeutic antibiotic additions to animal feed for growth promotion. This was first recognized in poultry and other livestock such as swine but *C. perfringens* also causes necrotizing enteritis in the small intestines of humans, which occurs sporadically in underdeveloped countries. Some factors that predispose to *C. perfringens* induced necrotic enteritis include protozoan and helminth infections. *C. perfringens* type associated diarrhea is one of the top 5 causes of food borne bacterial diarrheal disease ranked by CDC in the U.S. Alpha-toxin is particularly responsible for sublethal effects on enterocytes that could lead to malabsorption and stunting in children in developing countries. Studies also show the possible etiologic significance of early intestinal *C. perfringens* colonization and development of necrotizing enterocolitis in newborns. *Yersinia enterocolitica* and *Y. pseudotuberculosis* are other intestinal colonizers that may contribute to human diarrheal disease, but these enteropathogens have not been well studied as contributors to intestinal disease of humans in the developing world.

The problems of travelers in acquiring diarrheal diseases when abroad are legend and often ascribed to ETEC and EPEC strains but just as likely might be due to Norwalk and rotaviruses, *Campylobacter, Listeria* or *Giardia*, all predominantly waterborne or foodborne infections. Although enteric pathogens have a much larger detrimental effect on health in the developing world, these infections are not without major economic consequences in the U.S. and other developed countries. The USDA estimated that infections with *Campylobacter, Salmonella* (non-typhoidal), EHEC, STEC and *Listeria* had a 6.9 billion dollar negative economic impact. *E. coli* is the leading cause of both community-acquired and nosocomial urinary tract infections (UTI). As many as 50% of women have had at least one episode of UTI in their lifetime. *E. coli* also causes 12-50% of nosocomial infections. In regard to bacterial enteropathogens, a major problem, except for host-adapted *Salmonella* (i.e., *S. Typhi* and *S. Paratyphi*), *Shigella* sp. and some ETEC and EPEC strains, is the vast animal reservoir of *Salmonella enterica* serotypes (over 2000), *Clostridium* sp., *Yersinia* sp., APEC and other *E. coli* pathovars, *Listeria* and *Campylobacter*. Animals including companion animals, wildlife, and agriculturally important food animals are causes of water contamination or transmission of bacterial enteric pathogens through the food chain to humans. As such, a vaccine that reduces the probability of infection by necessitating higher infection doses or a vaccine that lessens the consequences of infection offers a definite public health benefit, especially in the developing world.

Approximately 1.4 million humans are infected with *Salmonella enterica* serotypes each year in the U.S. primarily causing gastroenteritis and lost time from work, but with a low incidence of more severe infections, sometimes leading to death in the very young, the elderly or in individuals with an immunocompromising condition, such as advanced HIV infection. In the U.S., *Salmonella* accounts for 31% of the fatalities due to foodborne pathogens whereas *Listeria monocytogenes* accounts for 28% and *C. jejuni*, which causes many more infections (2.5 million), accounts for 1% of the deaths. Twenty percent of all *Salmonella* cases or isolates are from children under 5 years of age.

*Salmonella enterica* has been subdivided into seven subspecies *differentiated* by biochemical and genetic tests, with subspecies I containing most of the serotypes that are implicated in warm-blooded animal and human infection. Although data collected from year to year and from country to country differ, it would appear that poultry (contaminated eggs and meat) constitute the major source of food-borne *Salmonella* infection in humans with contaminated pork, dairy products and vegetable/fruit crops accounting for the rest, but in decreasing frequency of causation. In a recent study, the Food Safety and Inspection Service (FSIS) determined *Salmonella* serotypes isolated from swine, ground turkey, ground beef and broilers in processing plants participating in the Hazard Analysis and Critical Control Point (HACCP) systems for pathogen reduction and found that 87% of the *Salmonella* isolates were from poultry sources. Using data from the Centers for Disease Control and Prevention collected in 2005, it is evident that some *Salmonella* serotypes that are most frequently isolated from humans are also very prevalent in poultry, with 8 of the *Salmonella* serotypes predominantly isolated from poultry being represented in the top 20 serotypes isolated from humans.

*Salmonella* is a gram-negative bacterium, best known for causing enteric diseases. Within the *Salmonella* genus, there are two main species, *S. bongori* and *S. enterica*. However, within each species, there are over 2500 serovars. These numerous serovars are found in a wide variety of different environments and are associated with many different diseases. The vast majority of human isolates (>99.5%) are subspecies *S. enterica*. To simplify taxonomy, the Centers for Disease Control and Prevention recommend that *Salmonella* species be referred to only by their genus and serovar, e.g., *Salmonella Typhi* (or *S. Typhi*) instead of the more technically correct designation, *Salmonella enterica* subspecies *enterica* serovar Typhi.

One important use of genetically engineered microorganisms, such as *Salmonella*, is as a live vaccine for inducing immunity. The use of *Salmonella* for vaccine purposes requires that the *Salmonella* be attenuated such that the administration thereof does not induce disease symptoms associated with wild type *Salmonella* infection. In addition, the *Salmonella* vaccine also has to exhibit a high degree of immunogenicity. As such, the objective of much research on *Salmonella*-based vaccines is to construct a safe and efficacious *Salmonella* vector system that can be used repeatedly for multiple recombinant attenuated *Salmonella* vaccines (RASVs) and additionally, induce some level of cross-protective immunity to diarrheal diseases caused by the diverse *S. enterica* serotypes and other pathogenic enteric bacteria (e.g., *Shigella* sp. and *E. coli* pathovars).

In theory, the ideal attenuated *Salmonella* vaccine should exhibit wild-type abilities that are capable of withstanding all types of biological stress that is entailed with living in an individual. Examples of these types of biological stresses include: exposure to enzymes, acid, bile, osmotic pressures and ion stress. In addition, the ideal attenuated *Salmonella* vaccine should also be able to withstand host defenses encountered following administration (e.g., orally or intranasally). Further, the ideal attenuated *Salmonella* vaccine should also be able to colonize and invade host lymphoid tissues before displaying its attenuation and its inability to cause disease symptoms.

Another existing problem is that the recipient's immune system reacts to the *Salmonella* serotype-specific antigen. The combination of minimizing a recipient's immune response to the *Salmonella* serotype-specific antigen while maximizing the immune response against the undesired bacterial pathogens has not been effectively accomplished in the art. What is needed are compositions and/or vaccines of *Salmonella* that are capable of decreased or absent expression of *Salmonella* serotype-specific antigens that can elicit immune responses to antigens expressed by bacterial enteric pathogens.

All references, patents, and patent applications cited here are each incorporated by reference in their entirety for all purposes.

SUMMARY OF THE INVENTION

One aspect of the present invention encompasses a recombinant *Salmonella* bacterium. The bacterium is typically capable of the expression of at least one nucleic acid encoding at least two enteric antigens. When administered to a host, the bacterium is generally capable of eliciting an immune response against at least two enteric pathogens in addition to at least one *Salmonella* serotype.

Another aspect of the present invention encompasses a vaccine composition. The vaccine composition comprises a recombinant *Salmonella* bacterium. The bacterium is typically capable of the expression of at least one nucleic acid encoding at least two enteric antigens. When administered to a host, the bacterium is generally capable of eliciting an immune response against at least two enteric pathogens in addition to at least one *Salmonella* serotype.

Yet another aspect of the invention encompasses a method of inducing an immune response against an enteric pathogen. The method comprises administering a vaccine composition comprising a recombinant *Salmonella* bacterium. The bacterium is typically capable of the expression of at least one nucleic acid encoding at least two enteric antigens. When administered to a host, the bacterium is generally capable of eliciting an immune response against at least two enteric pathogens in addition to at least one *Salmonella* serotype.

Other aspects and iterations of the invention are described more thoroughly below.

BRIEF DESCRIPTION OF THE FIGURES

FIG. 1 (A-B) depicts chromosomal maps of unmarked deletion mutations. (C) depicts chromosomal maps of unmarked deletion-insertion mutations.

FIG. 2 depicts a diagram of vector pYA3681.

FIG. 3 shows cross detection of OMPS of *Salmonella serotypes, E. coli, Shigella* and *Yersinia* with serum from mice immunized with RASV χ9088 and χ9241. The abbreviations and nomenclature used in this figures are as follows: Bacteria: Vv, *Vibrio vulnificus* MO6-24/O; Stm, *Salmonella Typhimurium* χ3761; Sty, *S. Typhi* χ3744; Spa, *S. Paratyphi* χ8387; Sga, *S. Gallinarum* χ3796; Sen, *S. Enteritidis* χ8494; Stm1, *S. Typhimurium* χ9088 (pYA3337); Sin, *S. Infantis* χ3213; She, *S. Heidelberg* χ3767; Shg1, *Shigella flexneri* BS12 (2457O; Hela invasion negative; sereny negative); Shg2, *S. flexneri* BS155 (lac−; Henle invasion+; Pcr+); Shg3, *S. flexneri* BS98 (spontaneous avirulant isolate from 2457T); YpeI, *Yersinia pestis* KIM; Ype2, *Y. pestis* C092; Yen 1, *Y. enterocolitica* C20; Yps1, *Y. pseudotuberculosis* B14; Eco1, *E. coli* χ7122 (O78:K80:H9; APEC); Eco2, *E. coli* χ7030 (O2:K2:H5; APEC); Eco3, *E. coli* χ7235 (O1:K1:H7; APEC); Eco4, *E. coli* TW01393 (O91:H21; STEC); Eco5, *E. coli* TW01407 (O156:H21; STEC); Eco6, *E. coli* TW02916 (O52:H25; STEC); Eco7, *E. coli* TW07593 (O159; STEC); and Eco8, *E. coli* TW07892 (O142:H21; EPEC). Media: LB, LB medium; Fe, LB medium containing $FeSO_4$ (50 μM); Di, LB medium containing dipyridyl (200 μM).

FIG. 4 depicts the construction of six $\Delta P_{mntR}$::TT araC $P_{BAD}$ mntR mutations. $\Delta P_{mntR26}$::TT araC $P_{BAD}$ mntR: SEQ ID NO:1; $\Delta P_{mntR20}$::TT araC $P_{BAD}$ mntR: SEQ ID NO:2; $\Delta P_{mntR21}$::TT araC $P_{BAD}$ mntR: SEQ ID NO:3; $\Delta P_{mntR22}$::TT araC $P_{BAD}$ mntR: SEQ ID NO:4; $\Delta P_{mntR19}$::TT araC $P_{BAD}$ mntR: SEQ ID NO:5; $\Delta P_{mntR27}$::TT araC $P_{BAD}$ mntR: SEQ ID NO:6.

FIG. 5 depicts a blot showing the determination of arabinose-regulated MntR protein expression among different recombinant strains. Lane 1: 0% arabinose; Lane 2: 0.002% arabinose; Lane 3: 0.02% arabinose; Lane 4 0.2% arabinose.

FIG. 6 depicts a blot showing the arabinose regulated expression of SitA. Lane 1: 0% arabinose; Lane 2 0.2% arabinose.

FIG. 7 depicts the DNA (SEQ ID NO:7) and amino acid (SEQ ID NO:8) sequences of the spvABCD operon with improved promoter inserted into the cysG deletion mutation (χ9876).

FIG. 8A depicts survival curves of mice after oral immunization with RASV-V antigen, RASV control, or BSG after PO *Yersinia pseudotuberculosis* challenge. The abbreviations and nomenclature used in this figure are as follows: RASV: recombinant *Salmonella* attenuated vaccine, vector control χ8501(pYA3620); RASV-Vag: RASV that express the truncated Vag (131-1327 aa), from *Y. pestis* (KIM) χ8501 (pYA3841); Challenge: *Y. pseudotuberculosis* (PB1/+), High dose: $10^8$ or Low dose: $10^7$.

FIG. 8B depicts survival curves of mice after oral immunization with RASV-V antigen, RASV control, or BSG after PO *Yersinia pseudotuberculosis* challenge. The abbreviations and nomenclature used in this figure are as follows: RASV: recombinant *Salmonella* attenuated vaccine, vector control χ8501(pYA3620) and χ9641(pYA3620); RASV-Vag: RASV that express the truncated Vag (131-1327 aa), from *Y. pestis* (KIM) χ8501(pYA3841) and χ9641(pYA3841); Challenge: *Y. pseudotuberculosis* (PB1/+), dose: $10^8$.

FIG. 8C depicts survival curves of mice after oral immunization with RASV-V antigen, RASV control, or BSG after PO *Yersinia enterocolitica* challenge. The abbreviations and nomenclature used in this figure are as follows: RASV: recombinant *Salmonella* attenuated vaccine, vector control χ8501(pYA3620); RASV-Vag: RASV that express the truncated Vag (131-1327 aa), from *Y. pestis* (KIM) χ8501 (pYA3841); Challenge: *Y. pseudotuberculosis* (PB1/+), dose: $10^9$.

FIG. 9 depicts the DNA (SEQ ID NO:9) and amino acid (SEQ ID NO:10) sequences of codon optimized psn of *Yersinia* and iucABCD iutA of *Shigella* inserted into cvaA and cvaB deletions of pAPEC-1.

FIG. 11 depicts the *Shigella* ipaD DNA (SEQ ID NO:11 and 12 (optimized)) and amino acid (SEQ ID NO:13) sequences.

Figure 12:
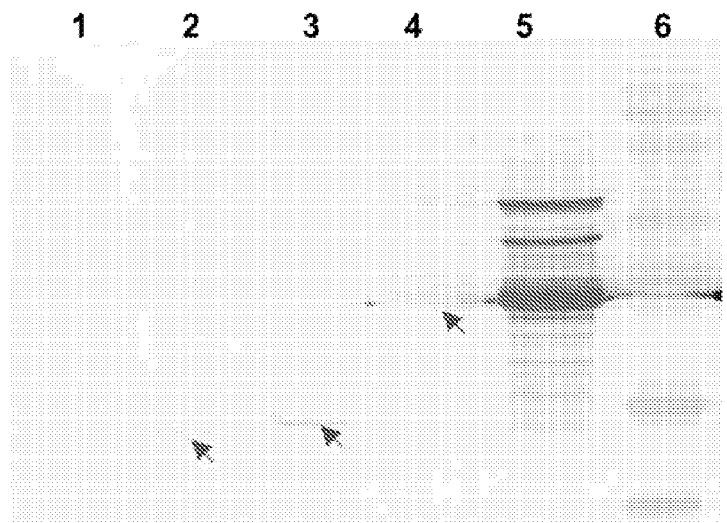

FIG. 12 depicts a blot showing the expression of ID1, ID2, ID and IDw fragments in χ7385. ID1 is 329 bp, corresponds to aa 60-162, and is ~11.7 kDa. ID2 is 377 bp, corresponds to aa 185-303, and is ~13.1 kDa. ID is 686 bp, corresponds to aa 10-162+185-303, and is ~24.8 kDa. IDw is 971 bp, corresponds to aa 23-333, and is ~34.4 kDa. Lane 1 is χ7385 (pYA3493); Lane 2 is χ7385 (pYA4415; ID1); Lane 3 is χ7385 (pYA4416; ID2); Lane 4 is χ7385 (pYA4417;ID); Lane 5 is χ7385 (pYA4418;IDw); Lane 6 is a molecular weight marker.

Figure 13:
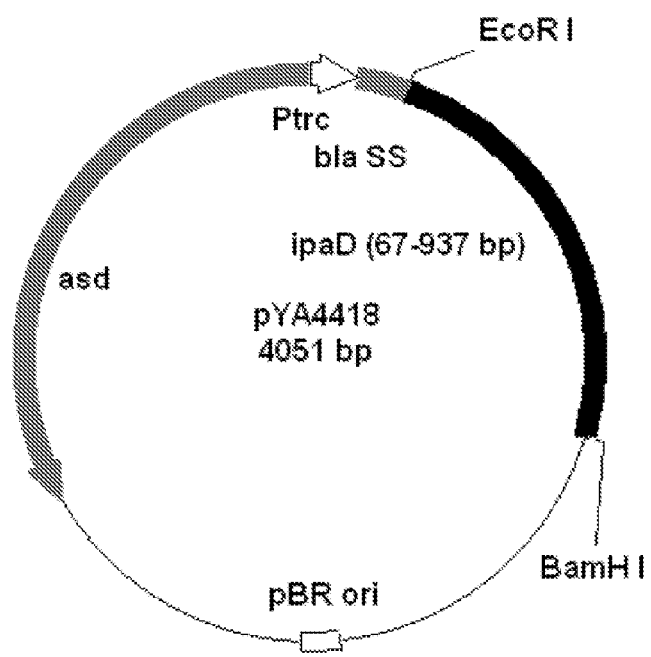

FIG. 13 depicts a diagram of pYA4418.

Figure 14A:
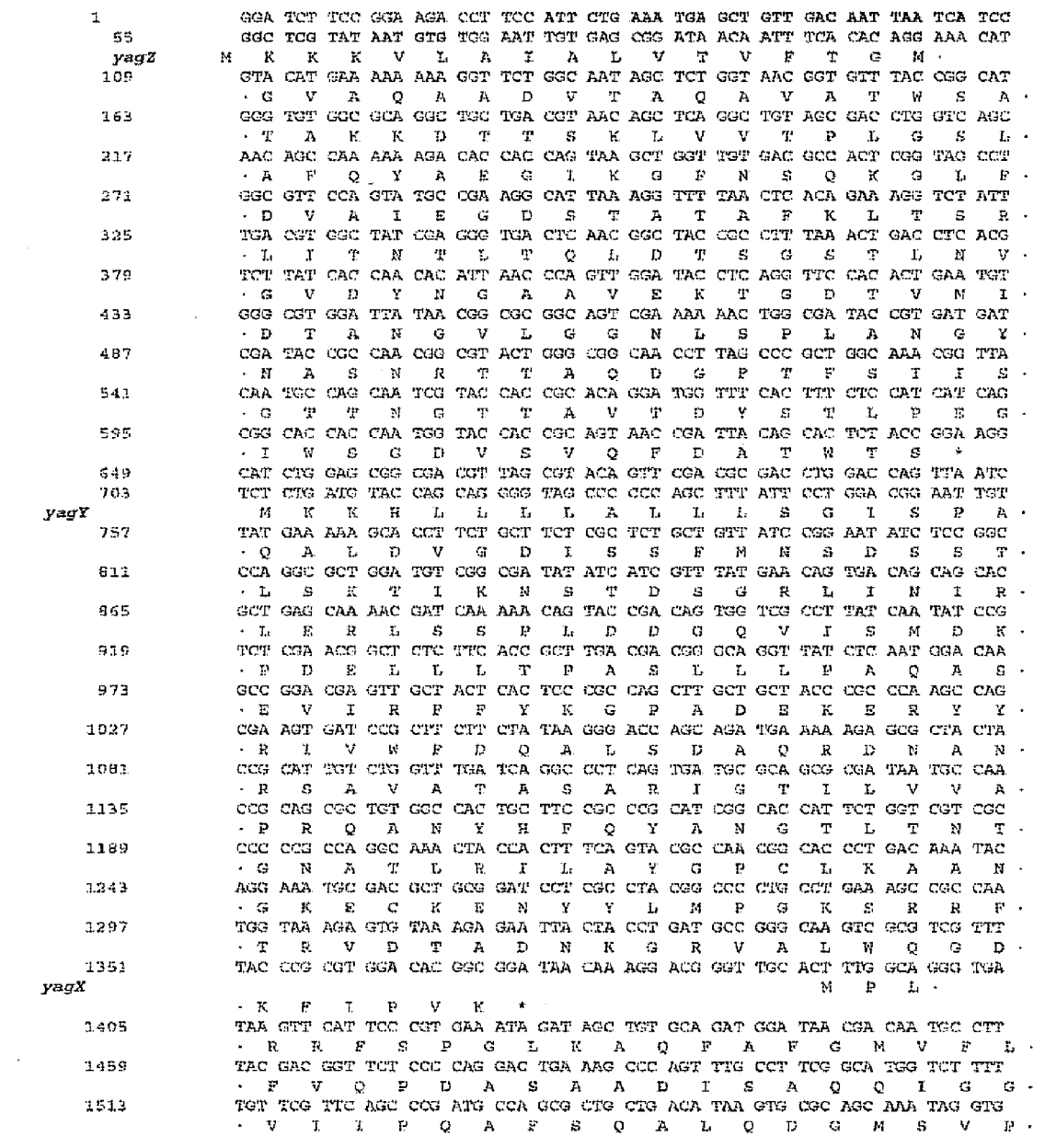

FIG. 14 depicts the DNA (SEQ ID NO:14) and amino acid (SEQ ID NO:15) sequence of vector pYA4428.

Figure 15:
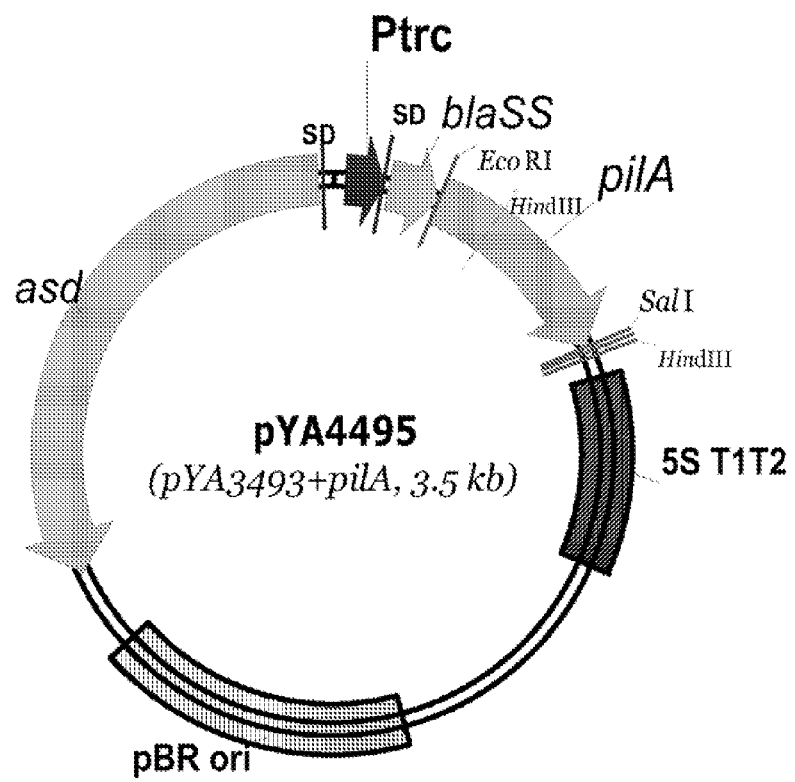

FIG. 15 depicts a diagram of pYA4495. pilA was cloned into the Asd+ expression plasmid pYA3493 to yield pYA4495.

Figure 16:
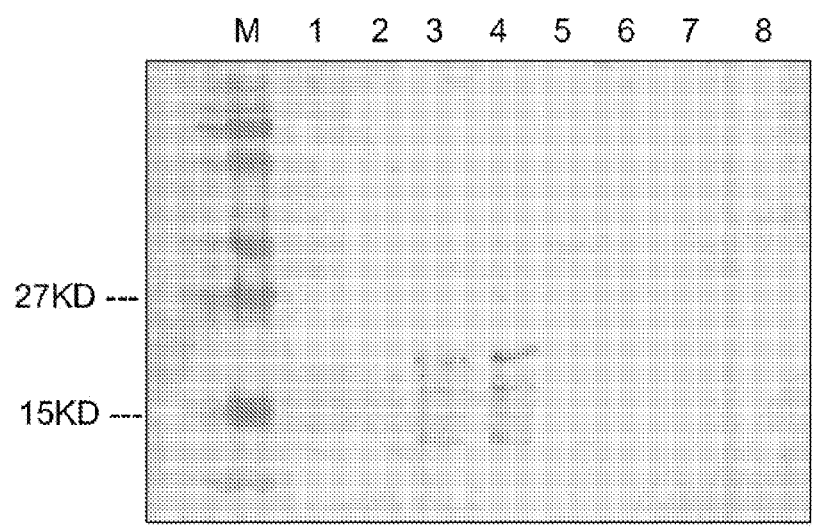

FIG. 16 depicts a blot showing the detection of PilA fusion protein in *S. Typhimurium* strain χ9088 (pYA4495). The western blot was probed with anti-PilA antibody. Lane M—Fermentas pre-stained protein ladder; Lane 1—χ9088 (pYA3493) negative control; Lane 2—NA; Lane 3—χ9088 (pYA4495) isolate 1; Lane 4—χ9088 (pYA4495) isolate 2.

FIG. 17 depicts the nucleic acid sequence (SEQ ID NO:16), the codon and G+C optimized pilA gene with G+C=45% (original G+C=32%) (SEQ ID NO:17), and the amino acid sequence (SEQ ID NO:18) of PilA.

FIG. 18 depicts the nucleic acid sequence (SEQ ID NO:19), codon and G+C optimized cjaA gene with G+C=44% (original G+C=32%) (SEQ ID NO:20), and the amino acid sequence (SEQ ID NO:21) of CjaA.

Figure 19:
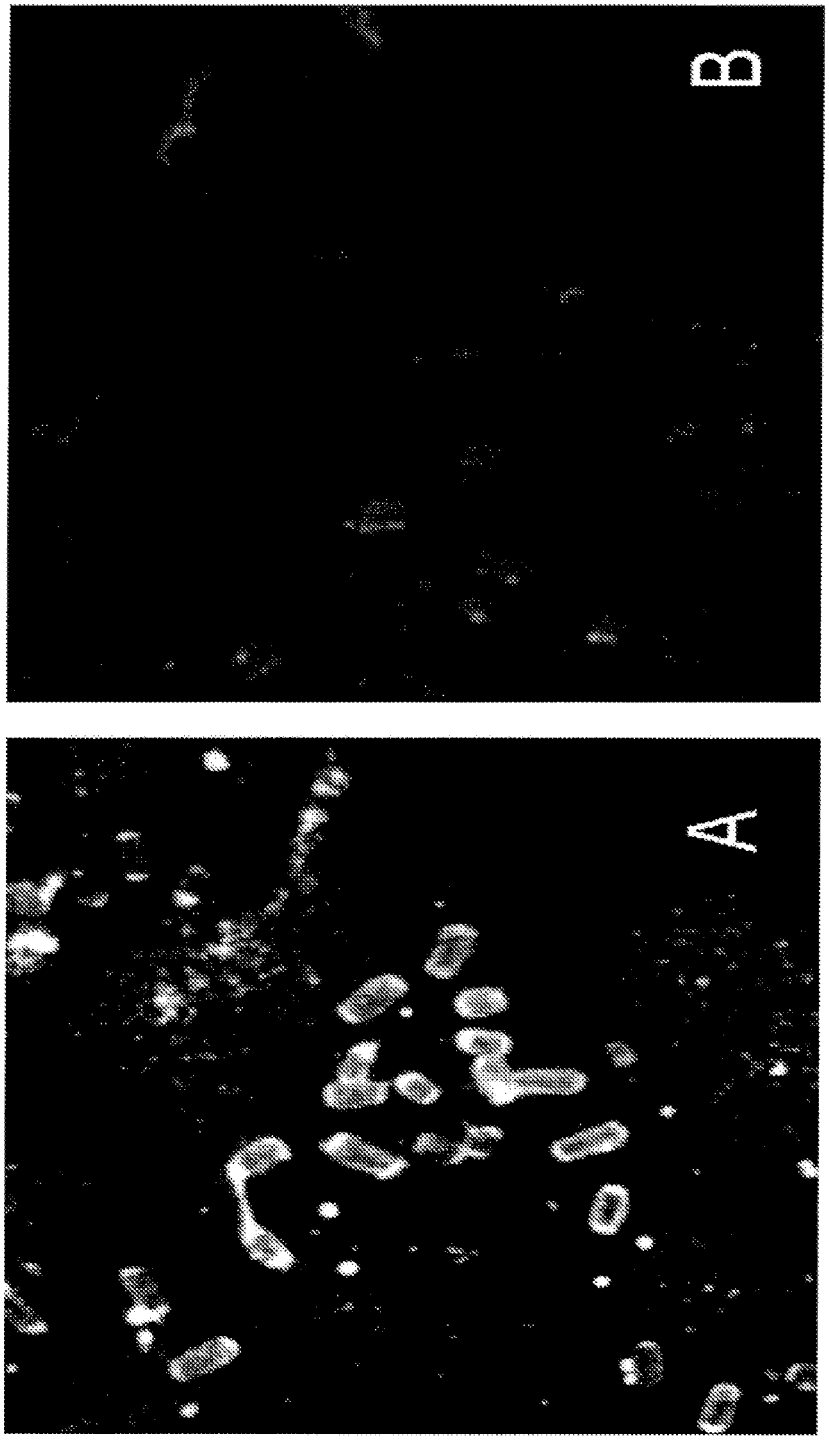

FIG. 19 depicts indirect immunofluorescence assay on *C. perfringens* bacteria with serum obtained from chickens immunized with recombinant PlcC (A) and control serum (B).

FIG. 20 depicts the predicted amino acid sequence (SEQ ID NO:22) of α-toxin (Plc) mature protein sequence of CP995 a NE isolate. Underlined fragment, amino acid 248-370, represents the C-terminal domain (PlcC), the antigen used to elicit an immune response.

FIG. 21 depicts a diagram of the plasmids for expression of plcC in a recombinant *Salmonella* bacterium.

FIG. 22 depicts the nucleic acid sequence (SEQ ID NO:23), the codon and G+C content optimized plcC gene with G+C=45% (original G+C=32%) (SEQ ID NO:24), and the amino acid sequence (SEQ ID NO:25) of PlcC.

FIG. 23 depicts the nucleic acid sequence (SEQ ID NO:26), the codon and G+C content optimized netB gene with G+C=45% (original G+C=27%) (SEQ ID NO:27), and the amino acid sequence (SEQ ID NO:28) of NetB.

Figure 24:
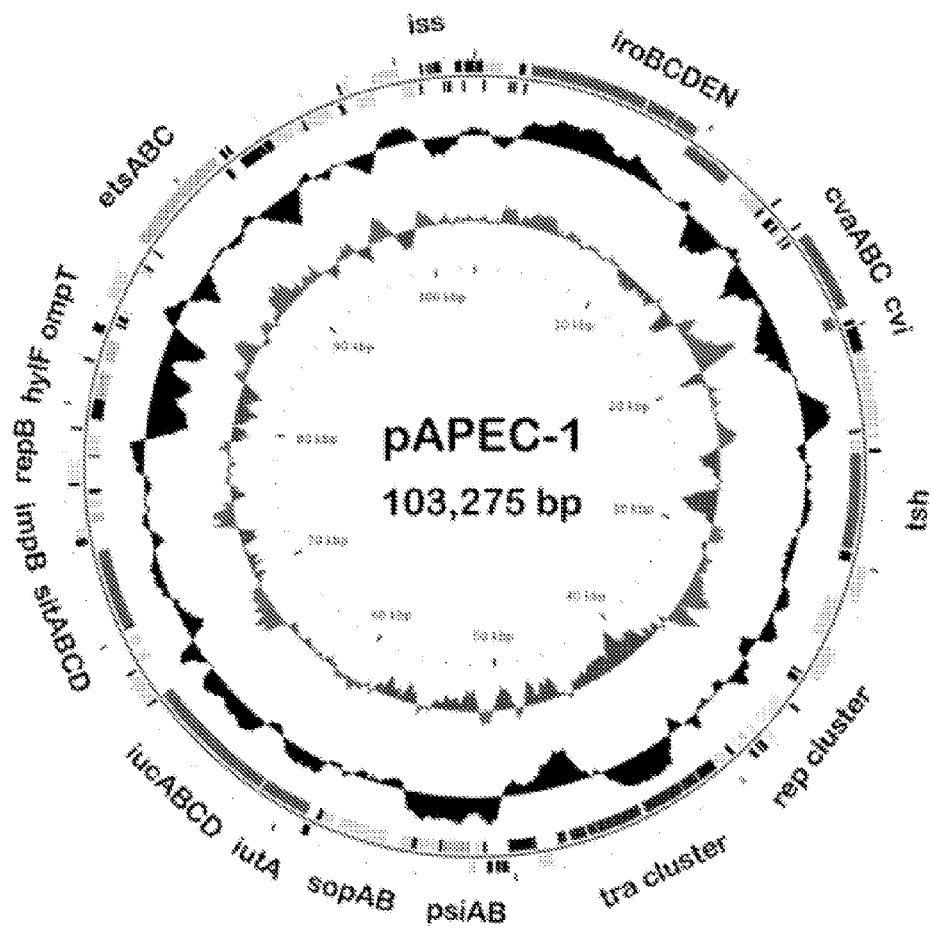

FIG. 24 depicts a diagram of pAPEC-1.

Figure 25:
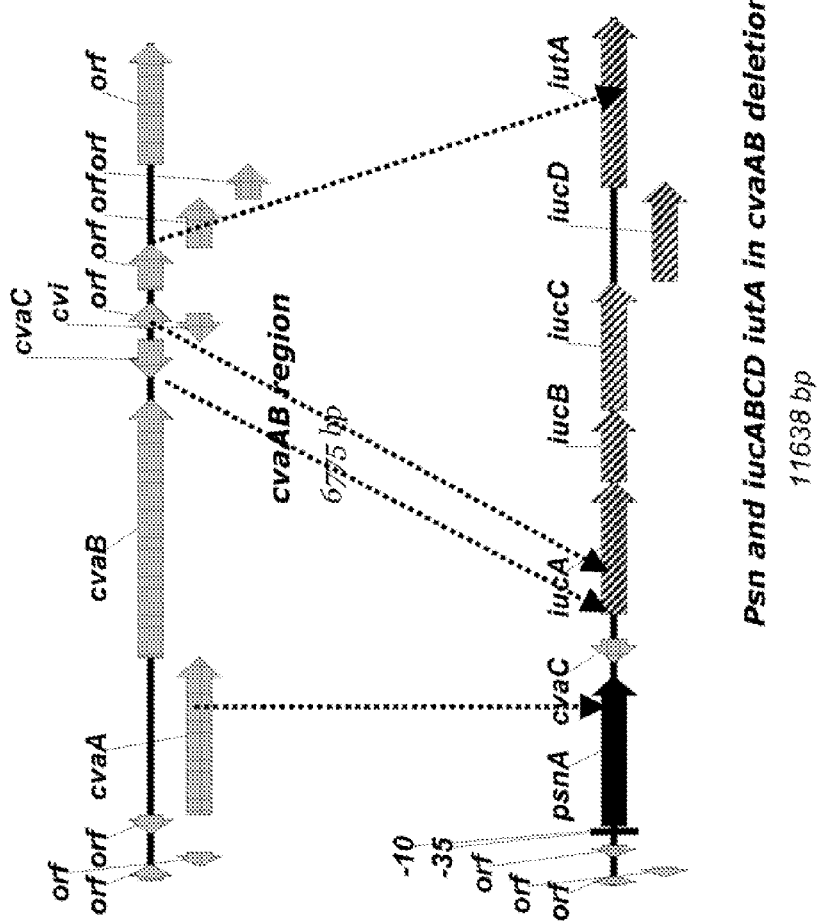

FIG. 25 depicts psn and iucABCD iutA in cvaAB deletions.

FIG. 26 depicts mutations to modify sites of LCRV interaction with the receptor (SEQ ID NO:29 and 30).

DETAILED DESCRIPTION OF THE INVENTION

The present invention provides a recombinant bacterium capable of eliciting an immune response against at least two enteric pathogens in addition to at least one *Salmonella* serotype. In some embodiments, the recombinant bacterium elicits an immune response against at least two *Salmonella* serotypes and at least two additional enteric pathogens. In an exemplary embodiment, the recombinant bacterium does not substantially induce an immune response to the serotype of the recombinant bacterium. The invention also encompasses a vaccine composition comprising the recombinant bacterium and methods for using the recombinant bacterium.

I. Recombinant Bacterium

One aspect of the present invention encompasses a recombinant *Salmonella* bacterium. Generally speaking, the recombinant bacterium is capable of the expression of at least one nucleic acid encoding at least two enteric antigens. The bacterium, when administered to a host, typically elicits an immune response against at least two enteric pathogens and at least one *Salmonella* serotype. In exemplary embodiments, the recombinant bacterium does not substantially induce an immune response specific to the serotype of the recombinant bacterium.

In additional exemplary embodiments, a recombinant *Salmonella* bacterium of the invention is capable of colonizing a host to substantially the same extent as a wild-type bacterium of the same serotype. A bacterium of the invention, however, will preferably be substantially avirulent after colonization.

In some embodiments, the recombinant bacterium may be a *Salmonella enterica* serovar. In an exemplary embodiment, a bacterium of the invention may be derived from *S. Typhimurium, S. Typhi, S. Paratyphi, S. Gallinarum, S. Enteritidis, S. Choleraesius, S. Arizonae,* or *S. Dublin.* In an exemplary embodiment, a bacterium of the invention may be derived from *S. Typhimurium, S. Paratyphi,* or *S. Typhi.* In all cases, a recombinant bacterium of the invention generally does not comprise any drug resistance nucleic acid sequences or other sequence scars in the chromosomes of the recombinant strain.

(a) Regulated Expression of a Nucleic Acid Encoding at Least One Serotype-Specific Antigen Generally speaking, a recombinant bacterium of the invention is capable of the regulated expression of a nucleic acid encoding at least one serotype-specific antigen. As used herein, the phrase "serotype-specific antigen" refers to an antigen that elicits an immune response specific for the bacterial vector serotype. In some embodiments, the immune response to a serotype-specific antigen may also recognize closely related strains in the same serogroup, but in a different, but related, serotype. Non-limiting examples of serotype-specific antigens may include LPS O-antigen, one or more components of a flagellum, and Vi capsular antigen. In some embodiments, the expression of at least one, at least two, at least three, or at least four nucleic acid sequences encoding a serotype-specific antigen are regulated in a bacterium of the invention.

The phrase "regulated expression of a nucleic acid encoding at least one serotype-specific antigen" refers to expression of the nucleic acid encoding a serotype-antigen such that the bacterium does not substantially induce an immune response specific to the bacterial vector serotype. In one embodiment, the expression of the serotype-specific antigen is eliminated. In another embodiment, the expression is substantially reduced. In yet another embodiment, the expression of the serotype-specific antigen is reduced in a temporally controlled manner. For instance, the expression of the serotype-specific antigen may be reduced during growth of the bacterium in a host, but not during in vitro growth.

The expression of a nucleic acid encoding a *Salmonella* serotype-specific antigen may be measured using standard molecular biology and protein chemistry techniques known to one of skill in the art. As used herein, "substantial reduction" of the expression of a nucleic acid encoding a serotype-specific antigen refers to a reduction of at least about 1% to at least about 99.9% as compared to a *Salmonella* bacterium in which no attempts have been made to reduce serotype-specific antigen expression. In one embodiment, the expression of a nucleic acid encoding a serotype-specific antigen is reduced by 100% by using a deletion mutation. In other embodiments of the invention, the expression of a nucleic acid encoding a serotype-specific antigen is reduced by at least about 99.9%, 99.5%, 99%, 98%, 97%, 96%, 95%, 94%, 93%, 92%, 91% or 90%. In yet other embodiments of the invention, the expression of a nucleic acid encoding a serotype-specific antigen is reduced by at least about 89%, 88%, 87%, 86%, 85%, 84%, 83%, 82%, 81% or 80%. In still other embodiments of the invention, the expression of a nucleic acid encoding a serotype-specific antigen is reduced by at least about 75%, 70%, 65%, 60%, 55%, or 50%. In additional embodiments, the expression of a nucleic acid encoding a serotype-specific antigen is reduced by at least about 45%, 40%, 35%, 30%, 25%, or 20%. In yet additional embodiments, the expression of a nucleic acid encoding a serotype-specific antigen is reduced by at least about 15%, 10%, 5%, 4%, 3%, 2% or 1%.

Methods of regulating expression of a nucleic acid encoding at least one serotype-specific antigen are discussed in detail below, and in the examples.

i. Regulating the Expression of a Nucleic Acid Encoding LPS O-Antigen

In one embodiment, the expression of a nucleic acid encoding the serotype-specific antigen LPS O-antigen is regulated by mutating the pmi nucleic acid sequence, which encodes a phosphomannose isomerase needed for the bacterium to interconvert fructose-6-P and mannose-6-P. In some instances, the bacterium comprises a Δpmi mutation, such as a Δpmi-2426 mutation. (See FIGS. 1A and 1B) A bacterium comprising a Δpmi-2426 mutation, grown in the presence of mannose, is capable of synthesizing a complete LPS O-antigen. But non-phosphorylated mannose, which is the form required for bacterial uptake, is unavailable in vivo. Hence, a bacterium comprising a Δpmi-2426 mutation loses the ability to synthesize LPS O-antigen serotype specific side chains after a few generations of growth in vivo. The LPS that is synthesized comprises a core structure that is substantially similar across many diverse *Salmonella* serotypes. This results in a bacterium that is capable of eliciting an immune response against at least two *Salmonella* serotypes without substantially inducing an immune response specific to the serotype of the bacterial vector.

A bacterium of the invention that comprises a Δpmi mutation may also comprise other mutations that ensure that mannose available to the bacterium during in vitro growth is used for LPS O-antigen synthesis. For instance, a bacterium may comprise a Δ(gmd-fcl)-26 mutation. This mutation deletes two nucleic acid sequences that encode enzymes for conversion of GDP-mannose to GDP-fucose. This ensures that mannose available to the bacterium during in vitro growth is used for LPS O-antigen synthesis and not colanic acid production. Similarly, a bacterium may comprise the Δ(wcaM-wza)-8 mutation, which deletes all 19 nucleic acid sequences necessary for colanic acid production, and also precludes conversion of GDP-mannose to GDP-fucose.

In addition to regulating LPS O-antigen synthesis with mannose, the synthesis of LPS O-antigen may be regulated by arabinose, which is also absent in vivo. For instance, a bacterium may comprise the mutation $\Delta P_{rfc}$::TT araC $P_{BAD}$ rfc. (P stands for promoter and TT stands for transcription terminator.) The rfc nucleic acid sequence is necessary for the addition of O-antigen subunits, which typically comprise three or four sugars, in a repeat fashion. When the rfc nucleic acid sequence is absent, only one O-antigen repeat subunit is added to the LPS core polysaccharide. Normally, the serotype-specific O-antigen contains some 50 or so repeats of the O-antigen subunit, catalyzed by the enzyme encoded by the rfc nucleic acid sequence. In the case of a bacterium comprising the $\Delta P_{rfc}$::TT araC $P_{BAD}$ rfc deletion-insertion mutation, expression of the rfc nucleic acid sequence is dependant on the presence of arabinose that can be supplied during in vitro growth of the strain, but that is absent in vivo. Consequently, rfc expression ceases in vivo, resulting in the cessation of assembly of the O-antigen repeat structure. This reduces the bacterium's ability to induce an immune response against the serotype-specific O-antigen.

Another means to regulate LPS O-antigen expression is to eliminate the function of galE in a recombinant bacterium of the invention. The galE nucleic acid sequence encodes an enzyme for the synthesis of UDP-Gal, which is a substrate for LPS O-antigen, the outer LPS core and colanic acid. Growth of a bacterium comprising a suitable galE mutation in the presence of galactose leads to the synthesis of O-antigen and the LPS core. Non-phosphorylated galactose is unavailable in vivo, however, and in vivo synthesis of UDP-Gal ceases, as does synthesis of the O-antigen and the LPS outer core. One example of a suitable galE mutation is the Δ(galE-ybhC)-851 mutation.

In certain embodiments, a bacterium of the invention may comprise one or more of the Δpmi, $\Delta P_{rfc}$::TT araC $P_{BAD}$ rfc, and ΔgalE mutations, with or without a Δ(gmd-fcl)-26 or Δ(wcaM-wza)-8 mutation. Such a combination may yield a recombinant bacterium that synthesizes all components of the LPS core and O-antigen side chains when grown in vitro (i.e. in the presence of suitable concentrations of mannose, arabinose and galactose), but that ceases to synthesize the LPS outer core and O-antigen in vivo due to the unavailability of free unphosphorylated mannose, arabinose or galactose. Also, a recombinant bacterium with the inability to synthesize the LPS outer core and/or O-antigen is attenuated, as the bacterium is more susceptible to macrophages and/or complement-mediated cytotoxicity. Additionally, a bacterium with the inability to synthesize the LPS outer core and O-antigen in vivo, induces only a minimal immune response to the serotype-specific LPS O-antigen.

The regulated expression of one or more nucleic acids that enable synthesis of LPS O-antigen allows a recombinant bacterium of the invention to be supplied with required sugars such as mannose, arabinose and/or galactose during in vitro growth of the bacterium, ensuring complete synthesis of the LPS O-antigen. This is important, because the presence of the O-antigen on the recombinant bacterium cell surface is indispensable for the strain to invade and colonize lymphoid tissue, a necessary prerequisite for being immunogenic. In vivo, LPS O-antigen synthesis ceases due to the unavailability of the free unphosphorylated sugars. Consequently, the recombinant bacterium is attenuated, becoming more susceptible to complement-mediated cytotoxicity and macrophage phagocytosis. Also, when LPS O-antigen synthesis ceases, the LPS core is exposed. The core is a cross-reactive antigen with a similar structure in all *Salmonella* serotypes. In addition, when LPS O-antigen synthesis ceases, any cross-reactive outer membrane proteins expressed by the recombinant bacterium are exposed for surveillance by the host immune system.

ii. The Expression of a Nucleic Acid Encoding a Component of a Flagellum

In one embodiment, the expression of a nucleic acid encoding a serotype-specific component of a flagellum is regulated by mutating the nucleic acid that encodes FljB or FliC. For instance, a bacterium of the invention may comprise a ΔfljB217 mutation. Alternatively, a bacterium may comprise a ΔfliCI80 mutation. The ΔfljB217 mutation deletes the structural nucleic acid sequence that encodes the Phase II flagellar antigen whereas the ΔfliCI80 mutation deletes the 180 amino acids encoding the antigenically variable serotype-specific domain of the Phase I FliC flagellar antigen. The portion of the flagellar protein that interacts with TLR5 to recruit/stimulate innate immune responses represents the conserved N- and C-terminal regions of the flagellar proteins and this is retained and expressed by strains with the ΔfliCI80 mutation. In addition, the ΔfliCI80 mutation retains the CD4-dependent T-cell epitope. It should be noted, that expression of the Phase I flagellar antigen and not the Phase II flagellar antigen potentiates *S. Typhimurium* infection of mice. *S. Typhimurium* recombinant bacteria with the Δpmi-2426, AfljB2I7 and ΔfliC180 mutations, when grown in the absence of mannose, are not agglutinated with antisera specific for the B-group O-antigen or the *S. Typhimurium* specific anti-flagellar sera. These recombinant bacteria are also non-motile since the FliC180 protein that is synthesized at high levels is not efficiently incorporated into flagella. When these recombinant bacteria are evaluated using HEK293 cells specifically expressing TLR5, the level of NFκB production is about 50% higher than when using a ΔfliB217 F1iC$^{+}$ strain that assembles flagellin into flagella and exhibits motility (there is no NFκB production by the control ΔfljB217 ΔfliC2426 strain with no flagella). Similarly, recombinant bacteria with the Δ(galE-ybhC)-851, ΔfljB217 and ΔfliC180 mutations, when grown in the absence of galactose, are not agglutinated with antisera specific for the B-group O-antigen or the *S. Typhimurium* specific anti-flagellar sera. These bacteria are also non-motile.

iii. The Expression of a Nucleic Acid Encoding the Vi Capsular Antigen

Certain *Salmonella* strains, such as *S. Typhi* and *S. Dublin*, express the Vi capsular antigen. This antigen is serotype-specific, inhibits invasion, and acts to suppress induction of a protective immune response. Consequently, when a recombinant bacterium of the invention is derived from a strain comprising the Vi capsular antigen, one or more nucleic acids encoding the Vi capsular antigen will be deleted such that the Vi capsular antigen is not synthesized.

(b) Expression of at Least One Enteric Antigen

Generally speaking, a recombinant bacterium of the invention is capable of the expression of at least one nucleic acid encoding at least two enteric antigens. As used herein, the phrase "enteric antigen" refers to an antigen that elicits an immune response against an enteric pathogen. Non-limiting examples of enteric antigens from *Yersinia* may include the V antigen and the psn nucleic acid product involved in iron acquisition. Non-limiting examples of enteric antigens from *E. coli* may include salmochelin, aerobactin, the sit operon antigens involved in iron and manganese uptake, the fimbriae encoded by the yagZ fimbrial operon, other fimbriae encoded by nucleic acids in various ETEC, EPEC, EHEC, APEC, UPEC and/or ExPEC strains, the tsh nucleic acid product, the iss nucleic acid product, and LTB, the non-toxic cell binding domain of the LT toxin. Non-limiting examples of enteric antigens from *Shigella* may include the IpaD and aerobactin antigens. Non-limiting examples of enteric antigens from *C. jejuni* may include PilA and CjaA antigen. Non-limiting examples of enteric antigens from *C. perfringens* may include the α-toxin and NetB antigens.

It is not necessary that the nucleic acid encoding an enteric antigen comprise the complete nucleic acid sequence of the antigen. It is only necessary that the enteric antigen sequence used be capable of eliciting an immune response. The antigen may be one that was not found in that exact form in the parent organism. For example, a sequence coding for an antigen comprising 100 amino acid residues may be transferred in part into a recombinant bacterium so that a peptide comprising only 75, 65, 55, 45, 35, 25, 15, or even 10, amino acid residues is produced by the recombinant bacterium. Alternatively, if the amino acid sequence of a particular enteric antigen or fragment thereof is known, it may be possible to chemically synthesize the nucleic acid fragment or analog thereof by means of automated nucleic acid sequence synthesizers, PCR, or the like and introduce said nucleic acid sequence into the appropriate copy number vector.

In certain embodiments, an enteric antigen of the invention may comprise a B cell epitope or a T cell epitope. Alternatively, an antigen to which an immune response is desired may be expressed as a fusion to a carrier protein that contains a strong promiscuous T cell epitope and/or serves as an adjuvant and/or facilitates presentation of the antigen to enhance, in all cases, the immune response to the antigen or its component part. This can be accomplished by methods known in the art. Fusion to tetnus toxin fragment C, CT-B, LT-B, hepatitis virus B core, and woodchuck hepatitis virus core are particularly useful for these purposes, although other epitope presentation systems are well known in the art.

In certain embodiments, the expression of at least one nucleic acid encoding at least two enteric antigens may be regulated. In further embodiments, a nucleic acid sequence encoding an antigen of the invention may comprise a secretion signal. In other embodiments, an antigen of the invention may be toxic to the recombinant bacterium.

A recombinant bacterium may comprise a long sequence of nucleic acid encoding several nucleic acid sequence products, one or all of which may be enteric antigens. In some embodiments, the expression of at least one, at least two, at least three, at least four, at least five, at least six, or more nucleic acids encoding enteric antigens is regulated in a bacterium of the invention. These antigens may be encoded by two or more open reading frames operably linked to be expressed coordinately as an operon, wherein each antigen is synthesized independently. Alternatively, the two or more antigens may be encoded by a single open reading frame such that the antigens are synthesized as a fusion protein. In another alternative, the two or more antigens may be encoded by overlapping open reading frames.

In many cases, the high level expression of a nucleic acid sequence encoding an antigen in a bacterium reduces the bacterium's fitness, such that the bacterium grows slowly, is susceptible to stresses encountered in the host, and is generally less able to effectively colonize effector lymphoid tissues. High level expression of a nucleic acid sequence encoding an antigen, however, is highly desirable to maximize induction of an immune response against the antigen. Consequently, the phrase "regulated expression of at least one nucleic acid encoding at least two enteric antigens" refers to expression at least one nucleic acid encoding at least two enteric antigens in a bacterium such that the bacterium is capable of colonizing a host at levels similar to a wild-type bacterium, and yet is still capable of eliciting an immune response against an enteric pathogens when administered to the host. Methods of expressing, or regulating the expression of, at least one nucleic acid encoding at least two enteric antigens are discussed in detail below, and in the examples.

i. Chromosomally Integrated Nucleic Acid Sequence Encoding a Repressor

In one embodiment, the expression of a nucleic acid sequence encoding an enteric antigen is regulated by a chromosomally integrated nucleic acid sequence encoding a repressor and a vector. For instance, a recombinant bacterium of the invention that is capable of the regulated expression of a nucleic acid sequence encoding at least one enteric antigen may comprise, in part, at least one chromosomally integrated nucleic acid sequence encoding a repressor. Typically, the nucleic acid sequence encoding a repressor is operably linked to a regulatable promoter. The nucleic acid sequence encoding a repressor and/or the promoter may be modified from the wild-type nucleic acid sequence so as to optimize the expression level of the nucleic acid sequence encoding the repressor.

Methods of chromosomally integrating a nucleic acid sequence encoding a repressor operably-linked to a regulatable promoter are known in the art and detailed in the examples. Generally speaking, the nucleic acid sequence encoding a repressor should not be integrated into a locus that disrupts colonization of the host by the recombinant bacterium, or attenuates the bacterium. In one embodiment, the nucleic acid sequence encoding a repressor may be integrated into the relA nucleic acid sequence. In another embodiment, the nucleic acid sequence encoding a repressor may be integrated into the endA nucleic acid sequence.

In some embodiments, at least one nucleic acid sequence encoding a repressor is chromosomally integrated. In other embodiments, at least two, or at least three nucleic acid sequences encoding repressors may be chromosomally integrated into the recombinant bacterium. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

A. Repressor

As used herein, "repressor" refers to a biomolecule that represses transcription from one or more promoters. Generally speaking, a suitable repressor of the invention is synthesized in high enough quantities during the in vitro growth of the bacterial strain to repress the transcription of the nucleic acid encoding an antigen of interest on the vector, as detailed below, and not impede the in vitro growth of the strain. Additionally, a suitable repressor will generally be substantially stable, i.e. not subject to proteolytic breakdown. Furthermore, a suitable repressor will be diluted by about half at every cell division after expression of the repressor ceases, such as in a non-permissive environment (e.g. an animal or human host).

The choice of a repressor depends, in part, on the species of the recombinant bacterium used. For instance, the repressor is usually not derived from the same species of bacteria as the recombinant bacterium. For instance, the repressor may be derived from *E. coli* if the recombinant bacterium is from the genus *Salmonella*. Alternatively, the repressor may be from a bacteriophage.

Suitable repressors are known in the art, and may include, for instance, LacI of *E. coli*, C2 encoded by bacteriophage P22, or C1 encoded by bacteriophage λ. Other suitable repressors may be repressors known to regulate the expression of a regulatable nucleic acid sequence, such as nucleic acid sequences involved in the uptake and utilization of sugars. In one embodiment, the repressor is LacI. In another embodiment, the repressor is C2. In yet another embodiment, the repressor is C1.

B. Regulatable Promoter

The chromosomally integrated nucleic acid sequence encoding a repressor is operably linked to a regulatable promoter. The term "promoter", as used herein, may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. The term "operably linked," as used herein, means that expression of a nucleic acid is under the control of a promoter with which it is spatially connected. A promoter may be positioned 5' (upstream) of the nucleic acid under its control. The distance between the promoter and a nucleic acid to be expressed may be approximately the same as the distance between that promoter and the native nucleic acid sequence it controls. As is known in the art, variation in this distance may be accommodated without loss of promoter function.

The regulated promoter used herein generally allows transcription of the nucleic acid sequence encoding a repressor while in a permissive environment (i.e. in vitro growth), but ceases transcription of the nucleic acid sequence encoding a repressor while in a non-permissive environment (i.e. during growth of the bacterium in an animal or human host). For instance, the promoter may be sensitive to a physical or chemical difference between the permissive and non-permissive environment. Suitable examples of such regulatable promoters are known in the art.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{BAD}$ system. The araC-$P_{BAD}$ system is a tightly regulated expression system that has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{BAD}$. For use as described herein, a cassette with the araC nucleic acid sequence and the araC-araBAD promoter may be used. This cassette is referred to herein as araC-P$_{BAD}$. The AraC protein is both a positive and negative regulator of P$_{BAD}$. In the presence of arabinose, the AraC protein is a positive regulatory element that allows expression from P$_{BAD}$. In the absence of arabinose, the AraC protein represses expression from P$_{BAD}$. This can lead to a 1,200-fold difference in the level of expression from P$_{BAD}$.

Other enteric bacteria contain arabinose regulatory systems homologous to the araC araBAD system from *E. coli*. For example, there is homology at the amino acid sequence level between the *E. coli* and the *S. Typhimurium* AraC proteins, and less homology at the DNA level. However, there is high specificity in the activity of the AraC proteins. For example, the *E. coli* AraC protein activates only *E. coli* P$_{BAD}$ (in the presence of arabinose) and not *S. Typhimurium* P$_{BAD}$. Thus, an arabinose regulated promoter may be used in a recombinant bacterium that possesses a similar arabinose operon, without substantial interference between the two, if the promoter and the operon are derived from two different species of bacteria.

Generally speaking, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In other embodiments, the promoter may be responsive to the level of maltose in the environment. Generally speaking, maltose may be present during the in vitro growth of a bacterium, while typically absent from host tissue. The malT nucleic acid encodes MalT, a positive regulator of four maltose-responsive promoters (P$_{PQ}$, P$_{EFG}$, P$_{KBM}$, and P$_S$). The combination of malT and a mal promoter creates a tightly regulated expression system that has been shown to work as a strong promoter induced by the addition of maltose (6). Unlike the araC-P$_{BAD}$ system, malT is expressed from a promoter (P$_T$) functionally unconnected to the other mal promoters. P$_T$ is not regulated by MalT. The malEFG-malKBM promoter is a bidirectional promoter controlling expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by the malT nucleic acid sequence product, is referred to herein as P$_{KBM}$, and the portion of the malEFG-malKBM promoter that mediates expression of the malEFG nucleic acid sequence, and that is controlled by the malT nucleic acid sequence product, is referred to herein as P$_{EFG}$. Full induction of P$_{KBM}$ requires the presence of the MalT binding sites of P$_{EFG}$. For use in the vectors and systems described herein, a cassette with the malT nucleic acid sequence and one of the mal promoters may be used. This cassette is referred to herein as ma/T-P$_{mal}$. In the presence of maltose, the MalT protein is a positive regulatory element that allows expression from P$_{mal}$.

In still other embodiments, the promoter may be sensitive to the level of rhamnose in the environment. Analogous to the araC-P$_{BAD}$ system described above, the rhaRS-P$_{rhaB}$ activator-promoter system is tightly regulated by rhamnose. Expression from the rhamnose promoter (P$_{rha}$) is induced to high levels by the addition of rhamnose, which is common in bacteria but rarely found in host tissues. The nucleic acid sequences rhaBAD are organized in one operon that is controlled by the P$_{rhaBAD}$ promoter. This promoter is regulated by two activators, RhaS and RhaR, and the corresponding nucleic acid sequences belong to one transcription unit that is located in the opposite direction of the rhaBAD nucleic acid sequences. If L-rhamnose is available, RhaR binds to the P$_{rhaRS}$ promoter and activates the production of RhaR and RhaS. RhaS together with L-rhamnose in turn binds to the P$_{rhaBAD}$ and the P$_{rhaT}$ promoter and activates the transcription of the structural nucleic acid sequences. Full induction of rhaBAD transcription also requires binding of the Crp-cAMP complex, which is a key regulator of catabolite repression.

Although both L-arabinose and L-rhamnose act directly as inducers for expression of regulons for their catabolism, important differences exist in regard to the regulatory mechanisms. L-Arabinose acts as an inducer with the activator AraC in the positive control of the arabinose regulon. However, the L-rhamnose regulon is subject to a regulatory cascade; it is therefore subject to even tighter control than the araC P$_{BAD}$ system. L-Rhamnose acts as an inducer with the activator RhaR for synthesis of RhaS, which in turn acts as an activator in the positive control of the rhamnose regulon. In the present invention, rhamnose may be used to interact with the RhaR protein and then the RhaS protein may activate transcription of a nucleic acid sequence operably-linked to the P$_{rhaBAD}$ promoter.

In still other embodiments, the promoter may be sensitive to the level of xylose in the environment. The xylR-P$_{xylA}$ system is another well-established inducible activator-promoter system. Xylose induces xylose-specific operons (xylE, xylFGHR, and xylAB) regulated by XylR and the cyclic AMP-Crp system. The XylR protein serves as a positive regulator by binding to two distinct regions of the xyl nucleic acid sequence promoters. As with the araC-P$_{BAD}$ system described above, the xylR-P$_{xylAB}$ and/or xylR-P$_{xylFGH}$ regulatory systems may be used in the present invention. In these embodiments, xylR P$_{xylAB}$ xylose interacting with the XylR protein activates transcription of nucleic acid sequences operably-linked to either of the two P$_{xyl}$ promoters.

The nucleic acid sequences of the promoters detailed herein are known in the art, and methods of operably-linking them to a chromosomally integrated nucleic acid sequence encoding a repressor are known in the art and detailed in the examples.

C. Modification to Optimize Expression

A nucleic acid sequence encoding a repressor and regulatable promoter detailed above, for use in the present invention, may be modified so as to optimize the expression level of the nucleic acid sequence encoding the repressor. The optimal level of expression of the nucleic acid sequence encoding the repressor may be estimated, or may be determined by experimentation. Such a determination should take into consideration whether the repressor acts as a monomer, dimer, trimer, tetramer, or higher multiple, and should also take into consideration the copy number of the vector encoding the antigen of interest, as detailed below. In an exemplary embodiment, the level of expression is optimized so that the repressor is synthesized while in the permissive environment (i.e. in vitro growth) at a level that substantially inhibits the expression of a nucleic acid sequence encoding an enteric antigen, and is substantially not synthesized in a non-permissive environment, thereby allowing expression of the nucleic acid encoding an enteric antigen.

As stated above, the level of expression may be optimized by modifying the nucleic acid sequence encoding the repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor.

For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding the repressor may be altered so as to mimic the codons from highly synthesized proteins of a particular organism. In a further embodiment, modify may refer to altering the GC content of the nucleic acid sequence encoding the repressor to change the level of translation of the mRNA encoding the repressor.

In some embodiments, more than one modification or type of modification may be performed to optimize the expression level of the nucleic acid sequence encoding the repressor. For instance, at least one, two, three, four, five, six, seven, eight, or nine modifications, or types of modifications, may be performed to optimize the expression level of the nucleic acid sequence encoding the repressor.

By way of non-limiting example, when the repressor is LacI, then the nucleic acid sequence of LacI and the promoter may be altered so as to increase the level of LacI synthesis. In one embodiment, the start codon of the LacI repressor may be altered from GTG to ATG. In another embodiment, the SD sequence may be altered from AGGG to AGGA. In yet another embodiment, the codons of lacI may be optimized according to the codon usage for highly synthesized proteins of *Salmonella*. In a further embodiment, the start codon of lacI may be altered, the SD sequence may be altered, and the codons of lacI may be optimized.

Methods of modifying the nucleic acid sequence encoding the repressor and/or the regulatable promoter are known in the art and detailed in the examples.

D. Transcription Termination Sequence

In some embodiments, the chromosomally integrated nucleic acid sequence encoding the repressor further comprises a transcription termination sequence. A transcription termination sequence may be included to prevent inappropriate expression of nucleic acid sequences adjacent to the chromosomally integrated nucleic acid sequence encoding the repressor and regulatable promoter.

E. Vector

A recombinant bacterium of the invention may also comprise a vector. For instance a bacterium that is capable of the regulated expression of at least one nucleic acid sequence encoding at least one enteric antigen may also comprise, in part, a vector. The vector comprises a nucleic acid sequence encoding at least one enteric antigen operably linked to a promoter. The promoter is preferably regulated by the chromosomally encoded repressor, such that the expression of the nucleic acid sequence encoding an antigen is repressed during in vitro growth of the bacterium, but the bacterium is capable of high level synthesis of the antigen in an animal or human host. In some cases, however, such regulated expression is not necessary, such as for expression of fimbrial adhesins encoded on a low copy number vector or where the synthesis of the enteric protective antigen does not compromise the growth and/or colonizing ability of the vaccine strain.

As used herein, "vector" refers to an autonomously replicating nucleic acid unit. The present invention can be practiced with any known type of vector, including viral, cosmid, phasmid, and plasmid vectors. The most preferred type of vector is a plasmid vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses or mucosal immune responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR on or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

A vector may comprise at least one nucleic acid sequence encoding at least two enteric antigens as detailed above.

F. Promoter Regulated by Repressor

The vector may comprise a nucleic acid sequence encoding at least one enteric antigen operably-linked to a promoter regulated by the repressor, encoded by a chromosomally integrated nucleic acid sequence. One of skill in the art would recognize, therefore, that the selection of a repressor dictates, in part, the selection of the promoter operably-linked to a nucleic acid sequence encoding an antigen of interest. For instance, if the repressor is LacI, then the promoter may be selected from the group consisting of LacI responsive promoters, such as $P_{trc}$, $P_{lac}$, $P_{T7lac}$ and $P_{tac}$. If the repressor is C2, then the promoter may be selected from the group consisting of C2 responsive promoters, such as P22 promoters $P_L$ and $P_R$.

If the repressor is C1, then the promoter may be selected from the group consisting of C1 responsive promoters, such as λ promoters $P_L$ and $P_R$.

In each embodiment herein, the promoter regulates expression of a nucleic acid sequence encoding the antigen, such that expression of the nucleic acid sequence encoding an antigen is repressed when the repressor is synthesized (i.e. during in vitro growth of the bacterium), but expression of the nucleic acid sequence encoding an antigen is high when the repressor is not synthesized (i.e. in an animal or human host). Generally speaking, the concentration of the repressor will decrease with every cell division after expression of the nucleic acid sequence encoding the repressor ceases. In some embodiments, the concentration of the repressor decreases enough to allow high level expression of the nucleic acid sequence encoding an enteric antigen after about 2, 3, 4, 5, 6, 7, 8, 9, 10, 11, or 12 divisions of the bacterium. In an exemplary embodiment, the concentration of the repressor decreases enough to allow high level expression of the nucleic acid sequence encoding an enteric antigen after about 5 divisions of the bacterium in an animal or human host.

In certain embodiments, the promoter may comprise other regulatory elements. For instance, the promoter may comprise lacO if the repressor is LacI. This is the case with the lipoprotein promoter $P_{lpp}$ that is regulated by LacI since it possesses the LacI binding domain lacO.

In one embodiment, the repressor is a LacI repressor and the promoter is $P_{trc}$.

G. Expression of the Nucleic Acid Sequence Encoding an Antigen

As detailed above, generally speaking the expression of the nucleic acid sequence encoding the enteric antigen should be repressed when the repressor is synthesized. For instance, if the repressor is synthesized during in vitro growth of the bacterium, expression of the nucleic acid sequence encoding the enteric antigen should be repressed. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceeding low, it is likely to be detectable using very sensitive methods since repression can never by absolute.

Conversely, the expression of the nucleic acid sequence encoding the antigen should be high when the expression of the nucleic acid sequence encoding the repressor is repressed. For instance, if the nucleic acid sequence encoding the repressor is not expressed during growth of the recombinant bacterium in the host, the expression of the nucleic acid sequence encoding the antigen should be high. As used herein, "high level" expression refers to expression that is strong enough to elicit an immune response to the antigen. Consequently, the copy number correlating with high level expression can and will vary depending on the antigen and the type of immune response desired. Methods of determining whether an antigen elicits an immune response such as by measuring antibody levels or antigen-dependant T cell populations or antigen-dependant cytokine levels are known in the art, and methods of measuring levels of expression of antigen encoding sequences by measuring levels of mRNA transcribed or by quantitating the level of antigen synthesis are also known in the art. For more details, see the examples.

ii. Other Ways of Regulating the Expression of a Nucleic Acid Encoding at Least One Enteric Antigen The invention also encompasses other means of regulating the expression of a nucleic acid sequence encoding at least one enteric antigen in a recombinant bacterium. For instance, in one embodiment, the enteric antigen of interest may be encoded on an extra-chromosomal vector. This can be used in the context of a balanced-lethal host-vector or balanced-attenuation host-vector system. Alternatively, the nucleotide sequence encoding the antigen of interest may be inserted into the chromosome but have its expression controlled by a regulatable system, e.g., LacI or C2, as with the regulated gene encoding the antigen of interest on an extra-chromosomal vector (e.g., a plasmid).

(c) Attenuation of the Recombinant Bacterium

In each of the above embodiments, a recombinant bacterium of the invention may also be attenuated. "Attenuated" refers to the state of the bacterium wherein the bacterium has been weakened from its wild type fitness by some form of recombinant or physical manipulation. This includes altering the genotype of the bacterium to reduce its ability to cause disease. However, the bacterium's ability to colonize the gastrointestinal tract (in the case of *Salmonella*) and induce immune responses is, preferably, not substantially compromised. For instance, in one embodiment, regulated attenuation allows the recombinant bacterium to express one or more nucleic acids encoding products important for the bacterium to withstand stresses encountered in the host after immunization. This allows efficient invasion and colonization of lymphoid tissues before the recombinant bacterium is regulated to display the attenuated phenotype.

In one embodiment, a recombinant bacterium may be attenuated as described in section I(a)i above, i.e. regulating LPS O-antigen. In another embodiment, a recombinant bacterium may be attenuated as described in section (c)i below. In which case, both regulated attenuation and regulated expression of an enteric antigen encoding sequence may be dependent upon an arabinose regulatable system. Consequently, the concentration of arabinose needed for optimal expression of the regulated enteric antigen encoding sequence may not be the same as the concentration for optimal expression of attenuation. In an exemplary embodiment, the concentration of arabinose for the optimization of both regulated attenuation and regulated expression of sequences encoding antigen will be substantially the same.

Accordingly, the promoter and/or the nucleic acid sequence encoding an attenuation protein may be modified to optimize the system. Methods of modification are detailed above. Briefly, for example, the SD ribosome binding sequence may be altered, and/or the start codon may be altered from ATG to GTG for the nucleic acid sequences fur and phoPQ, so that the production levels of Fur and PhoPQ are optimal for both the regulated attenuation phenotype and the regulated expression when growing strains with a given concentration of arabinose. One of skill in the art will appreciate that other nucleic acid sequences, in addition to fur and phoPQ, may also be altered as described herein in combination with other well-known protocols. In addition, these attenuating nucleic acid sequences may be regulated by other systems using well-established protocols known to one of skill in the art. For example, they may be regulated using with promoters dependent on addition of maltose, rhamnose, or xylose rather than arabinose.

Other methods of attenuation are known in the art. For instance, attenuation may be accomplished by altering (e.g., deleting) native nucleic acid sequences found in the wild type bacterium. For instance, if the bacterium is *Salmonella*, non-limiting examples of nucleic acid sequences which may be used for attenuation include: a pab nucleic acid sequence, a pur nucleic acid sequence, an aro nucleic acid sequence, asd, a dap nucleic acid sequence, nadA, pncB, galE, pmi, fur, rpsL, ompR, htrAi, hemA, cdt, cya, crp, dam, phoP, phoQ, rfc, poxA, galU, mviA, sodC, recA, ssrA, sirA, inv, hilA, rpoE, flgM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

The bacterium may also be modified to create a balanced-lethal host-vector system, although other types of systems may also be used (e.g., creating complementation heterozygotes). For the balanced-lethal host-vector system, the bacterium may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP. In one example, the bacterium is modified by using a ΔasdA mutation to eliminate the bacterium's ability to produce β-aspartate semialdehyde dehydrogenase, an enzyme essential for the synthesis of DAP. One of skill in the art can also use the teachings of U.S. Pat. No. 6,872,547 for other types of mutations of nucleic acid sequences that result in the abolition of the synthesis of DAP. These nucleic acid sequences may include, but are not limited to, dapA, dapB, dapC, dapD, dapE, dapF, and asd. Other modifications that may be employed include modifications to a bacterium's ability to synthesize D-alanine or to synthesize D-glutamic acid (e.g., ΔmurI mutations), which are both unique constituents of the peptidoglycan layer of the bacterial cell wall Yet another balanced-lethal host-vector system comprises modifying the bacterium such that the synthesis of an essential constituent of the rigid layer of the bacterial cell wall is dependent on a nutrient (e.g., arabinose) that can be supplied during the growth of the microorganism. For example, a bacterium may comprise the $\Delta P_{murA}$::TT araC $P_{BAD}$ murA deletion-insertion mutation. This type of mutation makes synthesis of muramic acid (another unique essential constituent of the peptidoglycan layer of the bacterial cell wall) dependent on the presence of arabinose that can be supplied during growth of the bacterium in vitro.

When arabinose is absent, however, as it is in an animal or human host, the essential constituent of the peptidoglycan layer of the cell wall is not synthesized. This mutation represents an arabinose dependant lethal mutation. In the absence of arabinose, synthesis of muramic acid ceases and lysis of the bacterium occurs because the peptidoglycan layer of the cell wall is not synthesized. It is not possible to generate ΔmurA mutations because they are lethal. The necessary nutrient, a phosphorylated muramic acid, cannot be exogenously supplied because enteric bacteria cannot take the nutrient up from the media. Recombinant bacteria with a $\Delta P_{murA}$::TT araC $P_{BAD}$ murA deletion-insertion mutation grown in the presence of arabinose exhibit effective colonization of effector lymphoid tissues after oral vaccination prior to undergoing lysis due to the inability to synthesize muramic acid.

Similarly, various embodiments may comprise the araC $P_{BAD}$ c2 cassette inserted into the asd nucleic acid sequence that encodes aspartate semialdehyde dehydrogenase. Since the araC nucleic acid sequence is transcribed in a direction that could lead to interference in the expression of adjacent nucleic acid sequences and adversely affect vaccine strain performance, a transcription termination (TT) sequence is generally inserted 3' to the araC nucleic acid sequence. The chromosomal asd nucleic acid sequence is typically inactivated to enable use of plasmid vectors encoding the wild-type asd nucleic acid sequence in the balanced lethal host-vector system. This allows stable maintenance of plasmids in vivo in the absence of any drug resistance attributes that are not permissible in live bacterial vaccines. In some of these embodiments, the wild-type asd nucleic acid sequence may be encoded by the vector described above.

In one embodiment, ΔasdA27::TT araC $P_{BAD}$ c2 has an improved SD sequence and a codon optimized c2 nucleic acid sequence. The C2 repressor synthesized in the presence of arabinose is used to repress nucleic acid sequence expression from P22 $P_R$ and $P_L$ promoters. In another embodiment, ΔasdA27::TT araC $P_{BAD}$ c2 has the 1104 base-pair asd nucleic acid sequence deleted (1 to 1104, but not including the TAG stop codon) and the 1989 base-pair fragment containing T4 ipIII TT araC $P_{BAD}$ c2 inserted. The c2 nucleic acid sequence in ΔasdA27::TT araC $P_{BAD}$ c2 has a SD sequence that was optimized to TAAGGAGGT. It also has an improved $P_{BAD}$ promoter such that the −10 sequence is improved from TACTGT to TATAAT. Furthermore, it has a codon optimized c2 nucleic acid sequence, in which the second codon was modified from AAT to AAA.

Figure 2:
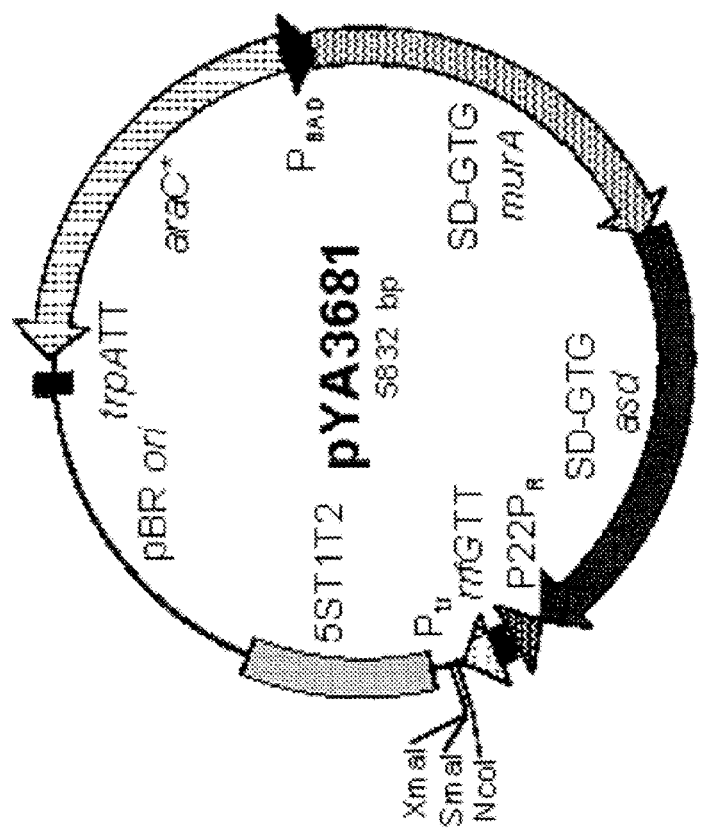
Figure 3:
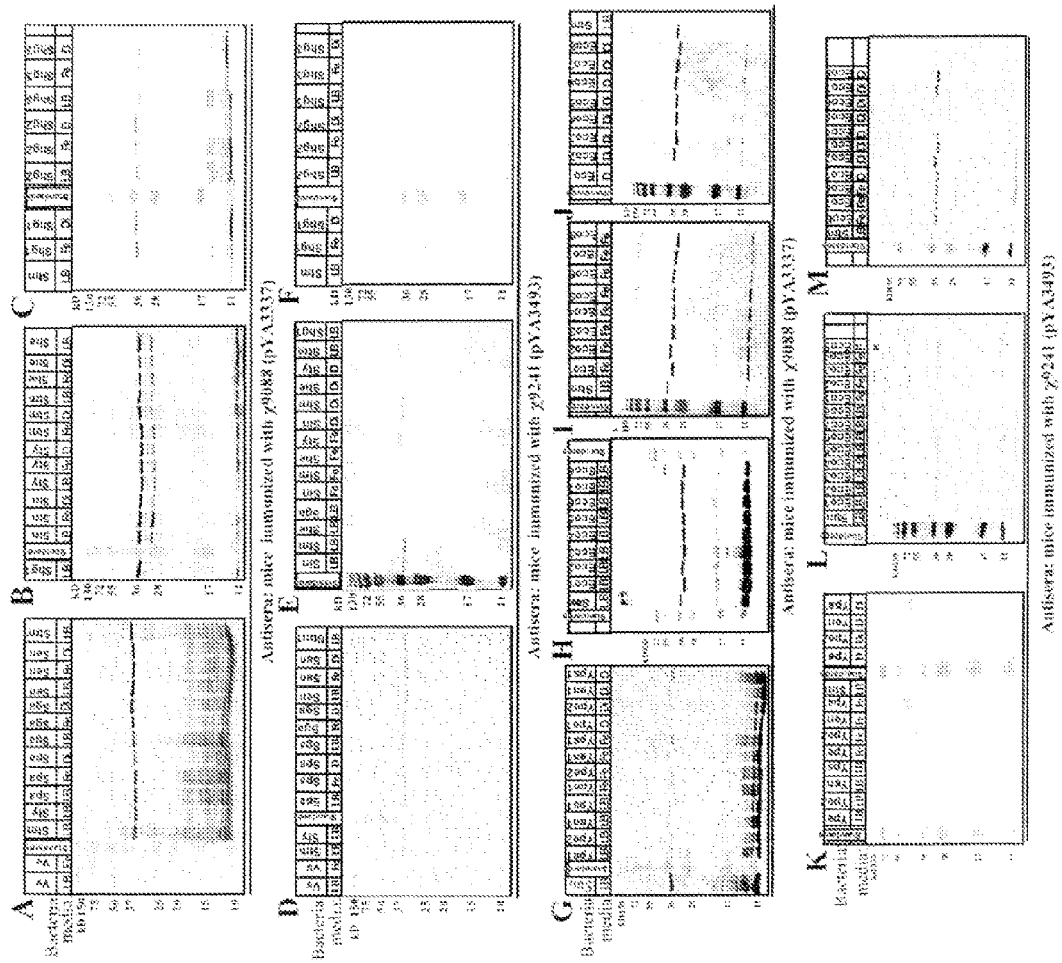

In further embodiments, the bacterium may be attenuated by regulating the murA nucleic acid sequence encoding the first enzyme in muramic acid synthesis and the asd nucleic acid sequence essential for DAP synthesis. These embodiments may comprise the chromosomal deletion-insertion mutations ΔasdA19::TT araC $P_{BAD}$ c2 or ΔasdA27::TT araC $P_{BAD}$ c2 and $\Delta P_{murA7}$::TT araC $P_{BAD}$ murA or $\Delta P_{murA12}$::TT araC $P_{BAD}$ murA or $\Delta P_{murA25}$::TT araC $P_{BAD}$ murA. This host-vector grows in LB broth with 0.1% L-arabinose, but is unable to grow in or on media devoid of arabinose since it undergoes cell wall-less death by lysis. In some embodiments of the invention, the recombinant bacterium may comprise araBAD and araE mutations to preclude breakdown and leakage of internalized arabinose such that asd and murA nucleic acid sequence expression continues for a cell division or two after oral immunization into an environment that is devoid of external arabinose. (For example a strain with the $\Delta P_{murA7}$::TT araC $P_{BAD}$ murA deletion-insertion mutation undergoes about two cell divisions and then commences to lyse in media made of mouse or chicken feed or chicken breast meat, unless they are supplemented with arabinose). Either GTG or TTG start codons for the murA and asd nucleic acid sequences are important to decrease translation efficiency on multi-copy plasmids. For instance plasmid vector pYA3681 (FIG. 2) contains the murA nucleic acid sequence (with altered start codon sequences to decrease translation efficiency) under the control of an araC $P_{BAD}$ promoter. Also the second nucleic acid sequence under the direction of this promoter is the asd nucleic acid sequence (with altered start codon sequences to decrease translation efficiency). The P22 $P_R$ promoter is in the anti-sense direction of both the asd nucleic acid sequence and the murA nucleic acid sequence. The P22 $P_R$ is repressed by the C2 repressor made during growth of the strain in media with arabinose (due to the ΔasdA19::TT araC $P_{BAD}$ c2 deletion-insertion). However C2 concentration decreases due to cell division in vivo to cause $P_R$ directed synthesis of anti-sense mRNA to further block translation of asd and murA mRNA. The araC $P_{BAD}$ sequence is also not from *E. coli* B/r as originally described but represents a sequence derived from *E. coli* K-12 strain χ289 with tighter control and less leakiness in the absence of arabinose. In the preferred embodiment, transcription terminators (TT) flank all of the domains for controlled lysis, replication, and expression so that expression in one domain does not affect the activities of another domain. As a safety feature, the plasmid asd nucleic acid sequence does not replace the chromosomal asd mutation since they have a deleted sequence in common, consequently, the *E. coli* murA nucleic acid sequence was used in the plasmid instead of using the *Salmonella* murA nucleic acid sequence. The recombinant bacterium of this embodiment is avirulent at oral doses in excess of $10^9$ CFU to BALB/c mice. In addition to being fully attenuated, this construction exhibits complete biological containment with no in vivo recombinant bacteria survivors detectable after 21 days and no recombinant bacteria survivors during or after excretion. This property enhances vaccine safety and minimizes the potential for vaccination of individuals not intended for vaccination.

i. Regulated Attenuation

The present invention also encompasses a recombinant bacterium capable of regulated attenuation. Generally speaking, the bacterium comprises a chromosomally integrated regulatable promoter. The promoter replaces the native promoter of, and is operably linked to, at least one nucleic acid sequence encoding an attenuation protein, such that the absence of the function of the protein renders the bacterium attenuated. In some embodiments, the promoter is modified to optimize the regulated attenuation.

In each of the above embodiments described herein, more than one method of attenuation may be used. For instance, a recombinant bacterium of the invention may comprise a regulatable promoter chromosomally integrated so as to replace the native promoter of, and be operably linked to, at least one nucleic acid sequence encoding an attenuation protein, such that the absence of the function of the protein renders the bacterium attenuated, and the bacterium may comprise another method of attenuation detailed in section I above.

A. Attenuation Protein

Herein, "attenuation protein" is meant to be used in its broadest sense to encompass any protein the absence of which attenuates a bacterium. For instance, in some embodiments, an attenuation protein may be a protein that helps protect a bacterium from stresses encountered in the gastrointestinal tract or respiratory tract. Non-limiting examples may be the RpoS, PhoPQ, OmpR, Fur, and Crp proteins. In other embodiments, the protein may be necessary to synthesize a component of the cell wall of the bacterium, or may itself be a necessary component of the cell wall such as the protein encoded by murA. In still other embodiments, the protein may be listed in Section i above.

The native promoter of at least one, two, three, four, five, or more than five attenuation proteins may be replaced by a regulatable promoter as described herein. In one embodiment, the promoter of one of the proteins selected from the group comprising RpoS, PhoPQ, OmpR, Fur, and Crp may be replaced. In another embodiment, the promoter of two, three, four or five of the proteins selected from the group comprising RpoS, PhoPQ, OmpR, Fur, and Crp may be replaced.

If the promoter of more than one attenuation protein is replaced, each promoter may be replaced with a regulatable promoter, such that the expression of each attenuation protein encoding sequence is regulated by the same compound or condition. Alternatively, each promoter may be replaced with a different regulatable promoter, such that the expression of each attenuation protein encoding sequence is regulated by a different compound or condition such as by the sugars arabinose, maltose, rhamnose or xylose.

B. Regulatable Promoter

The native promoter of a nucleic acid encoding an attenuation protein is replaced with a regulatable promoter operably linked to the nucleic acid sequence encoding an attenuation protein. The term "operably linked," is defined above.

The regulatable promoter used herein generally allows transcription of the nucleic acid sequence encoding the attenuation protein while in a permissive environment (i.e. in vitro growth), but cease transcription of the nucleic acid sequence encoding an attenuation protein while in a non-permissive environment (i.e. during growth of the bacterium in an animal or human host). For instance, the promoter may be responsive to a physical or chemical difference between the permissive and non-permissive environment. Suitable examples of such regulatable promoters are known in the art and detailed above.

In some embodiments, the promoter may be responsive to the level of arabinose in the environment, as described above. In other embodiments, the promoter may be responsive to the level of maltose, rhamnose, or xylose in the environment, as described above. The promoters detailed herein are known in the art, and methods of operably linking them to a nucleic acid sequence encoding an attenuation protein are known in the art.

In certain embodiments, a recombinant bacterium of the invention may comprise any of the following: $\Delta P_{fur}$::TT araC $P_{BAD}$ fur, $\Delta P_{crp}$::TT araC $P_{BAD}$ crp, $\Delta P_{phoPQ}$::TT araC $P_{BAD}$ phoPQ, or a combination thereof. Growth of such strains in the presence of arabinose leads to transcription of the fur, phoPQ, and/or crp nucleic acid sequences, but nucleic acid sequence expression ceases in a host because there is no free arabinose. Attenuation develops as the products of the fur, phoPQ, and/or the crp nucleic acid sequences are diluted at each cell division. Strains with the $\Delta P_{fur}$ and/or the $\Delta P_{phoPQ}$ mutations are attenuated at oral doses of $10^9$ CFU, even in three-week old mice at weaning. Generally speaking, the concentration of arabinose necessary to induce expression is typically less than about 2%. In some embodiments, the concentration is less than about 1.5%, 1%, 0.5%, 0.2%, 0.1%, or 0.05%. In certain embodiments, the concentration may be about 0.04%, 0.03%, 0.02%, or 0.01%. In an exemplary embodiment, the concentration is about 0.05%. Higher concentrations of arabinose or other sugars may lead to acid production during growth that may inhibit desirable cell densities. The inclusion of mutations such as ΔaraBAD or mutations that block the uptake and/or breakdown of maltose, rhamnose, or xylose, however, may prevent such acid production and enable use of higher sugar concentrations with no ill effects.

When the regulatable promoter is responsive to arabinose, the onset of attenuation may be delayed by including additional mutations, such as ΔaraBAD23, which prevents use of arabinose retained in the cell cytoplasm at the time of oral immunization, and/or ΔaraE25 that enhances retention of arabinose. Thus, inclusion of these mutations may be beneficial in at least two ways: first, enabling higher culture densities, and second enabling a further delay in the display of the attenuated phenotype that may result in higher densities in effector lymphoid tissues to further enhance immunogenicity.

C. Modifications

Attenuation of the recombinant bacterium may be optimized by modifying the nucleic acid sequence encoding an attenuation protein and/or promoter. Methods of modifying a promoter and/or a nucleic acid sequence encoding an attenuation protein are the same as those detailed above with respect to repressors in Section (b).

In some embodiments, more than one modification may be performed to optimize the attenuation of the bacterium. For instance, at least one, two, three, four, five, six, seven, eight or nine modifications may be performed to optimize the attenuation of the bacterium.

In various exemplary embodiments of the invention, the SD sequences and/or the start codons for the fur and/or the phoPQ virulence nucleic acid sequences may be altered so that the production levels of these nucleic acid products are optimal for regulated attenuation. FIG. 1 depicts $\Delta P_{fur77}$::TT araC $P_{BAD}$ fur, whose start codon is changed from ATG to GTG, and $\Delta P_{fur81}$::TT araC $P_{BAD}$ fur, that has a weakened SD sequence as well as the start codon changed from ATG to GTG. FIG. 1C depicts $\Delta P_{phopQ173}$::TT araC $P_{BAD}$ phoPQ, that has modifications to the start codon as well as the second codon, which was changed from ATG to GTG. FIG. 1C also depicts $\Delta P_{phoPQ177}$::TT araC $P_{BAD}$ phoPQ, wherein the SD sequence has been changed to the weaker AAGG sequence, the start codon was modified, and the second codon was modified from ATG to GTG.

(d) Eliciting an Immune Response Against at Least Two *Salmonella* Serotypes

A recombinant bacterium of the invention may be capable of eliciting an immune response against at least two *Salmonella* serotypes. This may be accomplished, for instance, by eliminating the serotype-specific LPS O-antigen side chains as discussed above. The remaining LPS core will elicit an immune response, inducing the production of antibodies against the LPS core. Since this LPS core is substantially identical in the several thousand *Salmonella enterica* serotypes, the antibodies potentially provide immunity against several diverse *Salmonella enterica* serotypes, such as Typhimurium, Heidelberg, Newport, Infantis, Dublin, Virchow, Typhi, Enteritidis, Berta, Seftenberg, Ohio, Agona, Braenderup, Hadar, Kentucky, Thompson, Montevideo, Mbandaka, Javiana, Oranienburg, Anatum, Paratyphi A, Schwarzengrund, Saintpaul, and Munchen.

In addition, the elimination of the LPS O-antigen provides the host immune system with better access to the outer membrane proteins of the recombinant bacterium, thereby enhancing induction of immune responses against these outer membrane proteins. In some embodiments, as described below, the outer membrane proteins may be upregulated to further enhance host immune responses to these proteins. Non-limiting examples of outer membrane proteins include proteins involved in iron and manganese uptake, as described below. Iron and manganese are essential nutrients for enteric pathogens and the induction of antibodies that inhibit iron and manganese uptake in effect starves the pathogens, conferring protective immunity on the host. Additionally, since these proteins are homologous among the enteric bacteria, such host immune responses provide immunity against multiple *Salmonella enterica* serotypes as well as to other enteric bacterial pathogens such as strains of *Yersinia, Shigella* and *Escherichia*. As evidence of this, the attenuated *S. Typhimurium* vaccine vector strain not expressing any *Yersinia* antigen is able to induce significant protective immunity to high doses of orally administered *Y. pseudotuberculosis* (see Example 9 and FIGS. 8A, B and C).

The elicited immune response may include, but is not limited to, an innate immune response, a humoral immune response and a cell-mediated immune response. In one embodiment, Th2-dependent mucosal and systemic antibody responses to the enteric antigen(s) are observed. Immune responses may be measured by standard immunological assays known to one of skill in the art. In an exemplary embodiment, the immune response is protective.

(e) Eliciting an Immune Response Against at Least Two Enteric Pathogens

Generally speaking, a recombinant bacterium of the invention is also capable of eliciting an immune response against at least two enteric pathogens in addition to *Salmonella*. This may be accomplished, for instance, by regulating the expression of an enteric antigen as described above. In an alternative embodiment, the enteric antigen may be an iron-regulated outer membrane protein (IROMP) or a manganese-regulated outer membrane protein (MnROMP). For instance, the mutation $\Delta P_{fur}$::TT araC $P_{BAD}$ fur in a *Salmonella* recombinant bacterium may cause up-regulation of IROMPS while the bacterium is growing in the host. This up-regulation may elicit a host immune response against the IROMPS of the *Salmonella* recombinant bacterium that cross-reacts with similar proteins from *Shigella, E. coli*, and *Yersinia.*

An "enteric pathogen," as used herein, refers to a pathogen capable of invading and colonizing the intestines of a host and causing pathology. The pathology, however, is not limited to the gastrointestinal tract. Many enteric pathogens cause extra intestinal diseases such as typhoid fever, meningitis, septicemia, and urinary tract infections, and use the intestines as a route of entry or as a reservoir from which to spread to other sites of entry. Additionally, some enteric bacteria can invade and colonize via the respiratory tract. This is most common in birds, such as chickens and turkeys that scratch to aerosolize enteric bacteria that can invade the lungs and airsacs during breathing. These same enteric bacteria are also ingested by birds such that they are equally capable of residing in the intestinal tract. In either case, these enteric bacteria are still able to colonize internal tissues to cause disease independent of whether the invasion occurred via the gastrointestinal or respiratory tracks. Non-limiting examples of enteric pathogens may include *E. coli* serotypes O124, O86:B7, H37, O27, O124:B17, O6:H16, O25:H+, O27:H2O, O157:H7; *Shigella* Serogroup A or *S. dysenteriae* (12 serotypes), Serogroup B or *S. flexneri* (6 serotypes), Serogroup C or *S. boydii* (23 serotypes), Serogroup D or *S. sonnei* (1 serotype); *Clostridium perfringens; Yersinia enterocolitica; Yersina pseudotuberculosis*; and *Campylobacter jejuni.*

The elicited immune response may include, but is not limited to, an innate immune response, a humoral immune response and a cell-mediated immune response. In one embodiment, Th2-dependent mucosal and systemic antibody responses to the enteric antigen(s) are observed. Immune responses may be measured by standard immunological assays known to one of skill in the art. In an exemplary embodiment, the immune response is protective.

(f) crp Cassette

In some embodiments, a recombinant bacterium of the invention may also comprise a $\Delta P_{crp}$::TT araC $P_{BAD}$ crp deletion-insertion mutation. Since the araC $P_{BAD}$ cassette is dependent both on the presence of arabinose and the binding of the catabolite repressor protein Crp, a $\Delta P_{crp}$::TT araC $P_{BAD}$ crp deletion-insertion mutation may be included as an additional means to reduce expression of any nucleic acid sequence under the control of the $P_{BAD}$ promoter. This means that when the bacterium is grown in a non-permissive environment (i.e. no arabinose) both the repressor itself and the Crp protein cease to be synthesized, consequently eliminating both regulating signals for the araC $P_{BAD}$ regulated nucleic acid sequence. This double shut off of araC $P_{BAD}$ may constitute an additional safety feature ensuring the genetic stability of the desired phenotypes.

Generally speaking, the activity of the Crp protein requires interaction with cAMP, but the addition of glucose, which may inhibit synthesis of cAMP, decreases the ability of the Crp protein to regulate transcription from the araC $P_{BAD}$ promoter. Consequently, to avoid the effect of glucose on cAMP, glucose may be substantially excluded from the growth media, or variants of crp may be isolated that synthesize a Crp protein that is not dependent on cAMP to regulate transcription from $P_{BAD}$. This strategy may also be used in other systems responsive to Crp, such as the systems responsive to rhamnose and xylose described above.

(g) Reduction in Fluid Secretion

In some embodiments, a recombinant bacterium of the invention may be modified so as to reduce fluid secretion in the host. For instance, the bacterium may comprise the ΔsopB1925 mutation. Alternatively, the bacterium may comprise the ΔmsbB48 mutation. For more details, see the Examples.

(h) Biological Containment

Under certain embodiments, a live recombinant bacterium may possess the potential to survive and multiply if excreted from a host. This leads to the possibility that individuals not electing to be immunized may be exposed to the recombinant bacterium. Consequently, in certain embodiments, a recombinant bacterium of the invention may comprise one or more mutations that decrease, if not preclude, the ability of Salmonella vaccines to persist in the GI tract of animals.

In another embodiment, a recombinant bacterium of the invention may comprise one or more of the Δ(gmd fcl)-26 or Δ(wcaM-wza)-7, ΔagfBAC811 or Δ($P_{agfD}$ agfG)-4, ΔbcsABZC2118 or ΔbcsEFG2319 and Δ(yshA-yihW)-157 mutations that block synthesis of colanic acid, thin aggregative fimbriae (i.e., curli), cellulose and extracellular polysaccharide, respectively, all of which contribute to biofilm formation. In addition, the mutation ΔyhiR36 that prevents use of DNA as a nutrient, Δ(shdA-ratB)-64, ΔmisL2 and ΔbigA3 that encode four proteins that enable Salmonella to adhere to host extracellular matrix proteins and ΔackA233 that blocks use of acetate, may be used as a means for biological containment. In exemplary embodiments, a recombinant bacterium comprising a biological containment mutation are not adversely effected in their virulence.

In some embodiments, the recombinant bacterium may comprise a method of regulated delayed lysis in vivo that prevents bacterial persistence in vivo and survival if excreted. These chromosomal mutations may include: Δ(gmd fcl)-26 or Δ(wcaM-wza)-8 that precludes synthesis of colanic acid that can protect cells undergoing cell wall-less death from lysing completely, ΔagfBAC811 that blocks synthesis of thin aggregative fimbriae (curli) that are critical for biofilm formation to enable persistent colonization on bile stones in the gall bladder, ΔasdA27::TT araC $P_{BAD}$ c2 insertion-deletion mutation to impose a requirement for the peptidoglycan constituent DAP and Δ$P_{murA12}$::TTaraC $P_{BAD}$ murA insertion-deletion mutation as a conditional-lethal mutation blocking synthesis of the peptidoglycan constituent muramic acid. The latter two mutations are typically complemented by a regulated delayed lysis plasmid vector such as pYA3681 (FIG. 2) that has an arabinose-dependent expression of asdA and murA genes. A recombinant bacterium comprising such mutations grows normally in the presence of arabinose. In vivo, however, the bacterium ceases to express any nucleic acids encoding the AsdA and MurA enzymes, such that synthesis of the peptidoglycan cell wall layer ceases, ultimately resulting in the lysis of the bacterium. This lysis may result in the release of a bolus of antigen specific for an enteric pathogen, thereby serving as a means to enhance induction of immunity against that enteric pathogen while conferring complete biological containment.

II. Vaccine Compositions and Administration

A recombinant bacterium of the invention may be particularly suited for use as a vaccine. Infection of a host with a Salmonella strain typically leads to colonization of the gut-associated lymphoid tissue (GALT) or Peyer's patches, which leads to the induction of a generalized mucosal immune response to the recombinant bacterium. Further penetration of the bacterium into the mesenteric lymph nodes, liver and spleen may augment the induction of systemic and cellular immune responses directed against the bacterium. Thus the use of recombinant Salmonella for oral immunization stimulates all three branches of the immune system, which is particularly important for immunizing against infectious disease agents that colonize on and/or invade through mucosal surfaces.

A recombinant bacterium of the invention may be administered to a host as a vaccine composition. As used herein, a vaccine composition is a composition designed to elicit an immune response to the recombinant bacterium, including any antigens that may be expressed by the bacterium. In an exemplary embodiment, the immune response is protective. As used herein, "protective" means that the immune response contributes to the lessening of any symptoms associated with infection of a host with the pathogen the antigen was derived from or designed to elicit a response against. For example, a protective antigen from a pathogen, such as Shigella, may induce an immune response that helps to ameliorate symptoms associated with Shigella infection or reduce the morbidity and mortality associated with infection with the pathogen. The use of the term "protective" in this invention does not necessarily require that the host is completely protected from the effects of the pathogen.

Immune responses to antigens are well studied and widely reported. A survey of immunology is given by Paul, W E, Stites D et al. and Ogra P L. et al. Mucosal immunity is also described by Ogra P L et al.

Vaccine compositions of the present invention may be administered to any host capable of mounting an immune response. Such hosts may include all vertebrates, for example, mammals, including domestic animals, agricultural animals, laboratory animals, and humans, and various species of birds, including domestic birds and birds of agricultural importance. Preferably, the host is a warm-blooded animal. The vaccine can be administered as a prophylactic or for treatment purposes.

In exemplary embodiments, the recombinant bacterium is alive when administered to a host in a vaccine composition of the invention. Suitable vaccine composition formulations and methods of administration are detailed below.

(a) Vaccine Composition

A vaccine composition comprising a recombinant bacterium of the invention may optionally comprise one or more possible additives, such as carriers, preservatives, stabilizers, adjuvants, and other substances.

In one embodiment, the vaccine comprises an adjuvant. Adjuvants, such as aluminum hydroxide or aluminum phosphate, are optionally added to increase the ability of the vaccine to trigger, enhance, or prolong an immune response. In exemplary embodiments, the use of a live attenuated recombinant bacterium may act as a natural adjuvant. The vaccine compositions may further comprise additional components known in the art to improve the immune response to a vaccine, such as T cell co-stimulatory molecules or antibodies, such as anti-CTLA4. Additional materials, such as cytokines, chemokines, and bacterial nucleic acid sequences naturally found in bacteria, like CpG, are also potential vaccine adjuvants.

In another embodiment, the vaccine may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the vaccine is preferably presented in the form of an aerosol.

Care should be taken when using additives so that the live recombinant bacterium is not killed, or have its ability to effectively colonize lymphoid tissues such as the GALT, NALT and BALT compromised by the use of additives. Stabilizers, such as lactose or monosodium glutamate (MSG), may be added to stabilize the vaccine formulation against a variety of conditions, such as temperature variations or a freeze-drying process.

The dosages of a vaccine composition of the invention can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1 \times 10^7$ to about $1 \times 10^{10}$ CFU depending upon the age of the host to be immunized. In some embodiments, the initial oral dose may be about $1 \times 10^5$ to about $1 \times 10^{10}$ CFU. Generally speaking, intranasal doses are lower than the dose for oral immunization. For instance, in some embodiments, the intranasal dose may be between about 80 and about 120 times lower than the oral dose. Similarly, parenteral doses are lower than the dose for intranasal immunization. For example, the parenteral dose may be between about 5 and 15 times lower than the intranasal dose. Administering multiple dosages may also be used as needed to provide the desired level of protective immunity.

(b) Methods of Administration

In order to stimulate a preferred response of the GALT, NALT or BALT cells, administration of the vaccine composition directly into the gut, nasopharynx, or bronchus is preferred, such as by oral administration, intranasal administration, gastric intubation or in the form of aerosols, although other methods of administering the recombinant bacterium, such as intravenous, intramuscular, subcutaneous injection or intramammary, intrapenial, intrarectal, vaginal administration, or other parenteral routes, are possible.

In some embodiments, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like.

In an exemplary embodiment, the recombinant bacterium may be administered orally. Oral administration of a composition comprising a recombinant bacterium allows for greater ease in disseminating vaccine compositions for infectious agents to a large number of people in need thereof, for example, in Third World countries or during times of biological warfare. In addition, oral administration allows for attachment of the bacterium to, and invasion of, the gut-associated lymphoid tissues (GALT or Peyer's patches) and/or effective colonization of the mesenteric lymph nodes, liver, and spleen. This route of administration thus enhances the induction of mucosal immune responses as well as systemic and cellular immune responses.

III. Kits

The invention also encompasses kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally.

IV. Methods of Use

A further aspect of the invention encompasses methods of using a recombinant bacterium of the invention. For instance, in one embodiment the invention provides a method for modulating a host's immune system. The method comprises administering to the host an effective amount of a composition comprising a recombinant bacterium of the invention. One of skill in the art will appreciate that an effective amount of a composition is an amount that will generate the desired immune response (e.g., mucosal, humoral or cellular). Methods of monitoring a host's immune response are well-known to physicians, veternarians, and other skilled practitioners. For instance, assays such as ELISA, and ELISPOT may be used. Effectiveness may be determined by monitoring the amount of the antigen of interest remaining in the host, or by measuring a decrease in disease incidence caused by a given pathogen in a host. For certain pathogens, cultures or swabs taken as biological samples from a host may be used to monitor the existence or amount of pathogen in the individual.

In another embodiment, the invention provides a method for eliciting an immune response against an antigen in a host. The method comprises administering to the host an effective amount of a composition comprising a recombinant bacterium of the invention.

In still another embodiment, a recombinant bacterium of the invention may be used in a method for eliciting an immune response against an enteric pathogen in an individual in need thereof. In some embodiments, a recombinant bacterium of the invention may be used in a method for eliciting an immune response against at least 2, 3, 4, 5 or more than 5 enteric pathogens in an individual in need thereof. The method comprises administrating to the host an effective amount of a composition comprising a recombinant bacterium as described herein. In a further embodiment, a recombinant bacterium described herein may be used in a method for ameliorating one or more symptoms of an enteric disease in a host in need thereof. The method comprises administering an effective amount of a composition comprising a recombinant bacterium as described herein.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

Figure 1A:
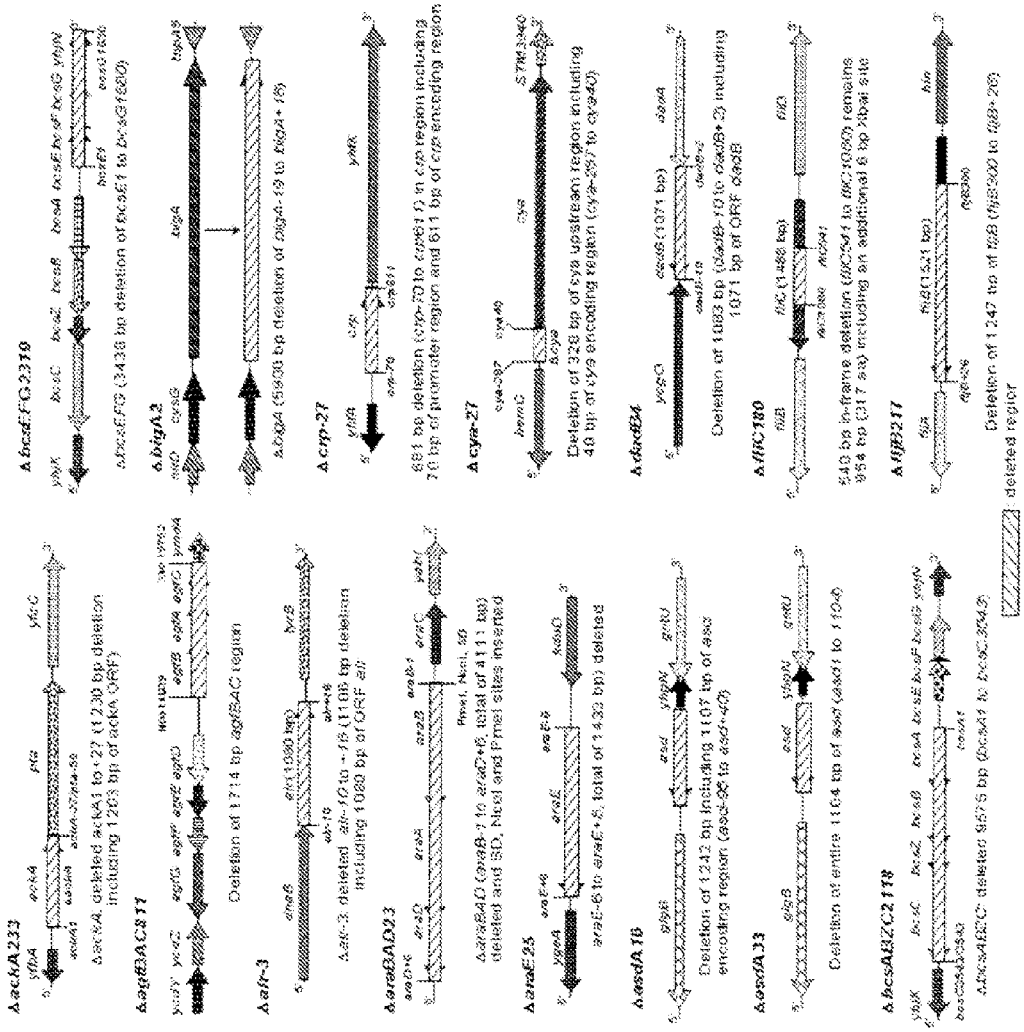
Figure 1B:
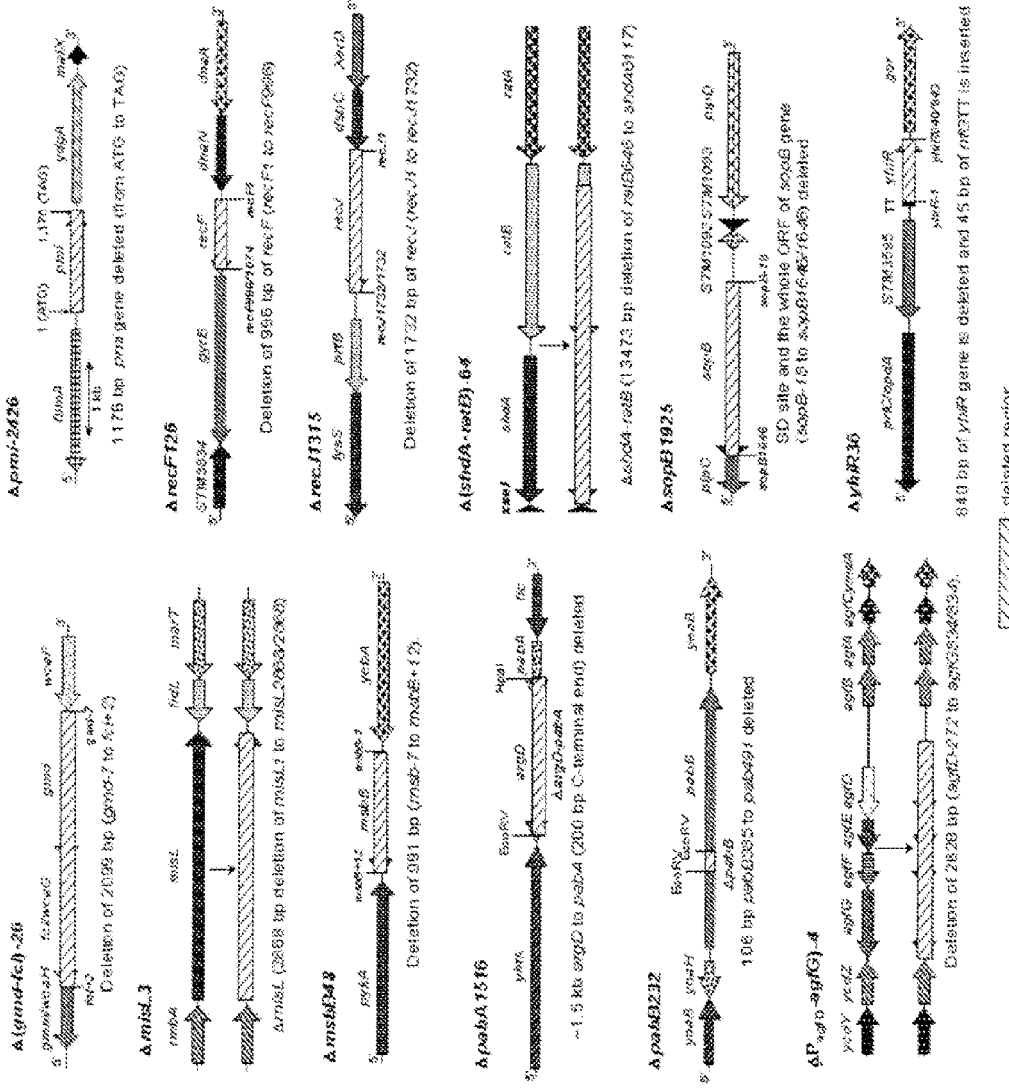

Construction of Vaccine Strain to Decrease or Eliminate Expression of Serotype-Specific Antigens and to Expose and Over-Express Cross Reactive Surface Antigens Three developed means to permit a regulated delayed attenuation phenotype were used so that vaccine strains at the time of immunization exhibit nearly wild-type attributes for survival and colonization of lymphoid tissues and after five to ten cell divisions in vivo become avirulent. In all cases, we generated precise deletion and deletion-insertion mutations using allele replacement and P22HTint transduction methods that do not leave any drug resistance genes or other sequence scars in the chromosomes of mutated strains. The first strategy makes use of pmi mutants that lack phosphomannose isomerase needed to interconvert fructose-6-P and mannose-6-P. Strains with the Δpmi-2426 mutation (diagrams of all deletion mutations are depicted in FIGS. 1A and 1B) grown in the presence of mannose synthesize a complete LPS O-antigen but lose LPS O-antigen side chains after about seven generations of growth in medium devoid of mannose or in tissues since non-phosphorylated mannose, required for uptake to synthesize O-antigen, is unavailable in vivo. To ensure that mannose provided to the vaccine during growth prior to immunization is directed at LPS O-antigen synthesis as well as to prevent colanic acid production, we included the Δ(gmd-fcl)-26 mutation that deletes two genes that encode enzymes for conversion of GDP-mannose to GDP-fucose and thus prevents synthesis of colanic acid that could protect lysing bacteria from death. We can and have also used the Δ(wcaM-wza)-8 mutation that deletes 19 genes involved in colanic acid synthesis. These mutations do not alter the attenuation, tissue-colonizing ability or immunogenicity of vaccine strains. Strains with the Δpmi-2426 mutation are about 1000-times less virulent than the wild-type parent and are highly immunogenic in inducing immunity to challenge.

In addition to the Δpmi-2426 mutation to reduce serotype-specific immune responses to the *S. Typhimurium* B group O-antigen, we can include the $\Delta P_{rfc}$:: TTaraC $P_{BAD}$ rfc deletion-insertion mutation (FIG. 1C) present in χ9736 to cause LPS O-antigen synthesis to be dependent on the presence of arabinose in addition to the presence of mannose. LPS O-antigen synthesis ceases in vivo since nonphosphylated mannose and arabinose are absent. As additional means to eliminate serotype-specific immune responses, we included the ΔfljB217 and ΔfliC180 mutations. The ΔfljB217 mutation deletes the structural gene for the Phase II flagellar antigen whereas the ΔfliC180 mutation deletes the 180 amino acids encoding the antigenically variable serotype-specific domain of the Phase I FliC flagellar antigen. The portion of the flagellar protein that interacts with TLR5 to recruit/stimulate innate immune responses represents the conserved N- and C-terminal regions of the flagellar proteins and this is retained and expressed by strains with the ΔfliC180 mutation. In addition, the ΔfliC180 mutation retains the CD4-dependent T-cell epitope. It should be noted, that expression of the Phase I flagellar antigen and not the Phase II flagellar antigen potentiates *S. Typhimurium* infection of mice. *S. Typhimurium* strains with the Δpmi-2426, ΔfljB217 and ΔfliC180 mutations when grown in the absence of mannose are not agglutinated with antisera specific for the B-group O-antigen or the *S. Typhimurium* specific anti-flagellar sera. This strain is also non-motile since the FliC180 protein that is synthesized at high level is not efficiently incorporated into flagella. When these cells are evaluated using HEK293 cells specifically expressing TLR5, the level of NF$_\kappa$B production is about 50% higher than when using a ΔfljB217 FliC$^+$ strain that assembles flagellin into flagella and exhibits motility (there is no NF$_\kappa$B production by the control ΔfljB217 ΔfliC2426 strain with no flagella).

To provide further attenuation, we use two additional means for regulated delayed attenuation in vivo, one causes over expression of immunologically cross-reactive iron-regulated outer membrane proteins (IROMPs). These additional means to achieve regulated delayed attenuation rely on using a more tightly regulated araC $P_{BAD}$ activator-promoter than the original sequence from *E. coli* B/r. We deleted the promoter, including sequences for activator or repressor protein binding, for the fur gene encoding the Fur protein that represses all genes involved in iron acquisition. The strains constructed thus possess the $\Delta P_{fur}$::TT araC $P_{BAD}$ fur and ΔPcrp::TT araC $P_{BAD}$ crp deletion-insertion mutations. Without being bound by theory, the absence of Fur possibly attenuates *Salmonella* due to iron overload. The crp gene encoding cAMP receptor protein that is necessary for virulence of *Salmonella* and that is also needed for maximal transcription from the $P_{BAD}$ promoter is similarly regulated by an araC $P_{BAD}$ cassette causing crp synthesis to also be dependent on arabinose which is unavailable in vivo.

Figure 1C:
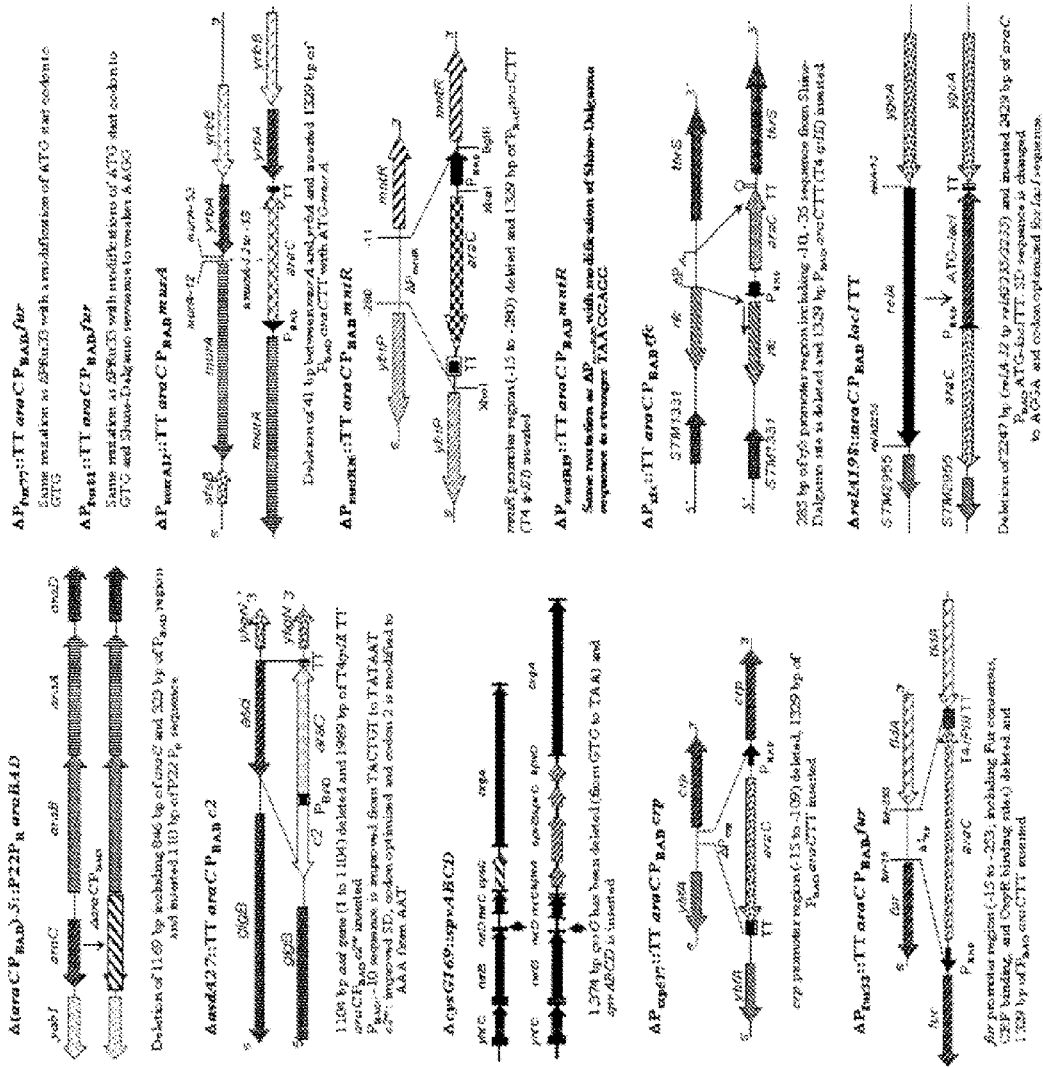

We then substituted the improved araC $P_{BAD}$ cassette to yield *Salmonella* strains with $\Delta P_{fur}$::TT araC $P_{BAD}$ fur and $\Delta P_{crp}$::TT araC $P_{BAD}$ crp deletion-insertion mutations (P stands for promoter, TT for transcription terminator) (all deletion-insertion mutations are diagrammed in FIG. 1C). In both constructions, a strong TT sequence is inserted at the C-terminal end of the araC gene to preclude continued synthesis of araC mRNA into adjacent genes that could interfere via production of anti-sense mRNA with the expression and function of these adjacent genes. As described below, we have also developed means for regulated delayed expression of cloned genes specifying production of antigens that also depend on using araC $P_{BAD}$ cassettes to cause arabinose-dependent expression of LacI and P22 C2 repressors. To decrease synthesis of such antigens regulated by $P_{trc}$ and P22 $P_R$ promoters, strains need to be grown in media with 0.2% arabinose to maximize LacI and C2 repressor synthesis. However, growth of strains with the $\Delta P_{fur33}$::TT araC $P_{BAD}$ fur mutation in such concentrations of arabinose synthesize so much Fur that the vaccine strain becomes iron starved and performs poorly in colonizing lymphoid tissues following oral immunization. We have therefore evaluated a number of $\Delta P_{fur}$::TT araC $P_{BAD}$ fur constructs in which we changed the fur gene start codon from ATG to GTG and have also altered the Shine-Dalgarno (SD) sequence for ribosome binding of mRNA to decrease such binding. We thus use the $\Delta P_{fur81}$::TT araC $P_{BAD}$ fur$^-$ mutation since the level of Fur synthesis when the strain is grown in LB broth with 0.2% arabinose still permits low level expression of Fur-regulated proteins to enable sufficient iron uptake for maximal vaccine strain colonization of lymphoid tissues. Such modification of the $\Delta P_{crp527}$::TT araC $P_{BAD}$ crp deletion-insertion mutation was not necessary and colonizing ability, attenuation and immunogenicity were all unaffected by the concentration of arabinose added to LB broth. Data on attenuation and immunogenicity of strains with these constructions were collected and recorded. Importantly, inclusion of the $\Delta P_{crp527}$::TT araC $P_{BAD}$ crp mutation provides a second means to shut off araC $P_{BAD}$ regulated genes since their expression is dependant on both arabinose that is not present in animal tissues and the Crp protein.

Timing in phenotypic expression of attenuation in strains with araC $P_{BAD}$ regulated genes for virulence can be delayed for one or two cell doublings by including the $\Delta araBAD23$ and $\Delta araE25$ mutations (FIGS. 1A and 1B) to preclude breakdown and leakage of internalized arabinose. A different means of achieving this that addresses the potential problem of arabinose liberation by intestinal flora is presented below. We have isolated His-tagged proteins for every gene product altered by any mutational construction and have rabbit anti-sera against all these proteins. We have thus evaluated stabilities (half lives) and decreased amounts of proteins as a function of cell divisions after strains are transferred to media without arabinose.

Example 2

Balanced-Lethal and Balanced-Attenuation Vector-Host Systems, Antigen Export and Regulated Delayed Expression To eliminate use of plasmid vectors with non-permitted drug resistance genes and to stabilize plasmid vectors in recombinant attenuated *Salmonella* vaccines (RASV) in vivo, we developed a balanced-lethal host-vector system using a vaccine host strain with deletion of the asd gene to impose an obligate requirement for diaminopimelic acid (DAP) and a plasmid vector with the wild-type asd gene. We now have two additional balanced-lethal vector-host systems based on genes for synthesis of D-alanine and muramic acid, two other unique essential constituents of the rigid layer of the bacterial cell wall. We have Asd$^+$, DadB$^+$ and MurA$^+$ vectors with the pSC101 ori, pI5A ori, pBR ori and pUC ori to give multiple options for levels of antigen expression based on gene copy number. We can thus use all three Asd$^+$, DadB$^+$ and MurA$^+$ vector systems in the same vaccine strain to encode multiple protective antigens. Such a vaccine host strain would have the $\Delta asdA33$ (or $\Delta asdA27$::TT araC $P_{BAD}$ c2, see below), $\Delta alr-3$, $\Delta dadB4$ and $\Delta P_{murA12}$::TTaraC $P_{BAD}$ murA ($\Delta P_{murA25}$::TTaraC $P_{BAD}$ murA) or mutations in addition to the $\Delta recF126$ chromosome mutation to prevent plasmid-plasmid recombination without altering virulence or colonizing ability. The chromosomal arabinose-dependant $\Delta P_{murA12}$:: TTaraC $P_{BAD}$ murA mutation is necessitated since $\Delta murA$ mutations are lethal since the muramic acid must be phosphorylated and *Salmonella* is unable to incorporate such phosphorylated muramic acid.

The export of antigens to the periplasm of vaccine strains yields superior antibody titers than if the protective antigen was retained in the cytoplasm of the vaccine strain. We initially used the β-lactamase Type II secretion system (SS) but now have validated use of the phoA and ompA SSs with equally good results. In these various vectors, we use either $P_{trc}$ or $P_{PR}$ as promoters with expression levels controlled by the LacI and C2 repressors, respectively. Over expression of protective antigens, which will be necessary to enable ability to induce protective immunity to diverse enteric pathogens by RASV strains, can reduce colonizing ability and thus immunogenicity. In specifying expression of recombinant protective antigens by RASV strains, we have controlled expression by the LacI regulatable $P_{trc}$ and the C2 regulatable P22 $P_R$ or $P_L$ promoters. We therefore generated the optimized $\Delta relA198$::araC $P_{BAD}$ lacI TT insertion-deletion mutation, so that vaccine strains growing in the presence of arabinose synthesize the LacI repressor to repress transcription from $P_{trc}$ on Asd$^+$ or MurA$^+$ expression vectors until after vaccination when the vaccine strain has already colonized internal lymphoid tissues. This technology has been improved to increase expression of the lacI gene 40-fold by changing the SD sequence from AGGG to AGGA, the lacI start codon from GTG to ATG and by changing lacI codons to maximize translation efficiency in *Salmonella*. In other constructions such as with the DadB$^+$ vectors, we use phage P22 $P_L$ and $P_R$ that are repressible by the C2 repressor. We have therefore constructed the $\Delta asdA27$::TT araC $P_{BAD}$ c2 deletion-insertion mutation in which we have increased C2 production by improving the −10 promoter sequence, the SD sequence, changed codon 2 to A-rich to enhance translation and optimized c2 codons for high-level expression in *Salmonella*.

We more recently developed a balanced-attenuation vector-host system to provide additional plasmid vectors to enable delivery by our attenuated *Salmonella* vaccine strains of more protective antigens specified by cloned DNA from diverse enteric pathogens. We therefore have constructed plasmid vectors with the wild-type alleles for the aroA, aroC, aroD, ilvC and ilvE genes that render *Salmonella* and other pathogens attenuated. These AroA$^+$, AroC$^+$, AroD$^+$, IlvC$^+$ and InvE$^+$ plasmid vectors possess the $P_{trc}$ promoter, a multiple cloning site, a transcription terminator and a pBR ori although other combinations of promoters and copy numbers are readily substituted to provide diversity of options for expression of antigen genes. The *Salmonella* vaccine stains thus have defined deletion mutations to result in strains with $\Delta aroA$, $\Delta aroC$, $\Delta aroD$, $\Delta ilvC$ and $\Delta ilvE$ mutations to establish the balanced-attenuation vector-host systems.

Many of the vectors defined in this Example are listed in Table 8.

Example 3

Construction of *S. Typhimurium* Vaccine Strains with Regulated Expression of Genes for the Synthesis of Essential Components of the Rigid Layer of the Bacterial Cell Wall Enabling Programmed Delayed Lysis after Colonization of Effector Lymphoid Tissues In Vivo We have devised a host-vector system with regulated expression of the murA gene encoding the first enzyme in muramic acid synthesis and the asd gene essential for DAP synthesis. Both muramic acid and DAP are essential unique constituents of the rigid layer of the bacterial cell wall. The vector pYA3681 is diagramed in FIG. 2. The host strain would possess the deletion and deletion-insertion mutations $\Delta asdA27$::TT araC $P_{BAD}$ c2, $\Delta P_{murA12}$::TT araC $P_{BAD}$ murA or ($\Delta P_{murA25}$::TT araC $P_{BAD}$ murA), $\Delta araBAD23$, $\Delta araE25$ and $\Delta relA198$::araC $P_{BAD}$ lacI TT. This host-vector grows in LB broth with 0.2% L-arabinose as well as the wild-type strain χ3761, but is unable to grow in or on media devoid of arabinose since it undergoes cell wall-less death by lysis. (A strain with the ΔP$_{mur}$::TT araC P$_{BAD}$ murA deletion-insertion mutation undergoes about two cell divisions and then commences to lyse in media made of mouse or chicken feed or chicken breast meat, unless they are supplemented with arabinose.) The pYA3681 vector construction is critical. The P22 P$_R$ is repressed by the C2 repressor made during growth of the strain in medium with arabinose (due to the ΔasdA27::TT araC P$_{BAD}$ c2 deletion-insertion). However, C2 concentration decreases due to cell division in vivo to cause synthesis of P$_R$ directed synthesis of anti-sense mRNA to further block translation of asdA and murA mRNA. The araC P$_{BAD}$ sequence, as stated above, represents a sequence with tighter control and less leakiness in the absence of arabinose. Transcription terminators (TT) flank all of the domains for controlled lysis, replication and expression so that expression of a function in one domain does not affect the activities of another domain. As a safety feature, the plasmid asdA and murA gene sequences cannot replace the chromosomal asdA and murA mutations since they have deleted sequences in common. The cloning of a sequence encoding a protective antigen under P$_{trc}$ control in pYA3681 enables the regulated delayed expression to facilitate vaccine strain colonization since growth of the vaccine strain in LB broth with 0.2% arabinose causes synthesis of LacI due to the ΔrelA198::araC P$_{BAD}$ lacI TT deletion-insertion mutation. Vaccine strains with this regulated delayed lysis system are totally avirulent at oral doses in excess of $10^9$ CFU to BALB/c mice and, by release of a bolus of protective antigen upon lysis, induce very good immune responses. This means of biological containment thus provides an independent means to achieve regulated delayed attenuation in vivo.

In some instances, however, lysis in the intestinal tract may not be complete. This may be due to low levels of arabinose generated by normal flora while degrading consumed food. This may allows the survival of some vaccine cells with the regulated delayed lysis in vivo phenotype. We have therefore developed a means by which *Salmonella* rapidly catabolizes in vivo arabinose that could otherwise enable survival in the intestinal tract. We have constructed the mutation Δ(araC P$_{BAD}$)-5::P22 P$_R$ araBAD (to replace the ΔaraBAD23 mutation) to use in a strain with the ΔasdA27::TT araC P$_{BAD}$ c2 mutation. Strains with this mutation exhibit constitutive transcription of the araBAD genes in vivo after several cell divisions to result in rapid degradation of any arabinose encountered.

Example 4

Induction of Antibody Responses to Surface Antigens of Diverse Enteric Bacteria

We had shown that *S. Typhimurium* strains (see Table 7) with either the Δpmi-2426 or ΔP$_{fur33}$::TTaraC P$_{BAD}$ fur mutation induced antibodies after a single oral immunization of female BALB/c mice that gave significant and similar titers by ELISA against outer membrane proteins isolated from diverse *Salmonella* serotypes and *E. coli* pathovars grown under conditions of iron limitation. We recently compared sera from mice orally immunized once with χ9088 (Δpmi-2426 Δ(gmd fcl)-26 ΔP$_{fur33}$::TT araC P$_{BAD}$ fur ΔasdA33 with an Asd$^+$ plasmid) and χ9241 (ΔpabA1516 ΔpabB232 ΔaraBAD23 ΔasdA16 ΔrelA198::araC P$_{BAD}$ lacI TT with an Asd$^+$ plasmid) by western blot analyses of polyacrylamide gels of OMPs isolated from a diversity of *Salmonella* serotypes, various *E. coli* pathovars, *Shigella flexneri* strains, and three different *Yersinia* species all grown with or without iron limitation. In all cases, more antibody reactivity was observed with sera from χ9088 immunized mice than χ9241 immunized mice (compare FIGS. 3*a-m*). We have also used these sera to demonstrate agglutination of cells, binding to intact cells using indirect immunofluorescence, and ELISA using whole bacteria to demonstrate immunological cross reaction of χ9088 induced antibodies to all these enteric strains. In contrast, western blot analyses of LPS components showed strong reactions to the LPS cores of all *Salmonella* serotypes but not to the LPS cores of other enterics. We did not see any antibody reactivity with surface components of *Vibrio vulnificus*. These results have encouraged us to further enhance induction of such cross protective immunity.

Example 5

Up-Regulation of Surface Antigens for Acquisition of Magnesium and Manganese

Figure 4:
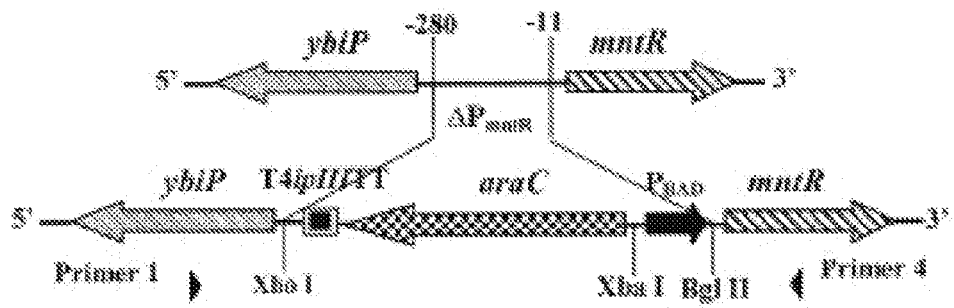

Acquisition of ion nutrients, in addition to iron, are undoubtedly essential for bacterial pathogen virulence. These abilities are likewise probably an essential means of host defense against these pathogens. We thus decided to genetically modify *Salmonella* vaccine strains to over express outer membrane proteins for acquisition of manganese and magnesium under the expectation that these will be cross-protective antigens. We therefore made constructions for regulated delayed constitutive expression of genes involved in these two transport functions. The repressor, MntR, regulates the expression of genes involved in manganese transport. Therefore, we have deleted the promoter, including sequences for activator or repressor protein binding, for the mntR gene and inserted the improved araC P$_{BAD}$ cassette to construct six different ΔP$_{mntR}$::TT araC P$_{BAD}$ mntR insertion-deletion mutations (FIG. 4) with different SD sequences and different start codons (ATG or GTG) to control the expression of MntH and SitABCD which encode two 2 major outer membrane Mn$^{2+}$ transporters that are highly conserved in *Salmonella, E. coli*, and *Shigella*. Surprisingly, strains with some of these deletion-insertion mutations display a 50-fold increase in virulence, but did not change the attenuation in combination with the Δpmi-2426 mutation. This result implies that uptake of an excess of manganese is non-toxic and non-attenuating in contrast to the consequences of excess iron intake. We have cloned the mntH and sitA genes, have generated and purified His-tagged proteins and raised antisera to both in rabbits. We injected mice with purified MntH and/or purified SitA and then challenged the mice with wild-type *S. Typhimurium* (Table 1). Mice immunized with either or both proteins were protected against challenge with 20× the LD$_{50}$ of the wild-type *S. Typhimurium* UK-1 strain χ3761, indicating that these proteins are important for virulence in *Salmonella*. Equally important, the over expression of these proteins in a *Salmonella* vaccine strain with a ΔP$_{mntR}$::TT araC P$_{BAD}$ mntR insertion-deletion mutation will induce antibodies to these proteins that should contribute to induction of cross-protective immunity to enterics that express these proteins. In addition, we have cloned the corA, mgtA, mntR, yaeT and yaeT (bsa surface domain) genes, have generated and purified His-tagged proteins, and raised rabbit antisera.

TABLE 1

Immunization with MntH or SitA proteins protects mice against challenge with virulent wild-type *S. Typhimurium*

| Purified Protein | Primary inoculating dose (μg) | Boost inoculating dose (μg) | Challenge inoculating dose (CFU) | Survivors/ total | Mean no. days to death |
|---|---|---|---|---|---|
| MntH | 50 | 50 | *Salmonella* χ3761: | | |
| | | | 0.94 × 10$^7$ | 3/3 | |
| | | | 0.94 × 10$^8$ | 2/3 | 2 |
| SitA | 50 | 50 | *Salmonella* χ3761: | | |
| | | | 0.94 × 10$^7$ | 3/3 | |
| | | | 0.94 × 10$^8$ | 2/3 | 27 |
| MntH + SitA | 50 + 50 | 50 + 50 | *Salmonella* χ3761: | | |
| | | | 0.94 × 10$^7$ | 3/3 | |
| | | | 0.94 × 10$^8$ | 2/3 | 13 |
| | | | 0.94 × 10$^9$ | 1/3 | 8 |

Figure 5:
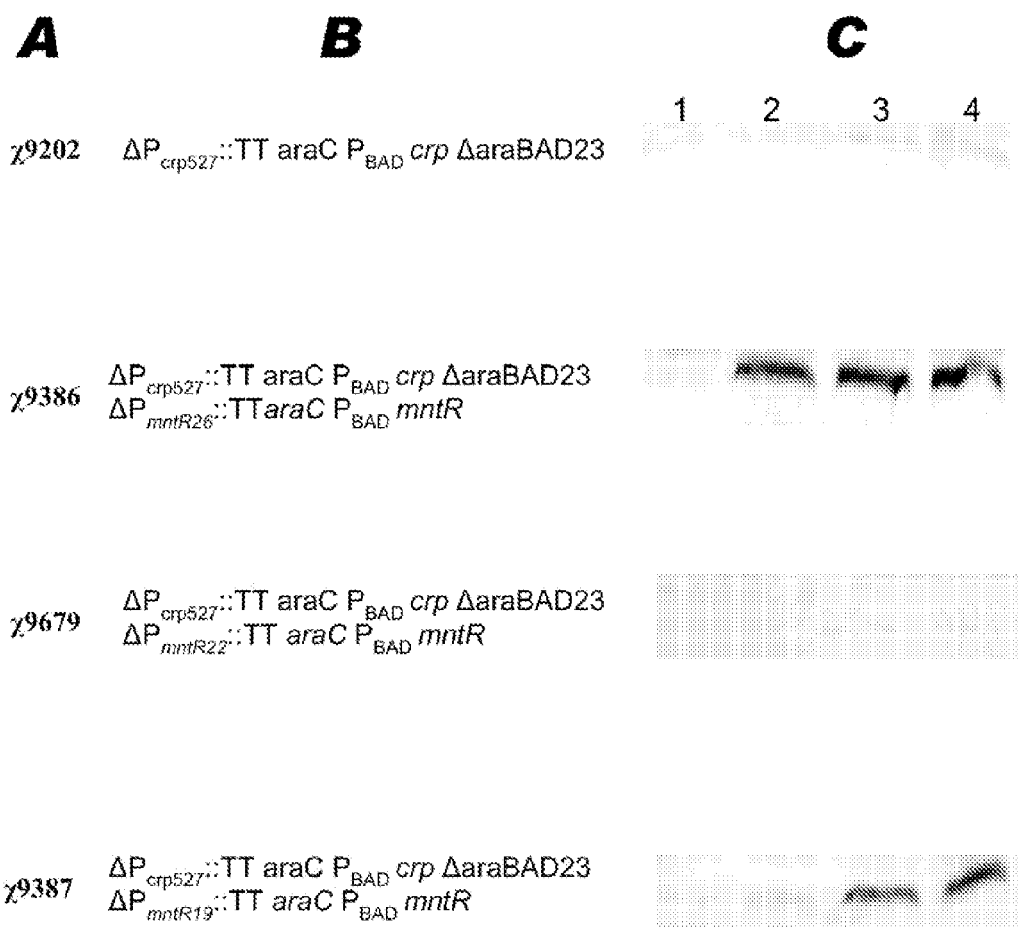
Figure 6:
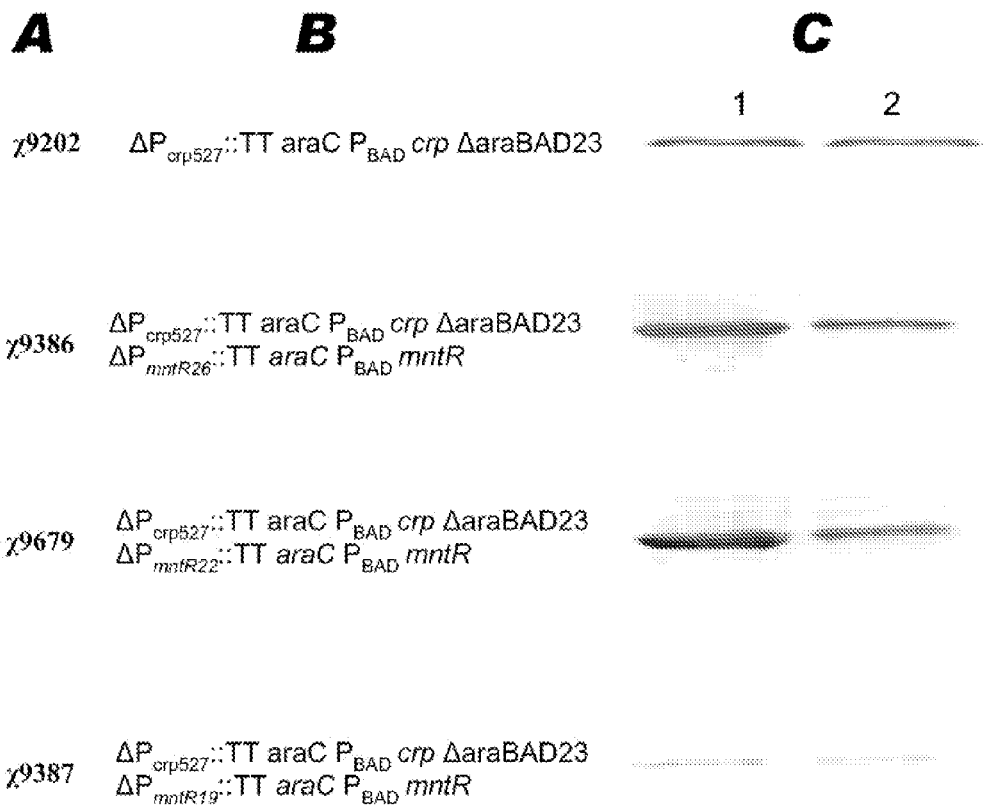

Adjuvant: complete and incomplete Freud's adjuvant; subcutaneous injection. The LD$_{50}$ for χ3761 in C3H/HeJ mice is approximately 4.4 × 10$^5$ CFU We introduced three of the ΔP$_{mntR}$::TT araC P$_{BAD}$ mntR insertion-deletion mutations (expected to give high, medium and low levels of synthesis of the MntR repressor protein when strains are grown with arabinose) into attenuated *S. Typhimurium* strain χ9202 (ΔP$_{crp527}$::TT araC P$_{BAD}$ crp Δara-BAD23). MntR synthesis in these constructs was regulated by arabinose availability as expected with the highest level of MntR synthesized by the strain with the ΔP$_{mntR26}$ and the lowest by the strain with the ΔP$_{mntR22}$ mutation (FIG. 5). In addition, we have confirmed that expression of SitA is higher when strains are grown in the absence of arabinose as expected (FIG. 6). We have also shown that MntH is also regulated by arabinose availability. We are evaluating the effect of these mutations on vaccine efficacy.

We are also studying regulated delayed in vivo over expressing corA, mntH and mgtA genes on Asd$^+$ vectors and yaeT and yaeT (bsa surface domain) genes on DadB$^+$ vectors to determine whether over expression of these gene products induces immune responses that are improved relative to inducing cross protective immunity to bacterial enteric pathogens. Further modifications of these genetic constructions and evaluations of their contributions on induction of cross protective immunity are discussed below.

Example 6

Vaccine Strain Alterations to Reduce Fluid Secretion in Vaccines

To reduce fluid secretion and potential mild gastroenteritis symptoms in human vaccinees, we include the ΔsopB1925 mutation, which we demonstrated to reduce fluid secretion and inflammation in rabbit ileal loop experiments. Others have demonstrated that sopB mutations also reduce induction of fluid secretion in calves. This mutation does not appreciably alter virulence or colonizing ability in mice. We have embarked on identification of mutations that render lipid A non toxic but retain ability to serve as a TLR4 agonist. One or more mutations conferring these attributes is included in a strain to be evaluated in humans. We had previously found that combination of the ΔsopB1925 and ΔmsbB48 mutations results in the least fluid secretion in rabbit ileal loops of any strain we tested. Strains with these two mutations are also well tolerated by newborn mice orally inoculated with 10$^7$ to 10$^8$ CFU on day of birth. An additional benefit of the ΔsopB1925 mutation is that it increases induced immune responses to expressed protective antigens.

Example 7

Progress in Achieving Biological Containment of Vaccine Strains

A difficulty with live bacterial vaccines is the potential to survive and multiply if excreted. This leads to the possibility that individuals not electing to be immunized get immunized. We have developed a method of regulated delayed lysis in vivo that prevents vaccine persistence in vivo and survival if excreted as described in Example 3. This means of biological containment also serves both as a means or regulated delayed attenuation and as a means to release a bolus of expressed protective antigens upon lysis in vivo. However, we are developing other means that decrease, if not preclude, the ability of *Salmonella* vaccines to persist in the GI tract of animals. In this regard, the chicken cecum is highly desirable environment for the *Salmonella*. Consequently we use chickens as our animal to evaluate our successes or lack thereof in achieving biological containment without resorting to cell lysis.

We have constructed and evaluated strains with the Δ(gmd fcl)-26 or Δ(wcaL-wza)-7, ΔagfBAC811 or Δ(P$_{agfD}$agfG)-4, ΔbcsABZC2118 or ΔbcsEFG2319 and Δ(yshA-yihW)-157 mutations that block synthesis of colanic acid, thin aggregative fimbriae (i.e., curli), cellulose and extracellular polysaccharide, respectively, all of which contribute to biofilm formation. Since the LPS O-antigen also enables biofilm formation, a strain with the Δpmi-2426, ΔP$_{rfc174}$::TT araC P$_{BAD}$ rfc, and Δ(galE-ybhC)-851 mutations with or without a Δ(gmd-fcl)-26 or Δ(wcaM-wza)-8 mutation would be expected to survive less well in nature because of a dependency on the availability of three sugars simultaneously, an unlikely occurrence. Such a strain would thus exhibit a rough phenotype making it less able to survive in soil or even in the intestinal environment. We also have mutations such as ΔyhiR36 that prevents use of DNA as a nutrient, Δ(shdA-ratB)-64, ΔmisL2 and ΔbigA3 that encode four proteins that enable *Salmonella* to adhere to host extracellular matrix proteins and ΔackA233 that blocks use of acetate. Some of these mutations have been reported to reduce *Salmonella* persistence in the intestinal track of calves and in mice, but this is not so in the intestinal track of chickens. We have yet to combine these mutations abolishing the ability to synthesize biofilms, the ability to synthesize LPS O-antigen, the ability to bind to extracellular matrix proteins, and the inability to use DNA and acetate as nutrients in a single bacterium, but we surmise that such a strain would exhibit a high level of biological containment and be unable to persist in the intestinal tracks of birds or mammals. Additionally, such a strain would not survive in the environment if excreted. A further anticipated benefit of such a strain is the further removal of macromolecules that might mask immunological surveillance of surface localized LPS core and cross reactive outer membrane antigens. Thus we anticipate an enhancement in levels of induced immune responses to expressed antigens. Indeed, vaccine strains with the Δ(wcaM-wza)-8 mutation synthesize five to ten percent more protective antigen and induce similarly higher antibody titers to this antigen.

Example 8

Use of Genetic Information from an APEC Strain to Enhance Induction of Cross Protective Immunity to Enteric Pathogens We have studied the avian pathogenic *E. coli* (APEC) strain χ7122 for some time and were first to describe an autotransporter (Type V secretion) protein (Tsh) in the Enterobacteriaceae, first to use genomic subtractive hybridization to define multiple genomic genetic islands in a pathogen, and first to use selective capture of transcribed sequences (SCOTS) to determine which genes are expressed in an animal. We have isolated and characterized three large plasmids from χ7122 and have sequenced the 103 kb pAPEC-1 plasmid that possesses the iroBCDN (salmochelin), tsh (hemoglobin protease, heme binding protein and hemagglutin), iucABCD iutA (aerobactin), sitABCD (iron and manganese uptake) and iss (serum resistance) loci known to contribute to virulence (and other loci that might also contribute). The iroBCDN and sitABCD previously identified as critical for ion acquisition and now the etsABC operon are ABC transport systems. Many of these genes involved in iron and/or manganese uptake are Fur and/or MntR regulated. Since pAPEC-1 is an IncF plasmid as is the *S. Typhimurium* virulence plasmid pSTV (184) (termed pSTUK100 for the UK-1 strain), we inserted the spvABCD operon that is responsible for the virulence attributes encoded on pSTUK100 into the cysG gene of the *S. Typhimurium* pSTUK100 cured strain χ9076 to yield χ9405 (ΔpSTUK100 ΔcysGI69::spvABCD). Oral infection of mice revealed that while the ΔpSTUK100 strain χ9076 was significantly attenuated compared to the pSTUK100 containing wild-type strain χ3761, strain χ9405 (ΔpSTUK100 ΔcysGI69::spvABCD) did not exhibit the expected virulence of χ3761 but was slightly attenuated. We therefore redesigned a stronger promoter for the inserted spvABCD operon and reconstructed the insertion into the cysG locus to result in the ΔcysG175::$P_{spv175}$ spvABCD deletion-insertion mutation in χ9876, which lacks the pSTUK100 virulence plasmid but now displays the same virulence as does the wild-type χ3761 strain. The nucleotide sequence for this improved spvABCD insertion is given in FIG. 7.

pAPEC-1 can now be introduced into χ9876 or other multiply mutant ΔpSTUK100 strains using χ7122 as the conjugational donor. The pAPEC-1 plasmid is not self-conjugative due to a deletion of tra genes so once transferred to *Salmonella* it is stably maintained. The introduction of pAPEC-1 into a suitably designed *Salmonella* vaccine is expected to further enhance inducing protective immunity to several enteric pathogens. This is so since the aerobactin operon on pAPEC-1 is used by all *Shigella* and *E. coli* STEC/EIEC pathovars, the salmochelin operon is widely distributed in *Salmonella* serotypes and in UPEC strains and the sit operon is present in *Salmonella, Shigella* and UPEC strains. Most importantly, the proteins encoded by these operons possess considerable amino acid sequence homology and the proteins also have similar if not nearly identical conformations. These properties contribute to the induction of cross-protective immunity. Further enhancement by modifications of pAPEC-1 in inducing protection to *Yersinia* and *Shigella* pathogens in provided below in Example 21.

Example 9

Figure 8B:
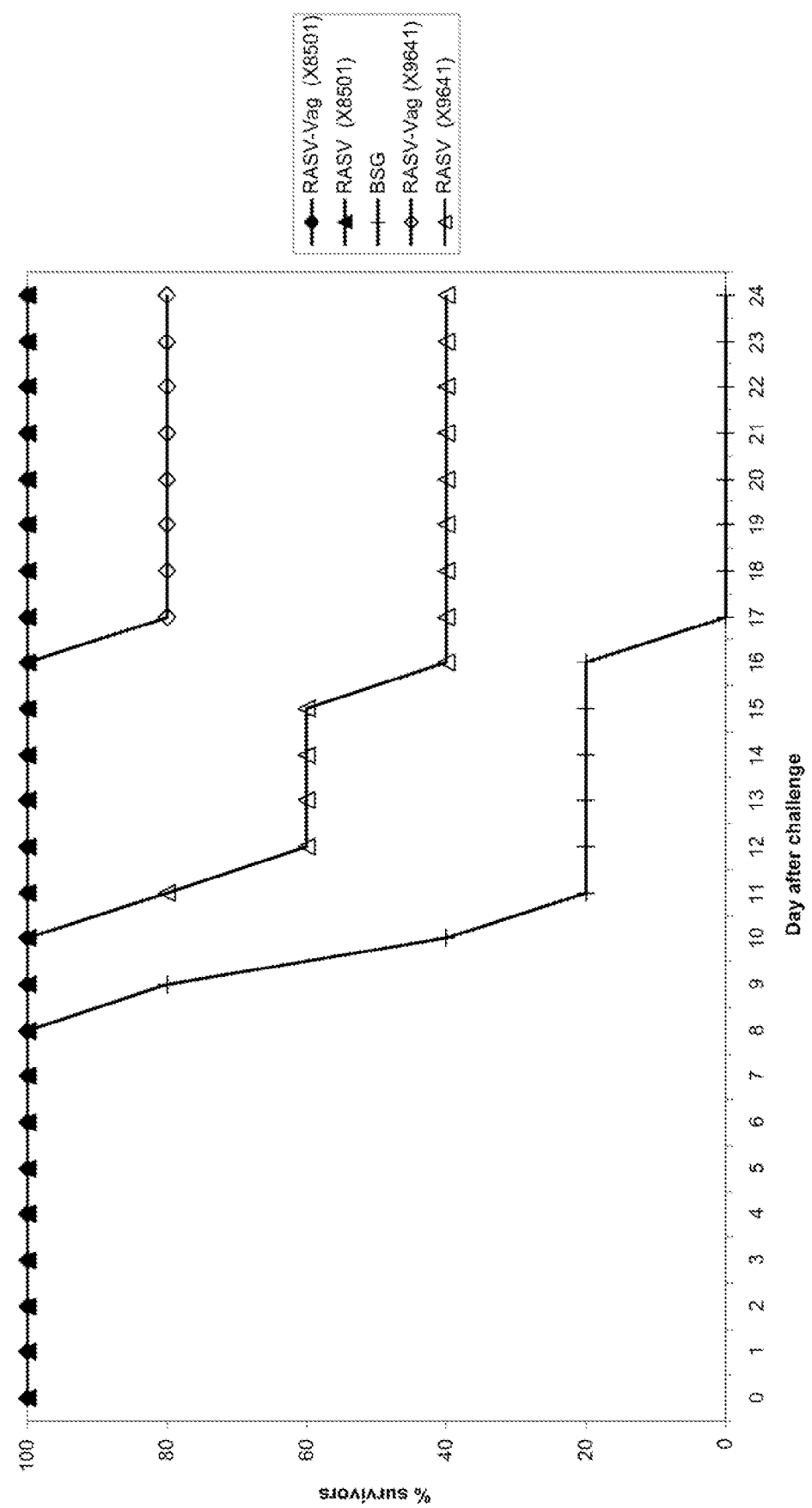
Figure 8C:
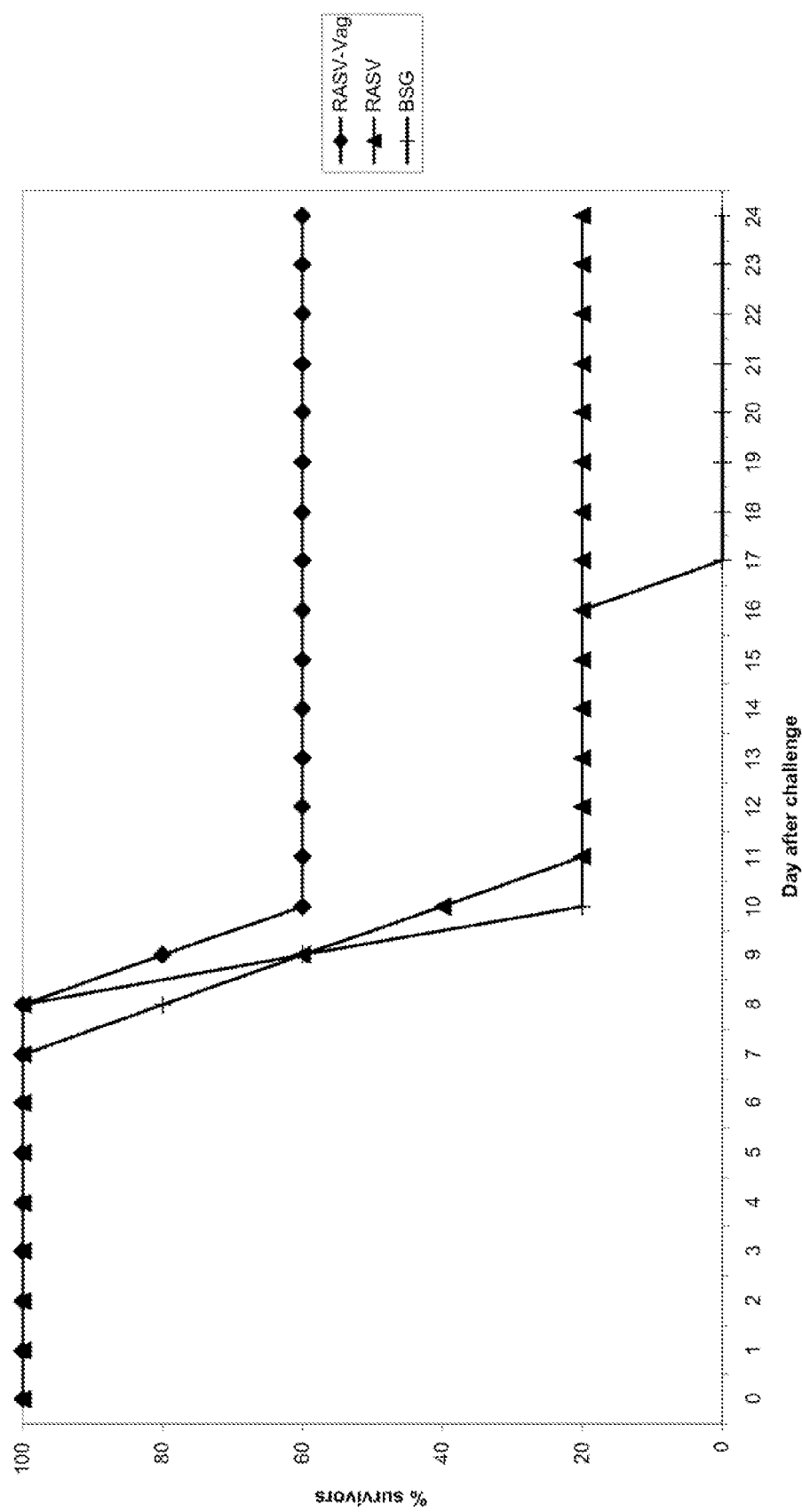

Ability of *S. Typhimurium* to Induce Protection to Challenge with *Yersinia* Species We have constructed various Asd⁺ plasmids encoding *Y. pestis* antigens for expression in *S. Typhimurium* χ8501 (Δcrp-28 ΔasdA16). Since the protective V antigen can interact with TLR2 to induce the non-inflammatory cytokine IL10 and this activity is encoded near the N-terminal end of the V antigen, we cloned a codon-optimized sequence encoding aa 131 to 327 as a β-lactamase SS fusion in the Asd⁺ vector pYA3620. Since this V antigen sequence is homologous to the V antigen sequence in the enteropathogens *Y. enterocolitica* and *Y. pseudotuberculosis*, we compared the ability of χ8501 with pYA3620 (vector control) versus χ8501 with the pYA3620-V antigen plasmid to induce protection. As indicated in FIG. 8A, the χ8501 control confers significant protection against challenge with *Y. pseudotuberculosis* strain pB1/+ with complete protection when mice were immunized with χ8501 delivering the truncated V antigen. This experiment has been repeated and we obtained the same level of protection. We also compared the ability of χ9641 with pYA3620 (vector control) versus χ9641 with the pYA3620-V antigen plasmid to induce protection. As indicated in FIG. 8B, the χ9641 control confers significant protection against challenge with *Y. pseudotuberculosis* strain pB1/+ with significantly greater protection when mice were immunized with χ9641 synthesizing the truncated V antigen. These results indicate that a *S. Typhimurium* strain such as χ9641 (Δpmi-2426 Δ(gmd-fcl)-26 ΔP$_{fur81}$::TT araC P$_{BAD}$ fur ΔP$_{crp527}$::TT araC P$_{BAD}$ crp ΔasdA27::TT araC P$_{BAD}$ c2 ΔaraE25 ΔaraBAD23 ΔrelA198::araC P$_{BAD}$ lacI TT ΔsopB1925 ΔagfBAC811 ΔfliC180 ΔfljB217) with many of the mutations described above induces very good cross protective immunity, even without delivery of the *Yersinia*-specific V antigen, to protect against the heterologous enteric pathogen *Y. pseudotuberculosis*. As indicated in FIG. 8C, significant protection against challenge with *Y. enterocolitica* strain 8081 was observed when mice were immunized with χ8501 synthesizing the truncated V antigen. No protection was conferred by strain χ8501 carrying the control plasmid and this was expected since this strain has none of the mutations (Δcrp-28 ΔasdA16) described above to enhance induction of cross protective immunity to heterologous enteric pathogens.

Since we now know the amino acid sequences that are necessary for interaction of the V antigen with TLR2 (Abramov et al, 2007, Sing et al, 2005), we engineered the truncated V antigen to express the N-terminal portion since it also contains protective epitopes. The sequence (979 bp) encoding AgV has been optimized for expression in *Salmonella* and cloned in pYA3620, generating the plasmid pYA4661. We have also introduced mutations into the sequence to modify sites of LCRV interaction with the receptor. (FIG. 26) The modifications include sequences encoding AgV (E33Q and E34Q), AgV (K42Q), AgV (E204Q and E205Q) and AgV (E33Q, E34Q, K42Q, E204Q and E205Q). Each of these four sequences has been cloned in pYA3620 generating respectively, plasmids pYA4662, pYA4663, pYA4664 and pYA4665. We are determining which of these modified AgV proteins will induce lower levels of Il-10 and a robust IgG response. The Psn OMP receptor for yersiniabactin is also highly conserved among all three *Yersinia* species and is encoded by a Fur regulated gene. We have used delivery of Psn and V antigen to induce protective immunity to *Y. pestis* challenge. Given the ability of *Yersinia* OMPs to be recognized by antibodies induced by χ9088 (Δpmi2426 Δ(gmd-fcl)-26 ΔP$_{fur33}$::TT araC P$_{BAD}$ fur ΔasdA33 with an Asd$^+$ plasmid) (see FIG. 3), we anticipate a higher level of protective immunity to the enteric *Yersinia* species will be achieved when immunizing with strains derived from χ9558 (Δpmi-2426 Δ(gmd fcl)-26 ΔP$_{fur81}$::TT araC P$_{BAD}$ fur ΔP$_{crp527}$::TT araC P$_{BAD}$ crp ΔasdA27::TTaraC P$_{BAD}$ c2 ΔaraE25 ΔaraBAD23 ΔrelA198::araCP$_{BAD}$lacITT ΔsopB1925 ΔagfBAC811) or its derivatives χ9592 that possesses the ΔfljB217 and ΔfliC180 mutations or χ9590 that also possesses the Δalr-3 and ΔdadB4 mutations to enable use of DadB$^+$ vectors to specify delivery of a protective antigen to enhance protective immunity to *Yersinia* species. In this regard, we have engineered expression of the Fur regulated and codon optimized psn gene on a derivative of pAPEC-1 described below in Example 21 to further enhance induction of protective immunity to *Yersinia* enteric pathogens. The psn DNA sequence has been codon optimized for expression in *Salmonella* and this sequence with its Fur regulated promoter has been inserted into a deletion of the pAPEC-1 cvaAB genes encoding colicin V (FIG. 9). To simplify constructions we simultaneously generated a construction that also contains the Fur regulated iucABCD and iutA genes of the *Shigella flexneri* aerobactin operon for insertion into the pAPEC-1 cvaAB deletion. Thus in a *Salmonella* vaccine strain with a ΔP$_{fur}$::TT araC P$_{BAD}$ fur deletion-insertion mutation there will be an over expression of psn and iutA genes in vivo to enhance induction of these important virulence antigens of *Yersinia* and *Shigella* strains.

Example 10

Evaluation of a Possible Universal Antigen to Protect Against Infection by *Shigella*

Figure 10:
FIG. 10 depicts a cladogram of IpaD protein in all *Shigella* species and in enteroinvasive *E. coli* serotypes.

The *Yersinia* V antigen, located at the tip of the Type III secretion needle, is essential for virulence and, if delivered in a modified form is a very protective antigen. The V antigen has structural homology to the IpaD protein of *Shigella* that is also located at the tip of the Type III secretion needle. FIG. 10 depicts a cladogram of the aa sequence data for the IpaD protein in all *Shigella* species and serotypes and in enteroinvasive *E. coli*. We have also closely examined the aa sequence (FIG. 11) and have made three separate clones including two with modifications in the amino acid sequence that is homologous to the sequences in the *Yersinia* V antigen known to interact with TLR2. These sequences have been cloned in the Asd$^+$ pYA3493 vector as β-lactamase SS fusions that are expressed (FIG. 12). Immunological evaluations were performed on one clone, pYA4188 (FIG. 13), encoding aa 23-333 of ipaD. Mice immunized with RASV χ9558 (pYA4188) were partially protected against challenge with virulent wild-type *Shigella flexneri* serovar 2a (Table 2). Immunological analyses on the remaining constructs are performed. As stated in Example 9 above and 21 below, the insertion of the *Shigella* aerobactin operon in pAPEC-1 will contribute another critical *Shigella* virulence trait and protective antigen to the *Salmonella* vaccine construct.

TABLE 2

IpaD provides protection against lethal challenge with *Shigella flexneri* serovar 2a strain 2457T[#]

| Strain | Antigen | % survivors |
|---|---|---|
| Buffer control | none | 0 |
| IpaD protein (injected) | IpaD | 40* |
| χ9558(pYA3634) | none | 0 |
| χ9558(pYA4418) | IpaD (IDw) | 40 |

[#]Mice were challenged using an intra-lung model.
*In a separate experiment, injection of IpaD provided >80% protection.

Example 11

Evaluation of a Universal Antigen of *E. coli*

Jorge Giron at the University of Arizona has described the sequence of the yagZ fimbrial operon that encodes the ECP pili displayed by essentially all *E. coli* pathovars and *Shigella* but has gone undetected for many years since these fimbriae are only synthesized and assembled in response to a signal encountered in vivo (*Proc. Natl. Acad. Sci. USA* 104:10637-10642 (2007)). We have cloned this fimbrial operon on the low copy number Asd$^+$ plasmid pYA3337 to yield pYA4428. This recombinant plasmid and the cloned pilus encoding DNA sequence are given in FIG. 14. The expression of this new fimbrial antigen under regulated P$_{trc}$ control by a multiply attenuated/mutated *S. Typhimurium* vaccine such as χ9592 is evaluated to determine whether it enhances induction of protective immunity to *E. coli* pathovars. Further studies including regulated expression of the fimbrial operon, are disclosed herein.

Example 12

Construction and Evaluation of a Vaccine Delivering Human LT-B

Although the delivery of the B subunit of LT does not confer adequate or complete protection against ETEC strains, its delivery in a vaccine of the type we are constructing will be helpful. In addition, LT is delivered to the outer membrane surface of *E. coli* with the B subunits outward facing to enable interaction with the GM-1 ganglioside present on the surface of most host cells. The delivery of LT from bacteria to host cells is facilitated by formation of outer membrane vesicles (OMVs). At least three of the mutations so far included in the *Salmonella* strains described herein cause a 100-fold increase in OMV formation when grown under the conditions encountered in vivo (at least in regard to availability of sugars). Our vaccine strains should ultimately be superior in inducing antibody responses to LT-B and accordingly, we are testing this hypothesis. We cloned the human LT-B sequence under P$_{trc}$ control in the Asd+ vectors pYA3337, pYA3332, pYA3342 and pYA3341 with pSC101 ori, p15A ori, pBR ori and pUC ori, respectively, and introduced these plasmids into χ9241 (ΔpabA1516 ΔpabB232 ΔaraBAD23 ΔasdA16 ΔrelA198::araC P$_{BAD}$ lacI TT). Only the plasmids with the pSC101 ori and to a lesser extent the p15A ori caused synthesis and export of LT-B from the *Salmonella* cells. We have determined that *S. Typhimurium* strains with the Δpmi-2426 Δ(gmd-fcl)-26 or ΔfliC180 ΔfljB217 mutations generate high yields of outer membrane vesicles (OMVs). Since we already know that production of OMV enhances induction of high levels of immunity to other recombinant expressed antigens, we believe that these mutations will enhance immunogenicity of *Salmonella* vaccine strains expressing LT-B. We are validating that the LT-B is present in OMVs and will then proceed to determine what genetic alterations of *Salmonella* will optimize LT-B expression and surface localization to facilitate attachment and presumably invasion of recombinant *Salmonella* vaccine cells into host cells.

Example 13

Evaluation of Possible Universal Antigens of *C. jejuni*

In this Example, we investigate whether a newly discovered pilus of critical importance for biofilm formation by and virulence and colonizing ability of *C. jejuni* can be used as an expressed antigen in our RASVs to induce immunity to *C. jejuni* colonization in chickens (and other target animals). The *C. jejuni* pilus gene was identified by isolating pilus proteins from cultures grown in a biofilm, separating them by SDS-PAGE, excising protein bands between 14.4-24 kDa that were subjected to trypsin digestion. The digests were subjected to liquid chromatography-mass spectrometer analysis and the sequence of each protein blasted against all known genomic sequences. The protein band at 18 kDa contained a sequence homologous to Ftp from *Hemophilus* spp and was then determined to be encoded by a gene designated pilA in the *C. jejuni* NCTC 11168 genome. The gene was disrupted by insertion of a chloramphenicol-resistance cassette. The *C. jejuni* pilA mutant was seeded onto polycarbonate membranes and cultured in Mueller-Hinton broth at 37° C. for 24 h. The pilA mutant produced sparse biofilms and SEM demonstrated the absence of pili in the mutant strain. Pili were not seen when the wild-type parent was grown under planktonic conditions. Fourteen day-old chicks were orally inoculated with $10^5$ NCTC 11168 *C. jejuni* or the pilus minus NCTC 11168 strain. The chicks were euthanized ten days post-inoculation and a gram of cecal contents from each chick were 10-fold diluted, and plated on CEFEX plates. The results of three colonization evaluations are included in Table and demonstrate a 1000-fold reduction in colonization by the Pil strain. The pilA gene is highly conserved (98 to 100%) in all *C. jejuni* sequences available, has been cloned and has been cloned into the $Asd^+$ expression vector pYA3493 and expressed as a β-lactamase SS fusion protein from pYA4495 (FIG. 15) in several recombinant *S. Typhimurium* vaccine strains, including χ9088 (Δpmi-2426 Δ(gmd-fcl)-26 $\Delta P_{fur33}$::TT araC $P_{BAD}$ fur ΔasdA33) (FIG. 16).

TABLE 3

| | Wild type (NCTC 11168) | | Δpil strain (Pil-) | |
|---|---|---|---|---|
| | No. of chicks colonized | Bacteria load CFU | No. of chicks colonized | Bacteria load CFU |
| Study 1 | 14/14 | $3.5 \times 10^7$ | 5/14 | $8.9 \times 10^4$ |
| Study 2 | 10/11 | $1.3 \times 10^8$ | 0/11 | $<1 \times 10^2$ |
| Study 3 | 14/15 | $7.8 \times 10^8$ | 5/15 | $7.7 \times 10^5$ |
| Average | 13/13 | $3.1 \times 10^8$ | 3/13 | $4.3 \times 10^5$ |

RASV strain χ9088(pYA4495) was used to orally immunize chicks. The birds were challenged with $10^5$ NCTC 11168 *C. jejuni*. A week later, cecal samples were collected and the number of CFU/g of cecal contents was determined. The results showed that immunization with χ9088(pYA4495), but not the control strain, resulted in a 4-log reduction *C. jejuni* recovered, indicating that the vaccine confers protection (Table 4).

TABLE 4

Vaccination of chickens with RASV expressing pilA reduces *C. jejuni* carriage in chickens.

| Vaccine | # chickens | challenge | Average CFU of *C. jejuni* recovered from ceca |
|---|---|---|---|
| none | 11 | none | 0 |
| none | 14 | *C. jejuni* | $2.7 \times 10^8$ |
| χ9088(pYA3493) | 11 | *C. jejuni* | $1.6 \times 10^8$ |
| χ9088(pYA4495) | 14 | *C. jejuni* | $6.8 \times 10^4$ |

The CjaA protein of *C. jejuni* is an outer membrane protein that is homologous to several prokaryotic solute-binding components of an ABC solute transporter system. Immunization of chickens with an attenuated *Salmonella* expressing CjaA has been shown to confer protection against *C. jejuni* challenge. We are constructing *Salmonella* vaccine strains that express both cjaA and pilA and are evaluating them in chickens.

The expression of *C. jejuni* genes in *Salmonella* can be problematic and lead to strain instability due to the low G+C content in the DNA of *C. jejuni* (31%) compared to the G+C content of *Salmonella* (50-53%). In addition, the codon usage in *C. jejuni* is different from *Salmonella*, which can lead to poor expression due to the presence of codons in the coding sequences that are rare in *Salmonella*. We have codon optimized the pilA and cjaA genes for expression in *Salmonella* (FIGS. 17 and 18). The G+C content of both genes was 32%. We have also modified the DNA sequence without changing the amino acid sequence to raise the G+C content of both genes to 44-45%, a value that is compatible with stable expression in *Salmonella*. We are cloning these modified genes into $Asd^+$ expression vectors and evaluating them for protein expression in *Salmonella*. Immunological analyses on these constructs are performed.

Example 14

RASV Strains Expressing *C. Perfringens* Antigens to Decrease *C. perfringens* Colonization, Virulence and Induction of Necrotic Enteritis All *C. perfringens* strains produce α-toxin, which is a potent phospholipase C enzyme with sphingomyelinase and hemolytic effects causing membrane disorganization (187). With MLD of <0.1 μg/mouse, it is the potent exotoxin among *C. perfringens* toxins that is explicitly implicated in gas-gangrene and as a major cause of necrotic enteritis. Chickens are considered 200 times more susceptible to α-toxin than β- or ε-toxin and develop severe necrotic enteritis or a widespread subclinical infection. In severe cases, necrotic enteritis causes significant destruction of the intestinal mucosa and mortality up to 30%. In sub clinical infections, α-toxin causes shortening of microvilli and thickens the intestinal mucosa to result in decreased nutrient uptake from digested food. To cause its lytic effect on cell membranes α-toxin has to bind to membranes by its C-terminal fragment and it has been shown that blockage of the C-terminus by specific antibody will neutralize α-toxin. Thus, we have cloned the C-terminal portion of the α-toxin gene onto the $Asd^+$ pYA3493 vector as β-lactamase SS fusions and several slightly different constructs introduced into χ8133 (Δcrp-27 Δcya-27 ΔasdA16), χ8914 (ΔpabA1516 ΔpabB232 ΔasdA16) and χ9241 (ΔpabA1516 ΔpabB232 ΔasdA16 ΔaraBAD23, ΔrelA198::araC $P_{BAD}$ lacI TT).

Mice orally immunized with any of these RASV constructs were protected from *C. perfringens*-induced gas gangrene following *C. perfringens* intramuscular challenge and showed significant reduction in numbers of bacteria recovered after challenge. Immunization of chicks with the RASV induced toxin neutralizing antibodies evaluated by inhibition of RBC hemolysis and by neutralizing lecithinase activity. These chickens developed less severe lesions in experimental necrotic enteritis challenge. Most interestingly, sera from immunized chickens could reduce the titers of *C. perfringens* almost 1000-fold in 12-hour cultures (see Table 5). A similar result was observed in vivo with regard to *C. perfringens* titers following repetitive challenge (4 days in a row). It appears that α-toxin, is essential for the survival and replication of the bacteria in vivo (muscle or intestine), and antibodies to α-toxin bind to $Tox^+$ *C. perfringens* cells (FIG. 19).

TABLE 5

| Conditions | *C. perfringens* CFU/ml 12 h culture | α-toxin neutralization (% RBC lysis) |
|---|---|---|
| No serum added | $2 \times 10^8$ | 92% |
| RASV Control (pYA3493 empty plasmid vector) | $1 \times 10^8$ | 75% |
| RASV-Cp pYA3977 Bla signal peptide secretion system | $8 \times 10^5$ | 57% |
| RASV-CP 4. pYA4149 Bla signal peptide secretion and Bla C-terminal fusion secretion system | $3 \times 10^5$ | 61% |
| RASV-Cp 5.PYA4110 OmpA signal peptide secretion system | $8 \times 10^5$ | 53% |
| Recombinant PlcC Subcu. Injection immunized | $5 \times 10^5$ | 34% |

A DNA sequence encoding the C-terminal 123 aa of plc, termed plcC (FIG. 20), produced the most stable construct in pYA3493. We also cloned plcC into $Asd^+$ expression vectors pYA3620, as a β-lactamase SS+CT fusion and pYA4102, as a phoA SS fusion, yielding plasmids pYA4149 and pYA4110, respectively (FIG. 21). These plasmids and pYA3977 were introduced into attenuated *S. Typhimurium* strain χ8914 (ΔpabA1516 ΔpabB232 ΔasdA16).

A study was undertaken wherein we orally immunized birds at days 3 and 13 of life with χ8914 derivatives carrying these plasmids and expressing the plcC fusion proteins. The birds were challenged with *C. perfringens* over a four-day period, two weeks later. The next day, birds were examined for signs of necrotic enteritis. The results showed that immunization with any of the three vaccine strains expressing plcC reduced the number of macroscopic and microscopic lesions associated with necrotic enteritis and positively influenced weight gain after challenge (Table 6).

TABLE 6

Gross and histopathology lesion scores and body weight (BW) differences in immunized and control chickens after challenge infection with virulent *C. perfringens*.

| Experimental group | Gross lesions[1] | Histopathology[2] Jejunum | Ileum | Body weight (g)[3] Pre-challenge | Post-challenge | % BW gain |
|---|---|---|---|---|---|---|
| RAS (χ8914, pYA3493) control | 3/5 | 3.0 | 3.3 | 365 ± 23 | $484 \pm 14^a$ | $32\%^a$ |
| RASV-1 (χ8914, pYA3977) | 1/5 | 2.4 | 1.7 | 331 ± 13 | $550 \pm 16^b$ | $66\%^b$ |
| RASV-2 (χ8914, pYA4110) | 1/5 | 1.5 | 1.0 | 330 ± 11 | $543 \pm 22^{b,c}$ | $65\%^b$ |
| RASV-3 (χ8914, pYA4149) | 1/5 | 1.6 | 1.8 | 369 ± 21 | $525 \pm 12^{b,c}$ | $42\%^c$ |
| rPlcC s.c. injection | 1/5 | 2.2 | 2.1 | 358 ± 18 | $571 \pm 25^b$ | $60\%^b$ |

All values are average of five chickens per group.

[1]Macroscopic lesions in the duodenum and jejunum.

[2]Frequency and severity of lesions were graded semi-quantitatively on scale of 0 to 5 (severe) in tissues collected one day after challenge.

[3]Body weight was measured before the *C. perfringens* challenge infection at day 35 of age and a week after the end of challenge infection, 44 days of age.

BW gain is expressed as percent difference from the weight before challenge. Different superscript letters in column designate significant differences ($p < 0.01$).

The netB gene encodes a protein that shows some homology with *C. perfringens* β-toxin. Among poultry isolates, it is found primarily in birds suffering from necrotic enteritis, but not from healthy animals and is required for the induction of necrotic enteritis symptoms in chickens. We have cloned the netB gene into a number of our Asd+ expression vectors and are performing immunological evaluations on *Salmonella* vaccine strains carrying these plasmids.

As mentioned above for *C. jejuni*, the expression of *C. perfringens* genes in *Salmonella* can be problematic and lead to strain instability due to the low G+C content in the DNA of *C. perfringens* (24-27%) compared to the G+C content of *Salmonella* (50-53%). In addition, the codon usage in *C. perfringens* is different from *Salmonella*, which can lead to poor expression due to the presence of codons in the coding sequences that are rare in *Salmonella*. We have optimized the sequences for plcC and netB for codon usage and G+C content (FIGS. 22 and 23). We are cloning these modified genes into $Asd^+$ expression vectors and performing immunological evaluations using *Salmonella* vaccine strains carrying these plasmids.

Example 15

Vaccine to Prevent *Giardia* Infection

We are investigating our RASV systems for induction of immunity to *Giardia* and this is in line with our recent success in inducing immunity to another intestinal parasite, *Eimeria acervulina* that causes coccidiosis in poultry. About 12 putative protective antigens have been identified by another party and our lab evaluated all the structures to determine how best to clone, express and deliver what parts of these antigens. The first four recombinants have been constructed. These are being evaluated in studies with mice.

Example 16

Construction of *S. Paratyphi* A Vaccine Strains

We have constructed *S. Paratyphi* A vaccine strains in parallel while constructing and characterizing *S. Typhimurium* vaccine strains. χ9608 has the genotype $\Delta P_{fur81}$::TT araC $P_{BAD}$ fur $\Delta P_{crp527}$::TT araC $P_{BAD}$ crp Δpmi-2426 Δ(gmd fcl)-26 ΔrelA198::araC $P_{BAD}$ lacI TT ΔaraBAD23 ΔaraE25 ΔagfBAC811 ΔsopB1925 ΔasdA33. We can easily add any constellation of mutations described above or in the examples to enable use of multiple balanced-lethal or balanced-attenuation vectors to specify synthesis of described antigens of *E. coli pathovars, Shigella, Yersinia, Campylobacter* and *Clostridium*, mutations to up regulate expression of manganese and magnesium uptake antigens in vivo, mutations to confer biological containment, mutations to eliminate serotype specific flagellar antigens while retaining TLR5 interactions, and mutations to better expose common cross reactive surface antigens. We can also introduce the modified pAPEC-1 plasmid to specify cross-reactive protective antigens from *E. coli, Salmonella, Shigella* and *Yersinia*. It should be evident that similar vaccine constructs derived from *S. Typhi* strains are also possible.

Example 17

Experimental Design and Methods

Bacterial Strains, Media and Bacterial Growth

Bacterial strains are listed in Table 7 and plasmids and plasmid vectors in Table 8. All strains for testing in mice and chickens are derived from the highly virulent *S. Typhimurium* strain UK-1 although some strains derived from SL1344 are also used. All bacterial strains that can be used are known to one of skill in the art including strains representing all *Salmonella* serotypes most frequently isolated from poultry, swine, cattle and humans. Defined deletion mutations with and without specific insertions that have been introduced into any of the strains constructed are depicted in FIGS. 1A and 1B and can be introduced into any other strain using suicide vectors and the transductional method described by Kang et al., *J. Bacteriol.,* 184:307-312 (2002). LB broth and agar were used as complex media for propagation and plating of bacteria. Nutrient broth (Difco), which is devoid of arabinose, and minimal salts medium and agar and MOPS media are also used. Some studies are done with bacterial strains grown in tissue culture medium to simulate environments to be encountered in vivo. MacConkey agar with 0.5% lactose (Lac), arabinose (Ara) or maltose (Mal) are used to enumerate bacteria from mice. We also use selenite broth, with or without supplements, for enrichment of *Salmonella* from tissues. Bacterial growth is monitored spectrophotometrically and quantitated by plate counts.

TABLE 7

Bacterial strains

| Strain | Genotype | Characterization |
|---|---|---|
| | *Salmonella* | |
| χ3213 | Wild type | *S. Infantis* NR29, group C1, O(6,7) H(r/1,5) |
| χ3744 | Wild type | *S. Typhi* |
| χ3761 | Wild type | *S. Typhimurium* UK-1 |
| χ3767 | Wild type | *S. Heidelber* |
| χ3796 | Wild type | *S. Gallinarum* |
| χ8133 | Δcya-27 Δcrp-27 ΔasdA16 | Defined deletions Δcya-27 Δcrp-27 ΔasdA16 were introduced into χ3761 |
| χ8387 | Wild type | *S. Paratyphi* |
| χ8494 | Wild type | *S. Enteritidis* |
| χ8501 | Δcrp-28 ΔasdA16 | Defined deletion ΔasdA16 was introduced into χ8499 background through allelic exchange with a suicide plasmid pMEG-443 |
| χ8650 | Δpmi-2426 | A defined deletion mutant made by conjugating χ3761 with χ7213 counting a suicide vector pYA3546 |
| χ8868 | Δpmi-2426 Δ(gmd-f cl)-26 | |
| χ8914 | ΔpabA1516 ΔpabB232ΔasdA16 | Transduced χ8442 with P22 (χ8276::pMEG443) and selected for Cm |
| χ9076 | ΔpSTV100 | *S. Typhimurium* UK-1 χ3761 cured of its large plasmid |
| χ9088 | Δpmi-2426 Δ(gmd-fcl)-26 $\Delta P_{fur33}$::TT araC $P_{BAD}$ fur ΔasdA33 | Transduced χ9063 with P22 (χ8958::pYA3736) and selected for CmR |
| χ9241 | ΔpabA1516 ΔpabB232 ΔasdA16 ΔaraBAD23 ΔrelA198::araC $P_{BAD}$ lacl TT | Defined deletion of relA-12 to 2235 and inserted 2429 by araCPBADlacl (ATG codon)TT in χ9097. Generated by conjugating χ9097 with χ7213 harboring pYA4064 |

TABLE 7-continued Bacterial strains

| Strain | Genotype | Characterization |
|---|---|---|
| χ9405 | ΔpSTV100 ΔcysG169::spvABCD | spvABCD region amplified from χ3761 and inserted into cysG chromosome of χ9076 by suing a suicide vector pRE112. |
| χ9424 | hsdL6 galE496 trpB2 flaA66 his-6165 rpsL120 xyl-404 metE551 metA22 lamB+(*E. coli*) Δzja::Tn10 hsdSA29 val ΔendA2311 ΔfimH1019 ΔrecF ΔrecJ ΔmsbB48 ΔfliC Δ(lpfABCDE)::Km fimA::Cm adf:Sm/Sp. | |
| χ9558 | Δpmi-2426 Δ(gmd fcl)-26 ΔP$_{fur81}$::TT araC P$_{BAD}$ fur ΔP$_{crp527}$::TT araC P$_{BAD}$ crp ΔasdA27::TTaraC P$_{BAD}$ c2 ΔaraE25 ΔaraBAD23 ΔrelA198::araCP$_{BAD}$lacITT ΔsopB1925 ΔagfBAC811 | Transduced χ9513 with P22 phage lysate grown on χ9477::pYA4109 |
| χ9590 | Δpmi-2426 Δ(gmd-fcl)-26 ΔP$_{fur33}$::TTaraCP$_{BAD}$fur ΔP$_{crp527}$::TTaraCP$_{BAD}$crp ΔasdA27::TTaraCP$_{BAD}$c2 ΔaraE25 ΔaraBAD23 ΔrelA198::araCP$_{BAD}$lacITT ΔsopB1925 Δakf-3 ΔdadB4 | Conjugated χ9588 with pYA3668 |
| χ9592 | Δpmi-2426 Δ(gmd-fcl)-26 ΔP$_{fur81}$::TT araC P$_{BAD}$ fur ΔP$_{crp527}$::TT araC P$_{BAD}$ crp ΔasdA27::TTaraC P$_{BAD}$ c2 ΔaraE25 ΔaraBAD23 ΔrelA 198::araC P$_{BAD}$ ΔacI TT ΔsopB1925 ΔagfBAC811ΔfliC180 ΔfljB3217 | Defined deletion of 19 genes from waz to wcaL in χ8958. Generated by conjugating χ7213 harboring pYA4366 |
| χ9606 | Δpmi-2426 Δ(gmd fcl)-26 ΔP$_{fur81}$::TT araC P$_{BAD}$ fur ΔP$_{crp527}$::TT araC P$_{BAD}$ crp ΔaraE25 ΔrelA198::araCP$_{BAD}$lacITT ΔsopB1925 ΔagfBAC811 | |
| χ9608 | ΔP$_{fur81}$::TT araC P$_{BAD}$ fur ΔP$_{crp527}$::TT araC P$_{BAD}$ crp Δpmi-2426 Δ(gmd fcl)-26 ΔrelA198::araC P$_{BAD}$ lacI TT ΔaraBAD23 ΔaraE25 ΔagfBAC811 ΔsopB1925 ΔasdA33 | |
| χ9641 | Δpmi-2426 Δ(gmd-fcl)-26 ΔP$_{fur81}$::TT araC P$_{BAD}$ fur ΔP$_{crp527}$::TT araC P$_{BAD}$ crp ΔasdA27::TTaraC P$_{BAD}$ c2 ΔaraE25 ΔaraBAD23 ΔrelA198::araCPBADlacITT ΔsopB192 ΔagfBAC811 ΔfliC180 ΔfljB217 | |
| χ9681 | ΔmntR28 | Defined deletion of mntR in χ3761 by conjugating with χ7213 harboring pYA3975 |

*Escherichia coli*

| Strain | Genotype | Characterization |
|---|---|---|
| χ289 | F$^-$ supE42 λ$^-$ T3$^R$ | Acridine orange cured F$^-$ derivative of χ15 |
| χ6097 | F$^-$ ara Δ lac-pro rpsL ΔasdA4 Δ(zhf$^2$::Tn10) Φ80d lacZDM15 | |
| χ6212 | Φ 80d lacZ DM15 deoR Δ(lacZYA-argF)U169 supE44 λ gyrA96 recA1 relA1 endA1 ΔasdA4 Δzhf-2::Tn10 hsdR17 (R$^-$ M$^+$) | Rec$^-$(UV$^s$) Asd$^-$ Lac$^-$ Nal$^r$ Tet$^s$, This is a Δasd derivative of DH5α providing a recA hsd background for the Asd$^+$ vectors. It was obtained by transforming χ6101 with pYA2000 (a recA clone) transducing this intermediate to Tet$^r$ Dap$^-$ using P1L4 grown on χ2981 then plating on fusaric acid medium containing DAP to select for Tet$^S$ isolate. This isolate no longer requires thiamine and appears to grow slower than either parent. (pYA2000 is not present in strain due to selection for Ap$^s$ isolate). |
| χ7030 | Wild type | Avian Pathogenic *E. coli* (APEC), O2:K1:H5 |
| χ7122 | Wild type | Avian Pathogenic *E. coli* (APEC), O78:K80:H9 |
| χ7213 | Thi-1 thr-1 supE44 tonA21 lacY1 recA RP4-2-Tc::M λpir ΔasdA4 Δzhf-2::Tn10 | DAP-, universal donor for conjugating pir-dependent suicide vectors |
| χ7235 | Wild type | Avian Pathogenic *E. coli* (APEC), O1:K1:H7 |
| χ7378 | thr-1 leuB6 fhuA21 lacY1 glnV44 ΔdadX recA1 ΔasdA4 Δ(zhf-2 :: Tn10) thi-1 RP4-2-Tc :: Mu [λ-pir] Δalr | χ7213 derivative with Δalr and ΔdadX |
| χ7385 | F$^-$ araD139 Δ(ara-leu)-7697 Δ(lacAYZOPI)-X74 Δlon-4 ΔompT0523(ΔompT::TT-araCP$_{BAD}$-T7pol-TT) galK deoR ΔcsgA mcrA galU f80dlacZΔM15 | This strain lacks lacI gene. Thus a target gene under control of the Ptrc promoter might be |

TABLE 7-continued

| | Bacterial strains | |
|---|---|---|
| Strain | Genotype | Characterization |
| | ΔfliC38 Δ(wcaL-wza)-19 recA1 endA1 nupG rpsL Δasd ΔfimA-H Δ(mcrBC-hsdRMS-mrr) | expressed constitutively without regulation. |
| TW01393 | Wild type | Shiga toxin-producing *E. coli* (STEC), O91:H21 |
| TWO1407 | Wild type | Shiga toxin-producing *E. coli* (STEC), O156:H21 |
| TW02916 | Wild type | Shiga toxin-producing *E. coli* (STEC), O52:H25 |
| TW07593 | Wild type | Shiga toxin-producing *E. coli* (STEC), O159 |
| TW07892 | Wild type | Enteropathogenic *E. coli* (EPEC), O142:H21 |
| | *Shigella* | |
| BS12 | Wild type | *S. flexneri* 2457O, Hela invasion -; sereny negative |
| BS155 | Wild type | *S. flexneri*, Hela invasion +; Pcr+ |
| BS98 | Spontaneous avirulent | *S. flexneri* 2a, nonpigmented mutant derivative of wild-type 2457T, pcr-11 |
| | *Yersinia* | |
| KIM6 | Wild type | *Y. pestis*, Subtype *medievalis* |
| CO92 | Wild type | *Y. pestis*, Subtype *orientalis* |
| C20 | Wild type | *Y. enterocolitica* |
| PB1/+ | Wild type | *Y. pseudotuberculosis*, Serotype IB |
| | *Clostridium perfringens* | |
| CP 15 | Wild type | *C. perfringens*, Type A, Isolate from chicken feces, moderate hemolysis and lecithinase activity. |
| CP 35 | Wild type | *C. perfringens*, wild type, Type A Isolate from chicken feces, low hemolysis and lecithinase activity |
| CP 167 | Wild type | *C. perfringens*, wild type, Type A, Isolate from Broiler litter, low hemolysis and lecithinase activity |
| CP 273 | Wild type | *C. perfringens* Type A, Isolate from Darkling beetle, low hemolysis and lecithinase activity |
| CP 284 | Wild type | Type A, Isolate from Darkling beetle larvae, low hemolysis and lecithinase activity. |
| CP 404 | Wild type | Type A, Isolate from isolated from Beef, moderate hemolysis and lecithinase activity. |

TABLE 8

| | Vectors |
|---|---|
| Plasmid | Properties |
| pYA232 | pSC101 on lacI$^q$, 10.2 kb, Tc$^R$ |
| pYA812 | pBR ori lacI$^q$, 5.46 kb, AP$^R$ |
| pYA3167 | pBR ori Asd$^+$, HBV core preS gene fragment of pYNS27-53PS2, 4125 bp |
| pYA3332 | p15A ori Asd$^+$, 3425 bp |
| pYA3337 | pSC101 ori Asd$^+$, 4343 bp |
| pYA3341 | pUC ori Asd$^+$, 2771 bp |
| pYA3342 | pBR ori Asd$^+$, 3012 bp |
| pYA3493 | pBR ori bla SS, Asd$^+$, 3113 bp, |
| pYA3620 | pBR ori bla SS bla CT, Asd$^+$, 3169 bp |
| pYA3634 | pBR ori bla SS, Asd$^+$ PspA/Rx1 |
| pYA3681 | pBR ori araC P$_{BAD}$ SD-GTG murA SD-GTG asd, P22P$_R$ antisense RNA P$_{trc}$, 5832 bp, prokaryotic expression regulated lysis vector |
| pYA3747 | pBR on ompA SS P$_{lpp}$ Asd$^+$ PspA aa 3-286 |
| pYA3791 | pUC ori P$_{trc}$ Asd$^+$, core aa 1-78 preS1 aa 20-47 core aa 79-144 preS2 aa 120-151 core aa 145-147, core aa 179-183, 3472 bp |
| pYA3792 | pBR ori P$_{trc}$ Asd$^+$, core aa 1-78 preS1 aa 20-47 core aa 79-144 preS2 aa 120-151 core aa 145-147, core aa 179-183, 3662 bp |

TABLE 8-continued

Vectors

| Plasmid | Properties |
| --- | --- |
| pYA3793 | pUC ori $P_{trc}$ Asd$^+$ core aa 1-77 preS1 aa 20-47 core aa 84-144 preS2 aa 120-151 core aa 145-147, core aa 179-183, 4599 bp |
| pYA3794 | pBR ori $P_{trc}$ Asd$^+$ core aa1-77 preS1 aa 20-47 core aa 84-144 preS2 aa 120-151 core aa 145-147, core aa 179-183, 3454 bp |
| pYA3795 | pUC ori $P_{trc}$ Asd$^+$ core aa 1-74 preS1 aa 20-47 core aa 87-144 preS2 aa 120-151 core aa 145-147, core aa 179-183, 3644 bp |
| pYA3796 | pBR ori $P_{trc}$ Asd$^+$ core aa 1-74 preS1 aa 20-47 core aa 87-144 preS2 aa 120-151 core aa 145-147, core aa179-183, 4581 bp |
| pYA3797 | pUC ori $P_{trc}$ Asd$^+$ core aa1-69 preS1 aa 20-47 core aa 91-144 preS2 aa 120-151 core aa 145-147, core aa 179-183, 3436 bp |
| pYA3798 | pBR ori $P_{trc}$ Asd$^+$ core aa 1-69 preS1 aa 20-47 core aa 91-144 preS2 aa 120-151 core aa 145-147, core aa 179-183, 3626 bp |
| pYA3802 | pBR ori bla SS bla CT Asd$^+$ $P_{trc}$ PspA aa 3-286, 3995 bp |
| pYA3826 | $P_{trc}$, bla ss, asd, pBRori, PlcC$_{241-370}$ |
| pYA3841 | pYA3841: pBR ori $P_{trc}$ IcrV$_{393-981}$ blaSS blaCT 5ST1 T2 Asd$^+$ LcrV as protein is fragment corresponding to aa131-aa327, 3734 bp |
| pYA3847 | pBR ori araC $P_{BAD}$ asd $P_{trc}$ bla SS::Ag85-A::ESAT-6::bla CT, 5616 bp |
| pYA3869 | pSC101 ori Asd$^+$ SopE$^+$, 4399 bp |
| pYA3870 | p15A ori Asd$^+$ SopE$^+$, 3481 bp |
| pYA3920 | p15A ori $P_{asd}$ asd $P_{sopE}$ sopE (Nt)::ESAT-6, 3758 bp |
| pYA3940 | pBR ori bla SS::Ag85A asd, 3989 bp |
| pYA3941 | pBR ori bla SS::Ag85A::bla CT asd, 4037 bp |
| pYA3950 | p15A ori $P_{asd}$ asd $P_{sopE}$ sopE::CFP-10::ESAT-6, 4036 bp |
| pYA3977 | $P_{trc}$, bla ss, asd, pBRori, PlcC$_{248-370}$ |
| pYA4013 | p15A ori MurA$^+$, 2984 bp |
| pYA4014 | p15A ori DadB$^+$, 2743 bp |
| pYA4015 | pBR ori DadB$^+$, 3017 bp |
| pYA4016 | pUC ori DadB$^+$, 2796 bp |
| pYA4028 | pBR ori bla SS Asd$^+$ $P_{trc}$ PspC aa 4-404, 4322 bp |
| pYA4029 | pBR ori bla SS Asd$^+$ $P_{trc}$ PspC aa 4-445 with the proline rich domain, 4452 bp |
| pYA4050 | pUC ori araC $P_{BAD}$ SD-GTG murA SD-GTG asd, P22P$_R$ antisense RNA with DNA nuclear targeting sequence and poly A from SV40, 6941 bp |
| pYA4088 | pBR ori bla SS Asd$^+$ $P_{trc}$ PspA aa 3-286, 3927 bp |
| pYA4100 | pBR ori ompA SS Asd$^+$ $P_{lpp}$ PspC aa 4-404 |
| pYA4102 | pBR ori ompA SS Asd$^+$, 3075 bp |
| pYA4106 | pBR ori phoA SS Asd$^+$, 3076 bp |
| pYA4110 | $P_{lpp}$, ompA ss*, asd, pBRori, PlcC$_{248-370}$, (3.6 kb) |
| pYA4111 | $P_{trc}$, asd, pBRori, gst, GST-PlcC$_{248-370}$, 4.2 kb |
| pYA4139 | pUC ori araC $P_{BAD}$ SD-GTG murA SD-GTG asd, P22P$_R$ antisense RNA sopE2 (Nt):: mtb39A SV40 poly A SV40 enhancer, 8481 bp |
| pYA4140 | pUC ori araC $P_{BAD}$ SD-GTG murA SD-GTG asd, P22P$_R$ antisense RNA, DNA nuclear targeting sequence and poly A from SV40 with sopE2 (Nt):: mtb39A, 8410 bp |
| pYA4149 | $P_{trc}$, bla ss, bla-C*, asd, pBRori, PlcC$_{248-370}$ |
| pYA4152 | pBR ori araC $P_{BAD}$ SD-GTG murA SD-GTG asd, P22P$_R$ antisense RNA $P_{trc}$ WHc-M2e (codon optimized) 6379 bp, |
| pYA4202 | pBR ori ompA SS Asd$^+$ $P_{trc}$ PspC aa 4-404, 4284 bp |
| pYA4211 | pBR ori araC $P_{BAD}$ asd $P_{trc}$, 4538 bp |
| pYA4240 | pBR ori MurA$^+$, 3249 bp |
| pYA4241 | pUC ori MurA$^+$, 3028 bp |
| pYA4251 | p15A ori $P_{asd}$ asd $P_{sopE}$sopE(Nt)::ESAT-6::ESAT-6::ESAT-6, 4322 bp |
| pYA4257 | p15A ori $P_{asd}$ asd $P_{sopE}$sopE(Nt)::ESAT-6::ESAT-6::CFP-10, 4327 bp |
| pYA4266 | pBR ori ompA SS Asd$^+$ $P_{trc}$ PspA aa 3-286, 3927 bp |
| pYA4267 | pBR ori phoA SS AAsd$^+$ $P_{trc}$ PspA aa 3-286, 3928 bp |
| pYA4269 | pBR ori bla SS bla CT Asd$^+$ $P_{trc}$ PspC aa 4-404, 4378 bp |
| pYA4271 | pUC ori araC $P_{BAD}$ SD-GTG murA SD-GTG asd, P22P$_R$ antisense RNA with DNA nuclear targeting sequence and poly A from SV40, contains EGFP |
| pYA4272 | pUC ori araC $P_{BAD}$ SD-GTG murA SD-GTG asd, P22P$_R$ antisense RNA, contains EGFP |
| pYA4407 | pSC101 ori Asd$^+$, IpaD aa 60-162 (LEEI-VQQI) 4637 bp |
| pYA4408 | pSC101 ori Asd$^+$, IpaD aa 185-303 (LEEL-VQQV) 4685 bp |
| pYA4409 | p15A ori Asd$^+$, IpaD aa 60-162 (LEEI-VQQI) 3604 bp |
| pYA4410 | p15A ori Asd$^+$, IpaD aa 185-303 (LEEL-VQQV) 3752 bp |
| pYA4411 | p15A ori Asd$^+$, IpaD aa 60-160 (LEEI-VQQI), IpaD aa 185-303 (LEEL-VQQV), 3963 bp |
| pYA4412 | pUC ori Asd$^+$, IpaD aa 60-162 (LEEI-VQQI) 3065 bp |

TABLE 8-continued

Vectors

| Plasmid | Properties |
| --- | --- |
| pYA4413 | pUC ori Asd+, IpaD aa 185-303 (LEEL-VQQV) 3113 bp |
| pYA4414 | pUC ori Asd+, IpaD aa 60-162 (LEEI-VQQI), IpaD aa 185-303 (LEEL-VQQV) 3424 bp |
| pYA4415 | pBR ori bla SS, Asd+, IpaD aa 60-162 (LEEI-VQQI) 3407 bp |
| pYA4416 | pBR ori bla SS, Asd+, IpaD aa 185-303 (LEEL-VQQV) 3455 bp |
| pYA4417 | pBR ori bla SS, Asd+, IpaD aa 60-162 (LEEI-VQQI), IpaD aa 185-303 (LEEL-VQQV) 3766 bp |
| pYA4418 | pBR ori bla SS, Asd+, IpaD aa 23-333 4051 bp |
| pYA4419 | pUC ori Asd+, MntH 4007 bp |
| pYA4420 | p15A ori Asd+, CorA 4490 bp |
| pYA4421 | pUC ori Asd+, CorA 3836 bp |
| pYA4422 | p15A ori Asd+, MgtA aa 350-650 4313 bp |
| pYA4423 | pUC ori Asd+, MgtA aa 350-650 3659 bp |
| pYA3740 | Suicide vector to generate $\Delta P_{mntR}19::TTaraCP_{BAD}$ mntR 914 bp flanking region, deleting 269 bp promoter sequence (mntR-11 to -280), plus 1329 by $P_{BAD}$ araC TT(T4 iplll) is inserted in SacI-SphI sites of pRE112 |
| pYA3742 | Suicide vector to generate $\Delta P_{mntR}26::TTaraCP_{BAD}$ mntR 909 bp flanking region, deleting 269 by promoter sequence (mntR-11 to -280), plus 1329 by $P_{BAD}$ araC TT(T4 iplll) is inserted in SacI-SphI sites of pRE112 |
| pYA4424 | Suicide vector to generate $\Delta P_{mntR}20::TTaraCP_{BAD}$ mntR 909 bp flanking region, deleting 269 by promoter sequence (mntR-11 to -280), plus 1329 by $P_{BAD}$ araC TT(T4 iplll) is inserted in SacI-SphI sites of pRE112 |
| pYA4425 | Suicide vector to generate $\Delta P_{mntR}21::TTaraCP_{BAD}$ mntR 912 bp flanking region, deleting 269 by promoter sequence (mntR-11 to -280), plus 1329 by $P_{BAD}$ araC TT(T4 iplll) is inserted in SacI-SphI sites of pRE112 |
| pYA4426 | Suicide vector to generate $\Delta P_{mntR}22::TTaraCP_{BAD}$mntR 912 bp flanking region, deleting 269 bp promoter sequence (mntR-11 to -280), plus 1329 by $P_{BAD}$ araC TT(T4 iplll) is inserted in SacI-SphI sites of pRE112 |
| pYA4427 | Suicide vector to generate $\Delta P_{mntR}27::TTaraCP_{BAD}$ mntR 914 bp flanking region, deleting 269 bp promoter sequence (mntR-11 to -280), plus 1329 by $P_{BAD}$ araC TT(T4 iplll) is inserted in SacI-SphI sites of pRE112 |
| pYA4428 | pSC101 ori, Asd+ YagZYXW 9743 bp |
| pYA4468 | GST-cpbX fusion (GST-netB) |
| pYA4488 | ipxR flanking regions with $P_{lpp}$ pagL cloned into suicide vector pRE112, this suicide vector can replace the IpxR with $P_{lpp}$ pagL which leads to constitutive expression of pagL |
| pYA4492 | netB (cpbX) in pYA3342-netB fragment |
| pYA4493 | netB (cpbX) in pYA3393-netB fragment |
| pYA4494 | pilA in pYA3342 |
| pYA4495 | pilA in pYA3493 |
| pYA4661 | pYA384: pBR ori $P_{trc}$ IcrV$_{1-981}$ blaSS blaCT 5ST1 T2 Asd+ LcrV as protein is fragment corresponding to aa131-aa327, 4127 bp |
| pYA4662 | pYA384: pBR on $P_{trc}$ ICrV$_{1-981}$ blaSS blaCT 5ST1 T2 Asd+ LcrV as protein (E33Q and E34Q),, 4127 bp |
| pYA4663 | pYA384: pBR ori $P_{trc}$ IcrV$_{1-981}$ blaSS blaCT 5ST1 T2 Asd+ LcrV as protein (K42Q), 4127 bp |
| pYA4664 | pYA384: pBR on $P_{trc}$ IcrV$_{1-981}$ blaSS blaCT 5ST1 T2 Asd+ LcrV as protein (E204Q and E205Q), 4127 bp |
| pYA4665 | pYA384: pBR ori $P_{trc}$ IcrV$_{393-981}$ blaSS blaCT 5ST1 T2 Asd+ LcrV as protein (E33Q, E34Q, K42Q, E204Q and E205Q), 4127 bp |
| pAPEC-1 | Virulence plasmid of APEC χ7122 (103 kb) |
| pCR2.1-TOPO | pUC on Ap$^R$, Kan$^R$ PCR cloning vector, 3931 bp |
| Vectors for expressing His- and GST-tagged proteins | |
| pET23d(+) | pBR ori $P_{T7}$ N-terminal T7 tag/C-terminal His-tag, Ap$^R$, 3663 bp |
| pET28b(+) | pBR ori $P_{T7}$ lacO N-terminal His-tag/thrombin/T7-tag/C-terminal His-tag, Kan$^R$, 5368 bp |
| pET30a(+) | pBR ori $P_{T7}$ lacO N-terminal His-tag/thrombin/S-tag/C-terminal His-tag, Kan$^R$, 5422 bp |
| pGEX4T-2 | pBR ori GST gene fusion vector Ap$^R$, 4970 bp |
| pBAD/HisB | $P_{BAD}$ promoter, araC+, pBRori, amp$^R$, His fusion vector 4.1 kb |
| pGEX-4T-2 | $P_{trc}$ promoter, pBRori, amp$^R$, GST fusion vector 4.5 kb |
| pYA4111 | pBR ori Asd+ GST gene fusion vector, 3.7 kb |

In addition, we have collected nine additional *S. enterica* serotypes frequently associated with carriage in bovine, porcine and poultry species and/or transmitted, presumably through the food chain, to cause disease in humans. We have also discovered seventy other serotypes from our collection. Thus, there is a very extensive collection to use in our studies on induction of immune response to *Salmonella* of diverse serotypes. We have three new *C. jejuni* strains and eleven new *Shigella* strains representing diverse species and serotypes. Other strains from diverse locations are being collected.

As a new suicide vector donor strain, we constructed $\chi$7378 with $\Delta$alr-9 and $\Delta$dadX8 mutations in addition to the $\Delta$asdA4 mutation to enable counter selection with omission of either D-alanine or DAP. This strain can also be used for conjugational delivery of recombinant DadB$^+$ or Asd$^+$ vectors while retaining a means for counter selection with a lethal marker. We also have a diversity of *E. coli* cloning hosts derived from $\chi$6097 and $\chi$6212 with the $\Delta$alr-9 and $\Delta$dadX8 mutations in addition to the $\Delta$asdA4 mutation.

Molecular and Genetic Procedures.

Methods for DNA isolation, restriction enzyme digestion, DNA cloning and use of PCR for construction and verification of vectors are standard. DNA sequence analysis was performed at nominal charge in the DNA Sequence Laboratory in the School of Life Sciences at ASU. All oligonucleotide and/or gene segment syntheses were done commercially. Site-directed mutagenesis was used to optimize codons for translational efficiency in *Salmonella*. Stabilization of mRNA to prolong its half-life will involve site-directed mutagenesis to destroy RNase E cleavage sites and/or by fusing the ompA leader mRNA encoding sequence at the transcription start site for a gene encoding an antigen of interest. Phage P22HTint are used to transduce mutations of a selectable phenotype from one *S. Typhimurium* strain into other strains. Conjugational transfer of suicide vectors was performed by standard methods using the suicide vector donor strain $\chi$7213 or its derivative with alr and dadB mutations $\chi$7378. Plasmid constructs was evaluated by DNA sequencing, ability to complement various *S. Typhimurium* mutant strains and for ability to specify synthesis of proteins using gel electrophoresis and western blot analyses. His-tagged proteins was produced in $\chi$7385, a new *E. coli* host, and used to obtain anti-protein rabbit antisera for western blot analyses.

Vaccine strains are fully characterized at each step in their construction and before use for immunization studies. These strains are compared with vector control strains for stability of plasmid maintenance, integrity and antigen synthesis ability when strains are grown in the presence of arabinose and/or DAP and/or D-alanine over a 50 generation period. Molecular genetic attributes are confirmed by use of PCR and/or Southern blot analyses with appropriate probes. Measurement of lipopolysaccharide or its absence is performed after electrophoresis using silver stained gels. This analysis is done after every step in any strain construction to eliminate rough variants if they arise. Motility tests and use of specific antisera for given flagellar antigens are used to reveal presence or absence of flagella. Presence of fimbrial adhesins are assayed using agglutination of yeast and red blood cells in the presence and absence of mannose as a function of growth conditions, Congo red binding assays and by transmission electron microscopy (TEM) using negative staining with phosphotungstic acid. Metabolic attributes of candidate vaccine strains are evaluated using API-20E tests.

Cell Biology.

The ability of various constructed *Salmonella* strains to attach to, invade into and survive in various murine and human macrophage cell lines are quantitated by well established methods used routinely. Similarly, ability to induce pyroptosis/apoptosis will use standard methods.

Animal Experimentation.

BALB/c and C57BL/6 female mice, six to eight weeks of age, are used for most experiments. Inbred mice with other MHC haplotypes and Swiss Webster outbred mice are also used in some studies. Mice are held in quarantine one-week before use in experiments. They are deprived of food and water 6 h before oral immunization. No bicarbonate is administered. Bacterial strains are grown under conditions to optimize expression of SPI-I encoded genes needed to facilitate invasion and colonization of lymphoid tissues. Food and water are returned 30 min after immunization. A second boosting immunization is given one, two or four weeks after the first dose, but after saphenous vein bleeding to collect serum and to collect feces and/or vaginal secretions for quantitation of SIgA. Candidate vaccine strains are quantitatively enumerated in various tissues as a function of time after inoculation. Generally, three mice are used per time point. The inoculation procedures are the same as in the immunization studies. All animals are housed in BL2 containment with filter bonnet covered cages. If high immunogenicity is observed in initial tests after primary immunization, subsequent studies are done to determine the lowest level of vaccine inocula to induce a significant immune response. Challenge studies involve many different bacterial pathogens all grown under optimal conditions for that pathogen and with the route of challenge also selected to reveal strengths and weaknesses of the immunizing strain or regime. We then calculate $LD_{50}$ and mean day of death (MDD) values.

Antigen Preparation

We have made purified antigens as His-tagged proteins from recombinant *E. coli* $\chi$7385 for all antigens encoded by genes from various pathogens and specified by RASVs. $\chi$7385 has been engineered to eliminate potential contamination of proteins with appendage proteins and LPS O-antigen. *Salmonella* LPS O-antigen is obtained commercially although purification of O-antigen and LPS core are in progress to facilitate determination of antibody titers. We have prepared an *S. Typhimurium* outer membrane protein (SOMP) fraction from $\chi$9424 that has been engineered to be unable to produce flagella, all in vitro-expressed pilus antigens, and LPS O-antigen and a heat killed extract of the wild-type *S. Typhimurium* UK-1 strain $\chi$3761. These antigens will be used as controls in western blots as well as for immunoassays as described below. We have OMP extracts from many *Salmonella* serotypes, *E. coli*, *Shigella* and *Yersinia* strains. Synthetic peptides for various T-cell epitopes to use in T-cell proliferation assays are prepared commercially.

ELISA

Serum antibodies are measured in blood collected by saphenous vein bleeding and mucosal antibodies as extracted copro antibodies from feces or in vaginal secretions. In initial studies, sera and secretions are pooled from all mice in a group but in later studies with successful constructs, antibody titers are monitored in individual mice. We employ a doubling dilution method with the end point titer being the dilution giving an $OD_{410}$ three times that for the reagent or unimmunized animal control. SIgA titers against the various antigens are monitored by ELISA in the same way. Since we are interested in distinguishing between a Th1 and Th2 response, the titers of IgG1 versus IgG2A are determined by standard methods known to one of skill in the art.

ELISPOT Analysis

ELISPOT analysis is used to quantitate IgA secreting peripheral blood lymphocytes in evaluating RASVs for inducing mucosal immunity and for INF-$\gamma$ produced by T cells from mice immunized with RASVs to stimulate T-cell immunity. INF-γ produced as a result of co-cultures of the lymphocytes and T cells are determined using a described ELISPOT assay.

T-Cell Proliferation Assays

These are performed on spleenocyte preparations obtained from groups of mice one, two and four weeks post-vaccination using standard methods. Lymphocytes are purified by Histopaque 1077 gradient centrifugation and examined for incorporation of [$^3$H]-thymidine after stimulation with His-tagged antigens. Stimulation with specific peptides containing T-cell epitopes is also employed. Stimulation with S. Typhimurium outer membrane proteins and concanavalin A serve as controls.

CTL Assays

CTL responses to T-cell epitopes are quantitated, if necessary, using the appropriate murine cell lines (P815 or EL-4) transfected with plasmids encoding the epitopes to serve as targets for assays of BALB/c or C57BL/6 immunized mice. Effector cells are obtained from spleens of non-immunized and immunized mice. Part of the effector cell population is used immediately in a Cytotox 96 nonradioactive CTL assay (Promega). The remaining cells are re-stimulated with the appropriate antigen for five to seven days prior to use in the CTL assay. The CTL assay measures lactate dehydrogenase released due to lysis of target cells. The values obtained are used to calculate the percentage of target cells lysed relative to the quantity of effector cells added. We have had very good success with this assay, but have also used the $^{51}$Cr release assay.

Statistical Analysis

All results are analyzed using the most appropriate statistical test from the SAS program to evaluate the relative significance or lack thereof of results obtained.

Further Genetic Modification of S. Typhimurium

To minimize induction of immune responses to serotype-specific antigens and maximize induction of cross protective immunity to common related antigens of S. enterica strains of diverse serotypes and to other bacterial enteric pathogens, especially E. coli pathovars, Shigella species and Yersinia species, further work was undertaken for genetic modification of S. Typhimurium.

We have one S. Typhimurium UK-1 starting strain χ9592 (Δpmi-2426 Δ(gmd-fcl)-26 ΔP$_{fur81}$::TT araC P$_{BAD}$ fur ΔP$_{crp527}$::TT araC P$_{BAD}$ crp ΔasdA27::TTaraC P$_{BAD}$ c2 ΔaraE25 ΔaraBAD23 ΔrelA198::araC P$_{BAD}$ ΔlacI TT ΔsopB1925 ΔagfBAC811ΔfliC180 ΔflijB217). We add mutations to this strain as their inclusion is validated by the experiments proposed in this and following sections. In addition, we then add the ΔrecF126 mutation and then derive three strains, one with the Δalr-3, ΔdadB4 mutations, one with the ΔP$_{murA12}$::TTaraC P$_{BAD}$ murA mutation and one with all three mutations. In another case, we will derive strains from S. Typhimurium χ9903 Δpmi-2426 Δ(wcaM-wza)-8 ΔP$_{fur81}$::TT araC P$_{BAD}$ fur ΔP$_{crp527}$::TT araC P$_{BAD}$ crp ΔasdA27::TT araC P$_{BAD}$ c2 ΔaraE25 ΔaraBAD23 ΔrelA198::araC P$_{BAD}$ lacI TT ΔsopB1925 ΔagfBAC811 Δlrp-23.

Constructing the Platform Strains.

We use our suicide vectors and P22 transduction methods to generate all the strain genotypes listed in the Introduction section above to generate stains lited in Table 7 and derivatives of χ9592 (Δpmi-2426 Δ(gmd-fcl)-26 ΔP$_{fur81}$::TT araC P$_{BAD}$ fur ΔP$_{crp527}$::TT araC P$_{BAD}$ crp ΔasdA27::TT araC P$_{BAD}$ c2 ΔaraE25 ΔaraBAD23 ΔrelA198::araC P$_{BAD}$ lacI TT ΔsopB1925 ΔagfBAC811 ΔfljB217 ΔfliC180) and derivatives of χ9903 Δpmi-2426 Δ(wcaM-wza)-8 ΔP$_{fur81}$::TT araC P$_{BAD}$ fur ΔP$_{crp527}$::TT araC P$_{BAD}$ crp ΔasdA27::TT araC P$_{BAD}$ c2 ΔaraE25 ΔaraBAD23 ΔrelA198::araC P$_{BAD}$ lacI TT ΔsopB1925 ΔagfBAC811 Δlrp-23. In making derivatives we will select from among the following mutations: ΔP$_{rfc174}$::TT araC P$_{BAD}$ rfc, Δ(galE-ybhC)-851, ΔP$_{mntR22}$::TT araC P$_{BAD}$ mntR, Δ(yshA-yihW)-207, ΔcysG175::P$_{spv175}$ spvABCD, ΔrecF126, Δalr-3 and ΔdadB4, ΔP$_{murA25}$::TTaraC P$_{BAD}$ murA, Δ(P$_{agfD}$ agfG)-4, ΔbcsABZC2118 or ΔbcsEFG2319, ΔyhiR36, Δ(shdA-ratB)-64, ΔmisL2, ΔbigA3, ΔackA233, ΔaroA21419, ΔaroC, ΔaroD, ΔilvE and ΔilvC.

At each step in the constructions we perform the strain characterizations described above. It should be noted that if improvements to the core genotype are developed prior to the completion of the construction plan above, one should include these improvements at the earliest step possible.

Example 18

Animal Protection Studies

Studies were conducted to fully evaluate how best to maximize induction of cross-protective immunity, consequences of vaccination on normal flora, efficacy of mixtures of vaccines designed to protect against Salmonella and one or two other species versus a vaccine designed to protect against multiple bacterial enteric pathogens, and means to experimentally validate a vaccine designed to protect against multiple pathogens.

Introduction

After making progress in constructing strains and vectors and in understanding how to best optimize vaccine efficacy, we are conducting a series of studies to examine optimal immunization regimens and doses, work out methods to evaluate induction of cross protective immunity without having to resort to hundreds of challenge studies, determine whether there are adverse consequences of vaccination on normal flora that impact the nutritional health of vaccinated individuals, determine whether antigen interference is observed such that vaccination with a mixture of vaccine strains will give better protection that achieved with a single genetically engineered vaccine, and devise means to validate vaccine-induced protection against multiple pathogens.

Determining Optimal Immunization Regimens and Doses

Initially we select two recombinant vaccines, one in which we expect protection against a lethal challenge (such as by EIEC or STEC) and the other in which we expect reduction in intestinal colonization (such as for C. perfringens or C. jejuni) in the mouse. We initially immunize orally with $10^7$, $10^8$ and $10^9$ CFU of vaccine, monitor selected immune responses by ELISA and ELISPOT at two-week intervals for 8 to 10 weeks and then administer a boost immunization and follow antibody titers for another four weeks followed by challenge with the pathogen of choice at a reasonable dose. A second set of experiments is done with the best regimen followed by a range of challenge doses with the pathogens of choice. We then use two different vaccines to see if similar results were observed such as protection against S. Enteriditis or Y. enterocolitica or colonization by UPEC or EHEC pathovars.

Evaluating Induction of Cross Protective Immunity

The experiments described above are directed to defining an approach to this problem. In regard to cross protective immunity with Salmonella serotypes, the vast majority of strains are not very virulent in mice or chickens. We thus take four very virulent strains (for mice) of S. Typhimurium, S. Choleraesuis, S. Dublin and S. Enteriditis representative of serogroups B, C, D and D, respectively. If the vaccine prevents infection and severe disease with these strains, it can be inferred that the vaccine would induce protective immunity to strains of lower virulence. In other words, if we can identify strains of high virulence for any of the enteric pathogens and demonstrate protection to challenge either in terms of preventing disease symptoms or in eliminating persistent infection, we can infer protection and vaccine efficacy. During the course of these studies we can also determine whether antibody titers to a particular pathogen antigen increase as a consequence of challenge. In fact, we are examining this using cross-reactive antigens encoded by genes from enteric pathogens other than from the challenge strain. The issue is whether a challenge stimulates increased antibody titers to both homologous and some related cross-reactive antigens.

In other cases, we use strains of serotypes that do not cause lethal infection in mice or chickens, and determine whether immunization with a vaccine construct reduces colonization levels and/or persistence by these strains, especially in the gastrointestinal tract.

Evaluating Potential Adverse Consequences of Vaccination on Normal Flora

These studies are an extension of those described above in which we examine whether vaccination with a S. Typhimurium strain designed to maximize induction of cross protective immunity to enteric pathogens also engineered to express an ubiquitous E. coli pilus antigen does or does not have an adverse effect on normal E. coli flora. Thus, in addition to following titers of resident E. coli strains, we also measure weights, food consumption and general health over a period of some six months. If adverse consequences are observed, we examine whether administering probiotic microbial populations counters the adverse effect of vaccination.

Determining Whether Antigen Interference is Observed Such that Vaccination with a Mixture of Vaccine Strains Will Give Better Protection that Achieved with a Single Genetically Engineered Vaccine.

By careful analysis of data collected throughout these studies, we observe whether antibody titers to a particular antigen(s) decrease when a particular carrier vaccine strain is modified to deliver additional protective antigens. The rigorous test involves constructing a strain that expresses multiple antigens from the same vector or two or more vectors in the same strain. In this regard, we have fusions of two pneumococcal antigens on the same plasmid and the immune responses to each are independent of the order of antigens in the fusion. We thus engineer Asd$^+$, DadB$^+$ and MurA$^+$ vectors to express the various antigens described in the studies described as above. In fact, we have a fourth balanced-lethal vector system using plasmid expression and chromosome deletion of the murI gene encoding glutamate racemase. The comparison with the multi-valiant vaccine would involve making a mixture of the individual vaccines generated among those proposed.

Methods to Validate Vaccine-Induced Protection Against Multiple Pathogens Ultimately Useful in the Conduct of Human Trials.

The basic idea to evaluate first is whether sera from immunized mice can passively protect naive unimmunized mice from any of the invasive pathogens capable of a lethal outcome. The studies described above likely identify strains of Salmonella, E. coli, Shigella (administered intranasally), Yersinia and C. perfringens suitable for these evaluations. We also investigate whether immunity could be transferred by transfer of periferal blood lymphocytes. Another assay would be to determine whether sera from immunized mice prevented invasion of any of the pathogens into cells in culture or protect against transcytosis using polarized cell monolayers. Our collective studies provide additional means by which a multi-valent vaccine protective against many enteropathogens could be evaluated for protective efficacy against the individual pathogens. Ultimate clinical evaluation would be by immunization of travelers and having them record bouts of diarrhea or other enteric disease during their subsequent travels.

Example 19

Design, Construction and Evaluation of an Attenuated S. Paratyphi a Vaccine(s) with Similar Genetic Attributes as the S. Typhimurium Vaccine(s) Constructed Introduction Although not common, S. enterica strains of the non-typhoidal type can occasionally be associated with Reiter's syndrome or adjuvant arthritis. There is no present way to determine what Salmonella gene differences are responsible or whether our extensive genetic manipulation of the S. Typhimurium vaccine strain might decrease or even increase the possibility for such adverse sequela. For these reasons, we are developing S. Paratyphi A strains in parallel to the construction of the S. Typhimurium vaccine strains in case the risks of using a S. Typhimurium based vaccine in the developed world are judged to be unacceptably high.

Construction and Evaluation of S. Paratyphi a Vaccine

We have constructed χ9608 (Δpmi-2426 Δ(gmd-fcl)-26 ΔP$_{fur81}$::TT araC P$_{BAD}$ fur ΔP$_{phoPQ107}$::TT araC P$_{BAD}$ phoPQ ΔP$_{crp527}$::TT araC P$_{BAD}$ crp ΔagfBAC811 ΔaraE25 ΔaraBAD23 ΔrelA198::araC P$_{BAD}$ lacI TT ΔsopB1925 ΔasdA33) which has the ΔP$_{phoPQ107}$::TT araC P$_{BAD}$ phoPQ mutation not present in χ9558, the ΔasdA33 instead of the ΔasdA27:: TT araC P$_{BAD}$ c2 mutation that are easily interchangeable. Safety of χ9608 has been demonstrated by oral inoculation of 10$^8$ CFU into day-of-birth mice. Since we have now shown that the presence of various ΔP$_{phopQ}$::TT araC P$_{BAD}$ phoPQ constructions reduced induction of mucosal and serum antibody responses to protective antigens delivered by RASV strains, we have replaced the ΔP$_{phoPQ107}$::TT araC P$_{BAD}$ phoPQ deletion-insertion mutation with the wild-type phoPQ alleles and now have several S. Paratyphi A strains all with the Δpmi-2426 Δ(gmd fcl)-26 ΔP$_{fur81}$::TT araC P$_{BAD}$ fur ΔP$_{crp527}$::TT araC P$_{BAD}$ crp ΔaraE25 ΔrelA198::araCP$_{BAD}$- lacITT ΔsopB1925 ΔagfBAC811 mutations (as present in χ9606) and derivatives with ΔaraBAD23, with ΔaraBAD23 and ΔasdA33 or with Δ(araC-P$_{BAD}$)-5::P22$_{PR}$ araBAD mutation (χ9651, χ9762, χ9763). We have inserted additional mutations for use with multiple Asd$^+$, DadB$^+$ and MurA$^+$ vectors, to confer biological containment and to add other desirable attributes based on our results with S. Typhimurium vaccine strains.

Example 20

Protection Against APEC and UPEC Infections

The difficulty in making a vaccine against extra-intestinal E. coli (ExPEC) in birds, animals and humans is related to the diversity of these strains. Targeting common genes among ExPEC strains will be the best strategy to have an efficient vaccine against ExPEC. pAPEC-1 encodes for different iron acquisition systems, common among ExPEC strains, mostly involved in their extra-intestinal life. Salmonella vaccine cured of pSTUK100 with the ΔcysG/75::$_{Pspv175}$ spvABCD deletion-insertion mutation and containing pAPEC-1 will be tested in chickens for its ability to protect against APEC infection, airsaculitis and septicemia, by challenging birds with APEC from worldwide serogroups O1, O2, and O78.

The vaccine will be also tested in mice for its ability to protect against UPEC infections, by challenging mice with UPEC via urethral inoculation.

Example 21

Modify pAPEC-1 to Enhance Protection Against Yersinia and Shigella

We are cloning the codon-optimized virulence genes psn from Yersinia and aerobactin operon (iutA iucABCD) from Shigella (FIG. 9) into the Colicin V operon (FIG. 25) of pAPEC-1 (FIG. 24). Salmonella vaccine containing the modified pAPEC-1 with the ΔcvaAB::psn iutA iucABCD insertion as shown in FIG. 25 should protect against not only APEC, UPEC and Salmonella serotypes but also confer some enhanced protection against Yersinia and Shigella. It should be noted that the insertion construction (FIG. 25) retains the Fur regulated promoters of the psn and iutA iucABCD genes such that they will be up regulated in vaccine strains with the $\Delta P_{fur77}$::TT araC $P_{BAD}$ fur or $\Delta P_{fur81}$::TT araC $P_{BAD}$ fur mutations to further enhance induction of cross-protective immunity.

Example 22

Developing Vaccines to Confer Protective Immunity Against Multiple Enteric Pathogens We recently constructed derivatives of χ9590 (Δpmi-2426 Δ(gmd-fcl)-26 $\Delta P_{fur81}$::TT araC $P_{BAD}$ fur $\Delta P_{crp527}$::TT araC $P_{BAD}$ crp ΔasdA27:: TT araC $P_{BAD}$ c2 ΔaraE25 ΔaraBAD23 ΔrelA198::araC $P_{BAD}$ lacI TT ΔsopB1925 ΔagfBAC811 Δalr-3 ΔdadB4) (Table 7) with various types of rec mutations to investigate possible difficulties in the stable maintenance of two plasmids specifying two different protective anigens and with either the AsdA⁺ or DadB⁺ selective marker but with some DNA sequences in common due to using the same $P_{trc}$ promoter, termination sequence and pBR ori. Although we determined that recombination between plasmids as well as within plasmids was exceedingly rare (frequency of no more than 10⁻³ after full growth of a culture for some 30 generations), we found even greater stability in the χ9590 derivative strain χ9760 that has the ΔrecF126 allele in which recombination between plasmids was reduced another 10-fold. The inclusion of the ΔrecF126 deletion mutation in the wild-type S. Typhimurium UK-1 strain χ3761 has no effect on virulence having the same LD₅₀. We will therefore include the ΔrecF126 mutation in strains to maintain multiple plasmids specifying synthesis and delivery of multiple protective antigens from diverse enteric pathogens. In addition to χ9760 that can stably maintain both AsdA⁺ and DadB⁺ plasmid vectors encoding two different protective antigens and in one case with one vector encoding a fusion to synthesize two different protective antigens to result in a strain delivering three different protective antigens, we have constructed χ9822 (Δpmi-2426 Δ(gmd-fcl)-26 $\Delta P_{fur77}$::TT araC $P_{BAD}$ fur $\Delta P_{crp527}$::TT araC $P_{BAD}$ crp ΔasdA27::TTaraC$P_{BAD}$ c2 ΔaraE25 Δara-BAD23 Δrel1A98:: araC $P_{BAD}$ lacI TT $\Delta P_{murA7}$::TT araC $P_{BAD}$ murA) to permit co-maintenance of AsdA⁺ and MurA⁺ plasmids each specifying one (or two as a fusion) different protective antigens.

It should be evident that inserts encoding protective antigens from enteric pathogens in AsdA⁺ vectors such as the Shigella IpaD antigen in pYA4418 (FIG. 13), the Campylobacter jejuni PilA antigen in pYA4495 (FIG. 15), the Yersinia V antigen in pYA3841 (FIG. 8) or the C. perfringens antigen PlcC in pYA4149 (FIG. 21) can be easily excised and placed in DadB⁺ and/or MurA⁺ vectors to enable construction of derivatives of either χ9760 or χ9822 to develop vaccine strains capable of inducing protective immunity to Yersinia and Shigella, or Yersinia and C. perfringens, or Yersinia and C. jejuni or Shigella and C. jejuni, or Shigella and C. perfringens or C. jejuni and C. perfringens infections as revealed after challenge studies as described in Example 18. All of these vaccine would also induce protective immunity to diverse S. enterica serotypes as would be revealed by challenge studies with strains of S. enterica of the serotypes Typhimurium, Heidelberg, Newport, Infantis, Dublin, Virchow, Typhi, Enteritidis, Berta, Seftenberg, Ohio, Agona, Braenderup, Hadar, Kentucky, Thompson, Montevideo, Mbandaka, Javiana, Oranienburg, Anatum, Paratyphi A, Schwarzengrund, Saintpaul, and Munchen.

Further enhancement in induction of cross-protective immunity against diverse enteric pathogens can be achieved as by introduction of the $\Delta P_{mnt22}$::TT araC $P_{BAD}$ mntR deletion-insertion mutation to cause an up-regulation of protein antigens for the uptake of manganese, an essential nutrient, in vaccine strains as has been done in χ9914 (Δpmi-2426 Δ(gmd-fcl)-26 $\Delta P_{fur81}$::TT araC $P_{BAD}$ fur $\Delta P_{crp527}$::TT araC $P_{BAD}$ crp ΔasdA27:: TT araC $P_{BAD}$ c2 ΔaraE25 ΔaraBAD23 ΔrelA198::araC $P_{BAD}$ lacI TT ΔsopB1925 ΔagfBAC811 ΔaraBAD23 $\Delta P_{mnt22}$:TT araC $P_{BAD}$ mntR).

Further enhancement in inducing cross-protective immunity to diverse enteric pathogens is achieved by curing the S. Typhimurium virulence plasmid with insertion of the virulence plasmid-specified spvABCD operon as accomplished by the addition of the ΔcysG175::$P_{spv175}$ spvABCD deletion-insertion mutation in χ9876 (Example 8) followed by addition of pAPEC-1 that encodes many cross-reactive iron acquisition, manganese acquisition and serum resistance surface antigens that would be over expressed in vaccine strains with the $\Delta P_{fur81}$::TT araC $P_{BAD}$ fur $\Delta P_{mnt22}$::TT araC $P_{BAD}$ mntR $\Delta P_{crp527}$::TT araC $P_{BAD}$ crp mutations. By introducing multiple additional mutations to enable use of diverse balanced-lethal and balanced-attenuation plasmid vectors one can cause synthesis of the many other protective antigens from diverse enteric pathogens as described in Examples 8, 9, 10, 11, 12, 13, 14, 15 20 and 21.

In design of a vaccine for humans, we would further modify a strain of S. Paratyphi A as described above in Examples 16 and 19. It should be noted that S. Paratyphi A does not have a virulence plasmid so it is immediately possible to introduce the modified pAPEC-1 plasmid with the ΔcvaAB::psn iutA iucABCD insertion described in Example 21 above. It is evident that all other modifications noted above could easily be introduced into such S. Paratyphi A derivative vaccines for humans.

What is claimed is:
1. A recombinant Salmonella bacterium, wherein
(a) the recombinant bacterium is selected from the group consisting of S. Typhimurium, S. Paratyphi, or S. Typhi, and comprises one or more mutations that reduce serotype-specific immune responses caused by at least one serotype-specific antigen selected from LPS O-antigen, a component of a flagellum, or the Vi capsular antigen, wherein the one or more mutations are selected from the group consisting of:
(i) a pmi mutation that results in lack of function of the pmi gene product,
(ii) a rfc mutation, such that LPS O-antigen synthesis is greater during in vitro growth compared to in vivo growth of the recombinant bacterium,

(iii) a galE mutation that results in lack of function of the galE gene product, (iv) a fliB mutation that reduces expression of the structural gene for Phase II flagellar antigen, (v) a fliC mutation that reduces expression of the antigenically variable serotype-specific domain of the Phase I FliC flagellar antigen, and (vi) or a Vi capsular antigen mutation that reduces synthesis of the Vi capsular antigen;

(b) the recombinant bacterium expresses at least one nucleic acid encoding at least two enteric antigens, wherein the enteric antigens are selected from the groups consisting of:

(i) *Salmonella enterica* iron regulated outer membrane protein (IROMP) or manganese regulated outer membrane protein (MnROMP), (ii) *Yersinia entercolitica* V antigen or psn nucleic acid product, (iii) *Shigella* species IpaD or aerobactin, (iv) *E. coli* salmochelin, aerobactin, sit operon nucleic acid product, vaqZ nucleic acid product, a fimbrial operon nucleic acid product, tsh nucleic acid product, iss nucleic acid product, or LTB, (v) *C. jejuni* PilA or CjaA, and (vi) *C. perfringens* alpha-toxin or NetB, such that the recombinant bacterium, when administered to a host, is capable of eliciting an immune response against at least two enteric pathogens; and (c) the recombinant bacterium comprises at least one mutation in a nucleic acid regulating the expression of a nucleic acid encoding an IROMP or MnROMP, such that expression of IROMP or MnROMP is greater during in vivo growth of the bacterium compared to in vitro growth of the bacterium.

2. The recombinant bacterium of claim 1, wherein the serotype-specific antigen is LPS O-antigen.

3. The recombinant bacterium of claim 1, wherein the recombinant bacterium comprises the mutation Δpmi-2426.

4. The recombinant bacterium of claim 1, wherein the serotype-specific antigen is a component of a flagellum.

5. The recombinant bacterium of claim 1, wherein the serotype-specific antigen is produced by fliB or fliC.

6. The recombinant bacterium of claim 5, wherein the recombinant bacterium comprises the ΔfljB217 and/or the ΔfliC180 mutation.

7. The recombinant bacterium of claim 1, wherein the recombinant bacterium comprises the mutation $\Delta P_{rfc}$::TT araC $P_{BAD}$rfc.

8. The recombinant bacterium of claim 1, wherein (a) the recombinant bacterium further comprises at least one chromosomally integrated nucleic acid sequence encoding a repressor operably linked to a regulatable promoter, wherein the repressor is selected from the group consisting of LacI, C2, and C1, and the regulatable promoter is selected from the group consisting of $P_{BAD}$, a promoter regulated by maltose, a promoter regulated by rhamnose, and a promoter regulated by xylose; and (b) the at least one nucleic acid sequence encoding at least two enteric antigens expressed by the recombinant bacterium is operably linked to a promoter regulated by the repressor in (a), such that the expression of the nucleic acid sequence encoding the enteric antigens is repressed during in vitro growth of the recombinant bacterium, but the recombinant bacterium is capable of high level expression of the nucleic acid sequence encoding the enteric antigen in vivo.

9. The recombinant bacterium of claim 8, wherein the recombinant bacterium comprises at least two chromosomally integrated nucleic acid sequences, each encoding a repressor operably linked to a regulatable promoter.

10. The recombinant bacterium of claim 9, wherein each repressor is independently selected from the group consisting of LacI, C2, and C1.

11. The recombinant bacterium of claim 8, wherein the regulatable promoter is $P_{BAD}$, or a promoter regulated by maltose, rhamnose, or xylose.

12. The recombinant bacterium of claim 8, wherein the bacterium further comprises the mutation $\Delta P_{crp}$::TT araC $P_{BAD}$ crp.

13. The recombinant bacterium of claim 8, wherein the codons of the nucleic acid sequence encoding the repressor have been modified so as to optimize the expression level of the nucleic acid sequence encoding the repressor.

14. The recombinant bacterium of claim 8, wherein the repressor comprises a modified Shine-Dalgarno sequence and optimized codons so as to optimize the expression level of the nucleic acid sequence encoding the repressor.

15. The recombinant bacterium of claim 8, wherein the nucleic acid encoding an enteric antigen is operably linked to a promoter regulated by a repressor selected from the group consisting of LacI, C1, and C2.

16. The recombinant bacterium of claim 8, wherein the nucleic acid encoding an antigen of interest is operably linked to a $P_{trc}$ promoter.

17. The recombinant bacterium of claim 1, wherein the bacterium further comprises the mutation $\Delta P_{crp}$::TT araC $P_{BAD}$ crp.

18. The recombinant *Salmonella* bacterium of claim 1, the bacterium comprising a Δpmi mutation, a $\Delta P_{rfc}$::TT araC $P_{BAD}$ rfc mutation, and a ΔgalE mutation.

19. The recombinant *Salmonella* bacterium of claim 1, the bacterium comprising a $\Delta P_{fur}$::TT araC $P_{BAD}$ fur mutation, a $\Delta P_{mntR}$::TT araC $P_{BAD}$ mntR mutation and a $\Delta P_{crp}$::TT araC $P_{BAD}$ crp deletion-insertion mutation.

20. The recombinant *Salmonella* bacterium of claim 1, the bacterium comprising the pAPEC-1 plasmid with a ΔcvaAB::psn iutA iucABCD insertion.

21. The recombinant *Salmonella* bacterium of claim 1, the bacterium comprising a Δpmi mutation, a $\Delta P_{rfc}$::TT araC $P_{BAD}$ rfc mutation, a ΔgalE mutation, a $\Delta P_{fur}$::TT araC $P_{BAD}$ fur deletion-insertion mutation, a $\Delta P_{mntR}$::TT araC $P_{BAD}$ mntR deletion-insertion mutation and a $\Delta P_{crp}$::TT araC $P_{BAD}$ crp deletion-insertion mutation, and containing the pAPEC-1 plasmid with the ΔcvaAB::psn iutA iucABCD insertion.

22. The recombinant bacterium of claim 8, wherein the at least one nucleic acid sequence encoding at least two enteric antigens expressed by the recombinant bacterium and operably linked to a promoter regulated by the repressor is on a vector.

23. The recombinant bacterium of claim 22, wherein the vector is a plasmid.

24. The recombinant bacterium of claim 22, wherein the vector further comprises a nucleic acid sequence encoding a secretion signal for the antigen of interest.

25. The recombinant bacterium of claim 22, wherein the repressor is selected from the group consisting of LacI, C2, and C1; the regulatable promoter is $P_{BAD}$; the vector is a plasmid; and the nucleic acid encoding an enteric antigen is operably linked to the $P_{trc}$ promoter.

26. A vaccine composition, the composition comprising a recombinant *Salmonella* bacterium of claim 1.

27. A recombinant *Salmonella* bacterium, wherein (a) the recombinant bacterium is from the group consisting of *S. Typhimurium, S. Paratyphi*, and *S. Typhi*, and comprises one or more mutations that reduce serotype-specific immune responses caused by at least one serotype-specific antigen selected from LPS O-antigen, a component of a flagellum, or the Vi capsular antigen, wherein the one or more mutations are selected from the group consisting of:

(i) a pmi mutation that results in lack of function of the pmi gene product, (ii) a rfc mutation, such that LPS O-antigen synthesis is greater during in vitro growth compared to in vivo growth of the recombinant bacterium, (iii) a galE mutation that results in lack of function of the galE gene product, (iv) a fliB mutation that reduces expression of the structural gene for Phase II flagellar antigen, (v) a fliC mutation that reduces expression of the antigenically variable serotype-specific domain of the Phase I FliC flagellar antigen, and (vi) or a Vi capsular antigen mutation that reduces synthesis of the Vi capsular antigen;

(b) the recombinant bacterium comprises the mutation $\Delta P_{crp}$::TT araC $P_{BAD}$ crp; and (c) the recombinant bacterium comprises at least one mutation in fur or mntR.

28. A recombinant *Salmonella* bacterium, wherein (a) the recombinant bacterium is derived-selected from the group consisting of *S. Typhimurium, S. Paratyphi*, or *S. Typhi*, and comprises one or more mutations that reduce serotype-specific immune responses caused by at least one serotype-specific antigen selected from LPS O-antigen, a component of a flagellum, or the Vi capsular antigen, wherein the one or more mutations are selected from the group consisting of:

(i) a pmi mutation that results in lack of function of the pmi gene product, (ii) a rfc mutation, such that LPS O-antigen synthesis is greater during in vitro growth compared to in vivo growth of the recombinant bacterium, (iii) a galE mutation that results in lack of function of the galE gene product, (iv) a fliB mutation that reduces expression of the structural gene for Phase II flagellar antigen, (v) a fliC mutation that reduces expression of the antigenically variable serotype-specific domain of the Phase I FliC flagellar antigen, and (vi) or a Vi capsular antigen mutation that reduces synthesis of the Vi capsular antigen;

(b) the recombinant bacterium comprises the mutation $\Delta P_{crp}$::TT araC $P_{BAD}$ Crp;

(c) the recombinant bacterium comprises at least one mutation in fur or mntR; and (d) the recombinant bacterium expresses at least one enteric antigen selected from the group consisting of (i) *Salmonella enterica* IROMP or MnROMP, (ii) *Yersinia entercolitica* V antigen nucleic acid product or psn nucleic acid product, (iii) *Shigella* species IpaD or aerobactin, (iv) *E. coli* salmochelin, aerobactin, sit operon nucleic acid product, yagZ nucleic acid product, a fimbrial operon nucleic acid product, tsh nucleic acid product, iss nucleic acid product, or LTB, (v) *C. jejuni* PilA or CjaA, and (vi) *C. perfringens* alpha-toxin or NetB.

* * * * *